United States Patent
Kim et al.

(10) Patent No.: US 9,932,412 B2
(45) Date of Patent: Apr. 3, 2018

(54) BISPECIFIC ANTIGEN BINDING PROTEIN COMPLEX AND PREPARATION METHODS OF BISPECIFIC ANTIBODIES

(71) Applicant: Samsung Electronics Co., Ltd., Suwon-si, Gyeonggi-do (KR)

(72) Inventors: Min-kyung Kim, Seoul (KR); JungWook Lee, Yongin-si (KR); SuJeong Hwang, Hwaseong-si (KR); Jaeil Lee, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/069,091

(22) Filed: Oct. 31, 2013

(65) Prior Publication Data
US 2014/0127210 A1    May 8, 2014

(30) Foreign Application Priority Data
Oct. 31, 2012    (KR) .................. 10-2012-0122559

(51) Int. Cl.
C07K 16/46    (2006.01)
C07K 16/22    (2006.01)
C07K 16/28    (2006.01)

(52) U.S. Cl.
CPC ............ C07K 16/468 (2013.01); C07K 16/22 (2013.01); C07K 16/2863 (2013.01); C07K 2317/569 (2013.01); C07K 2319/50 (2013.01)

(58) Field of Classification Search
None
See application file for complete search history.

(56) References Cited

U.S. PATENT DOCUMENTS

| | | | |
|---|---|---|---|
| 5,837,242 A | 11/1998 | Holliger et al. | |
| 5,932,448 A * | 8/1999 | Tso et al. | 435/69.6 |
| 6,121,424 A | 9/2000 | Whitlow et al. | |
| 6,294,353 B1 | 9/2001 | Pack et al. | |
| 7,498,024 B2 | 3/2009 | Fang et al. | |
| 7,696,320 B2 | 4/2010 | Ignatovich et al. | |
| 2004/0071696 A1 | 4/2004 | Adams et al. | |
| 2005/0136050 A1 | 6/2005 | Kufer et al. | |
| 2006/0088529 A1 | 4/2006 | Leung et al. | |
| 2006/0099205 A1 | 5/2006 | Adams et al. | |
| 2006/0147959 A1* | 7/2006 | Bell et al. | 435/6 |
| 2007/0020267 A1* | 1/2007 | Fuh et al. | 424/145.1 |
| 2008/0138339 A1 | 6/2008 | Huang et al. | |
| 2009/0010840 A1 | 1/2009 | Adams et al. | |
| 2009/0182127 A1 | 7/2009 | Kjaergaard et al. | |
| 2009/0202532 A1 | 8/2009 | Kumagai et al. | |
| 2009/0304696 A1* | 12/2009 | Lawson | C07K 16/00 424/135.1 |
| 2010/0092495 A1 | 4/2010 | Chari | |
| 2010/0189727 A1 | 7/2010 | Rodeck et al. | |
| 2010/0254989 A1 | 10/2010 | Bossenmaier et al. | |
| 2012/0230995 A1 | 9/2012 | Weidanz et al. | |
| 2013/0202596 A1 | 8/2013 | Salas et al. | |

FOREIGN PATENT DOCUMENTS

| | | |
|---|---|---|
| EP | 1136556 A1 | 9/2001 |
| EP | 0894135 B1 | 8/2004 |
| KR | 2008-0074231 A | 8/2008 |
| WO | WO 02-08293 A2 | 1/2002 |
| WO | WO 2002/090495 A2 | 11/2002 |
| WO | WO 2004-094613 A2 | 11/2004 |
| WO | WO 2012/006633 A1 | 1/2012 |
| WO | WO 2012/025530 A1 | 3/2012 |

OTHER PUBLICATIONS

Mabry et al. (Protein Engineering, Design, and Selection, 23: 115-127, 2010).*
Horak et al. (Cancer Biotherapy and Radiopharmaceuticals, 20: 603-613, 2005).*
Stols et al. (Protein Expression and Purification, 25: 8-15, 2002).*
Extended European Search Report for 13190818.8 mailed Feb. 18, 2014.
Arathoon et al., "A method for making multispecific antibodies having heteromultimeric and common components", *Expert Opinion on Therapeutic Patents*, 9 (6): 785-790 (1999).
Cochran et al., *J. Immunol. Meth.*, 287:147-158 (2004).
Jiang et al., *J. Biol. Chem.*, 280(6): 4656-4662 (2005).
Paul, *Fundamental Immunology* (textbook), 1993: 292-295 (1993).
Rudikoff et al., *Proc. Nat. Acad. Sci. USA*, 79: 1979-1983 (1982).
Stancoviski et al., *Proc. Nat. Acad. Sci.*, 88:8691-8695 (1991).
Yu et al., *Investigative Opthalmology & Visual Science*, 49(2): 522-527 (2008).
European Patent Office, Examination Report for Application No. 13 190 818.8 dated Aug. 3, 2017 (9 pages).
Asano et al. "Application of the Fc fusion format to generate tag-free bi-specific diabodies," *The FEBS Journal*, vol. 277, No. 2, pp. 477-487 (2009).
Terpe et al., "Overview of tag protein fusions: from molecular and biochecmical fundamentals to commercial systems," *Appl. Microbiol Biotechnol*, vol. 60, No. 5, pp. 523-533 (2003).

* cited by examiner

*Primary Examiner* — Nelson B Moseley, II
(74) *Attorney, Agent, or Firm* — Leydig, Voit & Mayer, Ltd.

(57) ABSTRACT

A bispecific antigen binding protein complex comprising a first polypeptide comprising a first antigen binding site at an N terminus; a second polypeptide comprising a second antigen binding site at an N terminus; and a linker connecting the first polypeptide and the second polypeptide; wherein the linker comprises a tag at one terminus thereof, and wherein the tag is connected to a C-terminus of the first polypeptide or to an N-terminus of the second polypeptide, and comprises a cleavable amino acid sequence; as well as related compositions and methods.

19 Claims, 5 Drawing Sheets

BISPECIFIC ANTIGEN BINDING PROTEIN COMPLEX AND PREPARATION METHODS OF BISPECIFIC ANTIBODIES

CROSS-REFERENCE TO RELATED APPLICATIONS

This application claims the benefit of Korean Patent Application No. 10-2012-0122559, filed on Oct. 31, 2012 in the Korean Intellectual Property Office, the entire disclosure of which is hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 425,467 Byte ASCII (Text) file named "712481-ST25-Updated.txt" created on Jan. 16, 2014.

BACKGROUND

1. Field

The present disclosure relates to bispecific antigen binding protein complexes, methods of preparing bispecific antibodies, and pharmaceutical purposes of the bispecific antibodies.

2. Description of the Related Art

Monoclonal antibodies have become a leader of new drugs in the market and accordingly, are being developed as drugs for a variety of targets. However, in many cases, the development of new drugs is limited; for example, there is no satisfactory efficacy, it is expensive to produce antibodies, or the like. As one solution to overcome these problems, a study on bispecific antibodies has been steadily explored since the mid-1980s, but in spite of a large effort, a dominant technology has not appeared yet.

In a conventional method of preparing bispecific antibodies, there are difficulties on mass production of homogeneous bispecific antibodies or practical difficulties due to low efficacy and side effects. In recent years, some competitive new antibody platforms have appeared based on the strength of the development of antibody engineering technology, but they are still in the verification phase.

Therefore, even by conventional technology, the development of a new platform for preparing an antibody having specificity to at least two heterogeneous antigens, and a method of producing the antibody are necessary.

SUMMARY

Provided are bispecific antigen binding protein complexes including two antibody binding sites according to an aspect of the present invention.

Specifically, the invention provides a bispecific antigen binding protein complex comprising: a first polypeptide comprising a first antigen binding site at an N terminus; a second polypeptide comprising a second antigen binding site at an N terminus; and a linker connecting the first polypeptide and the second polypeptide; wherein the linker includes a first tag and a second tag at both terminals, and wherein the first tag is connected to a C-terminus of the first polypeptide, the second tag is connected to an N-terminus of the second polypeptide, and the first tag and the second tag each includes a cleavable amino acid sequence.

Additionally, the invention provides a bispecific antigen binding protein complex comprising: a first polypeptide comprising a first antigen binding site at an N terminus; a second polypeptide comprising a second antigen binding site at an N terminus; and a linker connecting the first polypeptide and the second polypeptide; wherein the linker comprises a tag at one terminus, and wherein the tag is connected to a C-terminus of the first polypeptide or to an N-terminus of the second polypeptide, and comprises a cleavable amino acid sequence.

Provided are polynucleotides encoding the bispecific antigen binding protein complexes according to another aspect of the present invention.

Provided are methods of preparing bispecific antibodies using host cells transformed by recombinant expression vectors comprising the polynucleotides.

Provided are methods and pharmaceutical compositions including the bispecific antibodies (e.g., for the treatment or prevention of a disease). In particular, the invention provides a method for prevention or a treatment of a disease in a subject, comprising: preparing a pharmaceutical composition comprising a treatment effective dose of a bispecific antibody and a pharmaceutical acceptable carrier, an excipient, or a stabilizer, and administering the pharmaceutical composition to the subject, wherein the disease is selected from the group consisting of a proliferative disorder, a neoplastic disease, an inflammatory disease, an autoimmune disease, an infectious disease, a viral disease, an allergic condition, a graft-versus-host disease, and a host-versus-graft disease.

Provided are diagnostic methods and compositions including the bispecific antibodies. In one embodiment, the invention provides a method for diagnosing a disease comprising obtaining a biological sample from a subject and contacting the biological sample with a composition comprising a bispecific antibody, wherein the composition can detect an antigen specifically found in a disease by forming an antibody-antigen complex, and wherein the disease is selected from the group consisting of a proliferative disorder, a neoplastic disease, an inflammatory disease, an autoimmune disease, an infectious disease, a viral disease, an allergic condition, a graft-versus-host disease, and a host-versus-graft disease. In another embodiment, the invention provides a method for diagnosing a disease in a subject comprising injecting the subject with a composition comprising a bispecific antibody, wherein the composition can detect an antigen specifically found in a disease by forming an antibody-antigen complex, and wherein the disease is selected from the group consisting of a proliferative disorder, a neoplastic disease, an inflammatory disease, an autoimmune disease, an infectious disease, a viral disease, an allergic condition, a graft-versus-host disease, and a host-versus-graft disease.

Additional aspects will be set forth in part in the description which follows and, in part, will be apparent from the description, or may be learned by practice of the presented aspects.

BRIEF DESCRIPTION OF THE DRAWINGS

These and/or other aspects will become apparent and more readily appreciated from the following description of the aspects, taken in conjunction with the accompanying drawings in which.

DETAILED DESCRIPTION

Figure 1:
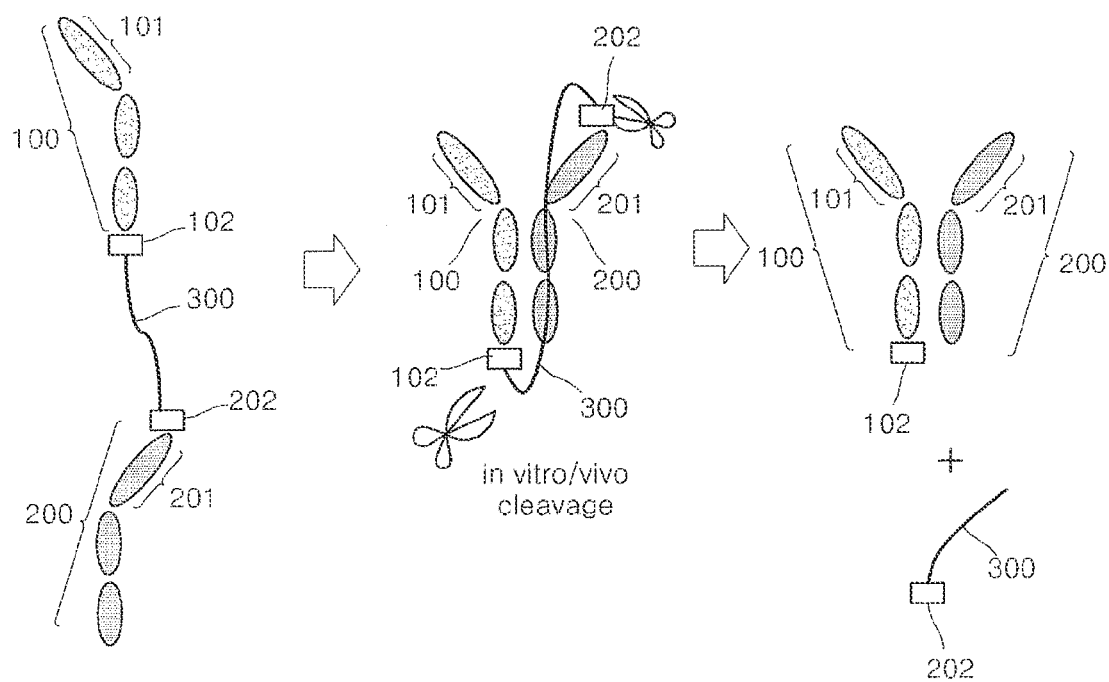
FIG. 1 is a schematic diagram of a bispecific antigen binding protein complex and a bispecific antibody according to an aspect of the present invention.

Reference will now be made in detail to aspects, examples of which are illustrated in the accompanying drawings, wherein like reference numerals refer to like elements throughout. In this regard, the present aspects may have different forms and should not be construed as being limited to the descriptions set forth herein. Accordingly, the aspects are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It should be understood that the exemplary aspects described herein should be considered in a descriptive sense only and not for purposes of limitation. Descriptions of features or aspects within each aspect should typically be considered as available for other similar features or aspects in other aspects.

According to an aspect of the present invention, provided is a bispecific antigen binding protein complex comprising, consisting essentially of, or consisting of a first polypeptide including a first antigen binding site at an N-terminus; a second polypeptide including a second antigen binding site at an N-terminus; and a linker connecting the first polypeptide and the second polypeptide, wherein the linker includes a first tag and a second tag at both termini, and wherein the first tag is connected to the C-terminus of the first polypeptide, the second tag is connected to the N-terminus of the second polypeptide, and the first tag and the second tag each includes a cleavable amino acid sequence.

According to another aspect of the present invention, provided is a bispecific antigen binding protein complex comprising, consisting essentially of, or consisting of a first polypeptide comprising a first antigen binding site at an N-terminus; a second polypeptide including a second antigen binding site at the N-terminus; and a linker connecting the first polypeptide and the second polypeptide, wherein the linker includes a tag at one terminus, and wherein the tag is connected to a C-terminus of the first polypeptide or an N-terminus of the second polypeptide and includes a cleavable amino acid sequence.

The term "bispecific" as used herein refers to two different antigens, or even when the two are the same antigens, each of them has a binding specificity for a different epitope. The epitope may have originated from different antigens or the same antigen. The terms "bispecific antigen binding protein complex" and "bispecific antigen," as used herein, refer to prepared products with a full-length antibody or a fragment having an antigen binding site. The antibody may be a human antibody, a non-human antibody, a humanized antibody, or a chimeric antibody. The term "antigen binding site" as used herein refers to a site in an antibody or antibody fragment, where an antigen or an epitope binds, and the antigen binding site may include a complementary determining region (CDR). The CDR refers to an amino acid sequence found in the hypervariable region of a heavy chain or a light chain of an immunoglobulin. Each of the heavy chain and the light chain may include three CDRs (e.g., CDRH1, CDRH2, CDRH3, and CDRL1, CDRL2, CDRL3). The CDR may provide a major contact residue for binding the antigen or the antibody to the epitope.

The term "heavy chain" as used herein is understood to include a full-length heavy chain including a variable region ($V_H$) having amino acid sequences that determine specificity for antigens and a constant region having three constant domains ($C_{H1}$, $C_{H2}$, and $C_{H3}$), and fragments thereof. Also, the term "light chain" as used herein includes a full-length light chain including a variable region ($V_L$) having amino acid sequences that determine specificity for antigens and a constant region ($C_L$), and fragments thereof.

According to an aspect of the present invention, the protein complex and the bispecific antibody may include a first antigen binding site and a second antigen binding site binding to different antigens or different epitopes. The antigen that may bind to the antigen binding site may not be expressed or may be expressed at a low level under normal condition; however, the antigen may show increased expression in a specific diseased condition, for example, in a neoplastic disease or in an immunological disease.

The antigen may be selected from the group consisting of VEGF, EGFR, EpCAM, CCR5, CD19, HER-2 neu, HER-3, HER-4, PSMA, CEA, MUC-1 (mucin), MUC2, MUC3, MUC4, MUC5 AC, MUC5 B, MUC7, βhCG, Lewis-Y, CD20, CD33, CD30, ganglioside GD3, 9-O-acetyl-GD3, GM2, Globo H, fucosyl GM1, poly SA, GD2, Carboanhydrase IX (MN/CA IX), CD44v6, Sonic Hedgehog (Shh), Wue-1, Plasma Cell Antigen, (membrane bound) IgE, Melanoma Chondroitin Sulfate Proteoglycan, MCSP, CCR8, TNF-α precursor, STEAP, mesothelin, A33 antigen, Prostate Stem Cell Antigen, PSCA, Ly-6, desmoglein 4, E-cadherin neoepitope, Fetal Acetylcholine Receptor, CD25, CA19-9 marker, CA-125 marker and Mullerian Inhibitory Substance, MIS II, sTn (sialylated Tn antigen; TAG-72), FAP (fibroblast activation protein), endosialin, EGFRvIII, LG, SAS and CD63. To achieve a uniform physiological effect, the protein complex and the bispecific antibodies binding to different antigens may use a combination of antigens that induces a synergistic effect of the two antigen-antibody reactions or enables a series of connected actions. The combination of antigens may include, for example, bispecific antibodies (BsAb) targeting a tumor cell antigen and a cytotoxic triggering molecule antigen, for example, anti-FcγRI/anti-CD15, anti-p185HER2/FcγRIII(CD16), anti-CD3/anti-malignant-B-cell (10), anti-CD3/anti-p185HER2, anti-CD3/anti-p97, anti-CD3/anti-renal cell carcinoma, anti-CD3/anti-OVCAR-3, anti-CD3/L-D1 (anti-colorectal cancer), anti-CD3/anti-melanin stimulating hormone analogues, anti-EGFR/anti-CD3, anti-CD3/anti-CAMA1, anti-CD3/anti-CD19, anti-CD3/MoV18, anti-neural cell adhesion molecule (NCAM)/anti-CD3, anti-folate binding protein (FBP)/anti-CD3, anti-pan carcinoma related antigen(AMOC-31)/anti-CD3; BsAb targeting tumor cell antigen and antitoxin antigen, for example, anti-saponin/anti-Id-1, anti-CD22/anti-saponin, anti-CD7/anti-saponin, anti-CD38/anti-saponin, anti-CEA/anti-lysine A chain, anti-interferon-α(IFN-α)/anti-hybridoma idiotype, anti-CEA/anti-Vinca alkaloid; BsAb for changing pro-drug activated by enzyme, for example, anti-CD30/anti-alkaline phosphatase (catalyzes changing mitomycin phosphatase pro-drug into mitomycin alcohol); BsAb used as fibrin decomposer, for example, anti-fibrin/anti-tissue plasminogen activator (tPA), anti-fibrin/anti-urokinase-type plasminogen activator (uPA); BsAb for targeting immunological complex in cell-surface receptor, for example, anti-low density lipoprotein (LDL)/anti-Fc receptor (example: FcγRI, FcγRII or FcγRIII); BsAb for treating infectious disease, for example, anti-CD3/anti-herpes simplex virus (HSV), anti-T-cell receptor:CD3 complex/anti-influenza, anti-FcγR/anti-HIV; BsAb for tumor detection in vitro or in vivo, for example, anti-CEA/anti-EOTUBE, anti-CEA/anti-DPTA, anti-p185HER2/anti-hapten); BsAb as a vaccine adjuvant; and BsAb as diagnostic means, for example, anti-rabbit IgG/anti-ferritin, anti-horse radish peroxidase (HRP)/anti-hormone, anti-somatostatin/anti-substance P, anti-HRP/anti-FITC, and anti-CEA/anti-β-galactosidase.

According to an aspect of the present invention, the polypeptide including the antigen binding site may be a complete antibody or a fragment of the complete antibody (antigen binding fragment).

The complete antibody has a structure of two full length light chains and two full length heavy chains, and each light chain and heavy chain is connected by a disulfide bond (S—S bond). A constant region of the antibody is divided into a heavy chain constant region and a light chain constant region, and the heavy chain constant region has gamma (γ), mu (ρ), alpha (α), delta (δ), and epsilon (ε) types, and has subclasses of gamma1 (γ1), gamma 2 (γ2), gamma 3 (γ3), gamma 4 (γ4), alpha1 (α1), and alpha 2 (α2). The constant region of the light chain has kappa (κ) and lambda (λ) types.

The term "antigen binding fragment" as used herein refers to a part of the complete antibody having antigen binding capability due to an antigen binding site. The antigen binding fragment included in this definition may include (i) light chain variable region (VL), a Fab fragment with a light chain constant region (CL), a heavy chain variable region (VH) and a first constant region of heavy chain (CH1); (ii) a Fab' fragment that is a Fab fragment having at least one cysteine residue at a C-terminus of the CH1 domain; (iii) a Fd fragment with VH and CH1 domains; (iv) Fd' fragment with at least one cysteine residue at VH, and CH1 domains, and the C-terminus of the CH1 domain; (v) Fv fragment that is a minimum antibody fragment having $V_L$ and $V_H$ domains on single arms of the antibody (two-chain Fv is connected by a non-covalently bond between the heavy chain variable region and the light chain variable region of the antibody, and single-chain Fv (scFv) is generally connected by a covalent bond through a peptide linker between the heavy chain variable region and the light chain variable region, or may form a dimer similar to a double stranded Fv because the single strand Fv is connected directly from the C-terminus; (vi) a dAb fragment composed of VH domains (Ward et al., Nature 341, 544-546 (1989)); (vii) an isolated CDR region; (viii) a F(ab')2 fragment which is bivalent fragment, that includes two Fab' fragments connected by a disulfide bridge at a hinge region; (ix) a single stranded antibody molecule (for example, single stranded Fv; scFv (Bird et al., Science 242:423-426 (1988); Huston et al., PNAS (USA) 85:5879-5883 (1988)); (x) a diabody having two antigen binding sites including the light chain variable region and the heavy chain variable region in the same polypeptide strand (Hollinger et al., Proc. Natl. Acad. Sci. USA, 90:6444-6448 (1993)); (xi) a linear antibody including a pair of tandem Fd segments (VH-CH1-VH-CH1) forming a pair of antigen binding regions along with a complementary light chain polypeptide (Zapata et al. Protein Eng. 8(10):1057-1062 (1995)); and (xii) a single-domain antibody including only a heavy chain composed of VH, CH2, and CH3. The antigen binding fragment may be obtained by a protease (for example, Fab may be obtained when the entire antibody is subject to restriction fragment with papain, and $F(ab')_2$ may be obtained when fragmented with pepsin), and the fragment may be prepared by the recombinant DNA technology.

According to an aspect of the present invention, a polypeptide including the antigen binding site may be a single domain antibody. The term "single-domain antibody" as used herein refers to a peptide chain having a single variable region ($V_H$) monomer, and composed of about 110 amino acids without a CH1 region of the light chain and the heavy chain. The single-domain antibody includes a heavy chain antibody, a naturally occurring single domain antibody (an antibody naturally without a light chain), a single-domain antibody that is derived from a conventional 4 chain antibody, an artificial antigen and a single domain scaffold that is not derived from an antigen. The single domain antibody molecule is very small, having a size about ¹/₁₀ of IgG molecule, and is a very stable single strand polypeptide, maintaining stability at conditions of extreme pH or temperature. Also, unlike conventional antibodies, the single domain antibody molecules have tolerance to protease activities, and may be mass produced with a high yield in vitro. The single domain antibody may include an antigen binding region or a fragment crystallizable (Fc) region. The antigen binding site, for example, may have the amino acid sequence of SEQ ID NO: 2 or SEQ ID NO: 3 when the conjugated antigen is VEGF, and may have amino acid sequence of SEQ ID NO: 5 or SEQ ID NO: 6 when the conjugated antigen is EFGR. The Fc region may include a hinge region or two constant regions ($C_{H2}$ and $C_{H3}$), for example, may have the amino acid sequence of SEQ ID NO: 4.

According to an aspect of the present invention, polypeptide including the antigen binding site may be selected from a group consisting of amino acid sequences having SEQ ID NOs: 8 to 44.

According to an aspect of the present invention, the protein complex may include a linker connecting the first polypeptide and the second polypeptide. The linker may be a peptide linker. Various linkers known in the art may be used, for example, the linker may be composed of a plurality of amino acids. According to an aspect of the present invention, the linker, for example, may be a polypeptide composed of about 1 to about 100 or about 2 to about 50 amino acids (this length does not include a potential tag as described below). The sequence of the linker may be random. Examples of suitable linkers include, but are not limited to, Gly-Gly and (Gly-Gly-Gly-Gly-Ser)n (SEQ ID NO: 82), wherein n is 1-10.

The peptide linker may be folded in functional secondary or tertiary structures by sufficiently separating the first polypeptide and the second polypeptide. For example, the peptide linker may include Gly, Asn, and Ser residues, and may include neutral amino acids such as Thr and Ala. Amino acid sequences suitable for the peptide linker are known in the art. On the other hand, a length of the linker may be variously decided, provided that the length does not affect the function of the fusion protein.

According to an aspect of the present invention, the linker may further include a tag on at least one terminal of the linker. Also, the tag (e.g., one or more tags) connects to the terminal of the linker, and may include a cleavable amino acid sequence.

The term "tag" as used herein refers to a protein or a polypeptide bound to an end of the fusion protein, and the tag is a medium for connecting different fusion proteins. The tag may be connected to an N-terminus or a C-terminus of the polypeptide. According to an aspect of the present invention, the tag may be cleavable in vitro or in vivo. The in vitro or in vivo cleaving may be processed by a protease.

According to an aspect of the present invention, the tag may be selected from the group consisting of ubiquitin, ubiquitin-like protein, and TEV cleavage peptide. Ubiquitin (Ub) is the most conservative protein found in nature that has 76 amino acids in sequence, and it is a water soluble protein showing a perfect homology among evolutionarily various species such as insect, rainbow trout, and humans. Also, ubiquitin is known as a protein stable with respect to pH changes, which does not denature easily at a high temperature, and is stable with respect to the protease.

The ubiquitin or the ubiquitin-like protein may be selected from the group consisting of wild type ubiquitin, wild type ubiquitin-like protein, mutant ubiquitin, and mutant ubiquitin-like protein. According to an aspect of the present invention, the ubiquitin may be composed of the amino acid sequence of SEQ ID NO: 7. The ubiquitin-like protein is a protein with similar properties as an ubiquitin, and may be selected from the group consisting of, for example, Nedd8, SUMO-1, SUMO-2, NUB1, PIC1, UBL3, UBL5, and ISG15. The mutant ubiquitin refers to a wild type ubiquitin wherein one or more amino acids have been changed (e.g., inserted, added, deleted, or substituted). For example, the mutant ubiquitin can include Lys of a wild type ubiquitin substituted by Arg, and a C-terminal RGG of a wild type ubiquitin substituted by RGA. According to an aspect of the present invention, regarding the mutant ubiquitin whose Lys has been substituted by Arg, the substitution may occur in Lys located in amino acid residues 6, 11, 27, 29, 33, 48, and 63 relative to the wild type ubiquitin sequence (Accession No. 3H7P_A), and the substitution may occur independently or in combination.

According to an aspect of the present invention, the ubiquitin or the ubiquitin-like protein may include an amino acid sequence cleavable by a protease at a C-terminus of the amino acid sequence in vitro or in vivo. The amino acid sequences cleavable by the protease may be found in a search database known in the art. For example, protease and cleavable amino acid sequences found using the PeptideCutter tool and database maintained by the Swiss Institute of Bioinformatics, Lausanne, Switzerland (Gasteiger E., Hoogland C., Gattiker A., Duvaud S., Wilkins M. R., Appel R. D., Bairoch A.; *Protein Identification and Analysis Tools on the ExPASy Server*; (In) John M. Walker (ed): The Proteomics Protocols Handbook, Humana Press (2005)). When a cleavable amino acid sequence is included, the protein complex may have its tag cleaved in vitro (e.g., in a host cell expressing the protein complex and an enzyme or other molecule capable of cleaving the tag, or after isolating the protein complex including the linker from the host cell) or in vivo such that the protein complex may form a tertiary structure as a bispecific antibody, thereby performing its function.

According to another aspect of the present invention, the protein complex may further include a signal sequence for secretion.

The signal sequence for secretion refers to a sequence inducing a secretion of a protein or a peptide expressed by connecting to an N-terminus of the coding sequence outside a cell membrane or a cell, and the signal sequence may be a peptide sequence composed of about 18 to about 30 amino acids. All proteins transportable outside the cell membrane have distinctive signal sequences, and the signal sequence is cleaved by a signal peptidase at the cell membrane. Generally, for a foreign protein not expressed naturally in a host cell, a signal sequence to secrete the protein to a periplasm or culture medium, or a modified sequence may be used.

According to an aspect of the invention, the amino acid sequence of the protein complex may be suitably changed, provided that an intended function or a property, for example, antigen specificity, is not actually changed. The change in amino acid occurs based on the similarity of an amino acid residue substitution product, for example, based on hydrophobic property, hydrophilic property, electric charge, and/or size, and for this, the amino acid hydrophobic index may be considered. The change, for example, may be a partial substitution, insertion, deletion, and/or addition of amino acid, and especially, the substitution may be a conservative substitution. The term "conservative substitution" as used herein refers to a substitution that does not change the biological activity of the resulting molecule, such that the substituted amino acid does not affect a tertiary structure of the protein or a local charge state. Amino acid substitutions that do not entirely change the molecular activity are known in the art, for example, may include amino acid substitutions of Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and/or Asp/Gly.

In another aspect of the present invention, a polynucleotide encoding the protein complex is provided.

The term "polynucleotide" as used herein refers to a polymer of deoxyribonucleotide or ribonucleotide existing in a single strand or in a double strand form. The polynucleotide includes RNA genome sequence, DNA (gDNA and cDNA), or RNA sequence transcribed from the DNA, and unless specifically mentioned, the polypeptide further includes a natural polynucleotide, sugar, or base changed analogues. According to an aspect of the present invention, the polynucleotide is a light chain polynucleotide.

The inventive polynucleotide includes a nucleotide sequence encoding the amino acid sequence of the protein complex, and also includes a nucleotide sequence complementary thereto. The complementary sequence includes a completely complementary sequence and a substantially complementary sequence, which refers to a sequence hybridizable to a nucleotide sequence encoding the amino acid sequence of the protein complex under a stringent condition known in the art.

Also, the nucleotide sequence encoding the protein complex amino acid sequence may be changed or mutated. The change includes an addition, an insertion, a deletion, or a non-conservative substitution or a conservative substitution. The polynucleotide encoding the protein complex amino acid sequence may be interpreted as including the nucleotide sequence showing a substantial identity with respect to the polynucleotide. The substantial identity aligns the nucleotide sequence and another random sequence in a way that they are maximally correspondent, and when the aligned sequence is analyzed using an algorithm generally used in the art, the sequence may show greater than 80% identity, greater than 90% identity, or greater than 95% identity.

According to an aspect of the present invention, the polynucleotide may have a base sequence selected from a group consisting of SEQ ID NO: 45 to SEQ ID NO: 81.

Genetic engineering technology and/or chemical synthesis known in the art can be used to prepare the protein complex or the corresponding polynucleotide. The genetic engineering technology may involve preparing a cloning vector or an expression vector encoding the target protein, transforming a host cell with the vector, and culturing the host cell to express the target protein.

Hence, an aspect of the present invention provides a method of preparing a bispecific antibody, the method including preparing a recombinant expression vector, wherein a polynucleotide encoding the above-mentioned protein complex is inserted, transforming a host cell with the recombinant expression vector, culturing the transformed host cell, and collecting a bispecific antibody expressed in the host cell.

The term "vector" as used herein refers to a method of expressing a target gene, and when the vector is introduced in the host cell, the cell produces copies of foreign DNA independently cloned and inserted in the vector and interior of the cell. The term "recombinant expression vector" as used herein refers to a vector wherein a foreign DNA fragment is inserted to amplify a target protein, and the foreign DNA fragment may be the polynucleotide encoding the protein complex. A method of manufacturing a vector system for expression or cloning is known in the art.

The vector may include a regulatory sequence operably linked to the polynucleotide sequence.

The term "regulatory sequence" as used herein refers to a nucleic acid sequence for expressing a coding sequence, and properties of the regulatory sequence may vary depending on the host organism. In a prokaryote, the regulatory sequence generally includes a promoter, a ribosome binding site, and transcription/translation terminators. In a eukaryotic organism, the regulatory sequence generally includes a promoter, a terminator, and in some cases, an enhancer, transactivators, or a transcription factor may be included. The term "operably linked" used herein refers to a juxtaposition caused by a functional binding such that the components may operate as intended. The regulatory sequence operably linked to the coding sequence is linked under a condition where the coding sequence expression may coexist with the regulatory sequence.

When a prokaryotic cell is used as a host, the recombinant vector may include a strong promoter that may process a transcription (for example, tac promoter, lac promoter, lacUV5 promoter, lpp promoter, pLA promoter, pRA promoter, rac5 promoter, amp promoter, recA promoter, SP6 promoter, trp promoter, and/or T7 promoter); a ribosome binding site for starting a translation; and transcription/translation terminators. When $E.\ coli$ (for example, HB101, BL21, or DH5a) is used as the host cell, $E.\ coli$ promoter and operator regions of the tryptophan biosynthesis pathway (Yanofsky, C. (1984), J. Bacteriol., 158:1018-1024), and/or leftward promoter of phage A (pLA promoter, Herskowitz, I. and Hagen, D. (1980), Ann. Rev. Genet., 14:399-445) may be used as a regulatory region. When an eukaryotic cell is used as a host, a promoter originated from a mammalian cell precursor (e.g., metallothionein promoter) or a promoter originated from a mammalian virus (e.g., adenovirus late promoter, a vaccinia virus promoter 7.5K, an SV40 promoter or a cytomegalovirus promoter, and atk promoter of HSV) may be used, and may have a polyadenylated sequence as the transcription terminator sequence.

In addition to the regulatory sequence, the recombinant expression vector may further include a restriction site, a marker gene such as a drug resistance gene, a signal sequence for secretion, or a leader sequence. The restriction site refers to a specific base sequence specifically recognized by the restriction enzyme. The restriction site may be sequences specifically recognized by restriction enzymes such as for example, EcoRI, BamHI, HindIII, kpn I, Not I, Pst I, Sma I, and/or Xho I. The marker gene acts as a selectable marker, and may be a drug resistance gene for drugs such as ampicillin, gentamicin, carbenicillin, chloramphenicol, streptomycin, kanamycin, geneticin, neomycin, and/or tetracycline. The signal sequence for secretion or a leader sequence are sequences inducing a synthesized protein to move to a cell compartment (for example, periplasmic space) or inducing a secretion of the synthesized protein into a culture medium exterior of the cell, and the sequence may be included in the coding sequence of the polynucleotide sequence. The sequence may be suitably selected by one of ordinary skill in the art to correspond to the introduced DNA, the types of the host cells, and/or the conditions of the culture medium.

Suitable vectors (which may include the above-described factors) include, but are not limited to, Okayama-Berg cDNA expression vector pcDV1 (Pharmacia), pCDM8, pRc/CMV, pcDNA1, pcDNA3 (Invitrogen)), pEF-DHFR, pEF-ADA or pEF-neo, or pSPORT1(GIBCO BRL).

According to an aspect of the present invention, the host cell may be prepared by transforming or transfecting the recombinant expression vector or the bispecific antigen binding protein complex into the host cell.

The host cell may be a prokaryotic cell or a eukaryotic cell known in the art that may stabilize the recombinant vector and may continuously clone and express the vector. The prokaryotic organism includes a bacterium into which a DNA molecule or an RNA molecule for protein expression may be transformed. For example, $Escherichia\ coli,\ Bacillus$ strains such as $Bacillus\ subtilis$, and $Bacillus\ thuringiensis,\ Streptomyces,\ Pseudomonas$ (for example, $Pseudomonas\ putida$), $Proteus\ mirabilis,\ Staphylococcus$ (for example, $Staphylococcus\ carnosus$), rat typhus ($S.\ typhimurium$), or $Serratia\ marcescens$, can be used. The eukaryotic cells include yeast, higher vegetation, insect or mammalian cells.

According to an aspect of the present invention, the host cell may be a mammalian cell. Examples of useful mammalian cells include simian kidney cell, CV1 cell line transformed into SV40 (COS-7, ATCC CRL 1651); a human embryonic kidney cell line (HEK-293 or subcloned hEK-293 cell for growth in suspension culture, Graham et al., J. Gen Virol. 36:59 (1977)); a baby hamster kidney cell (BHK, ATCC CCL 10); a Chinese hamster ovary cell/-DHFR (CHO, Urlaub et al., Proc. Natl. Acad. Sci. USA 77:4216 (1980)); a mouse sertoli cell (TM4, Mather, Biol. Reprod. 23:243-251 (1980)); a simian kidney cell (CV1 ATCC CCL 70); an African green monkey kidney cell (VERO-76, ATCC CRL-1587); a human cervical cancer cell (HELA, ATCC CCL 2); a canine kidney cell (MDCK, ATCC CCL 34); a buffalo rat liver cell (BRL 3A, ATCC CRL 1442); a human lung cell (W138, ATCC CCL 75); a human liver cell (Hep G2, HB 8065); a mouse breast cancer cell (MMT 060562, ATCC CCL51); a TR1 cell (Mather et al., Annals N.Y. Acad. Sci. 383:44-68 (1982)); an MRC 5 cell; an FS4 cell; and/or a human liver tumor cell line (Hep G2).

The transformation of the recombinant expression vector into the host cell may be performed by, for example, DEAE-dextran mediated transfection, electroporation, transduction, calcium phosphate transfection, cationic lipid-mediated transfection, scrape loading, and/or infection.

Culturing the host cell may be performed by using a suitable culture medium and culture conditions known in the art. A commercial culture medium, for example, Ham's F10 (Sigma), MEM (Minimal Essential Medium, Sigma), RPMI-1640 (Sigma), and/or DMEM (Dulbecco's Modified Eagle's Medium, Sigma) may be used. When needed, hormone or other growth factors, salt, buffer, nucleotides, antibiotics, trace elements and/or glucose may be added according to a suitable concentration known in the art. Culturing conditions, for example, a temperature and/or a pH, may depend on a selected host cell determined by one of ordinary skill in the art.

The bispecific antigen binding protein complex expressed by the host cell may be secreted out of the cell by a signal peptide for secretion, and in this case, the complex may be obtained by recovering the complex from the culturing solution or a culture medium. For example, by condensing a culturing supernatant using a protein filter, an antibody protein may be separated. However, when expressed without a signal sequence for secretion, the protein complex may be directly obtained from a cell lysate because the protein complex exists in periplasm of a cell. The process of isolating the secreted antibodies into the periplasm is known in the art, and may be generally removed by centrifuging a grain fragment (fragment of the host cell or a decomposed host cell) or by ultrafiltration.

Selectively, the bispecific antibodies obtained from the culture may be further purified using a method known in the art. For example, depending on the recovered antibodies, generally known protein purification methods such as chromatofocusing (e.g., ion exchange, hydrophilic, hydrophobic, and/or size-exclusion), SDS-PAGE, and/or fractional solution (for example, ammonium sulfate precipitation) may be used. According to an aspect of the present invention, the bispecific antibodies may be purified by affinity chromatography. As an affinity ligand, the suitability of protein A corresponds to Fc domain types and isotypes of an immunoglobulin existing in the antibody. A matrix to which the affinity ligand attaches may be an agarose, but is not limited thereto, and a mechanically stable matrix (for example, regulated pore glass or poly (styrene divinyl)benzene) may improve flow velocity and processing time compared to the agarose.

According to another aspect of the present invention, provided is a pharmaceutical composition including the above-mentioned bispecific antibody, and a pharmaceutical acceptable carrier, an excipient, or a stabilizer.

The pharmaceutical composition may be used for prevention and treatment of a disease by having a physiological effect caused by a binding reaction of the bispecific antigen-antibody acting as a treating mechanism, or the composition may be for targeting a lesion caused by an antigen-antibody reaction. According to an aspect of the present invention, the condition or the disease may be for example, a proliferative disorder, a neoplastic disease, an inflammatory disease, an autoimmune disease, an infectious disease, a viral disease, an allergic condition, a graft-versus-host disease, and/or a host-versus-graft disease.

For example, regarding an antibody specifically binding to VEGF, and EGFR, the pharmaceutical composition including the bispecific antibody may be used for prevention and/or treatment of a disease that may be improved by an inhibition of angiogenesis and/or an inhibition of epidermal growth, for example, a neoplastic disease. The neoplastic disease may be squamous cell carcinoma of lung, lung cancer (including small cell lung cancer, non-small cell lung cancer, adenocarcinoma of a lung, or squamous cell carcinoma of a lung), peritoneal cancer, hepatoma, gastric adenocarcinoma (including gastrointestinal cancer), pancreatic cancer, glioma, giloblastoma, cervical cancer, ovarian cancer, liver cancer, bladder cancer, hepatic tumor, breast cancer, colon cancer, colorectal cancer, endometrial cancer or uterine cancer, salivary gland tumor, renal cell carcinoma, prostate cancer, vulva cancer, thyroid cancer, hepatic carcinoma, and various forms of head and neck cancer; B-cell lymphoma (low grade/follicular non-Hodgkin's lymphoma (NHL); small lymphocytic lymphoma (SL) non-Hodgkin's lymphoma; intermediate grade/follicular non-Hodgkin's lymphoma; intermediate differentiating non-Hodgkin's lymphoma; high grade immunoblastic non-Hodgkin's lymphoma; high grade lymphoblastic non-Hodgkin's lymphoma; high grade small non-cleaved cell non-Hodgkin's lymphoma; bulky disease non-Hodgkin's lymphoma; mantle cell lymphoma; AIDS-related lymphoma; and Waldenstrom's macroglobulinemia; chronic lymphocytic leukemia (CLL); acute lymphoblastic leukemia (ALL); hairy cell leukemia; chronic myelocitic leukemia; post-transplant lymphoproliferative disorder (PTLD); and/or abnormal proliferation of vascular endothelial cells related to phacomatosis, edema (edema related to encephaloma), and/or Meige syndrome.

Therefore, the invention provides a method for prevention or a treatment of a disease in a subject, comprising preparing a pharmaceutical composition comparing a treatment effective dose of the bispecific antibody and a pharmaceutical acceptable carrier, an excipient, or a stabilizer, and administering the pharmaceutical composition to the subject. The disease can be any suitable disease, such as a disease selected from the group consisting of a proliferative disorder, a neoplastic disease, an inflammatory disease, an autoimmune disease, an infectious disease, a viral disease, an allergic condition, a graft-versus-host disease, and a host-versus-graft disease. The subject can be any suitable animal, such as a mammal including a primate (e.g., human), mouse, rat, hamster, guinea pig, cat, dog, pig, goat, cow, or horse.

According to an aspect of the present invention, bispecific antibody of the pharmaceutical composition may be bound to a second activator (biologically active agent or functional molecule). The second activator may be a functional molecule showing prevention or treatment of a target disease, and may include a compound, a peptide, a polypeptide, a nucleic acid, a carbohydrate, a lipid, or an inorganic particle. In the pharmaceutical composition, the bispecific antibody may have a treatment activity on its own; however, in addition or instead, it may perform a function of targeting the second activator to a specific disease region. The disease region may be an organ, a tissue, or a cell where antibodies specifically binding to the bispecific antigen are aggregated and distributed. Drugs targeted to the disease region exist in high concentration such that the drug efficacy may be increased compared to the amount of injection. Hence, the pharmaceutical composition is useful for the treatment of a drug resistant tumor, and may decrease side effects and adverse drug reactions resulting from a non-specific drug distribution.

The pharmaceutical composition may be prepared by mixing a bispecific antigen having an intended purity with a pharmaceutically permissible carrier, an excipient, or a stabilizer. The pharmaceutically permissible carrier, the excipient, or the stabilizer used are non-toxic to a receptor with respect to dose and concentration, and may include phosphate, citrate, and other organic acids; antioxidant (for example, ascorbic acid and methionine); antiseptic (for example, octadecyl dimethyl benzene ammonium chloride, hexamethonium chloride, benzalkonium chloride, phenol, butyl or benzyl, alcohol, alkyl paraben, catechol, resorcinol, cyclohexanol, 3-pentanol, or m-cresol); low molecular weight (less than about 10 fragments) polypeptide; protein, for example, serum albumin, gelatin, or immunoglobulin; hydrophilic polymer, for example polyvinyl pyrrolidone; amino acid (for example, glycine, glutamine, asparagine, histidine, arginine, or lysine); monosaccharide, disaccharide, and other carbohydrates (including for example, glucose, mannose, or dextrin); chelating agent (for example, EDTA); sugar (for example, sucrose, mannitol, trehalose, or sorbitol); salt-producing counterions; metal complex; and/or non-ionic surfactant (for example, including TWEEN™, PLURONICS™, or polyethylene glycol (PEG)). In addition, depending on the formulating method, a generally-used filler, diluent, binder, wetting agent, disintegrating agent, and/or surfactant may be suitably selected by one of ordinary skill in the art.

An activator including the bispecific antibody in the pharmaceutical composition may be entrapped in a microcapsule prepared by coacervation technology or interfacial polymerization, for example, hydroxymethyl cellulose, gelatin-microcapsule, poly-(methyl methacrylate) microcapsule, colloid drug delivery system (liposome, albumin microspore, microemulsion, nano-particle, and/or nanocapsule) or in microemulsion.

Also, the bispecific antigen may be formulated into an extended-release tablet. The extended-release tablet may be, for example, a semipermeable matrix of solid hydrophobic polymer including an antibody. The matrix may be in a film or a microcapsule form, and may be polyester, hydrogel (for example, poly(2-hydroxyethyl-methacrylate), or poly(vinyl alcohol)), polylactide (U.S. Pat. No. 3,773,919), a copolymer of L-glutamic acid and γ ethyl-L-glutamate, non-degradable ethylene-vinyl acetate, degradable copolymer of lactic acid-glycolic acid, for example, LUPRON DEPOT™ (an injectable microsphere including a copolymer of lactic acid-glycolic acid, and leuprolide acetate), and/or poly-D-(−)-3-hydroxybutyric acid. When an encapsulated antibody protein remains in a body for a long time, as a result of being exposed to humidity at a temperature of 37° C., the antibody may denature or aggregate, thus losing biological activity and causing changes in immunogenicity, and as a result, a suitable method for stabilizing the antibody may be considered. For example, when a coagulant is an S—S bonding between cells through a thio-disulfide exchange, the antibody may be stabilized by reforming a sulfhydryl fragment, freeze-drying from an acidic solution, controlling humidity content, using a suitable additive and/or by developing a specific polymer matrix.

According to another aspect of the present invention, provided is a method of prevention and/or treatment and administration of an treatment effective amount of the pharmaceutical composition for preventing and/or treating a condition selected from the group consisting of a proliferative disorder, a neoplastic disease, an inflammatory disease, an autoimmune disease, an infectious disease, a viral disease, an allergic condition, a graft-versus-host disease, and a host-versus-graft disease.

The pharmaceutical composition may be injected through various routes in entities including a rat, a mouse, a domestic animal, and/or a human. All injection methods are predictable, for example, oral, rectal, intravenous, nasal, abdominal, subcutaneous, or local injections are possible. The composition may be injected using other methods ((for example, methods introduced in recent Remington's Pharmaceutical Science), known in the art.

The "treatment effective amount" as used herein refers to a sufficient quantity for treating a disease according to a reasonable benefit or risk ratio. The treatment effective dose may vary depending on causes caused by a patient for example disease type, severity, onset, age of an entity, body weight, excretion speed, reaction susceptibility, health status, and/or complications; and/or causes caused by a patient for example drug activity, injection route, injection period and numbers, and/or drug combinations; and may also be suitably selected by one of ordinary skill in the art depending on the purpose of a treatment. The amount of injection, for example, may be randomly divided into numerous times such that the amount may be between about 0.001 to about 100 mg/kg with respect to an adult's weight.

In another aspect of the present invention, provided is a diagnostic composition including a bispecific antibody for a disease selected from a group consisting of a proliferative disorder, a neoplastic disease, an inflammatory disease, an autoimmune disease, an infectious disease, a viral disease, an allergic condition, a graft-versus-host disease, and a host-versus-graft disease.

According to an aspect of the present invention, the diagnostic composition is applied to a biological sample, and may be used to detect an antigen specifically found in a disease. The term "biological sample" may include cells, tissue, whole blood, plasma, a tissue autopsy sample (brain, skin, lymph node, and spinal cord), a cell culture supernatant, and/or a destroyed eukaryotic cell. An application of the composition may be performed in vitro with respect to collected biological sample or in vivo by injecting the composition into an investigated entity.

The term "detect" used herein refers to confirming the formation of an antigen-antibody composition by reacting the bispecific antibody of the diagnostic composition with the biological sample, and may be performed by a detectable label, and a detection method. The detection method may be a colormetric method, an electrochemical method, a fluorometric method, luminometry, a particle counting method, a visual assessment or scintillation counting method. The detectable label may be an enzyme, a fluorescent material, a luminous substance, a ligand, a nanoparticle, or a radioactive isotope. The enzyme used as the detection label may include acetylcholine esterase, alkaline phosphatase, β-D-galactosidase, horseradish peroxidase, and/or β-lactamase. The fluorescent material may include fluorescein, $Eu^3+$, $Eu^3+$ chelate or cryptate. The luminous substance may include acridinium ester and/or isoluminol derivate, the ligand may include biotin derivative, the nanoparticle may include colloid or gold colored latex, the radioactive isotope may include $^{57}Co$, $^3H$, $^{125}I$, $^{125}I$-Bonton, and/or Hunter samples. According to an aspect of the present invention, detection of the antigen-antibody complex may be performed by enzyme-linked immunosorbent assay (ELISA). Also, when detecting an antigen-antibody reaction by injecting the diagnostic composition into an entity, the detectable label may be injected by binding or coupling the label to the bispecific antibody.

Therefore, the invention provides a method for diagnosing a disease comprising obtaining a biological sample from a subject and contacting the biological sample with a composition comprising a bispecific antibody, wherein the composition can detect an antigen specifically found in a disease by forming an antibody-antigen complex.

The invention also provides a method for diagnosing a disease in a subject comprising injecting a subject with a composition comprising a bispecific antibody prepared, wherein the composition can detect an antigen specifically found in a disease by forming an antibody-antigen complex, and wherein the disease is selected from the group consisting of a proliferative disorder, a neoplastic disease, an inflammatory disease, an autoimmune disease, an infectious disease, a viral disease, an allergic condition, a graft-versus-host disease, and a host-versus-graft disease.

The disease to be diagnosed can be any suitable disease, such as a disease is selected from the group consisting of a proliferative disorder, a neoplastic disease, an inflammatory disease, an autoimmune disease, an infectious disease, a viral disease, an allergic condition, a graft-versus-host disease, and a host-versus-graft disease. In one embodiment, the composition for use in the diagnostic methods comprises a detectable label attached to the bispecific antibody.

In another aspect of the present invention, provided is a kit including the above-mentioned bispecific antibody. The kit, as the above-mentioned components, may be a medical kit for diagnosing, preventing, and/or treating a condition selected from a group consisting of a proliferative disorder, a neoplastic disease, an inflammatory disease, an autoimmune disease, an infectious disease, a viral disease, an allergic condition, a graft-versus-host disease, and a host-versus-graft disease.

By using a protein complex according to an aspect of the present invention, an efficient preparation of a bispecific antibody recognizing two antigens, or two epitopes of a same antigen is possible. The bispecific antibody may be used for the purpose of diagnosing, preventing, and/or treating a disease such as a cell proliferative disease or an immunological disease.

Figure 2:
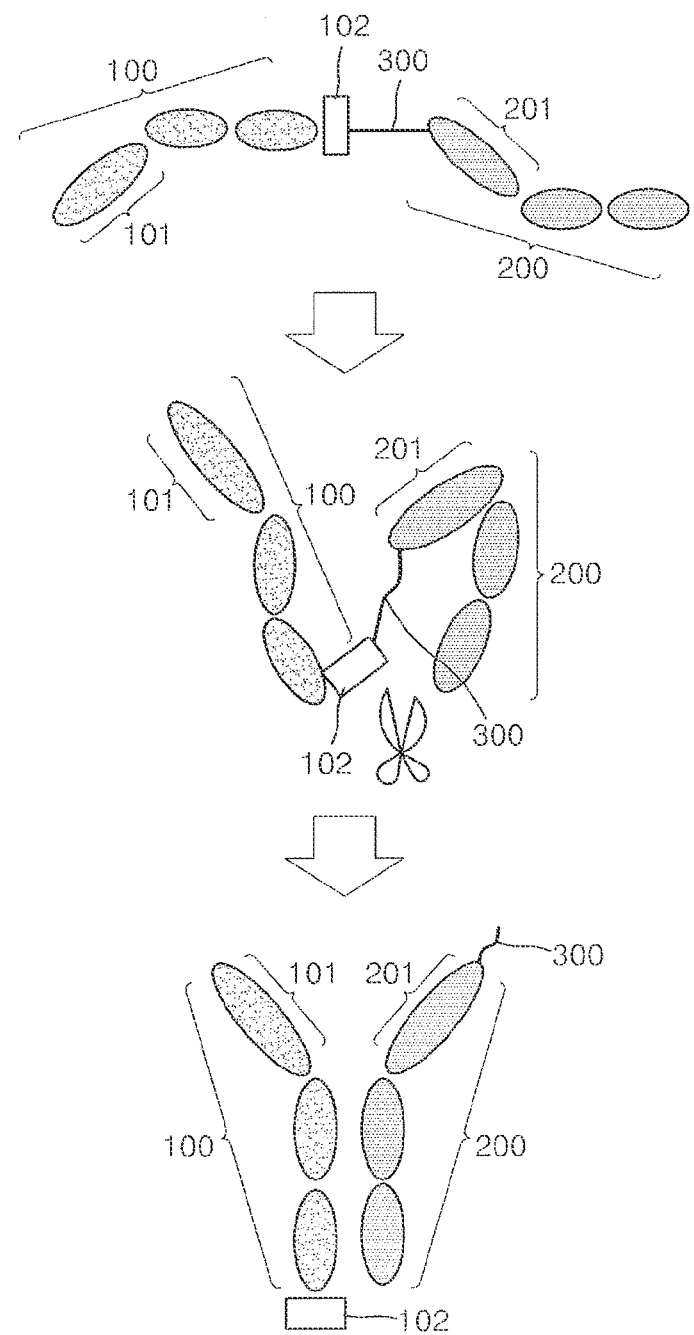
FIG. 2 is a schematic diagram of a bispecific antigen binding protein complex and a bispecific antibody according to an aspect of the present invention.

FIGS. 1 and 2 are schematic diagrams of a bispecific antigen binding protein complex including an antigen binding site, and a bispecific antibody according to an aspect of the present invention.

As shown in FIG. 1, a first tag 102, and a second tag 202 are respectively connected to a first polypeptide 100 including a first antigen binding site 101, and a second polypeptide 200 including a second antigen binding site 201, and the first tag 102 and the second tag 202 are connected to an end of a linker 300 is composed of a polypeptide. The first tag 102 and the second tag 202 are cleavable in vitro or in vivo because they are composed of proteins such as ubiquitin or ubiquitin-like protein. Whether in vitro or in vivo, the first polypeptide 100 including the first antigen binding site 101, and the second polypeptide 201 including the second antigen binding site 201 may form bispecific antibodies each having different antigen binding sites through a completely spontaneous binding.

FIG. 2 illustrates an example of a protein complex including two or more polypeptides including antigen biding site according to one embodiment disclosed in FIG. 1, without a second tag 202. As described above, the protein complex forms a bispecific antibody including different antigen binding sites through an in vitro or an in vivo cleaving; however, because the protein complex of FIG. 2 does not have the second tag 202, it exists in a form where the linker 300 is bonded to the second polypeptide 200 including the second antigen binding site 201; however, because the linker 300 includes a short amino acid sequence of about 2 to about 50 amino acids such that it does not affect the function of the second polypeptide 200 including the second antigen binding site 201.

Example 1: Preparing an Anti-VEGF-EGFR Bispecific Antibody Expression Vector To prepare a bispecific antibody including specific binding sites with respect to a vascular endothelial growth factor (VEGF) and an endothelial growth factor receptor (EGFR), an expression vector of a protein complex of the bispecific antibody was prepared by GeneArt by request, and pcDNA 3.1 myc/his A (Invitrogen) was used as a vector for protein overexpression.

Figure 3:
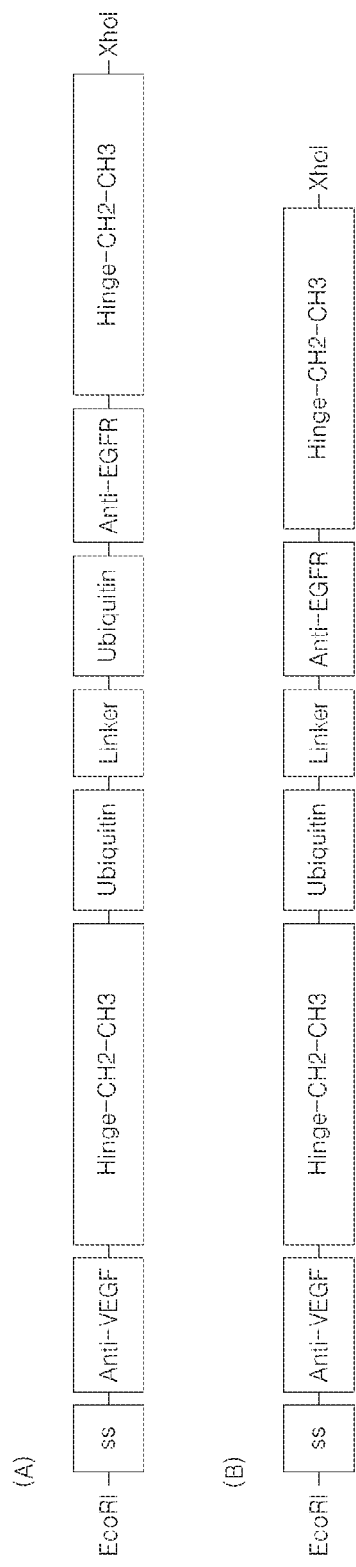
FIGS. 3A and 3B illustrate amino acid sequence structures of a bispecific antigen binding protein complex according to an aspect of the present invention.

In particular, as shown in FIGS. 3 (A) and (B), a signal sequence, (ss) (SEQ ID NO: 1), VEGF binding site V1 or V2 (SEQ ID NO: 2 or 3), and a single-domain antibody composed of an Fc domain (SEQ ID NO: 4) including a hinge, EGFR binding sites E1 or E2 (SEQ ID NO: 5 or 6) and the single-domain antibody including the Fc domain (SEQ ID NO: 4) including a hinge, at least one ubiquitin tag (SEQ ID NO: 7), and a single stranded DNA (total 37 corresponding to combination of a length of V1/V2 and E1/E2, a length of linker, and the number of ubiquitin) corresponding to an amino acid sequence of a protein complex composed of a linker (Gly-Gly or (Gly-Gly-Gly-Gly-Ser)n (SEQ ID NO: 82) peptide, wherein n can be 1-10) were synthesized. Nucleotide sequences of a DNA fragment inserted into a plasmid to express the protein complex are represented by SEQ ID NOS: 45 to 81. The inserted DNA fragment includes a nucleotide sequence that may be cleaved by EcoRI at a 5' terminal, and a nucleotide sequence that may be cleaved by XhoI at a 3' terminal, and thus may be inserted into the EcoRI-XhoI restriction site of pcDNA3.1 myc/his A vector.

Example 2: Expression and Purification of Bispecific VEGF-EGFR

The recombinant vector comprising the nucleotide sequence of SEQ ID NO: 78 obtained according to Example 1 was transfected by using a liposome in HEK-293 cell line (Human Embryonic Kidney-293 cell) (Korean Cell Line Bank), and from this, anti-VEGF-EGFR bispecific antibody was expressed and purified.

In a 500 mL Erlenmeyer flask, HEK-293 cells were seeded by using 100 mL of Freestyle 293 culture medium at a concentration of $1 \times 10^6$ cells/mL, and Freestyle™ MAX was used to prepare a DNA-liposome mixture. To prepare a DNA-liposome complex, the mixture was reacted for 10 minutes at room temperature, and the complex mixture was added to the HEK-293 cells. Protein expression was induced by culturing the cell for 7 days at a temperature of 37° C. in an 8% $CO_2$ shaking incubator.

Figure 4:
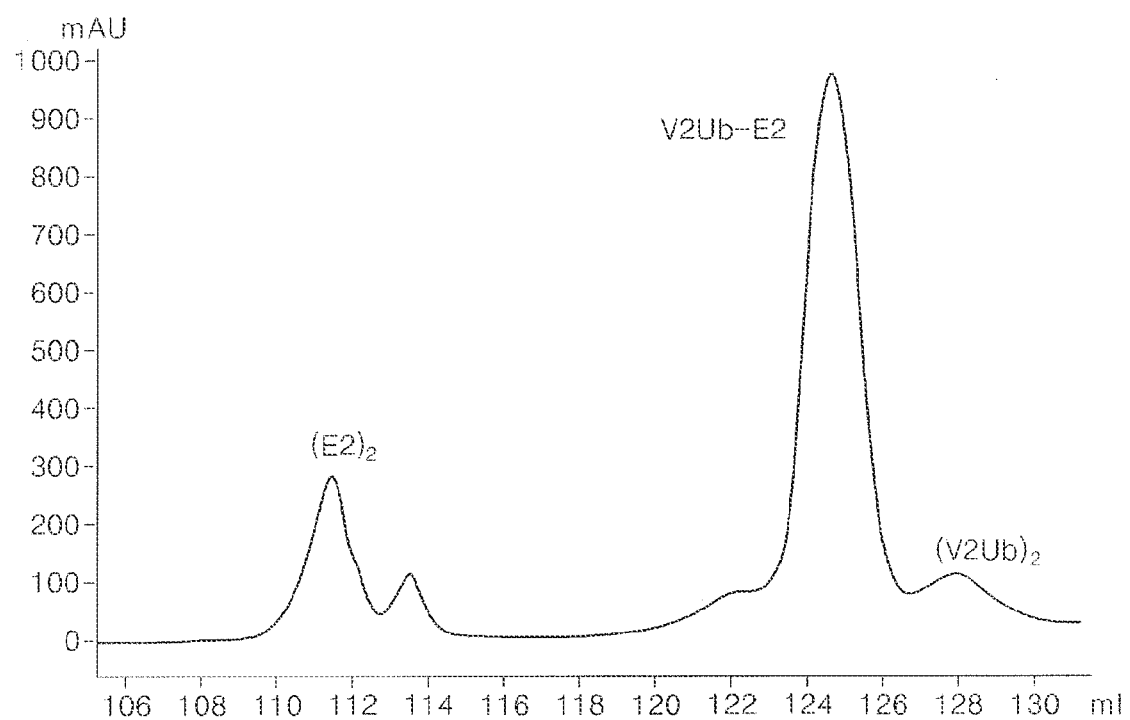
FIG. 4 is a graph that illustrates a result of an ion substitution chromatography of expression and purification of a bispecific antibody according to an aspect of the present invention, wherein the y-axis indicates absorbance (mAU) and the x-axis indicates volume (mL) and wherein E2 is an EGFR binding site, V2 is a VEGF binding site, and Ub is ubiquitin.

The culture medium of cells expressing the bispecific antibody was filtered using a 0.2 μm filter. Chromatography of the cell culture medium was performed using a protein A affinity column (GE healthcare). The bispecific antibody included in the cell culture medium was coupled to a protein A column, washed with phosphate-buffered saline (PBS) (pH 7.4), and an effluent (100 mM Glycine-HCl, pH 2.7) was used to elute the antibody from the protein A column. Tris buffer (1 M Tris-HCl, pH 9.0) with ¹⁄₁₀ the volume was inserted to the effluent to neutralize the effluent. The effluent was exchanged with a buffering solution (30 mM Tris-HCl, pH 9.0) by using a desalting column, and applied to a MonoS column (GE healthcare) to perform ion-exchange chromatography. As a result, as shown in FIG. 4, the bispecific antibody was eluted.

The presence of the bispecific antibody in the obtained effluent was confirmed through SDS-PAGE. The bispecific antibody was treated with β-mercaptoethanol to confirm a molecular weight of the monomer form bispecific antibody. As a result, it was confirmed that a one-armed antibody including a VEGF binding site, and a one-armed antibody including an EGFR binding site were detected in a monomer form.

Example 3: Verification of Antigen Bonding Capacity of Anti-VEGF-EGFR Bispecific Antibody To confirm a bispecific antigen-antibody reaction of the bispecific antibody prepared in Example 2, a BiacoreT100 machine (GE Healthcare Bio-Sciences AB) was used to verify an antibody binding capacity to the VEGF and the EGFR proteins. Human VEGF (R&D Systems) was immobilized on a CM5 chip at a concentration of about 2000 RU (response unit) through an amine-coupling chemical reaction. The bispecific antibody prepared in Example 2 was flowed for one minute at a flow velocity of 10 µL/minute. After confirming the coupling, human EGFR extracellular domain (Prospec) was flowed for one minute at a flow velocity of 10 µL/minute. After confirming the coupling, a Glycine-HCl (GE Healthcare) solution (pH 2.0) was flowed for one minute at a flow velocity of 10 µL/minute to regenerate a surface.

Figure 5:
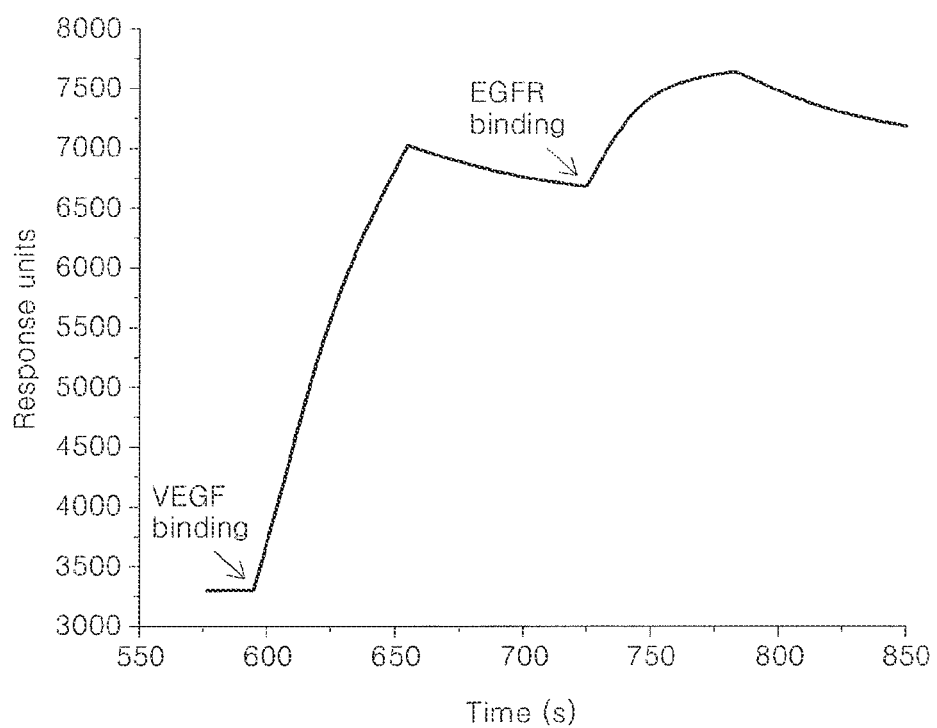
FIG. 5 is a sensogram illustrating a dual antigen binding reaction of a bispecific antibody, wherein response units are indicated on the y-axis and time (seconds) is indicated on the x-axis.

As a result of the above analysis, the bispecific antibody was confirmed to have a simultaneous bonding capacity to the human VEGF and to the human EGFR proteins (FIG. 5).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A bispecific antigen binding protein complex comprising:
   a first polypeptide comprising a first antigen binding site at an N terminus;
   a second polypeptide comprising a second antigen binding site at an N terminus; and
   a peptide linker connecting the first polypeptide and the second polypeptide; wherein the linker consists of 2 to 50 amino acids;
   wherein the peptide linker comprises a tag attached to at least one terminus thereof, and wherein the tag is connected to at least one of a C-terminus of the first polypeptide and an N-terminus of the second polypeptide, and comprises a protease-cleavable amino acid sequence.

2. The protein complex of claim 1, wherein the peptide linker includes a first tag at one terminus of the linker and a second tag at another terminus of the peptide linker, and wherein the first tag is connected to a C-terminus of the first polypeptide, the second tag is connected to an N-terminus of the second polypeptide, and the first tag and the second tag each includes a protease-cleavable amino acid sequence.

3. The protein complex of claim 1, wherein at least one of the first polypeptide and the second polypeptide comprises an antibody heavy chain, an antibody light chain, a single-domain antibody, or an antibody fragment selected from a group consisting of Fab, Fab', Fv, and scFv.

4. The protein complex of claim 1, wherein the tag is selected from a group consisting of ubiquitin, ubiquitin-like protein, and TEV cleavage peptide.

5. The protein complex of claim 1, wherein the first antigen binding site and the second antigen binding site each independently comprises a site binding specifically to a target antigen selected from the group consisting of VEGF, EGFR, EpCAM, CCRS, CD19, HER-2 neu, HER-3, HER-4, EGFR, PSMA, CEA, MUC-1 (mucin), MUC2, MUC3, MUC4, MUC5 AC, MUC5 B, MUC7, βhCG, Lewis-Y, CD20, CD33, CD30, ganglioside GD3, 9-O-acetyl-GD3, GM2, Globo H, fucosyl GM1, poly SA, GD2, Carboanhydrase IX (MN/CA IX), CD44v6, Sonic Hedgehog (Shh), Wue-1, Plasma Cell Antigen, (membrane bound) IgE, Melanoma Chondroitin Sulfate Proteoglycan (MCSP), CCR8, TNF-alpha precursor, STEAP, mesothelin, A33 antigen, Prostate Stem Cell Antigen (PSCA) antigen, Ly-6, desmoglein 4, E-cadherin neoepitope, Fetal Acetylcholine Receptor, CD25, CA19-9 marker, CA-125 marker, Mullerian Inhibitory Substance (MIS) II receptor, sTn (sialyated Tn antigen; TAG-72), FAP (fibroblast activation antigen), endosialin, EGFRvIII, LG, SAS, and CD63.

6. The protein complex of claim 1, wherein the first and second polypeptides each comprise an amino acid sequence independently selected from the group consisting of SEQ ID NOs: 8 to 44.

7. A polynucleotide encoding the protein complex of claim 1.

8. The polynucleotide of claim 7, wherein the polynucleotide comprises a nucleotide sequence selected from the group consisting of SEQ ID NOs: 45 to 81.

9. A method of preparing a bispecific protein complex, the method comprising:
   transforming a host cell with a recombinant expression vector comprising a polynucleotide of claim 7;
   culturing the transformed host cell so as to express a bispecific protein complex; and
   isolating the bispecific protein complex.

10. The method of claim 9, wherein the tag is cleaved.

11. A method for treatment of a disease in a subject, comprising:
    administering a bispecific protein complex of claim 1 to the subject, wherein the disease is a proliferative disorder, a neoplastic disease, an inflammatory disease, an autoimmune disease, an infectious disease, a viral disease, an allergic condition, a graft-versus-host disease, or a host-versus-graft disease.

12. The method of claim 11, wherein the protein complex is bound to a second active agent, and targets the second active agent to a disease site.

13. A method for diagnosing a disease comprising obtaining a biological sample from a subject and contacting the biological sample with a composition comprising a bispecific protein complex of claim 1, wherein the composition can detect an antigen specifically found in a disease, and wherein the disease is selected from the group consisting of a proliferative disorder, a neoplastic disease, an inflammatory disease, an autoimmune disease, an infectious disease, a viral disease, an allergic condition, a graft-versus-host disease, and a host-versus-graft disease.

14. The method of claim 13, wherein the composition comprises a detectable label attached to the bispecific protein complex.

15. A method for diagnosing a disease in a subject comprising injecting the subject with a composition comprising a bispecific protein complex of claim 1, wherein the composition can detect an antigen specifically found in a disease, and wherein the disease is selected from the group consisting of a proliferative disorder, a neoplastic disease, an inflammatory disease, an autoimmune disease, an infectious disease, a viral disease, an allergic condition, a graft-versus-host disease, and a host-versus-graft disease.

16. The method of claim 15, wherein the composition comprises a detectable label attached to the bispecific protein complex.

17. A composition comprising the protein complex of claim 1 and a detectable label attached to the protein complex.

18. The protein complex of claim 1, wherein the first polypeptide and second polypeptide each comprise a Fc region.

19. The protein complex of claim 18, wherein the Fc region comprises a hinge region and CH2 and CH3 region.

* * * * *

SEQUENCE LISTING

```
<160> NUMBER OF SEQ ID NOS: 81

<210> SEQ ID NO 1
<211> LENGTH: 19
<212> TYPE: PRT
<213> ORGANISM: Artificial Sequence
<220> FEATURE:
<223> OTHER INFORMATION: Synthetic signal sequence

<400> SEQUENCE: 1

Met Gly Trp Ser Cys Ile Ile Leu Phe Leu Val Ala Thr Ala Thr Gly
1               5                   10                  15

Val His Ser

<210> SEQ ID NO 2
<211> LENGTH: 108
<212> TYPE: PRT
<213> ORGANISM: Artificial Sequence
<220> FEATURE:
<223> OTHER INFORMATION: Synthetic Vl(binding site of VEGF)

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Pro Glu
            20                  25                  30
```

```
Leu Ser Trp Tyr Gln Gln Lys Pro Gly Lys Ala Pro Lys Leu Leu Ile
            35                  40                  45

Tyr His Thr Ser Ile Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Phe Gln Pro Arg
                85                  90                  95

Thr Phe Gly Gln Gly Thr Lys Val Glu Ile Arg Arg
            100                 105

<210> SEQ ID NO 3
<211> LENGTH: 108
<212> TYPE: PRT
<213> ORGANISM: Artificial Sequence
<220> FEATURE:
<223> OTHER INFORMATION: Synthetic V2(binding site of VEGF)

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Lys Ile Phe Asn Gly
            20                  25                  30

Leu Ser Tr

```
                115                 120                 125
Arg Glu Pro Gln Val Tyr Thr Leu Pro Pro Ser Arg Glu Glu Met Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 5
<211> LENGTH: 108
<212> TYPE: PRT
<213> ORGANISM: Artificial Sequence
<220> FEATURE:
<223> OTHER INFORMATION: Synthetic E1(binding site of EGFR)

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ile Leu
            20                  25                  30

Val Asp Trp Tyr Gln Gln Lys Pro Gly Glu Ala Pro Lys Leu Leu Ile
        35                  40                  45

Tyr Tyr Ala Ser Phe Leu Gln Ser Gly Val Pro Ser Arg Phe Ser Gly
    50                  55                  60

Ser Gly Phe Gly Thr Asp Phe Thr Leu Thr Ile Ser Ser Leu His Pro
65                  70                  75                  80

Glu Asp Phe Ala Thr Tyr Tyr Cys Gln Gln Ala Asn Pro Ala Pro Leu
                85                  90                  95

Thr Phe Gly Gln Gly Thr Lys Val Glu Ile Lys Arg
            100                 105

<210> SEQ ID NO 6
<211> LENGTH: 108
<212> TYPE: PRT
<213> ORGANISM: Artificial Sequence
<220> FEATURE:
<223> OTHER INFORMATION: Synthetic E2(binding site of EGFR)

<400> SEQUENCE: 6

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Trp Ile Gly Asn Leu
            20                  25                  30

Leu Asp Trp Tyr Gln Gln Lys Pro Gly Glu Ala Pro Lys Leu Leu Ile
        35                  40                  45

Tyr Tyr Ala Ser Phe Leu Gln Ser Gly Val Pro Ser Arg Phe Ser Gly
    50                  55                  60

Gly Gly Phe Gly Thr Asp Phe Thr Leu Thr Ile Ser Ser Leu Gln Pro
65                  70                  75                  80
```

```
Glu Asp Phe Ala Thr Tyr Tyr Cys Gln Gln Ala Asn Pro Ala Pro Leu
                85                  90                  95

Thr Phe Gly Gln Gly Thr Lys Val Glu Ile Lys Arg
            100                 105
```

<210> SEQ ID NO 7
<211> LENGTH: 76
<212> TYPE: PRT
<213> ORGANISM: Artificial Sequence
<220> FEATURE:
<223> OTHER INFORMATION: Synthetic ubiquitin tag

<400> SEQUENCE: 7

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75
```

<210> SEQ ID NO 8
<211> LENGTH: 871
<212> TYPE: PRT
<213> ORGANISM: Artificial Sequence
<220> FEATURE:
<223> OTHER INFORMATION: Synthetic Protein complex comprising VEGF and
      EGFR specific binding peptides #1

<400> SEQUENCE: 8

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
                20                  25                  30

Ser Val Gly Asp Arg Val Thr Ile Thr Cys Arg Ala Ser

-continued

```
                195                 200                 205
Asn Ser Thr Tyr Arg Val Val Ser Val Leu Thr Val Leu His Gln Asp
210                 215                 220
Trp Leu Asn Gly Lys Glu Tyr Lys Cys Lys Val Ser Asn Lys Ala Leu
225                 230                 235                 240
Pro Ala Pro Ile Glu Lys Thr Ile Ser Lys Ala Lys Gly Gln Pro Arg
                245                 250                 255
Glu Pro Gln Val Tyr Thr Leu Pro Pro Ser Arg Glu Glu Met Thr Lys
                260                 265                 270
Asn Gln Val Ser Leu Thr Cys Leu Val Lys Gly Phe Tyr Pro Ser Asp
                275                 280                 285
Ile Ala Val Glu Trp Glu Ser Asn Gly Gln Pro Glu Asn Asn Tyr Lys
                290                 295                 300
Thr Thr Pro Pro Val Leu Asp Ser Asp Gly Ser Phe Phe Leu Tyr Ser
305                 310                 315                 320
Lys Leu Thr Val Asp Lys Ser Arg Trp Gln Gln Gly Asn Val Phe Ser
                325                 330                 335
Cys Ser Val Met His Glu Ala Leu His Asn His Tyr Thr Gln Lys Ser
                340                 345                 350
Leu Ser Leu Ser Pro Gly Lys Met Gln Ile Phe Val Lys Thr Leu Thr
                355                 360                 365
Gly Lys Thr Ile Thr Leu Glu Val Glu Pro Ser Asp Thr Ile Glu Asn
370                 375                 380
Val Lys Ala Lys Ile Gln Asp Lys Glu Gly Ile Pro Pro Asp Gln Gln
385                 390                 395                 400
Arg Leu Ile Phe Ala Gly Lys Gln Leu Glu Asp Gly Arg Thr Leu Ser
                405                 410                 415
Asp Tyr Asn Ile Gln Lys Glu Ser Thr Leu His Leu Val Leu Arg Leu
                420                 425                 430
Arg Gly Gly Gly Gly Gly Ser Gly Gly Gly Ser Gly Gly Gly
                435                 440                 445
Gly Ser Gly Gly Gly Ser Met Gln Ile Phe Val Lys Thr Leu Thr
450                 455                 460
Gly Lys Thr Ile Thr Leu Glu Val Glu Pro Ser Asp Thr Ile Glu Asn
465                 470                 475                 480
Val Lys Ala Lys Ile Gln Asp Lys Glu Gly Ile Pro Pro Asp Gln Gln
                485                 490                 495
Arg Leu Ile Phe Ala Gly Lys Gln Leu Glu Asp Gly Arg Thr Leu Ser
                500                 505                 510
Asp Tyr Asn Ile Gln Lys Glu Ser Thr Leu His Leu Val Leu Arg Leu
                515                 520                 525
Arg Gly Gly Asp Ile Gln Met Thr Gln Ser Pro Ser Ser Leu Ser Ala
                530                 535                 540
Ser Val Gly Asp Arg Val Thr Ile Thr Cys Arg Ala Ser Gln Trp Ile
545                 550                 555                 560
Gly Ile Leu Val Asp Trp Tyr Gln Gln Lys Pro Gly Glu Ala Pro Lys
                565                 570                 575
Leu Leu Ile Tyr Tyr Ala Ser Phe Leu Gln Ser Gly Val Pro Ser Arg
                580                 585                 590
Phe Ser Gly Ser Gly Phe Gly Thr Asp Phe Thr Leu Thr Ile Ser Ser
                595                 600                 605
Leu His Pro Glu Asp Phe Ala Thr Tyr Tyr Cys Gln Gln Ala Asn Pro
                610                 615                 620
```

```
Ala Pro Leu Thr Phe Gly Gln Gly Thr Lys Val Glu Ile Lys Arg Glu
625                 630                 635                 640

Pro Lys Ser Cys Asp Lys Thr His Thr Cys Pro Pro Cys Pro Ala Pro
            645                 650                 655

Glu Leu Leu Gly Gly Pro Ser Val Phe Leu Phe Pro Pro Lys Pro Lys
                660                 665                 670

Asp Thr Leu Met Ile Ser Arg Thr Pro Glu Val Thr Cys Val Val Val
            675                 680                 685

Asp Val Ser His Glu Asp Pro Glu Val Lys Phe Asn Trp Tyr Val Asp
        690                 695                 700

Gly Val Glu Val His Asn Ala Lys Thr Lys Pro Arg Glu Glu Gln Tyr
705                 710                 715                 720

Asn Ser Thr Tyr Arg Val Val Ser Val Leu Thr Val Leu His Gln Asp
                725                 730                 735

Trp Leu Asn Gly Lys Glu Tyr Lys Cys Lys Val Ser Asn Lys Ala Leu
            740                 745                 750

Pro Ala Pro Ile Glu Lys Thr Ile Ser Lys Ala Lys Gly Gln Pro Arg
        755                 760                 765

Glu Pro Gln Val Tyr Thr Leu Pro Pro Ser Arg Glu Glu Met Thr Lys
770                 775                 780

Asn Gln Val Ser Leu Thr Cys Leu Val Lys Gly Phe Tyr Pro Ser Asp
785                 790                 795                 800

Ile Ala Val Glu Trp Glu Ser Asn Gly Gln Pro Glu Asn Asn Tyr Lys
                805                 810                 815

Thr Thr Pro Pro Val Leu Asp Ser Asp Gly Ser Phe Phe Leu Tyr Ser
            820                 825                 830

Lys Leu Thr Val Asp Lys Ser Arg Trp Gln Gln Gly Asn Val Phe Ser
        835                 840                 845

Cys Ser Val Met His Glu Ala Leu His Asn His Tyr Thr Gln Lys Ser
    850                 855                 860

Leu Ser Leu Ser Pro Gly Lys
865                 870

<210> SEQ ID NO 9
<211> LENGTH: 876
<212> TYPE: PRT
<213> ORGANISM: Artificial Sequence
<220> FEATURE:
<223> OTHER INFORMATION: Synthetic Protein complex comprising VEGF and
      EGFR specific binding peptides #2

<400> SEQUENCE: 9

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Trp Ile
        35                  40                  45

Gly Pro Glu Leu Ser Trp Tyr Gln Gln Lys Pro Gly Lys Ala Pro Lys
    50                  55                  60

Leu Leu Ile Tyr His Thr Ser Ile Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Met Phe
```

```
                100                 105                 110
    Gln Pro Arg Thr Phe Gly Gln Gly Thr Lys Val Glu Ile Arg Arg Glu
                    115                 120                 125
    Pro Lys Ser Cys Asp Lys Thr His Thr Cys Pro Pro Cys Pro Ala Pro
                    130                 135                 140
    Glu Leu Leu Gly Gly Pro Ser Val Phe Leu Phe Pro Pro Lys Pro Lys
    145                 150                 155                 160
    Asp Thr Leu Met Ile Ser Arg Thr Pro Glu Val Thr Cys Val Val Val
                    165                 170                 175
    Asp Val Ser His Glu Asp Pro Glu Val Lys Phe Asn Trp Tyr Val Asp
                    180                 185                 190
    Gly Val Glu Val His Asn Ala Lys Thr Lys Pro Arg Glu Glu Gln Tyr
                    195                 200                 205
    Asn Ser Thr Tyr Arg Val Val Ser Val Leu Thr Val Leu His Gln Asp
                    210                 215                 220
    Trp Leu Asn Gly Lys Glu Tyr Lys Cys Lys Val Ser Asn Lys Ala Leu
    225                 230                 235                 240
    Pro Ala Pro Ile Glu Lys Thr Ile Ser Lys Ala Lys Gly Gln Pro Arg
                    245                 250                 255
    Glu Pro Gln Val Tyr Thr Leu Pro Pro Ser Arg Glu Glu Met Thr Lys
                    260                 265                 270
    Asn Gln Val Ser Leu Thr Cys Leu Val Lys Gly Phe Tyr Pro Ser Asp
                    275                 280                 285
    Ile Ala Val Glu Trp Glu Ser Asn Gly Gln Pro Glu Asn Asn Tyr Lys
                    290                 295                 300
    Thr Thr Pro Pro Val Leu Asp Ser Asp Gly Ser Phe Phe Leu Tyr Ser
    305                 310                 315                 320
    Lys Leu Thr Val Asp Lys Ser Arg Trp Gln Gln Gly Asn Val Phe Ser
                    325                 330                 335
    Cys Ser Val Met His Glu Ala Leu His Asn His Tyr Thr Gln Lys Ser
                    340                 345                 350
    Leu Ser Leu Ser Pro Gly Lys Met Gln Ile Phe Val Lys Thr Leu Thr
                    355                 360                 365
    Gly Lys Thr Ile Thr Leu Glu Val Glu Pro Ser Asp Thr Ile Glu Asn
                    370                 375                 380
    Val Lys Ala Lys Ile Gln Asp Lys Glu Gly Ile Pro Pro Asp Gln Gln
    385                 390                 395                 400
    Arg Leu Ile Phe Ala Gly Lys Gln Leu Glu Asp Gly Arg Thr Leu Ser
                    405                 410                 415
    Asp Tyr Asn Ile Gln Lys Glu Ser Thr Leu His Leu Val Leu Arg Leu
                    420                 425                 430
    Arg Gly Gly Gly Gly Gly Ser Gly Gly Gly Ser Gly Gly Gly
                    435                 440                 445
    Gly Ser Gly Gly Gly Ser Gly Gly Gly Ser Met Gln Ile Phe
                    450                 455                 460
    Val Lys Thr Leu Thr Gly Lys Thr Ile Thr Leu Glu Val Glu Pro Ser
    465                 470                 475                 480
    Asp Thr Ile Glu Asn Val Lys Ala Lys Ile Gln Asp Lys Glu Gly Ile
                    485                 490                 495
    Pro Pro Asp Gln Gln Arg Leu Ile Phe Ala Gly Lys Gln Leu Glu Asp
                    500                 505                 510
    Gly Arg Thr Leu Ser Asp Tyr Asn Ile Gln Lys Glu Ser Thr Leu His
                    515                 520                 525
```

Leu Val Leu Arg Leu Arg Gly Gly Asp Ile Gln Met Thr Gln Ser Pro
    530                 535                 540

Ser Ser Leu Ser Ala Ser Val Gly Asp Arg Val Thr Ile Thr Cys Arg
545                 550                 555                 560

Ala Ser Gln Trp Ile Gly Ile Leu Val Asp Trp Tyr Gln Gln Lys Pro
                565                 570                 575

Gly Glu Ala Pro Lys Leu Leu Ile Tyr Tyr Ala Ser Phe Leu Gln Ser
            580                 585                 590

Gly Val Pro Ser Arg Phe Ser Gly Ser Gly Phe Gly Thr Asp Phe Thr
        595                 600                 605

Leu Thr Ile Ser Ser Leu His Pro Glu Asp Phe Ala Thr Tyr Tyr Cys
    610                 615                 620

Gln Gln Ala Asn Pro Ala Pro Leu Thr Phe Gly Gln Gly Thr Lys Val
625                 630                 635                 640

Glu Ile Lys Arg Glu Pro Lys Ser Cys Asp Lys Thr His Thr Cys Pro
                645                 650                 655

Pro Cys Pro Ala Pro Glu Leu Leu Gly Gly Pro Ser Val Phe Leu Phe
            660                 665                 670

Pro Pro Lys Pro Lys Asp Thr Leu Met Ile Ser Arg Thr Pro Glu Val
        675                 680                 685

Thr Cys Val Val Val Asp Val Ser His Glu Asp Pro Glu Val Lys Phe
    690                 695                 700

Asn Trp Tyr Val Asp Gly Val Glu Val His Asn Ala Lys Thr Lys Pro
705                 710                 715                 720

Arg Glu Glu Gln Tyr Asn Ser Thr Tyr Arg Val Val Ser Val Leu Thr
                725                 730                 735

Val Leu His Gln Asp Trp Leu Asn Gly Lys Glu Tyr Lys Cys Lys Val
            740                 745                 750

Ser Asn Lys Ala Leu Pro Ala Pro Ile Glu Lys Thr Ile Ser Lys Ala
        755                 760                 765

Lys Gly Gln Pro Arg Glu Pro Gln Val Tyr Thr Leu Pro Pro Ser Arg
    770                 775                 780

Glu Glu Met Thr Lys Asn Gln Val Ser Leu Thr Cys Leu Val Lys Gly
785                 790                 795                 800

Phe Tyr Pro Ser Asp Ile Ala Val Glu Trp Glu Ser Asn Gly Gln Pro
                805                 810                 815

Glu Asn Asn Tyr Lys Thr Thr Pro Pro Val Leu Asp Ser Asp Gly Ser
            820                 825                 830

Phe Phe Leu Tyr Ser Lys Leu Thr Val Asp Lys Ser Arg Trp Gln Gln
        835                 840                 845

Gly Asn Val Phe Ser Cys Ser Val Met His Glu Ala Leu His Asn His
    850                 855                 860

Tyr Thr Gln Lys Ser Leu Ser Leu Ser Pro Gly Lys
865                 870                 875

<210> SEQ ID NO 10
<211> LENGTH: 881
<212> TYPE: PRT
<213> ORGANISM: Artificial Sequence
<220> FEATURE:
<223> OTHER INFORMATION: Synthetic Protein complex comprising VEGF and
      EGFR specific binding peptides #3

<400> SEQUENCE: 10

Met Gly Trp Ser Cys Ile Ile Leu Phe Leu Val Ala Thr Ala Thr Gly

```
1               5                   10                  15
Val His Ser Asp Ile Gln Met Thr Gln Ser Pro Ser Ser Leu Ser Ala
                20                  25                  30
Ser Val Gly Asp Arg Val Thr Ile Thr Cys Arg Ala Ser Gln Trp Ile
                35                  40                  45
Gly Pro Glu Leu Ser Trp Tyr Gln Gln Lys Pro Gly Lys Ala Pro Lys
                50                  55                  60
Leu Leu Ile Tyr His Thr Ser Ile Leu Gln Ser Gly Val Pro Ser Arg
65                  70                  75                  80
Phe Ser Gly Ser Gly Ser Gly Thr Asp Phe Thr Leu Thr Ile Ser Ser
                85                  90                  95
Leu Gln Pro Glu Asp Phe Ala Thr Tyr Tyr Cys Gln Gln Tyr Met Phe
                100                 105                 110
Gln Pro Arg Thr Phe Gly Gln Gly Thr Lys Val Glu Ile Arg Arg Glu
                115                 120                 125
Pro Lys Ser Cys Asp Lys Thr His Thr Cys Pro Pro Cys Pro Ala Pro
                130                 135                 140
Glu Leu Leu Gly Gly Pro Ser Val Phe Leu Phe Pro Pro Lys Pro Lys
145                 150                 155                 160
Asp Thr Leu Met Ile Ser Arg Thr Pro Glu Val Thr Cys Val Val Val
                165                 170                 175
Asp Val Ser His Glu Asp Pro Glu Val Lys Phe Asn Trp Tyr Val Asp
                180                 185                 190
Gly Val Glu Val His Asn Ala Lys Thr Lys Pro Arg Glu Glu Gln Tyr
                195                 200                 205
Asn Ser Thr Tyr Arg Val Val Ser Val Leu Thr Val Leu His Gln Asp
                210                 215                 220
Trp Leu Asn Gly Lys Glu Tyr Lys Cys Lys Val Ser Asn Lys Ala Leu
225                 230                 235                 240
Pro Ala Pro Ile Glu Lys Thr Ile Ser Lys Ala Lys Gly Gln Pro Arg
                245                 250                 255
Glu Pro Gln Val Tyr Thr Leu Pro Pro Ser Arg Glu Glu Met Thr Lys
                260                 265                 270
Asn Gln Val Ser Leu Thr Cys Leu Val Lys Gly Phe Tyr Pro Ser Asp
                275                 280                 285
Ile Ala Val Glu Trp Glu Ser Asn Gly Gln Pro Glu Asn Asn Tyr Lys
                290                 295                 300
Thr Thr Pro Pro Val Leu Asp Ser Asp Gly Ser Phe Phe Leu Tyr Ser
305                 310                 315                 320
Lys Leu Thr Val Asp Lys Ser Arg Trp Gln Gln Gly Asn Val Phe Ser
                325                 330                 335
Cys Ser Val Met His Glu Ala Leu His Asn His Tyr Thr Gln Lys Ser
                340                 345                 350
Leu Ser Leu Ser Pro Gly Lys Met Gln Ile Phe Val Lys Thr Leu Thr
                355                 360                 365
Gly Lys Thr Ile Thr Leu Glu Val Glu Pro Ser Asp Thr Ile Glu Asn
                370                 375                 380
Val Lys Ala Lys Ile Gln Asp Lys Glu Gly Ile Pro Pro Asp Gln Gln
385                 390                 395                 400
Arg Leu Ile Phe Ala Gly Lys Gln Leu Glu Asp Gly Arg Thr Leu Ser
                405                 410                 415
Asp Tyr Asn Ile Gln Lys Glu Ser Thr Leu His Leu Val Leu Arg Leu
                420                 425                 430
```

```
Arg Gly Gly Gly Gly Gly Ser Gly Gly Gly Ser Gly Gly
    435                 440             445
Gly Ser Gly Gly Gly Ser Gly Gly Gly Ser Gly Gly Gly
    450             455             460
Ser Met Gln Ile Phe Val Lys Thr Leu Thr Gly Lys Thr Ile Thr Leu
465             470                 475                 480
Glu Val Glu Pro Ser Asp Thr Ile Glu Asn Val Lys Ala Lys Ile Gln
            485                 490                 495
Asp Lys Glu Gly Ile Pro Pro Asp Gln Gln Arg Leu Ile Phe Ala Gly
            500                 505                 510
Lys Gln Leu Glu Asp Gly Arg Thr Leu Ser Asp Tyr Asn Ile Gln Lys
    515                 520                 525
Glu Ser Thr Leu His Leu Val Leu Arg Leu Arg Gly Gly Asp Ile Gln
    530                 535                 540
Met Thr Gln Ser Pro Ser Ser Leu Ser Ala Ser Val Gly Asp Arg Val
545                 550                 555                 560
Thr Ile Thr Cys Arg Ala Ser Gln Trp Ile Gly Ile Leu Val Asp Trp
                565                 570                 575
Tyr Gln Gln Lys Pro Gly Glu Ala Pro Lys Leu Leu Ile Tyr Tyr Ala
            580                 585                 590
Ser Phe Leu Gln Ser Gly Val Pro Ser Arg Phe Ser Gly Ser Gly Phe
    595                 600                 605
Gly Thr Asp Phe Thr Leu Thr Ile Ser Ser Leu His Pro Glu Asp Phe
    610                 615                 620
Ala Thr Tyr Tyr Cys Gln Gln Ala Asn Pro Ala Pro Leu Thr Phe Gly
625                 630                 635                 640
Gln Gly Thr Lys Val Glu Ile Lys Arg Glu Pro Lys Ser Cys Asp Lys
                645                 650                 655
Thr His Thr Cys Pro Pro Cys Pro Ala Pro Glu Leu Leu Gly Gly Pro
            660                 665                 670
Ser Val Phe Leu Phe Pro Pro Lys Pro Lys Asp Thr Leu Met Ile Ser
    675                 680                 685
Arg Thr Pro Glu Val Thr Cys Val Val Val Asp Val Ser His Glu Asp
    690                 695                 700
Pro Glu Val Lys Phe Asn Trp Tyr Val Asp Gly Val Glu Val His Asn
705                 710                 715                 720
Ala Lys Thr Lys Pro Arg Glu Glu Gln Tyr Asn Ser Thr Tyr Arg Val
                725                 730                 735
Val Ser Val Leu Thr Val Leu His Gln Asp Trp Leu Asn Gly Lys Glu
            740                 745                 750
Tyr Lys Cys Lys Val Ser Asn Lys Ala Leu Pro Ala Pro Ile Glu Lys
    755                 760                 765
Thr Ile Ser Lys Ala Lys Gly Gln Pro Arg Glu Pro Gln Val Tyr Thr
    770                 775                 780
Leu Pro Pro Ser Arg Glu Glu Met Thr Lys Asn Gln Val Ser Leu Thr
785                 790                 795                 800
Cys Leu Val Lys Gly Phe Tyr Pro Ser Asp Ile Ala Val Glu Trp Glu
                805                 810                 815
Ser Asn Gly Gln Pro Glu Asn Asn Tyr Lys Thr Thr Pro Pro Val Leu
            820                 825                 830
Asp Ser Asp Gly Ser Phe Phe Leu Tyr Ser Lys Leu Thr Val Asp Lys
    835                 840                 845
```

```
Ser Arg Trp Gln Gln Gly Asn Val Phe Ser Cys Ser Val Met His Glu
    850                 855                 860

Ala Leu His Asn His Tyr Thr Gln Lys Ser Leu Ser Leu Ser Pro Gly
865                 870                 875                 880

Lys

<210> SEQ ID NO 11
<211> LENGTH: 886
<212> TYPE: PRT
<213> ORGANISM: Artificial Sequence
<220> FEATURE:
<223> OTHER INFORMATION: Synthetic Protein complex comprising VEGF and
      EGFR specific binding peptides #4

<400> SEQUENCE: 11

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Trp Ile
        35                  40                  45

Gly Pro Glu Leu Ser Trp Tyr Gln Gln Lys Pro Gly Lys Ala Pro Lys
    50                  55                  60

Leu Leu Ile Tyr His Thr Ser Ile Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Met Phe
            100                 105                 110

Gln Pro Arg Thr Phe Gly Gln Gly Thr Lys Val Glu Ile Arg Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320
```

-continued

```
Lys Leu Thr Val Asp Lys Ser Arg Trp Gln Gln Gly Asn Val Phe Ser
            325                 330                 335
Cys Ser Val Met His Glu Ala Leu His Asn His Tyr Thr Gln Lys Ser
            340                 345                 350
Leu Ser Leu Ser Pro Gly Lys Met Gln Ile Phe Val Lys Thr Leu Thr
            355                 360                 365
Gly Lys Thr Ile Thr Leu Glu Val Glu Pro Ser Asp Thr Ile Glu Asn
370                 375                 380
Val Lys Ala Lys Ile Gln Asp Lys Glu Gly Ile Pro Pro Asp Gln Gln
385                 390                 395                 400
Arg Leu Ile Phe Ala Gly Lys Gln Leu Glu Asp Gly Arg Thr Leu Ser
            405                 410                 415
Asp Tyr Asn Ile Gln Lys Glu Ser Thr Leu His Leu Val Leu Arg Leu
            420                 425                 430
Arg Gly Gly Gly Gly Gly Ser Gly Gly Gly Ser Gly Gly Gly
            435                 440                 445
Gly Ser Gly Gly Gly Ser Gly Gly Gly Ser Gly Gly Gly
450                 455                 460
Ser Gly Gly Gly Ser Met Gln Ile Phe Val Lys Thr Leu Thr Gly
465                 470                 475                 480
Lys Thr Ile Thr Leu Glu Val Glu Pro Ser Asp Thr Ile Glu Asn Val
            485                 490                 495
Lys Ala Lys Ile Gln Asp Lys Glu Gly Ile Pro Pro Asp Gln Gln Arg
            500                 505                 510
Leu Ile Phe Ala Gly Lys Gln Leu Glu Asp Gly Arg Thr Leu Ser Asp
            515                 520                 525
Tyr Asn Ile Gln Lys Glu Ser Thr Leu His Leu Val Leu Arg Leu Arg
            530                 535                 540
Gly Gly Asp Ile Gln Met Thr Gln Ser Pro Ser Ser Leu Ser Ala Ser
545                 550                 555                 560
Val Gly Asp Arg Val Thr Ile Thr Cys Arg Ala Ser Gln Trp Ile Gly
            565                 570                 575
Ile Leu Val Asp Trp Tyr Gln Gln Lys Pro Gly Glu Ala Pro Lys Leu
            580                 585                 590
Leu Ile Tyr Tyr Ala Ser Phe Leu Gln Ser Gly Val Pro Ser Arg Phe
            595                 600                 605
Ser Gly Ser Gly Phe Gly Thr Asp Phe Thr Leu Thr Ile Ser Ser Leu
            610                 615                 620
His Pro Glu Asp Phe Ala Thr Tyr Tyr Cys Gln Gln Ala Asn Pro Ala
625                 630                 635                 640
Pro Leu Thr Phe Gly Gln Gly Thr Lys Val Glu Ile Lys Arg Glu Pro
            645                 650                 655
Lys Ser Cys Asp Lys Thr His Thr Cys Pro Pro Cys Pro Ala Pro Glu
            660                 665                 670
Leu Leu Gly Gly Pro Ser Val Phe Leu Phe Pro Pro Lys Pro Lys Asp
            675                 680                 685
Thr Leu Met Ile Ser Arg Thr Pro Glu Val Thr Cys Val Val Val Asp
            690                 695                 700
Val Ser His Glu Asp Pro Glu Val Lys Phe Asn Trp Tyr Val Asp Gly
705                 710                 715                 720
Val Glu Val His Asn Ala Lys Thr Lys Pro Arg Glu Glu Gln Tyr Asn
            725                 730                 735
Ser Thr Tyr Arg Val Val Ser Val Leu Thr Val Leu His Gln Asp Trp
```

```
                   740                 745                 750
Leu Asn Gly Lys Glu Tyr Lys Cys Lys Val Ser Asn Lys Ala Leu Pro
            755                 760                 765

Ala Pro Ile Glu Lys Thr Ile Ser Lys Ala Lys Gly Gln Pro Arg Glu
        770                 775                 780

Pro Gln Val Tyr Thr Leu Pro Pro Ser Arg Glu Met Thr Lys Asn
785                 790                 795                 800

Gln Val Ser Leu Thr Cys Leu Val Lys Gly Phe Tyr Pro Ser Asp Ile
                805                 810                 815

Ala Val Glu Trp Glu Ser Asn Gly Gln Pro Glu Asn Asn Tyr Lys Thr
            820                 825                 830

Thr Pro Pro Val Leu Asp Ser Asp Gly Ser Phe Phe Leu Tyr Ser Lys
        835                 840                 845

Leu Thr Val Asp Lys Ser Arg Trp Gln Gln Gly Asn Val Phe Ser Cys
    850                 855                 860

Ser Val Met His Glu Ala Leu His Asn His Tyr Thr Gln Lys Ser Leu
865                 870                 875                 880

Ser Leu Ser Pro Gly Lys
                885

<210> SEQ ID NO 12
<211> LENGTH: 891
<212> TYPE: PRT
<213> ORGANISM: Artificial Sequence
<220> FEATURE:
<223> OTHER INFORMATION: Synthetic Protein complex comprising VEGF and
      EGFR specific binding peptides #5

<400> SEQUENCE: 12

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Trp Ile
        35                  40                  45

Gly Pro Glu Leu Ser Trp Tyr Gln Gln Lys Pro Gly Lys Ala Pro Lys
    50                  55                  60

Leu Leu Ile Tyr His Thr Ser Ile Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Met Phe
            100                 105                 110

Gln Pro Arg Thr Phe Gly Gln Gly Thr Lys Val Glu Ile Arg Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205
```

-continued

```
Asn Ser Thr Tyr Arg Val Val Ser Val Leu Thr Val Leu His Gln Asp
        210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Met Thr Lys
                260                 265                 270

Asn Gln Val Ser Leu Thr Cys Leu Val Lys Gly Phe Tyr Pro Ser Asp
                275                 280                 285

Ile Ala Val Glu Trp Glu Ser Asn Gly Gln Pro Glu Asn Asn Tyr Lys
        290                 295                 300

Thr Thr Pro Pro Val Leu Asp Ser Asp Gly Ser Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
                340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
        370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
                420                 425                 430

Arg Gly Gly Gly Gly Gly Ser Gly Gly Gly Ser Gly Gly Gly
        435                 440                 445

Gly Ser Gly Gly Gly Gly Ser Gly Gly Gly Gly Ser Gly Gly Gly Gly
        450                 455                 460

Ser Gly Gly Gly Gly Ser Gly Gly Gly Gly Ser Met Gln Ile Phe Val
465                 470                 475                 480

Lys Thr Leu Thr Gly Lys Thr Ile Thr Leu Glu Val Glu Pro Ser Asp
                485                 490                 495

Thr Ile Glu Asn Val Lys Ala Lys Ile Gln Asp Lys Glu Gly Ile Pro
                500                 505                 510

Pro Asp Gln Gln Arg Leu Ile Phe Ala Gly Lys Gln Leu Glu Asp Gly
                515                 520                 525

Arg Thr Leu Ser Asp Tyr Asn Ile Gln Lys Glu Ser Thr Leu His Leu
        530                 535                 540

Val Leu Arg Leu Arg Gly Gly Asp Ile Gln Met Thr Gln Ser Pro Ser
545                 550                 555                 560

Ser Leu Ser Ala Ser Val Gly Asp Arg Val Thr Ile Thr Cys Arg Ala
                565                 570                 575

Ser Gln Trp Ile Gly Ile Leu Val Asp Trp Tyr Gln Lys Pro Gly
                580                 585                 590

Glu Ala Pro Lys Leu Leu Ile Tyr Tyr Ala Ser Phe Leu Gln Ser Gly
                595                 600                 605

Val Pro Ser Arg Phe Ser Gly Ser Gly Phe Gly Thr Asp Phe Thr Leu
        610                 615                 620

Thr Ile Ser Ser Leu His Pro Glu Asp Phe Ala Thr Tyr Tyr Cys Gln
```

```
                    625                 630                 635                 640
        Gln Ala Asn Pro Ala Pro Leu Thr Phe Gly Gln Gly Thr Lys Val Glu
                        645                 650                 655
        Ile Lys Arg Glu Pro Lys Ser Cys Asp Lys Thr His Thr Cys Pro Pro
                        660                 665                 670
        Cys Pro Ala Pro Glu Leu Leu Gly Gly Pro Ser Val Phe Leu Phe Pro
                        675                 680                 685
        Pro Lys Pro Lys Asp Thr Leu Met Ile Ser Arg Thr Pro Glu Val Thr
                        690                 695                 700
        Cys Val Val Val Asp Val Ser His Glu Asp Pro Glu Val Lys Phe Asn
        705                 710                 715                 720
        Trp Tyr Val Asp Gly Val Glu Val His Asn Ala Lys Thr Lys Pro Arg
                        725                 730                 735
        Glu Glu Gln Tyr Asn Ser Thr Tyr Arg Val Val Ser Val Leu Thr Val
                        740                 745                 750
        Leu His Gln Asp Trp Leu Asn Gly Lys Glu Tyr Lys Cys Lys Val Ser
                        755                 760                 765
        Asn Lys Ala Leu Pro Ala Pro Ile Glu Lys Thr Ile Ser Lys Ala Lys
                770                 775                 780
        Gly Gln Pro Arg Glu Pro Gln Val Tyr Thr Leu Pro Pro Ser Arg Glu
        785                 790                 795                 800
        Glu Met Thr Lys Asn Gln Val Ser Leu Thr Cys Leu Val Lys Gly Phe
                        805                 810                 815
        Tyr Pro Ser Asp Ile Ala Val Glu Trp Glu Ser Asn Gly Gln Pro Glu
                        820                 825                 830
        Asn Asn Tyr Lys Thr Thr Pro Pro Val Leu Asp Ser Asp Gly Ser Phe
                        835                 840                 845
        Phe Leu Tyr Ser Lys Leu Thr Val Asp Lys Ser Arg Trp Gln Gln Gly
                        850                 855                 860
        Asn Val Phe Ser Cys Ser Val Met His Glu Ala Leu His Asn His Tyr
        865                 870                 875                 880
        Thr Gln Lys Ser Leu Ser Leu Ser Pro Gly Lys
                        885                 890

<210> SEQ ID NO 13
<211> LENGTH: 896
<212> TYPE: PRT
<213> ORGANISM: Artificial Sequence
<220> FEATURE:
<223> OTHER INFORMATION: Synthetic Protein complex comprising VEGF and

```
Leu Gln Pro Glu Asp Phe Ala Thr Tyr Tyr Cys Gln Gln Tyr Met Phe
                100                 105                 110
Gln Pro Arg Thr Phe Gly Gln Gly Thr Lys Val Glu Ile Arg Arg Glu
            115                 120                 125
Pro Lys Ser Cys Asp Lys Thr His Thr Cys Pro Pro Cys Pro Ala Pro
        130                 135                 140
Glu Leu Leu Gly Gly Pro Ser Val Phe Leu Phe Pro Pro Lys Pro Lys
145                 150                 155                 160
Asp Thr Leu Met Ile Ser Arg Thr Pro Glu Val Thr Cys Val Val Val
                165                 170                 175
Asp Val Ser His Glu Asp Pro Glu Val Lys Phe Asn Trp Tyr Val Asp
            180                 185                 190
Gly Val Glu Val His Asn Ala Lys Thr Lys Pro Arg Glu Glu Gln Tyr
        195                 200                 205
Asn Ser Thr Tyr Arg Val Val Ser Val Leu Thr Val Leu His Gln Asp
    210                 215                 220
Trp Leu Asn Gly Lys Glu Tyr Lys Cys Lys Val Ser Asn Lys Ala Leu
225                 230                 235                 240
Pro Ala Pro Ile Glu Lys Thr Ile Ser Lys Ala Lys Gly Gln Pro Arg
                245                 250                 255
Glu Pro Gln Val Tyr Thr Leu Pro Pro Ser Arg Glu Glu Met Thr Lys
            260                 265                 270
Asn Gln Val Ser Leu Thr Cys Leu Val Lys Gly Phe Tyr Pro Ser Asp
        275                 280                 285
Ile Ala Val Glu Trp Glu Ser Asn Gly Gln Pro Glu Asn Asn Tyr Lys
    290                 295                 300
Thr Thr Pro Pro Val Leu Asp Ser Asp Gly Ser Phe Phe Leu Tyr Ser
305                 310                 315                 320
Lys Leu Thr Val Asp Lys Ser Arg Trp Gln Gln Gly Asn Val Phe Ser
                325                 330                 335
Cys Ser Val Met His Glu Ala Leu His Asn His Tyr Thr Gln Lys Ser
            340                 345                 350
Leu Ser Leu Ser Pro Gly Lys Met Gln Ile Phe Val Lys Thr Leu Thr
        355                 360                 365
Gly Lys Thr Ile Thr Leu Glu Val Glu Pro Ser Asp Thr Ile Glu Asn
    370                 375                 380
Val Lys Ala Lys Ile Gln Asp Lys Glu Gly Ile Pro Pro Asp Gln Gln
385                 390                 395                 400
Arg Leu Ile Phe Ala Gly Lys Gln Leu Glu Asp Gly Arg Thr Leu Ser
                405                 410                 415
Asp Tyr Asn Ile Gln Lys Glu Ser Thr Leu His Leu Val Leu Arg Leu
            420                 425                 430
Arg Gly Gly Gly Gly Gly Ser Gly Gly Gly Ser Gly Gly
        435                 440                 445
Gly Ser Gly Gly Gly Gly Ser Gly Gly Gly Gly Ser Gly Gly Gly Gly
    450                 455                 460
Ser Gly Gly Gly Gly Ser Gly Gly Gly Ser Gly Gly Gly Ser
465                 470                 475                 480
Met Gln Ile Phe Val Lys Thr Leu Thr Gly Lys Thr Ile Thr Leu Glu
                485                 490                 495
Val Glu Pro Ser Asp Thr Ile Glu Asn Val Lys Ala Lys Ile Gln Asp
            500                 505                 510
Lys Glu Gly Ile Pro Pro Asp Gln Gln Arg Leu Ile Phe Ala Gly Lys
```

```
            515                 520                 525
Gln Leu Glu Asp Gly Arg Thr Leu Ser Asp Tyr Asn Ile Gln Lys Glu
    530                 535                 540

Ser Thr Leu His Leu Val Leu Arg Leu Arg Gly Gly Asp Ile Gln Met
545                 550                 555                 560

Thr Gln Ser Pro Ser Ser Leu Ser Ala Ser Val Gly Asp Arg Val Thr
                565                 570                 575

Ile Thr Cys Arg Ala Ser Gln Trp Ile Gly Ile Leu Val Asp Trp Tyr
            580                 585                 590

Gln Gln Lys Pro Gly Glu Ala Pro Lys Leu Leu Ile Tyr Tyr Ala Ser
        595                 600                 605

Phe Leu Gln Ser Gly Val Pro Ser Arg Phe Ser Gly Ser Gly Phe Gly
    610                 615                 620

Thr Asp Phe Thr Leu Thr Ile Ser Ser Leu His Pro Glu Asp Phe Ala
625                 630                 635                 640

Thr Tyr Tyr Cys Gln Gln Ala Asn Pro Ala Pro Leu Thr Phe Gly Gln
                645                 650                 655

Gly Thr Lys Val Glu Ile Lys Arg Glu Pro Lys Ser Cys Asp Lys Thr
            660                 665                 670

His Thr Cys Pro Pro Cys Pro Ala Pro Glu Leu Leu Gly Gly Pro Ser
        675                 680                 685

Val Phe Leu Phe Pro Pro Lys Pro Lys Asp Thr Leu Met Ile Ser Arg
    690                 695                 700

Thr Pro Glu Val Thr Cys Val Val Val Asp Val Ser His Glu Asp Pro
705                 710                 715                 720

Glu Val Lys Phe Asn Trp Tyr Val Asp Gly Val Glu Val His Asn Ala
                725                 730                 735

Lys Thr Lys Pro Arg Glu Glu Gln Tyr Asn Ser Thr Tyr Arg Val Val
            740                 745                 750

Ser Val Leu Thr Val Leu His Gln Asp Trp Leu Asn Gly Lys Glu Tyr
        755                 760                 765

Lys Cys Lys Val Ser Asn Lys Ala Leu Pro Ala Pro Ile Glu Lys Thr
    770                 775                 780

Ile Ser Lys Ala Lys Gly Gln Pro Arg Glu Pro Gln Val Tyr Thr Leu
785                 790                 795                 800

Pro Pro Ser Arg Glu Glu Met Thr Lys Asn Gln Val Ser Leu Thr Cys
                805                 810                 815

Leu Val Lys Gly Phe Tyr Pro Ser Asp Ile Ala Val Glu Trp Glu Ser
            820                 825                 830

Asn Gly Gln Pro Glu Asn Asn Tyr Lys Thr Thr Pro Pro Val Leu Asp
        835                 840                 845

Ser Asp Gly Ser Phe Phe Leu Tyr Ser Lys Leu Thr Val Asp Lys Ser
    850                 855                 860

Arg Trp Gln Gln Gly Asn Val Phe Ser Cys Ser Val Met His Glu Ala
865                 870                 875                 880

Leu His Asn His Tyr Thr Gln Lys Ser Leu Ser Leu Ser Pro Gly Lys
                885                 890                 895

<210> SEQ ID NO 14
<211> LENGTH: 901
<212> TYPE: PRT
<213> ORGANISM: Artificial Sequence
<220> FEATURE:
<223> OTHER INFORMATION: Synthetic Protein complex comprising VEGF and
      EGFR specific binding peptides #7
```

<400> SEQUENCE: 14

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Trp Ile
        35                  40                  45

Gly Pro Glu Leu Ser Trp Tyr Gln Gln Lys Pro Gly Lys Ala Pro Lys
    50                  55                  60

Leu Leu Ile Tyr His Thr Ser Ile Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Met Phe
            100                 105                 110

Gln Pro Arg Thr Phe Gly Gln Gly Thr Lys Val Glu Ile Arg Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
```

```
            405                 410                 415
Asp Tyr Asn Ile Gln Lys Glu Ser Thr Leu His Leu Val Leu Arg Leu
            420                 425                 430

Arg Gly Gly Gly Gly Gly Ser Gly Gly Gly Ser Gly Gly
            435                 440                 445

Gly Ser Gly Gly Gly Ser Gly Gly Gly Ser Gly Gly Gly
    450                 455                 460

Ser Gly Gly Gly Ser Gly Gly Gly Ser Gly Gly Gly Ser
465                 470                 475                 480

Gly Gly Gly Gly Ser Met Gln Ile Phe Val Lys Thr Leu Thr Gly Lys
                485                 490                 495

Thr Ile Thr Leu Glu Val Glu Pro Ser Asp Thr Ile Glu Asn Val Lys
            500                 505                 510

Ala Lys Ile Gln Asp Lys Glu Gly Ile Pro Pro Asp Gln Gln Arg Leu
            515                 520                 525

Ile Phe Ala Gly Lys Gln Leu Glu Asp Gly Arg Thr Leu Ser Asp Tyr
            530                 535                 540

Asn Ile Gln Lys Glu Ser Thr Leu His Leu Val Leu Arg Leu Arg Gly
545                 550                 555                 560

Gly Asp Ile Gln Met Thr Gln Ser Pro Ser Ser Leu Ser Ala Ser Val
                565                 570                 575

Gly Asp Arg Val Thr Ile Thr Cys Arg Ala Ser Gln Trp Ile Gly Ile
            580                 585                 590

Leu Val Asp Trp Tyr Gln Gln Lys Pro Gly Glu Ala Pro Lys Leu Leu
            595                 600                 605

Ile Tyr Tyr Ala Ser Phe Leu Gln Ser Gly Val Pro Ser Arg Phe Ser
            610                 615                 620

Gly Ser Gly Phe Gly Thr Asp Phe Thr Leu Thr Ile Ser Ser Leu His
625                 630                 635                 640

Pro Glu Asp Phe Ala Thr Tyr Tyr Cys Gln Gln Ala Asn Pro Ala Pro
                645                 650                 655

Leu Thr Phe Gly Gln Gly Thr Lys Val Glu Ile Lys Arg Glu Pro Lys
            660                 665                 670

Ser Cys Asp Lys Thr His Thr Cys Pro Pro Cys Pro Ala Pro Glu Leu
            675                 680                 685

Leu Gly Gly Pro Ser Val Phe Leu Phe Pro Pro Lys Pro Lys Asp Thr
            690                 695                 700

Leu Met Ile Ser Arg Thr Pro Glu Val Thr Cys Val Val Val Asp Val
705                 710                 715                 720

Ser His Glu Asp Pro Glu Val Lys Phe Asn Trp Tyr Val Asp Gly Val
                725                 730                 735

Glu Val His Asn Ala Lys Thr Lys Pro Arg Glu Glu Gln Tyr Asn Ser
            740                 745                 750

Thr Tyr Arg Val Val Ser Val Leu Thr Val Leu His Gln Asp Trp Leu
            755                 760                 765

Asn Gly Lys Glu Tyr Lys Cys Lys Val Ser Asn Lys Ala Leu Pro Ala
            770                 775                 780

Pro Ile Glu Lys Thr Ile Ser Lys Ala Lys Gly Gln Pro Arg Glu Pro
785                 790                 795                 800

Gln Val Tyr Thr Leu Pro Pro Ser Arg Glu Glu Met Thr Lys Asn Gln
                805                 810                 815

Val Ser Leu Thr Cys Leu Val Lys Gly Phe Tyr Pro Ser Asp Ile Ala
            820                 825                 830
```

Val Glu Trp Glu Ser Asn Gly Gln Pro Glu Asn Asn Tyr Lys Thr Thr
          835                 840                 845

Pro Pro Val Leu Asp Ser Asp Gly Ser Phe Phe Leu Tyr Ser Lys Leu
    850                 855                 860

Thr Val Asp Lys Ser Arg Trp Gln Gln Gly Asn Val Phe Ser Cys Ser
865                 870                 875                 880

Val Met His Glu Ala Leu His Asn His Tyr Thr Gln Lys Ser Leu Ser
            885                 890                 895

Leu Ser Pro Gly Lys
            900

<210> SEQ ID NO 15
<211> LENGTH: 871
<212> TYPE: PRT
<213> ORGANISM: Artificial Sequence
<220> FEATURE:
<223> OTHER INFORMATION: Synthetic Protein complex comprising VEGF and
      EGFR specific binding peptides #8

<400> SEQUENCE: 15

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Trp Ile
        35                  40                  45

Gly Pro Glu Leu Ser Trp Tyr Gln Gln Lys Pro Gly Lys Ala Pro Lys
    50                  55                  60

Leu Leu Ile Tyr His Thr Ser Ile Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Met Phe
            100                 105                 110

Gln Pro Arg Thr Phe Gly Gln Gly Thr Lys Val Glu Ile Arg Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp

```
                    275                 280                 285
Ile Ala Val Glu Trp Glu Ser Asn Gly Gln Pro Glu Asn Asn Tyr Lys
290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                    325                 330                 335

Cys Ser Val Met His Glu Ala Leu His Asn His Tyr Thr Gln Lys Ser
                340                 345                 350

Leu Ser Leu Ser Pro Gly Lys Met Gln Ile Phe Val Lys Thr Leu Thr
                355                 360                 365

Gly Lys Thr Ile Thr Leu Glu Val Glu Pro Ser Asp Thr Ile Glu Asn
370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
                420                 425                 430

Arg Gly Gly Gly Gly Gly Ser Gly Gly Gly Ser Gly Gly Gly
                435                 440                 445

Gly Ser Gly Gly Gly Ser Met Gln Ile Phe Val Lys Thr Leu Thr
450                 455                 460

Gly Lys Thr Ile Thr Leu Glu Val Glu Pro Ser Asp Thr Ile Glu Asn
465                 470                 475                 480

Val Lys Ala Lys Ile Gln Asp Lys Glu Gly Ile Pro Pro Asp Gln Gln
                485                 490                 495

Arg Leu Ile Phe Ala Gly Lys Gln Leu Glu Asp Gly Arg Thr Leu Ser
                500                 505                 510

Asp Tyr Asn Ile Gln Lys Glu Ser Thr Leu His Leu Val Leu Arg Leu
                515                 520                 525

Arg Gly Gly Asp Ile Gln Met Thr Gln Ser Pro Thr Ser Leu Ser Ala
530                 535                 540

Ser Val Gly Asp Arg Val Thr Ile Thr Cys Arg Ala Ser Gln Trp Ile
545                 550                 555                 560

Gly Asn Leu Leu Asp Trp Tyr Gln Gln Lys Pro Gly Glu Ala Pro Lys
                565                 570                 575

Leu Leu Ile Tyr Tyr Ala Ser Phe Leu Gln Ser Gly Val Pro Ser Arg
                580                 585                 590

Phe Ser Gly Gly Gly Phe Gly Thr Asp Phe Thr Leu Thr Ile Ser Ser
                595                 600                 605

Leu Gln Pro Glu Asp Phe Ala Thr Tyr Tyr Cys Gln Gln Ala Asn Pro
                610                 615                 620

Ala Pro Leu Thr Phe Gly Gln Gly Thr Lys Val Glu Ile Lys Arg Glu
625                 630                 635                 640

Pro Lys Ser Cys Asp Lys Thr His Thr Cys Pro Pro Cys Pro Ala Pro
                645                 650                 655

Glu Leu Leu Gly Gly Pro Ser Val Phe Leu Phe Pro Pro Lys Pro Lys
                660                 665                 670

Asp Thr Leu Met Ile Ser Arg Thr Pro Glu Val Thr Cys Val Val Val
                675                 680                 685

Asp Val Ser His Glu Asp Pro Glu Val Lys Phe Asn Trp Tyr Val Asp
                690                 695                 700
```

```
Gly Val Glu Val His Asn Ala Lys Thr Lys Pro Arg Glu Glu Gln Tyr
705                 710                 715                 720

Asn Ser Thr Tyr Arg Val Val Ser Val Leu Thr Val Leu His Gln Asp
                725                 730                 735

Trp Leu Asn Gly Lys Glu Tyr Lys Cys Lys Val Ser Asn Lys Ala Leu
            740                 745                 750

Pro Ala Pro Ile Glu Lys Thr Ile Ser Lys Ala Lys Gly Gln Pro Arg
        755                 760                 765

Glu Pro Gln Val Tyr Thr Leu Pro Pro Ser Arg Glu Glu Met Thr Lys
770                 775                 780

Asn Gln Val Ser Leu Thr Cys Leu Val Lys Gly Phe Tyr Pro Ser Asp
785                 790                 795                 800

Ile Ala Val Glu Trp Glu Ser Asn Gly Gln Pro Glu Asn Asn Tyr Lys
                805                 810                 815

Thr Thr Pro Pro Val Leu Asp Ser Asp Gly Ser Phe Phe Leu Tyr Ser
            820                 825                 830

Lys Leu Thr Val Asp Lys Ser Arg Trp Gln Gln Gly Asn Val Phe Ser
        835                 840                 845

Cys Ser Val Met His Glu Ala Leu His Asn His Tyr Thr Gln Lys Ser
850                 855                 860

Leu Ser Leu Ser Pro Gly Lys
865                 870

<210> SEQ ID NO 16
<211> LENGTH: 876
<212> TYPE: PRT
<213> ORGANISM: Artificial Sequence
<220> FEATURE:
<223> OTHER INFORMATION: Synthetic Protein complex comprising VEGF and
      EGFR specific binding peptides #9

<400> SEQUENCE: 16

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Trp Ile
        35                  40                  45

Gly Pro Glu Leu Ser Trp Tyr Gln Gln Lys Pro Gly Lys Ala Pro Lys
    50                  55                  60

Leu Leu Ile Tyr His Thr Ser Ile Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Met Phe
            100                 105                 110

Gln Pro Arg Thr Phe Gly Gln Gly Thr Lys Val Glu Ile Arg Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
```

```
                180              185              190
Gly Val Glu Val His Asn Ala Lys Thr Lys Pro Arg Glu Gln Tyr
            195              200              205
Asn Ser Thr Tyr Arg Val Val Ser Val Leu Thr Val Leu His Gln Asp
210              215              220
Trp Leu Asn Gly Lys Glu Tyr Lys Cys Lys Val Ser Asn Lys Ala Leu
225              230              235              240
Pro Ala Pro Ile Glu Lys Thr Ile Ser Lys Ala Lys Gly Gln Pro Arg
            245              250              255
Glu Pro Gln Val Tyr Thr Leu Pro Pro Ser Arg Glu Glu Met Thr Lys
            260              265              270
Asn Gln Val Ser Leu Thr Cys Leu Val Lys Gly Phe Tyr Pro Ser Asp
            275              280              285
Ile Ala Val Glu Trp Glu Ser Asn Gly Gln Pro Glu Asn Asn Tyr Lys
            290              295              300
Thr Thr Pro Pro Val Leu Asp Ser Asp Gly Ser Phe Phe Leu Tyr Ser
305              310              315              320
Lys Leu Thr Val Asp Lys Ser Arg Trp Gln Gln Gly Asn Val Phe Ser
                325              330              335
Cys Ser Val Met His Glu Ala Leu His Asn His Tyr Thr Gln Lys Ser
                340              345              350
Leu Ser Leu Ser Pro Gly Lys Met Gln Ile Phe Val Lys Thr Leu Thr
            355              360              365
Gly Lys Thr Ile Thr Leu Glu Val Glu Pro Ser Asp Thr Ile Glu Asn
            370              375              380
Val Lys Ala Lys Ile Gln Asp Lys Glu Gly Ile Pro Pro Asp Gln Gln
385              390              395              400
Arg Leu Ile Phe Ala Gly Lys Gln Leu Glu Asp Gly Arg Thr Leu Ser
                405              410              415
Asp Tyr Asn Ile Gln Lys Glu Ser Thr Leu His Leu Val Leu Arg Leu
                420              425              430
Arg Gly Gly Gly Gly Gly Ser Gly Gly Gly Ser Gly Gly Gly
            435              440              445
Gly Ser Gly Gly Gly Ser Gly Gly Gly Ser Met Gln Ile Phe
            450              455              460
Val Lys Thr Leu Thr Gly Lys Thr Ile Thr Leu Glu Val Glu Pro Ser
465              470              475              480
Asp Thr Ile Glu Asn Val Lys Ala Lys Ile Gln Asp Lys Glu Gly Ile
                485              490              495
Pro Pro Asp Gln Gln Arg Leu Ile Phe Ala Gly Lys Gln Leu Glu Asp
                500              505              510
Gly Arg Thr Leu Ser Asp Tyr Asn Ile Gln Lys Glu Ser Thr Leu His
            515              520              525
Leu Val Leu Arg Leu Arg Gly Gly Asp Ile Gln Met Thr Gln Ser Pro
            530              535              540
Thr Ser Leu Ser Ala Ser Val Gly Asp Arg Val Thr Ile Thr Cys Arg
545              550              555              560
Ala Ser Gln Trp Ile Gly Asn Leu Leu Asp Trp Tyr Gln Gln Lys Pro
                565              570              575
Gly Glu Ala Pro Lys Leu Leu Ile Tyr Tyr Ala Ser Phe Leu Gln Ser
                580              585              590
Gly Val Pro Ser Arg Phe Ser Gly Gly Phe Gly Thr Asp Phe Thr
            595              600              605
```

```
Leu Thr Ile Ser Ser Leu Gln Pro Glu Asp Phe Ala Thr Tyr Tyr Cys
            610                 615                 620

Gln Gln Ala Asn Pro Ala Pro Leu Thr Phe Gly Gln Gly Thr Lys Val
625                 630                 635                 640

Glu Ile Lys Arg Glu Pro Lys Ser Cys Asp Lys Thr His Thr Cys Pro
                645                 650                 655

Pro Cys Pro Ala Pro Glu Leu Leu Gly Gly Pro Ser Val Phe Leu Phe
            660                 665                 670

Pro Pro Lys Pro Lys Asp Thr Leu Met Ile Ser Arg Thr Pro Glu Val
        675                 680                 685

Thr Cys Val Val Val Asp Val Ser His Glu Asp Pro Glu Val Lys Phe
690                 695                 700

Asn Trp Tyr Val Asp Gly Val Glu Val His Asn Ala Lys Thr Lys Pro
705                 710                 715                 720

Arg Glu Glu Gln Tyr Asn Ser Thr Tyr Arg Val Val Ser Val Leu Thr
                725                 730                 735

Val Leu His Gln Asp Trp Leu Asn Gly Lys Glu Tyr Lys Cys Lys Val
            740                 745                 750

Ser Asn Lys Ala Leu Pro Ala Pro Ile Glu Lys Thr Ile Ser Lys Ala
        755                 760                 765

Lys Gly Gln Pro Arg Glu Pro Gln Val Tyr Thr Leu Pro Pro Ser Arg
770                 775                 780

Glu Glu Met Thr Lys Asn Gln Val Ser Leu Thr Cys Leu Val Lys Gly
785                 790                 795                 800

Phe Tyr Pro Ser Asp Ile Ala Val Glu Trp Glu Ser Asn Gly Gln Pro
                805                 810                 815

Glu Asn Asn Tyr Lys Thr Thr Pro Pro Val Leu Asp Ser Asp Gly Ser
            820                 825                 830

Phe Phe Leu Tyr Ser Lys Leu Thr Val Asp Lys Ser Arg Trp Gln Gln
        835                 840                 845

Gly Asn Val Phe Ser Cys Ser Val Met His Glu Ala Leu His Asn His
850                 855                 860

Tyr Thr Gln Lys Ser Leu Ser Leu Ser Pro Gly Lys
865                 870                 875

<210> SEQ ID NO 17
<211> LENGTH: 881
<212> TYPE: PRT
<213> ORGANISM: Artificial Sequence
<220> FEATURE:
<223> OTHER INFORMATION: Synthetic Protein complex comprising VEGF and
      EGFR specific binding peptides #10

<400> SEQUENCE: 17

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Trp Ile
        35                  40                  45

Gly Pro Glu Leu Ser Trp Tyr Gln Gln Lys Pro Gly Lys Ala Pro Lys
    50                  55                  60

Leu Leu Ile Tyr His Thr Ser Ile Leu Gln Ser Gly Val Pro Ser Arg
65                  70                  75                  80

Phe Ser Gly Ser Gly Ser Gly Thr Asp Phe Thr Leu Thr Ile Ser Ser
```

```
            85                  90                  95
Leu Gln Pro Glu Asp Phe Ala Thr Tyr Tyr Cys Gln Gln Tyr Met Phe
            100                 105                 110

Gln Pro Arg Thr Phe Gly Gln Gly Thr Lys Val Glu Ile Arg Arg Glu
            115                 120                 125

Pro Lys Ser Cys Asp Lys Thr His Thr Cys Pro Pro Cys Pro Ala Pro
            130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
                180                 185                 190

Gly Val Glu Val His Asn Ala Lys Thr Lys Pro Arg Glu Glu Gln Tyr
            195                 200                 205

Asn Ser Thr Tyr Arg Val Val Ser Val Leu Thr Val Leu His Gln Asp
            210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
            275                 280                 285

Ile Ala Val Glu Trp Glu Ser Asn Gly Gln Pro Glu Asn Asn Tyr Lys
            290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
                340                 345                 350

Leu Ser Leu Ser Pro Gly Lys Met Gln Ile Phe Val Lys Thr Leu Thr
            355                 360                 365

Gly Lys Thr Ile Thr Leu Glu Val Glu Pro Ser Asp Thr Ile Glu Asn
            370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Ser Gly Gly Gly Gly Ser Gly Gly Gly Gly
            435                 440                 445

Gly Ser Gly Gly Gly Gly Ser Gly Gly Gly Gly Ser Gly Gly Gly Gly
            450                 455                 460

Ser Met Gln Ile Phe Val Lys Thr Leu Thr Gly Lys Thr Ile Thr Leu
465                 470                 475                 480

Glu Val Glu Pro Ser Asp Thr Ile Glu Asn Val Lys Ala Lys Ile Gln
                485                 490                 495

Asp Lys Glu Gly Ile Pro Pro Asp Gln Gln Arg Leu Ile Phe Ala Gly
            500                 505                 510
```

```
Lys Gln Leu Glu Asp Gly Arg Thr Leu Ser Asp Tyr Asn Ile Gln Lys
            515                 520                 525

Glu Ser Thr Leu His Leu Val Leu Arg Leu Arg Gly Gly Asp Ile Gln
        530                 535                 540

Met Thr Gln Ser Pro Thr Ser Leu Ser Ala Ser Val Gly Asp Arg Val
545                 550                 555                 560

Thr Ile Thr Cys Arg Ala Ser Gln Trp Ile Gly Asn Leu Leu Asp Trp
                565                 570                 575

Tyr Gln Gln Lys Pro Gly Glu Ala Pro Lys Leu Leu Ile Tyr Tyr Ala
            580                 585                 590

Ser Phe Leu Gln Ser Gly Val Pro Ser Arg Phe Ser Gly Gly Gly Phe
        595                 600                 605

Gly Thr Asp Phe Thr Leu Thr Ile Ser Ser Leu Gln Pro Glu Asp Phe
610                 615                 620

Ala Thr Tyr Tyr Cys Gln Gln Ala Asn Pro Ala Pro Leu Thr Phe Gly
625                 630                 635                 640

Gln Gly Thr Lys Val Glu Ile Lys Arg Glu Pro Lys Ser Cys Asp Lys
            645                 650                 655

Thr His Thr Cys Pro Pro Cys Pro Ala Pro Glu Leu Leu Gly Gly Pro
        660                 665                 670

Ser Val Phe Leu Phe Pro Pro Lys Pro Lys Asp Thr Leu Met Ile Ser
675                 680                 685

Arg Thr Pro Glu Val Thr Cys Val Val Val Asp Val Ser His Glu Asp
690                 695                 700

Pro Glu Val Lys Phe Asn Trp Tyr Val Asp Gly Val Glu Val His Asn
705                 710                 715                 720

Ala Lys Thr Lys Pro Arg Glu Glu Gln Tyr Asn Ser Thr Tyr Arg Val
            725                 730                 735

Val Ser Val Leu Thr Val Leu His Gln Asp Trp Leu Asn Gly Lys Glu
        740                 745                 750

Tyr Lys Cys Lys Val Ser Asn Lys Ala Leu Pro Ala Pro Ile Glu Lys
755                 760                 765

Thr Ile Ser Lys Ala Lys Gly Gln Pro Arg Glu Pro Gln Val Tyr Thr
770                 775                 780

Leu Pro Pro Ser Arg Glu Glu Met Thr Lys Asn Gln Val Ser Leu Thr
785                 790                 795                 800

Cys Leu Val Lys Gly Phe Tyr Pro Ser Asp Ile Ala Val Glu Trp Glu
            805                 810                 815

Ser Asn Gly Gln Pro Glu Asn Asn Tyr Lys Thr Thr Pro Pro Val Leu
        820                 825                 830

Asp Ser Asp Gly Ser Phe Phe Leu Tyr Ser Lys Leu Thr Val Asp Lys
835                 840                 845

Ser Arg Trp Gln Gln Gly Asn Val Phe Ser Cys Ser Val Met His Glu
850                 855                 860

Ala Leu His Asn His Tyr Thr Gln Lys Ser Leu Ser Leu Ser Pro Gly
865                 870                 875                 880

Lys

<210> SEQ ID NO 18
<211> LENGTH: 886
<212> TYPE: PRT
<213> ORGANISM: Artificial Sequence
<220> FEATURE:
<223> OTHER INFORMATION: Synthetic Protein complex comprising VEGF and
```

EGFR specific binding peptides #11

<400> SEQUENCE: 18

```
Met Gly Trp Ser Cys Ile Ile Leu Phe Leu Val Ala Thr Ala Thr Gly
 1               5                  10                  15

Val His Ser Asp Ile Gln Met Thr Gln Ser Pro Ser Ser Leu Ser Ala
                20                  25                  30

Ser Val Gly Asp Arg Val Thr Ile Thr Cys Arg Ala Ser Gln Trp Ile
            35                  40                  45

Gly Pro Glu Leu Ser Trp Tyr Gln Gln Lys Pro Gly Lys Ala Pro Lys
        50                  55                  60

Leu Leu Ile Tyr His Thr Ser Ile Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Met Phe
            100                 105                 110

Gln Pro Arg Thr Phe Gly Gln Gly Thr Lys Val Glu Ile Arg Arg Glu
        115                 120                 125

Pro Lys Ser Cys Asp Lys Thr His Thr Cys Pro Pro Cys Pro Ala Pro
130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
370                 375                 380

Val Lys Ala Lys Ile Gln Asp Lys Glu Gly Ile Pro Pro Asp Gln Gln
385                 390                 395                 400
```

Arg Leu Ile Phe Ala Gly Lys Gln Leu Glu Asp Gly Arg Thr Leu Ser
                    405                 410                 415

Asp Tyr Asn Ile Gln Lys Glu Ser Thr Leu His Leu Val Leu Arg Leu
                420                 425                 430

Arg Gly Gly Gly Gly Gly Ser Gly Gly Gly Gly Ser Gly Gly Gly
            435                 440                 445

Gly Ser Gly Gly Gly Gly Ser Gly Gly Gly Gly Ser Gly Gly Gly
    450                 455                 460

Ser Gly Gly Gly Gly Ser Met Gln Ile Phe Val Lys Thr Leu Thr Gly
465                 470                 475                 480

Lys Thr Ile Thr Leu Glu Val Glu Pro Ser Asp Thr Ile Glu Asn Val
                485                 490                 495

Lys Ala Lys Ile Gln Asp Lys Glu Gly Ile Pro Pro Asp Gln Gln Arg
                500                 505                 510

Leu Ile Phe Ala Gly Lys Gln Leu Glu Asp Gly Arg Thr Leu Ser Asp
            515                 520                 525

Tyr Asn Ile Gln Lys Glu Ser Thr Leu His Leu Val Leu Arg Leu Arg
        530                 535                 540

Gly Gly Asp Ile Gln Met Thr Gln Ser Pro Thr Ser Leu Ser Ala Ser
545                 550                 555                 560

Val Gly Asp Arg Val Thr Ile Thr Cys Arg Ala Ser Gln Trp Ile Gly
                565                 570                 575

Asn Leu Leu Asp Trp Tyr Gln Gln Lys Pro Gly Glu Ala Pro Lys Leu
                580                 585                 590

Leu Ile Tyr Tyr Ala Ser Phe Leu Gln Ser Gly Val Pro Ser Arg Phe
            595                 600                 605

Ser Gly Gly Gly Phe Gly Thr Asp Phe Thr Leu Thr Ile Ser Ser Leu
    610                 615                 620

Gln Pro Glu Asp Phe Ala Thr Tyr Tyr Cys Gln Gln Ala Asn Pro Ala
625                 630                 635                 640

Pro Leu Thr Phe Gly Gln Gly Thr Lys Val Glu Ile Lys Arg Glu Pro
                645                 650                 655

Lys Ser Cys Asp Lys Thr His Thr Cys Pro Pro Cys Pro Ala Pro Glu
                660                 665                 670

Leu Leu Gly Gly Pro Ser Val Phe Leu Phe Pro Pro Lys Pro Lys Asp
            675                 680                 685

Thr Leu Met Ile Ser Arg Thr Pro Glu Val Thr Cys Val Val Val Asp
    690                 695                 700

Val Ser His Glu Asp Pro Glu Val Lys Phe Asn Trp Tyr Val Asp Gly
705                 710                 715                 720

Val Glu Val His Asn Ala Lys Thr Lys Pro Arg Glu Glu Gln Tyr Asn
                725                 730                 735

Ser Thr Tyr Arg Val Val Ser Val Leu Thr Val Leu His Gln Asp Trp
                740                 745                 750

Leu Asn Gly Lys Glu Tyr Lys Cys Lys Val Ser Asn Lys Ala Leu Pro
            755                 760                 765

Ala Pro Ile Glu Lys Thr Ile Ser Lys Ala Lys Gly Gln Pro Arg Glu
    770                 775                 780

Pro Gln Val Tyr Thr Leu Pro Pro Ser Arg Glu Met Thr Lys Asn
785                 790                 795                 800

Gln Val Ser Leu Thr Cys Leu Val Lys Gly Phe Tyr Pro Ser Asp Ile
                805                 810                 815

Ala Val Glu Trp Glu Ser Asn Gly Gln Pro Glu Asn Asn Tyr Lys Thr

```
                    820                 825                 830
Thr Pro Pro Val Leu Asp Ser Asp Gly Ser Phe Phe Leu Tyr Ser Lys
                835                 840                 845

Leu Thr Val Asp Lys Ser Arg Trp Gln Gln Gly Asn Val Phe Ser Cys
            850                 855                 860

Ser Val Met His Glu Ala Leu His Asn His Tyr Thr Gln Lys Ser Leu
865                 870                 875                 880

Ser Leu Ser Pro Gly Lys
                885

<210> SEQ ID NO 19
<211> LENGTH: 891
<212> TYPE: PRT
<213> ORGANISM: Artificial Sequence
<220> FEATURE:
<223> OTHER INFORMATION: Synthetic Protein complex comprising VEGF and
      EGFR specific binding peptides #12

<400> SEQUENCE: 19

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Trp Ile
        35                  40                  45

Gly Pro Glu Leu Ser Trp Tyr Gln Gln Lys Pro Gly Lys Ala Pro Lys
    50                  55                  60

Leu Leu Ile Tyr His Thr Ser Ile Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Met Phe
            100                 105                 110

Gln Pro Arg Thr Phe Gly Gln Gly Thr Lys Val Glu Ile Arg Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285
```

-continued

```
Ile Ala Val Glu Trp Glu Ser Asn Gly Gln Pro Glu Asn Asn Tyr Lys
290                 295                 300
Thr Thr Pro Pro Val Leu Asp Ser Asp Gly Ser Phe Phe Leu Tyr Ser
305                 310                 315                 320
Lys Leu Thr Val Asp Lys Ser Arg Trp Gln Gln Gly Asn Val Phe Ser
                325                 330                 335
Cys Ser Val Met His Glu Ala Leu His Asn His Tyr Thr Gln Lys Ser
            340                 345                 350
Leu Ser Leu Ser Pro Gly Lys Met Gln Ile Phe Val Lys Thr Leu Thr
        355                 360                 365
Gly Lys Thr Ile Thr Leu Glu Val Glu Pro Ser Asp Thr Ile Glu Asn
370                 375                 380
Val Lys Ala Lys Ile Gln Asp Lys Glu Gly Ile Pro Pro Asp Gln Gln
385                 390                 395                 400
Arg Leu Ile Phe Ala Gly Lys Gln Leu Glu Asp Gly Arg Thr Leu Ser
                405                 410                 415
Asp Tyr Asn Ile Gln Lys Glu Ser Thr Leu His Leu Val Leu Arg Leu
            420                 425                 430
Arg Gly Gly Gly Gly Gly Ser Gly Gly Gly Ser Gly Gly Gly
        435                 440                 445
Gly Ser Gly Gly Gly Ser Gly Gly Gly Ser Gly Gly Gly
    450                 455                 460
Ser Gly Gly Gly Gly Ser Gly Gly Gly Ser Met Gln Ile Phe Val
465                 470                 475                 480
Lys Thr Leu Thr Gly Lys Thr Ile Thr Leu Glu Val Glu Pro Ser Asp
                485                 490                 495
Thr Ile Glu Asn Val Lys Ala Lys Ile Gln Asp Lys Glu Gly Ile Pro
            500                 505                 510
Pro Asp Gln Gln Arg Leu Ile Phe Ala Gly Lys Gln Leu Glu Asp Gly
        515                 520                 525
Arg Thr Leu Ser Asp Tyr Asn Ile Gln Lys Glu Ser Thr Leu His Leu
530                 535                 540
Val Leu Arg Leu Arg Gly Gly Asp Ile Gln Met Thr Gln Ser Pro Thr
545                 550                 555                 560
Ser Leu Ser Ala Ser Val Gly Asp Arg Val Thr Ile Thr Cys Arg Ala
                565                 570                 575
Ser Gln Trp Ile Gly Asn Leu Leu Asp Trp Tyr Gln Lys Pro Gly
            580                 585                 590
Glu Ala Pro Lys Leu Leu Ile Tyr Tyr Ala Ser Phe Leu Gln Ser Gly
        595                 600                 605
Val Pro Ser Arg Phe Ser Gly Gly Gly Phe Gly Thr Asp Phe Thr Leu
610                 615                 620
Thr Ile Ser Ser Leu Gln Pro Glu Asp Phe Ala Thr Tyr Tyr Cys Gln
625                 630                 635                 640
Gln Ala Asn Pro Ala Pro Leu Thr Phe Gly Gln Gly Thr Lys Val Glu
                645                 650                 655
Ile Lys Arg Glu Pro Lys Ser Cys Asp Lys Thr His Thr Cys Pro Pro
            660                 665                 670
Cys Pro Ala Pro Glu Leu Leu Gly Gly Pro Ser Val Phe Leu Phe Pro
        675                 680                 685
Pro Lys Pro Lys Asp Thr Leu Met Ile Ser Arg Thr Pro Glu Val Thr
690                 695                 700
Cys Val Val Val Asp Val Ser His Glu Asp Pro Glu Val Lys Phe Asn
```

```
                    705                 710                 715                 720
Trp Tyr Val Asp Gly Val Glu Val His Asn Ala Lys Thr Lys Pro Arg
                        725                 730                 735

Glu Glu Gln Tyr Asn Ser Thr Tyr Arg Val Val Ser Val Leu Thr Val
                        740                 745                 750

Leu His Gln Asp Trp Leu Asn Gly Lys Glu Tyr Lys Cys Lys Val Ser
                        755                 760                 765

Asn Lys Ala Leu Pro Ala Pro Ile Glu Lys Thr Ile Ser Lys Ala Lys
                        770                 775                 780

Gly Gln Pro Arg Glu Pro Gln Val Tyr Thr Leu Pro Pro Ser Arg Glu
785                 790                 795                 800

Glu Met Thr Lys Asn Gln Val Ser Leu Thr Cys Leu Val Lys Gly Phe
                        805                 810                 815

Tyr Pro Ser Asp Ile Ala Val Glu Trp Glu Ser Asn Gly Gln Pro Glu
                        820                 825                 830

Asn Asn Tyr Lys Thr Thr Pro Pro Val Leu Asp Ser Asp Gly Ser Phe
                        835                 840                 845

Phe Leu Tyr Ser Lys Leu Thr Val Asp Lys Ser Arg Trp Gln Gln Gly
                        850                 855                 860

Asn Val Phe Ser Cys Ser Val Met His Glu Ala Leu His Asn His Tyr
865                 870                 875                 880

Thr Gln Lys Ser Leu Ser Leu Ser Pro Gly Lys
                        885                 890

<210> SEQ ID NO 20
<211> LENGTH: 896
<212> TYPE: PRT
<213> ORGANISM: Artificial Sequence
<220> FEATURE:
<223> OTHER INFORMATION: Synthetic Protein complex comprising VEGF and
      EGFR specific binding peptides #13

<400> SEQUENCE: 20

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
                20                  25                  30

Ser Val Gly Asp Arg Val Thr Ile Thr Cys Arg Ala Ser Gln Trp Ile
            35                  40                  45

Gly Pro Glu Leu Ser Trp Tyr Gln Gln Lys Pro Gly Lys Ala Pro Lys
        50                  55                  60

Leu Leu Ile Tyr His Thr Ser Ile Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Met Phe
                100                 105                 110

Gln Pro Arg Thr Phe Gly Gln Gly Thr Lys Val Glu Ile Arg Arg Glu
            115                 120                 125

Pro Lys Ser Cys Asp Lys Thr His Thr Cys Pro Pro Cys Pro Ala Pro
        130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175
```

```
Asp Val Ser His Glu Asp Pro Glu Val Lys Phe Asn Trp Tyr Val Asp
            180                 185                 190
Gly Val Glu Val His Asn Ala Lys Thr Lys Pro Arg Glu Glu Gln Tyr
        195                 200                 205
Asn Ser Thr Tyr Arg Val Val Ser Val Leu Thr Val Leu His Gln Asp
    210                 215                 220
Trp Leu Asn Gly Lys Glu Tyr Lys Cys Lys Val Ser Asn Lys Ala Leu
225                 230                 235                 240
Pro Ala Pro Ile Glu Lys Thr Ile Ser Lys Ala Lys Gly Gln Pro Arg
                245                 250                 255
Glu Pro Gln Val Tyr Thr Leu Pro Pro Ser Arg Glu Glu Met Thr Lys
            260                 265                 270
Asn Gln Val Ser Leu Thr Cys Leu Val Lys Gly Phe Tyr Pro Ser Asp
        275                 280                 285
Ile Ala Val Glu Trp Glu Ser Asn Gly Gln Pro Glu Asn Asn Tyr Lys
    290                 295                 300
Thr Thr Pro Pro Val Leu Asp Ser Asp Gly Ser Phe Phe Leu Tyr Ser
305                 310                 315                 320
Lys Leu Thr Val Asp Lys Ser Arg Trp Gln Gln Gly Asn Val Phe Ser
                325                 330                 335
Cys Ser Val Met His Glu Ala Leu His Asn His Tyr Thr Gln Lys Ser
            340                 345                 350
Leu Ser Leu Ser Pro Gly Lys Met Gln Ile Phe Val Lys Thr Leu Thr
        355                 360                 365
Gly Lys Thr Ile Thr Leu Glu Val Glu Pro Ser Asp Thr Ile Glu Asn
    370                 375                 380
Val Lys Ala Lys Ile Gln Asp Lys Glu Gly Ile Pro Pro Asp Gln Gln
385                 390                 395                 400
Arg Leu Ile Phe Ala Gly Lys Gln Leu Glu Asp Gly Arg Thr Leu Ser
                405                 410                 415
Asp Tyr Asn Ile Gln Lys Glu Ser Thr Leu His Leu Val Leu Arg Leu
            420                 425                 430
Arg Gly Gly Gly Gly Gly Ser Gly Gly Gly Gly Ser Gly Gly Gly Gly
        435                 440                 445
Gly Ser Gly Gly Gly Gly Ser Gly Gly Gly Gly Ser Gly Gly Gly Gly
    450                 455                 460
Ser Gly Gly Gly Gly Ser Gly Gly Gly Ser Gly Gly Gly Gly Ser
465                 470                 475                 480
Met Gln Ile Phe Val Lys Thr Leu Thr Gly Lys Thr Ile Thr Leu Glu
                485                 490                 495
Val Glu Pro Ser Asp Thr Ile Glu Asn Val Lys Ala Lys Ile Gln Asp
            500                 505                 510
Lys Glu Gly Ile Pro Pro Asp Gln Gln Arg Leu Ile Phe Ala Gly Lys
        515                 520                 525
Gln Leu Glu Asp Gly Arg Thr Leu Ser Asp Tyr Asn Ile Gln Lys Glu
    530                 535                 540
Ser Thr Leu His Leu Val Leu Arg Leu Arg Gly Gly Asp Ile Gln Met
545                 550                 555                 560
Thr Gln Ser Pro Thr Ser Leu Ser Ala Ser Val Gly Asp Arg Val Thr
                565                 570                 575
Ile Thr Cys Arg Ala Ser Gln Trp Ile Gly Asn Leu Leu Asp Trp Tyr
            580                 585                 590
Gln Gln Lys Pro Gly Glu Ala Pro Lys Leu Leu Ile Tyr Tyr Ala Ser
```

```
                    595                 600                 605
Phe Leu Gln Ser Gly Val Pro Ser Arg Phe Ser Gly Gly Phe Gly
        610                 615                 620

Thr Asp Phe Thr Leu Thr Ile Ser Ser Leu Gln Pro Glu Asp Phe Ala
625                 630                 635                 640

Thr Tyr Tyr Cys Gln Gln Ala Asn Pro Ala Pro Leu Thr Phe Gly Gln
                645                 650                 655

Gly Thr Lys Val Glu Ile Lys Arg Glu Pro Lys Ser Cys Asp Lys Thr
            660                 665                 670

His Thr Cys Pro Pro Cys Pro Ala Pro Glu Leu Leu Gly Gly Pro Ser
        675                 680                 685

Val Phe Leu Phe Pro Pro Lys Pro Lys Asp Thr Leu Met Ile Ser Arg
    690                 695                 700

Thr Pro Glu Val Thr Cys Val Val Val Asp Val Ser His Glu Asp Pro
705                 710                 715                 720

Glu Val Lys Phe Asn Trp Tyr Val Asp Gly Val Glu Val His Asn Ala
                725                 730                 735

Lys Thr Lys Pro Arg Glu Glu Gln Tyr Asn Ser Thr Tyr Arg Val Val
            740                 745                 750

Ser Val Leu Thr Val Leu His Gln Asp Trp Leu Asn Gly Lys Glu Tyr
        755                 760                 765

Lys Cys Lys Val Ser Asn Lys Ala Leu Pro Ala Pro Ile Glu Lys Thr
    770                 775                 780

Ile Ser Lys Ala Lys Gly Gln Pro Arg Glu Pro Gln Val Tyr Thr Leu
785                 790                 795                 800

Pro Pro Ser Arg Glu Glu Met Thr Lys Asn Gln Val Ser Leu Thr Cys
                805                 810                 815

Leu Val Lys Gly Phe Tyr Pro Ser Asp Ile Ala Val Glu Trp Glu Ser
            820                 825                 830

Asn Gly Gln Pro Glu Asn Asn Tyr Lys Thr Thr Pro Pro Val Leu Asp
        835                 840                 845

Ser Asp Gly Ser Phe Phe Leu Tyr Ser Lys Leu Thr Val Asp Lys Ser
    850                 855                 860

Arg Trp Gln Gln Gly Asn Val Phe Ser Cys Ser Val Met His Glu Ala
865                 870                 875                 880

Leu His Asn His Tyr Thr Gln Lys Ser Leu Ser Leu Ser Pro Gly Lys
                885                 890                 895

<210> SEQ ID NO 21
<211> LENGTH: 901
<212> TYPE: PRT
<213> ORGANISM: Artificial Sequence
<220> FEATURE:
<223> OTHER INFORMATION: Synthetic Protein complex comprising VEGF and
      EGFR specific binding peptides #14

<400> SEQUENCE: 21

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Trp Ile
        35                  40                  45

Gly Pro Glu Leu Ser Trp Tyr Gln Gln Lys Pro Gly Lys Ala Pro Lys
    50                  55                  60
```

```
Leu Leu Ile Tyr His Thr Ser Ile Leu Gln Ser Gly Val Pro Ser Arg
 65                  70                  75                  80

Phe Ser Gly Ser Gly Ser Gly Thr Asp Phe Thr Leu Thr Ile Ser Ser
                 85                  90                  95

Leu Gln Pro Glu Asp Phe Ala Thr Tyr Tyr Cys Gln Gln Tyr Met Phe
            100                 105                 110

Gln Pro Arg Thr Phe Gly Gln Gly Thr Lys Val Glu Ile Arg Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Ser Gly Gly Gly Gly
        435                 440                 445

Gly Ser Gly Gly Gly Gly Ser Gly Gly Gly Ser Gly Gly Gly Gly Gly
    450                 455                 460

Ser Gly Gly Gly Ser Gly Gly Gly Gly Ser Gly Gly Gly Gly Gly Ser
465                 470                 475                 480

Gly Gly Gly Gly Ser Met Gln Ile Phe Val Lys Thr Leu Thr Gly Lys
```

-continued

```
              485                 490                 495
Thr Ile Thr Leu Glu Val Glu Pro Ser Asp Thr Ile Glu Asn Val Lys
            500                 505                 510

Ala Lys Ile Gln Asp Lys Glu Gly Ile Pro Pro Asp Gln Gln Arg Leu
            515                 520                 525

Ile Phe Ala Gly Lys Gln Leu Glu Asp Gly Arg Thr Leu Ser Asp Tyr
            530                 535                 540

Asn Ile Gln Lys Glu Ser Thr Leu His Leu Val Leu Arg Leu Arg Gly
545                 550                 555                 560

Gly Asp Ile Gln Met Thr Gln Ser Pro Thr Ser Leu Ser Ala Ser Val
                565                 570                 575

Gly Asp Arg Val Thr Ile Thr Cys Arg Ala Ser Gln Trp Ile Gly Asn
            580                 585                 590

Leu Leu Asp Trp Tyr Gln Gln Lys Pro Gly Glu Ala Pro Lys Leu Leu
            595                 600                 605

Ile Tyr Tyr Ala Ser Phe Leu Gln Ser Gly Val Pro Ser Arg Phe Ser
            610                 615                 620

Gly Gly Gly Phe Gly Thr Asp Phe Thr Leu Thr Ile Ser Ser Leu Gln
625                 630                 635                 640

Pro Glu Asp Phe Ala Thr Tyr Tyr Cys Gln Gln Ala Asn Pro Ala Pro
                645                 650                 655

Leu Thr Phe Gly Gln Gly Thr Lys Val Glu Ile Lys Arg Glu Pro Lys
            660                 665                 670

Ser Cys Asp Lys Thr His Thr Cys Pro Pro Cys Pro Ala Pro Glu Leu
            675                 680                 685

Leu Gly Gly Pro Ser Val Phe Leu Phe Pro Pro Lys Pro Lys Asp Thr
            690                 695                 700

Leu Met Ile Ser Arg Thr Pro Glu Val Thr Cys Val Val Val Asp Val
705                 710                 715                 720

Ser His Glu Asp Pro Glu Val Lys Phe Asn Trp Tyr Val Asp Gly Val
                725                 730                 735

Glu Val His Asn Ala Lys Thr Lys Pro Arg Glu Glu Gln Tyr Asn Ser
            740                 745                 750

Thr Tyr Arg Val Val Ser Val Leu Thr Val Leu His Gln Asp Trp Leu
            755                 760                 765

Asn Gly Lys Glu Tyr Lys Cys Lys Val Ser Asn Lys Ala Leu Pro Ala
            770                 775                 780

Pro Ile Glu Lys Thr Ile Ser Lys Ala Lys Gly Gln Pro Arg Glu Pro
785                 790                 795                 800

Gln Val Tyr Thr Leu Pro Pro Ser Arg Glu Glu Met Thr Lys Asn Gln
                805                 810                 815

Val Ser Leu Thr Cys Leu Val Lys Gly Phe Tyr Pro Ser Asp Ile Ala
            820                 825                 830

Val Glu Trp Glu Ser Asn Gly Gln Pro Glu Asn Asn Tyr Lys Thr Thr
            835                 840                 845

Pro Pro Val Leu Asp Ser Asp Gly Ser Phe Phe Leu Tyr Ser Lys Leu
            850                 855                 860

Thr Val Asp Lys Ser Arg Trp Gln Gln Gly Asn Val Phe Ser Cys Ser
865                 870                 875                 880

Val Met His Glu Ala Leu His Asn His Tyr Thr Gln Lys Ser Leu Ser
                885                 890                 895

Leu Ser Pro Gly Lys
            900
```

```
<210> SEQ ID NO 22
<211> LENGTH: 871
<212> TYPE: PRT
<213> ORGANISM: Artificial Sequence
<220> FEATURE:
<223> OTHER INFORMATION: Synthetic Protein complex comprising VEGF and
      EGFR specific binding peptides #15

<400> SEQUENCE: 22

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
                20                  25                  30

Ser Val Gly Asp Arg Val Thr Ile Thr Cys Arg Ala Ser Gln Lys Ile
            35                  40                  45

Phe Asn Gly Leu Ser Trp Tyr Gln Gln Lys Pro Gly Lys Ala Pro Lys
        50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
                100                 105                 110

Tyr Pro Tyr Thr Phe Gly Gln Gly Thr Lys Val Glu Ile Lys Arg Glu
            115                 120                 125

Pro Lys Ser Cys Asp Lys Thr His Thr Cys Pro Pro Cys Pro Ala Pro
        130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
```

```
              355                 360                 365
Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
                420                 425                 430

Arg Gly Gly Gly Gly Gly Ser Gly Gly Gly Ser Gly Gly Gly
            435                 440                 445

Gly Ser Gly Gly Gly Ser Met Gln Ile Phe Val Lys Thr Leu Thr
    450                 455                 460

Gly Lys Thr Ile Thr Leu Glu Val Glu Pro Ser Asp Thr Ile Glu Asn
465                 470                 475                 480

Val Lys Ala Lys Ile Gln Asp Lys Glu Gly Ile Pro Pro Asp Gln Gln
                485                 490                 495

Arg Leu Ile Phe Ala Gly Lys Gln Leu Glu Asp Gly Arg Thr Leu Ser
                500                 505                 510

Asp Tyr Asn Ile Gln Lys Glu Ser Thr Leu His Leu Val Leu Arg Leu
                515                 520                 525

Arg Gly Gly Asp Ile Gln Met Thr Gln Ser Pro Ser Ser Leu Ser Ala
    530                 535                 540

Ser Val Gly Asp Arg Val Thr Ile Thr Cys Arg Ala Ser Gln Trp Ile
545                 550                 555                 560

Gly Ile Leu Val Asp Trp Tyr Gln Gln Lys Pro Gly Glu Ala Pro Lys
                565                 570                 575

Leu Leu Ile Tyr Tyr Ala Ser Phe Leu Gln Ser Gly Val Pro Ser Arg
                580                 585                 590

Phe Ser Gly Ser Gly Phe Gly Thr Asp Phe Thr Leu Thr Ile Ser Ser
    595                 600                 605

Leu His Pro Glu Asp Phe Ala Thr Tyr Tyr Cys Gln Gln Ala Asn Pro
    610                 615                 620

Ala Pro Leu Thr Phe Gly Gln Gly Thr Lys Val Glu Ile Lys Arg Glu
625                 630                 635                 640

Pro Lys Ser Cys Asp Lys Thr His Thr Cys Pro Pro Cys Pro Ala Pro
                645                 650                 655

Glu Leu Leu Gly Gly Pro Ser Val Phe Leu Phe Pro Pro Lys Pro Lys
                660                 665                 670

Asp Thr Leu Met Ile Ser Arg Thr Pro Glu Val Thr Cys Val Val Val
                675                 680                 685

Asp Val Ser His Glu Asp Pro Glu Val Lys Phe Asn Trp Tyr Val Asp
    690                 695                 700

Gly Val Glu Val His Asn Ala Lys Thr Lys Pro Arg Glu Glu Gln Tyr
705                 710                 715                 720

Asn Ser Thr Tyr Arg Val Val Ser Val Leu Thr Val Leu His Gln Asp
                725                 730                 735

Trp Leu Asn Gly Lys Glu Tyr Lys Cys Lys Val Ser Asn Lys Ala Leu
                740                 745                 750

Pro Ala Pro Ile Glu Lys Thr Ile Ser Lys Ala Lys Gly Gln Pro Arg
                755                 760                 765

Glu Pro Gln Val Tyr Thr Leu Pro Pro Ser Arg Glu Glu Met Thr Lys
770                 775                 780
```

```
Asn Gln Val Ser Leu Thr Cys Leu Val Lys Gly Phe Tyr Pro Ser Asp
785                 790                 795                 800

Ile Ala Val Glu Trp Glu Ser Asn Gly Gln Pro Glu Asn Asn Tyr Lys
                805                 810                 815

Thr Thr Pro Pro Val Leu Asp Ser Asp Gly Ser Phe Phe Leu Tyr Ser
            820                 825                 830

Lys Leu Thr Val Asp Lys Ser Arg Trp Gln Gln Gly Asn Val Phe Ser
        835                 840                 845

Cys Ser Val Met His Glu Ala Leu His Asn His Tyr Thr Gln Lys Ser
    850                 855                 860

Leu Ser Leu Ser Pro Gly Lys
865                 870

<210> SEQ ID NO 23
<211> LENGTH: 876
<212> TYPE: PRT
<213> ORGANISM: Artificial Sequence
<220> FEATURE:
<223> OTHER INFORMATION: Synthetic Protein complex comprising VEGF and
      EGFR specific binding peptides #16

<400> SEQUENCE: 23

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
```

-continued

```
                260                 265                 270
Asn Gln Val Ser Leu Thr Cys Leu Val Lys Gly Phe Tyr Pro Ser Asp
                275                 280                 285
Ile Ala Val Glu Trp Glu Ser Asn Gly Gln Pro Glu Asn Asn Tyr Lys
                290                 295                 300
Thr Thr Pro Pro Val Leu Asp Ser Asp Gly Ser Phe Phe Leu Tyr Ser
305                 310                 315                 320
Lys Leu Thr Val Asp Lys Ser Arg Trp Gln Gln Gly Asn Val Phe Ser
                325                 330                 335
Cys Ser Val Met His Glu Ala Leu His Asn His Tyr Thr Gln Lys Ser
                340                 345                 350
Leu Ser Leu Ser Pro Gly Lys Met Gln Ile Phe Val Lys Thr Leu Thr
                355                 360                 365
Gly Lys Thr Ile Thr Leu Glu Val Glu Pro Ser Asp Thr Ile Glu Asn
                370                 375                 380
Val Lys Ala Lys Ile Gln Asp Lys Glu Gly Ile Pro Pro Asp Gln Gln
385                 390                 395                 400
Arg Leu Ile Phe Ala Gly Lys Gln Leu Glu Asp Gly Arg Thr Leu Ser
                405                 410                 415
Asp Tyr Asn Ile Gln Lys Glu Ser Thr Leu His Leu Val Leu Arg Leu
                420                 425                 430
Arg Gly Gly Gly Gly Gly Ser Gly Gly Gly Ser Gly Gly Gly
                435                 440                 445
Gly Ser Gly Gly Gly Gly Ser Gly Gly Gly Ser Met Gln Ile Phe
                450                 455                 460
Val Lys Thr Leu Thr Gly Lys Thr Ile Thr Leu Glu Val Glu Pro Ser
465                 470                 475                 480
Asp Thr Ile Glu Asn Val Lys Ala Lys Ile Gln Asp Lys Glu Gly Ile
                485                 490                 495
Pro Pro Asp Gln Gln Arg Leu Ile Phe Ala Gly Lys Gln Leu Glu Asp
                500                 505                 510
Gly Arg Thr Leu Ser Asp Tyr Asn Ile Gln Lys Glu Ser Thr Leu His
                515                 520                 525
Leu Val Leu Arg Leu Arg Gly Gly Asp Ile Gln Met Thr Gln Ser Pro
                530                 535                 540
Ser Ser Leu Ser Ala Ser Val Gly Asp Arg Val Thr Ile Thr Cys Arg
545                 550                 555                 560
Ala Ser Gln Trp Ile Gly Ile Leu Val Asp Trp Tyr Gln Gln Lys Pro
                565                 570                 575
Gly Glu Ala Pro Lys Leu Leu Ile Tyr Tyr Ala Ser Phe Leu Gln Ser
                580                 585                 590
Gly Val Pro Ser Arg Phe Ser Gly Ser Gly Phe Gly Thr Asp Phe Thr
                595                 600                 605
Leu Thr Ile Ser Ser Leu His Pro Glu Asp Phe Ala Thr Tyr Tyr Cys
                610                 615                 620
Gln Gln Ala Asn Pro Ala Pro Leu Thr Phe Gly Gln Gly Thr Lys Val
625                 630                 635                 640
Glu Ile Lys Arg Glu Pro Lys Ser Cys Asp Lys Thr His Thr Cys Pro
                645                 650                 655
Pro Cys Pro Ala Pro Glu Leu Leu Gly Gly Pro Ser Val Phe Leu Phe
                660                 665                 670
Pro Pro Lys Pro Lys Asp Thr Leu Met Ile Ser Arg Thr Pro Glu Val
                675                 680                 685
```

```
Thr Cys Val Val Val Asp Val Ser His Glu Asp Pro Glu Val Lys Phe
    690                 695                 700

Asn Trp Tyr Val Asp Gly Val Glu Val His Asn Ala Lys Thr Lys Pro
705                 710                 715                 720

Arg Glu Glu Gln Tyr Asn Ser Thr Tyr Arg Val Val Ser Val Leu Thr
                725                 730                 735

Val Leu His Gln Asp Trp Leu Asn Gly Lys Glu Tyr Lys Cys Lys Val
            740                 745                 750

Ser Asn Lys Ala Leu Pro Ala Pro Ile Glu Lys Thr Ile Ser Lys Ala
        755                 760                 765

Lys Gly Gln Pro Arg Glu Pro Gln Val Tyr Thr Leu Pro Pro Ser Arg
    770                 775                 780

Glu Glu Met Thr Lys Asn Gln Val Ser Leu Thr Cys Leu Val Lys Gly
785                 790                 795                 800

Phe Tyr Pro Ser Asp Ile Ala Val Glu Trp Glu Ser Asn Gly Gln Pro
                805                 810                 815

Glu Asn Asn Tyr Lys Thr Thr Pro Pro Val Leu Asp Ser Asp Gly Ser
            820                 825                 830

Phe Phe Leu Tyr Ser Lys Leu Thr Val Asp Lys Ser Arg Trp Gln Gln
        835                 840                 845

Gly Asn Val Phe Ser Cys Ser Val Met His Glu Ala Leu His Asn His
    850                 855                 860

Tyr Thr Gln Lys Ser Leu Ser Leu Ser Pro Gly Lys
865                 870                 875

<210> SEQ ID NO 24
<211> LENGTH: 881
<212> TYPE: PRT
<213> ORGANISM: Artificial Sequence
<220> FEATURE:
<223> OTHER INFORMATION: Synthetic Protein complex comprising VEGF and
      EGFR specific binding peptides #17

<400> SEQUENCE: 24

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
```

```
            165                 170                 175
Asp Val Ser His Glu Asp Pro Glu Val Lys Phe Asn Trp Tyr Val Asp
            180                 185                 190
Gly Val Glu Val His Asn Ala Lys Thr Lys Pro Arg Glu Glu Gln Tyr
            195                 200                 205
Asn Ser Thr Tyr Arg Val Val Ser Val Leu Thr Val Leu His Gln Asp
            210                 215                 220
Trp Leu Asn Gly Lys Glu Tyr Lys Cys Lys Val Ser Asn Lys Ala Leu
225                 230                 235                 240
Pro Ala Pro Ile Glu Lys Thr Ile Ser Lys Ala Lys Gly Gln Pro Arg
                245                 250                 255
Glu Pro Gln Val Tyr Thr Leu Pro Pro Ser Arg Glu Glu Met Thr Lys
                260                 265                 270
Asn Gln Val Ser Leu Thr Cys Leu Val Lys Gly Phe Tyr Pro Ser Asp
                275                 280                 285
Ile Ala Val Glu Trp Glu Ser Asn Gly Gln Pro Glu Asn Asn Tyr Lys
            290                 295                 300
Thr Thr Pro Pro Val Leu Asp Ser Asp Gly Ser Phe Phe Leu Tyr Ser
305                 310                 315                 320
Lys Leu Thr Val Asp Lys Ser Arg Trp Gln Gln Gly Asn Val Phe Ser
                325                 330                 335
Cys Ser Val Met His Glu Ala Leu His Asn His Tyr Thr Gln Lys Ser
                340                 345                 350
Leu Ser Leu Ser Pro Gly Lys Met Gln Ile Phe Val Lys Thr Leu Thr
                355                 360                 365
Gly Lys Thr Ile Thr Leu Glu Val Glu Pro Ser Asp Thr Ile Glu Asn
            370                 375                 380
Val Lys Ala Lys Ile Gln Asp Lys Glu Gly Ile Pro Pro Asp Gln Gln
385                 390                 395                 400
Arg Leu Ile Phe Ala Gly Lys Gln Leu Glu Asp Gly Arg Thr Leu Ser
                405                 410                 415
Asp Tyr Asn Ile Gln Lys Glu Ser Thr Leu His Leu Val Leu Arg Leu
            420                 425                 430
Arg Gly Gly Gly Gly Gly Ser Gly Gly Gly Ser Gly Gly Gly Gly Gly
            435                 440                 445
Gly Ser Gly Gly Gly Gly Ser Gly Gly Gly Ser Gly Gly Gly Gly
            450                 455                 460
Ser Met Gln Ile Phe Val Lys Thr Leu Thr Gly Lys Thr Ile Thr Leu
465                 470                 475                 480
Glu Val Glu Pro Ser Asp Thr Ile Glu Asn Val Lys Ala Lys Ile Gln
                485                 490                 495
Asp Lys Glu Gly Ile Pro Pro Asp Gln Gln Arg Leu Ile Phe Ala Gly
                500                 505                 510
Lys Gln Leu Glu Asp Gly Arg Thr Leu Ser Asp Tyr Asn Ile Gln Lys
            515                 520                 525
Glu Ser Thr Leu His Leu Val Leu Arg Leu Arg Gly Gly Asp Ile Gln
            530                 535                 540
Met Thr Gln Ser Pro Ser Ser Leu Ser Ala Ser Val Gly Asp Arg Val
545                 550                 555                 560
Thr Ile Thr Cys Arg Ala Ser Gln Trp Ile Gly Ile Leu Val Asp Trp
                565                 570                 575
Tyr Gln Gln Lys Pro Gly Glu Ala Pro Lys Leu Leu Ile Tyr Tyr Ala
            580                 585                 590
```

Ser Phe Leu Gln Ser Gly Val Pro Ser Arg Phe Ser Gly Ser Gly Phe
            595                 600                 605

Gly Thr Asp Phe Thr Leu Thr Ile Ser Ser Leu His Pro Glu Asp Phe
        610                 615                 620

Ala Thr Tyr Tyr Cys Gln Gln Ala Asn Pro Ala Pro Leu Thr Phe Gly
625                 630                 635                 640

Gln Gly Thr Lys Val Glu Ile Lys Arg Glu Pro Lys Ser Cys Asp Lys
            645                 650                 655

Thr His Thr Cys Pro Pro Cys Pro Ala Pro Glu Leu Leu Gly Gly Pro
        660                 665                 670

Ser Val Phe Leu Phe Pro Pro Lys Pro Lys Asp Thr Leu Met Ile Ser
    675                 680                 685

Arg Thr Pro Glu Val Thr Cys Val Val Val Asp Val Ser His Glu Asp
690                 695                 700

Pro Glu Val Lys Phe Asn Trp Tyr Val Asp Gly Val Glu Val His Asn
705                 710                 715                 720

Ala Lys Thr Lys Pro Arg Glu Glu Gln Tyr Asn Ser Thr Tyr Arg Val
            725                 730                 735

Val Ser Val Leu Thr Val Leu His Gln Asp Trp Leu Asn Gly Lys Glu
        740                 745                 750

Tyr Lys Cys Lys Val Ser Asn Lys Ala Leu Pro Ala Pro Ile Glu Lys
    755                 760                 765

Thr Ile Ser Lys Ala Lys Gly Gln Pro Arg Glu Pro Gln Val Tyr Thr
770                 775                 780

Leu Pro Pro Ser Arg Glu Glu Met Thr Lys Asn Gln Val Ser Leu Thr
785                 790                 795                 800

Cys Leu Val Lys Gly Phe Tyr Pro Ser Asp Ile Ala Val Glu Trp Glu
            805                 810                 815

Ser Asn Gly Gln Pro Glu Asn Asn Tyr Lys Thr Thr Pro Pro Val Leu
        820                 825                 830

Asp Ser Asp Gly Ser Phe Phe Leu Tyr Ser Lys Leu Thr Val Asp Lys
    835                 840                 845

Ser Arg Trp Gln Gln Gly Asn Val Phe Ser Cys Ser Val Met His Glu
850                 855                 860

Ala Leu His Asn His Tyr Thr Gln Lys Ser Leu Ser Leu Ser Pro Gly
865                 870                 875                 880

Lys

<210> SEQ ID NO 25
<211> LENGTH: 886
<212> TYPE: PRT
<213> ORGANISM: Artificial Sequence
<220> FEATURE:
<223> OTHER INFORMATION: Synthetic Protein complex comprising VEGF and
    EGFR specific binding peptides #18

<400> SEQUENCE: 25

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

```
Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
            115                 120                 125

Pro Lys Ser Cys Asp Lys Thr His Thr Cys Pro Pro Cys Pro Ala Pro
            130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
                180                 185                 190

Gly Val Glu Val His Asn Ala Lys Thr Lys Pro Arg Glu Glu Gln Tyr
            195                 200                 205

Asn Ser Thr Tyr Arg Val Val Ser Val Leu Thr Val Leu His Gln Asp
210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
            275                 280                 285

Ile Ala Val Glu Trp Glu Ser Asn Gly Gln Pro Glu Asn Asn Tyr Lys
            290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
                340                 345                 350

Leu Ser Leu Ser Pro Gly Lys Met Gln Ile Phe Val Lys Thr Leu Thr
            355                 360                 365

Gly Lys Thr Ile Thr Leu Glu Val Glu Pro Ser Asp Thr Ile Glu Asn
            370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Ser Gly Gly Gly Ser Gly Gly Gly
            435                 440                 445

Gly Ser Gly Gly Gly Ser Gly Gly Gly Ser Gly Gly Gly
            450                 455                 460

Ser Gly Gly Gly Gly Ser Met Gln Ile Phe Val Lys Thr Leu Thr Gly
465                 470                 475                 480
```

```
Lys Thr Ile Thr Leu Glu Val Glu Pro Ser Asp Thr Ile Glu Asn Val
                485                 490                 495
Lys Ala Lys Ile Gln Asp Lys Glu Gly Ile Pro Pro Asp Gln Gln Arg
            500                 505                 510
Leu Ile Phe Ala Gly Lys Gln Leu Glu Asp Gly Arg Thr Leu Ser Asp
        515                 520                 525
Tyr Asn Ile Gln Lys Glu Ser Thr Leu His Leu Val Leu Arg Leu Arg
    530                 535                 540
Gly Gly Asp Ile Gln Met Thr Gln Ser Pro Ser Ser Leu Ser Ala Ser
545                 550                 555                 560
Val Gly Asp Arg Val Thr Ile Thr Cys Arg Ala Ser Gln Trp Ile Gly
                565                 570                 575
Ile Leu Val Asp Trp Tyr Gln Gln Lys Pro Gly Glu Ala Pro Lys Leu
            580                 585                 590
Leu Ile Tyr Tyr Ala Ser Phe Leu Gln Ser Gly Val Pro Ser Arg Phe
        595                 600                 605
Ser Gly Ser Gly Phe Gly Thr Asp Phe Thr Leu Thr Ile Ser Ser Leu
    610                 615                 620
His Pro Glu Asp Phe Ala Thr Tyr Tyr Cys Gln Gln Ala Asn Pro Ala
625                 630                 635                 640
Pro Leu Thr Phe Gly Gln Gly Thr Lys Val Glu Ile Lys Arg Glu Pro
                645                 650                 655
Lys Ser Cys Asp Lys Thr His Thr Cys Pro Pro Cys Pro Ala Pro Glu
            660                 665                 670
Leu Leu Gly Gly Pro Ser Val Phe Leu Phe Pro Pro Lys Pro Lys Asp
        675                 680                 685
Thr Leu Met Ile Ser Arg Thr Pro Glu Val Thr Cys Val Val Val Asp
    690                 695                 700
Val Ser His Glu Asp Pro Glu Val Lys Phe Asn Trp Tyr Val Asp Gly
705                 710                 715                 720
Val Glu Val His Asn Ala Lys Thr Lys Pro Arg Glu Glu Gln Tyr Asn
                725                 730                 735
Ser Thr Tyr Arg Val Val Ser Val Leu Thr Val Leu His Gln Asp Trp
            740                 745                 750
Leu Asn Gly Lys Glu Tyr Lys Cys Lys Val Ser Asn Lys Ala Leu Pro
        755                 760                 765
Ala Pro Ile Glu Lys Thr Ile Ser Lys Ala Lys Gly Gln Pro Arg Glu
    770                 775                 780
Pro Gln Val Tyr Thr Leu Pro Pro Ser Arg Glu Glu Met Thr Lys Asn
785                 790                 795                 800
Gln Val Ser Leu Thr Cys Leu Val Lys Gly Phe Tyr Pro Ser Asp Ile
                805                 810                 815
Ala Val Glu Trp Glu Ser Asn Gly Gln Pro Glu Asn Asn Tyr Lys Thr
            820                 825                 830
Thr Pro Pro Val Leu Asp Ser Asp Gly Ser Phe Phe Leu Tyr Ser Lys
        835                 840                 845
Leu Thr Val Asp Lys Ser Arg Trp Gln Gln Gly Asn Val Phe Ser Cys
    850                 855                 860
Ser Val Met His Glu Ala Leu His Asn His Tyr Thr Gln Lys Ser Leu
865                 870                 875                 880
Ser Leu Ser Pro Gly Lys
                885
```

```
<210> SEQ ID NO 26
<211> LENGTH: 891
<212> TYPE: PRT
<213> ORGANISM: Artificial Sequence
<220> FEATURE -continued

```
Gly Lys Thr Ile Thr Leu Glu Val Glu Pro Ser Asp Thr Ile Glu Asn
370                 375                 380
Val Lys Ala Lys Ile Gln Asp Lys Glu Gly Ile Pro Pro Asp Gln Gln
385                 390                 395                 400
Arg Leu Ile Phe Ala Gly Lys Gln Leu Glu Asp Gly Arg Thr Leu Ser
                405                 410                 415
Asp Tyr Asn Ile Gln Lys Glu Ser Thr Leu His Leu Val Leu Arg Leu
                420                 425                 430
Arg Gly Gly Gly Gly Gly Ser Gly Gly Gly Ser Gly Gly Gly
                435                 440                 445
Gly Ser Gly Gly Gly Gly Ser Gly Gly Gly Gly Ser Gly Gly Gly Gly
450                 455                 460
Ser Gly Gly Gly Ser Gly Gly Gly Ser Met Gln Ile Phe Val
465                 470                 475                 480
Lys Thr Leu Thr Gly Lys Thr Ile Thr Leu Glu Val Glu Pro Ser Asp
                485                 490                 495
Thr Ile Glu Asn Val Lys Ala Lys Ile Gln Asp Lys Glu Gly Ile Pro
                500                 505                 510
Pro Asp Gln Gln Arg Leu Ile Phe Ala Gly Lys Gln Leu Glu Asp Gly
                515                 520                 525
Arg Thr Leu Ser Asp Tyr Asn Ile Gln Lys Glu Ser Thr Leu His Leu
530                 535                 540
Val Leu Arg Leu Arg Gly Gly Asp Ile Gln Met Thr Gln Ser Pro Ser
545                 550                 555                 560
Ser Leu Ser Ala Ser Val Gly Asp Arg Val Thr Ile Thr Cys Arg Ala
                565                 570                 575
Ser Gln Trp Ile Gly Ile Leu Val Asp Trp Tyr Gln Lys Pro Gly
                580                 585                 590
Glu Ala Pro Lys Leu Leu Ile Tyr Tyr Ala Ser Phe Leu Gln Ser Gly
                595                 600                 605
Val Pro Ser Arg Phe Ser Gly Ser Gly Phe Gly Thr Asp Phe Thr Leu
                610                 615                 620
Thr Ile Ser Ser Leu His Pro Glu Asp Phe Ala Thr Tyr Tyr Cys Gln
625                 630                 635                 640
Gln Ala Asn Pro Ala Pro Leu Thr Phe Gly Gln Gly Thr Lys Val Glu
                645                 650                 655
Ile Lys Arg Glu Pro Lys Ser Cys Asp Lys Thr His Thr Cys Pro Pro
                660                 665                 670
Cys Pro Ala Pro Glu Leu Leu Gly Gly Pro Ser Val Phe Leu Phe Pro
                675                 680                 685
Pro Lys Pro Lys Asp Thr Leu Met Ile Ser Arg Thr Pro Glu Val Thr
                690                 695                 700
Cys Val Val Val Asp Val Ser His Glu Asp Pro Glu Val Lys Phe Asn
705                 710                 715                 720
Trp Tyr Val Asp Gly Val Glu Val His Asn Ala Lys Thr Lys Pro Arg
                725                 730                 735
Glu Glu Gln Tyr Asn Ser Thr Tyr Arg Val Val Ser Val Leu Thr Val
                740                 745                 750
Leu His Gln Asp Trp Leu Asn Gly Lys Glu Tyr Lys Cys Lys Val Ser
                755                 760                 765
Asn Lys Ala Leu Pro Ala Pro Ile Glu Lys Thr Ile Ser Lys Ala Lys
                770                 775                 780
Gly Gln Pro Arg Glu Pro Gln Val Tyr Thr Leu Pro Pro Ser Arg Glu
```

```
                785                 790                 795                 800
Glu Met Thr Lys Asn Gln Val Ser Leu Thr Cys Leu Val Lys Gly Phe
                    805                 810                 815

Tyr Pro Ser Asp Ile Ala Val Glu Trp Glu Ser Asn Gly Gln Pro Glu
                820                 825                 830

Asn Asn Tyr Lys Thr Thr Pro Pro Val Leu Asp Ser Asp Gly Ser Phe
                835                 840                 845

Phe Leu Tyr Ser Lys Leu Thr Val Asp Lys Ser Arg Trp Gln Gln Gly
850                 855                 860

Asn Val Phe Ser Cys Ser Val Met His Glu Ala Leu His Asn His Tyr
865                 870                 875                 880

Thr Gln Lys Ser Leu Ser Leu Ser Pro Gly Lys
                885                 890

<210> SEQ ID NO 27
<211> LENGTH: 896
<212> TYPE: PRT
<213> ORGANISM: Artificial Sequence
<220> FEATURE:
<223> OTHER INFORMATION: Synthetic Protein complex comprising VEGF and
      EGFR specific binding peptides #20

<400> SEQUENCE: 27

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
                20                  25                  30

Ser Val Gly Asp Arg Val Thr Ile Thr Cys Arg Ala Ser Gln Lys Ile
            35                  40                  45

Phe Asn Gly Leu Ser Trp Tyr Gln Gln Lys Pro Gly Lys Ala Pro Lys
        50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
                100                 105                 110

Tyr Pro Tyr Thr Phe Gly Gln Gly Thr Lys Val Glu Ile Lys Arg Glu
            115                 120                 125

Pro Lys Ser Cys Asp Lys Thr His Thr Cys Pro Pro Cys Pro Ala Pro
130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255
```

```
Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
        290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Ser Gly Gly Gly Ser Gly Gly Gly Gly
        435                 440                 445

Gly Ser Gly Gly Gly Gly Ser Gly Gly Gly Gly Ser Gly Gly Gly Gly
450                 455                 460

Ser Gly Gly Gly Gly Ser Gly Gly Gly Ser Gly Gly Gly Gly Ser
465                 470                 475                 480

Met Gln Ile Phe Val Lys Thr Leu Thr Gly Lys Thr Ile Thr Leu Glu
                485                 490                 495

Val Glu Pro Ser Asp Thr Ile Glu Asn Val Lys Ala Lys Ile Gln Asp
            500                 505                 510

Lys Glu Gly Ile Pro Pro Asp Gln Gln Arg Leu Ile Phe Ala Gly Lys
        515                 520                 525

Gln Leu Glu Asp Gly Arg Thr Leu Ser Asp Tyr Asn Ile Gln Lys Glu
    530                 535                 540

Ser Thr Leu His Leu Val Leu Arg Leu Arg Gly Gly Asp Ile Gln Met
545                 550                 555                 560

Thr Gln Ser Pro Ser Ser Leu Ser Ala Ser Val Gly Asp Arg Val Thr
                565                 570                 575

Ile Thr Cys Arg Ala Ser Gln Trp Ile Gly Ile Leu Val Asp Trp Tyr
            580                 585                 590

Gln Gln Lys Pro Gly Glu Ala Pro Lys Leu Leu Ile Tyr Tyr Ala Ser
        595                 600                 605

Phe Leu Gln Ser Gly Val Pro Ser Arg Phe Ser Gly Ser Gly Phe Gly
    610                 615                 620

Thr Asp Phe Thr Leu Thr Ile Ser Ser Leu His Pro Glu Asp Phe Ala
625                 630                 635                 640

Thr Tyr Tyr Cys Gln Gln Ala Asn Pro Ala Pro Leu Thr Phe Gly Gln
                645                 650                 655

Gly Thr Lys Val Glu Ile Lys Arg Glu Pro Lys Ser Cys Asp Lys Thr
            660                 665                 670

His Thr Cys Pro Pro Cys Pro Ala Pro Glu Leu Leu Gly Gly Pro Ser
```

```
                        675                 680                 685
Val Phe Leu Phe Pro Pro Lys Pro Lys Asp Thr Leu Met Ile Ser Arg
        690                 695                 700

Thr Pro Glu Val Thr Cys Val Val Asp Val Ser His Glu Asp Pro
705                 710                 715                 720

Glu Val Lys Phe Asn Trp Tyr Val Asp Gly Val Glu Val His Asn Ala
                725                 730                 735

Lys Thr Lys Pro Arg Glu Glu Gln Tyr Asn Ser Thr Tyr Arg Val Val
            740                 745                 750

Ser Val Leu Thr Val Leu His Gln Asp Trp Leu Asn Gly Lys Glu Tyr
                755                 760                 765

Lys Cys Lys Val Ser Asn Lys Ala Leu Pro Ala Pro Ile Glu Lys Thr
770                 775                 780

Ile Ser Lys Ala Lys Gly Gln Pro Arg Glu Pro Gln Val Tyr Thr Leu
785                 790                 795                 800

Pro Pro Ser Arg Glu Glu Met Thr Lys Asn Gln Val Ser Leu Thr Cys
                805                 810                 815

Leu Val Lys Gly Phe Tyr Pro Ser Asp Ile Ala Val Glu Trp Glu Ser
            820                 825                 830

Asn Gly Gln Pro Glu Asn Asn Tyr Lys Thr Thr Pro Pro Val Leu Asp
                835                 840                 845

Ser Asp Gly Ser Phe Phe Leu Tyr Ser Lys Leu Thr Val Asp Lys Ser
            850                 855                 860

Arg Trp Gln Gln Gly Asn Val Phe Ser Cys Ser Val Met His Glu Ala
865                 870                 875                 880

Leu His Asn His Tyr Thr Gln Lys Ser Leu Ser Leu Ser Pro Gly Lys
                885                 890                 895

<210> SEQ ID NO 28
<211> LENGTH: 901
<212> TYPE: PRT
<213> ORGANISM: Artificial Sequence
<220> FEATURE:
<223> OTHER INFORMATION: Synthetic Protein complex comprising VEGF and
      EGFR specific binding peptides #21

<400> SEQUENCE: 28

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
                20                  25                  30

Ser Val Gly Asp Arg Val Thr Ile Thr Cys Arg Ala Ser Gln Lys Ile
            35                  40                  45

Phe Asn Gly Leu Ser Trp Tyr Gln Gln Lys Pro Gly Lys Ala Pro Lys
        50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140
```

```
Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Ser Gly Gly Gly Ser Gly Gly Gly Gly Gly
        435                 440                 445

Gly Ser Gly Gly Gly Gly Ser Gly Gly Gly Gly Ser Gly Gly Gly Gly
450                 455                 460

Ser Gly Gly Gly Gly Ser Gly Gly Gly Gly Ser Gly Gly Gly Gly Ser
465                 470                 475                 480

Gly Gly Gly Gly Ser Met Gln Ile Phe Val Lys Thr Leu Thr Gly Lys
                485                 490                 495

Thr Ile Thr Leu Glu Val Glu Pro Ser Asp Thr Ile Glu Asn Val Lys
            500                 505                 510

Ala Lys Ile Gln Asp Lys Glu Gly Ile Pro Pro Asp Gln Gln Arg Leu
        515                 520                 525

Ile Phe Ala Gly Lys Gln Leu Glu Asp Gly Arg Thr Leu Ser Asp Tyr
    530                 535                 540

Asn Ile Gln Lys Glu Ser Thr Leu His Leu Val Leu Arg Leu Arg Gly
545                 550                 555                 560

Gly Asp Ile Gln Met Thr Gln Ser Pro Ser Ser Leu Ser Ala Ser Val
```

565                 570                 575
Gly Asp Arg Val Thr Ile Thr Cys Arg Ala Ser Gln Trp Ile Gly Ile
                580                 585                 590

Leu Val Asp Trp Tyr Gln Gln Lys Pro Gly Glu Ala Pro Lys Leu Leu
            595                 600                 605

Ile Tyr Tyr Ala Ser Phe Leu Gln Ser Gly Val Pro Ser Arg Phe Ser
        610                 615                 620

Gly Ser Gly Phe Gly Thr Asp Phe Thr Leu Thr Ile Ser Ser Leu His
625                 630                 635                 640

Pro Glu Asp Phe Ala Thr Tyr Tyr Cys Gln Gln Ala Asn Pro Ala Pro
                645                 650                 655

Leu Thr Phe Gly Gln Gly Thr Lys Val Glu Ile Lys Arg Glu Pro Lys
            660                 665                 670

Ser Cys Asp Lys Thr His Thr Cys Pro Pro Cys Pro Ala Pro Glu Leu
        675                 680                 685

Leu Gly Gly Pro Ser Val Phe Leu Phe Pro Pro Lys Pro Lys Asp Thr
    690                 695                 700

Leu Met Ile Ser Arg Thr Pro Glu Val Thr Cys Val Val Val Asp Val
705                 710                 715                 720

Ser His Glu Asp Pro Glu Val Lys Phe Asn Trp Tyr Val Asp Gly Val
                725                 730                 735

Glu Val His Asn Ala Lys Thr Lys Pro Arg Glu Glu Gln Tyr Asn Ser
            740                 745                 750

Thr Tyr Arg Val Val Ser Val Leu Thr Val Leu His Gln Asp Trp Leu
        755                 760                 765

Asn Gly Lys Glu Tyr Lys Cys Lys Val Ser Asn Lys Ala Leu Pro Ala
    770                 775                 780

Pro Ile Glu Lys Thr Ile Ser Lys Ala Lys Gly Gln Pro Arg Glu Pro
785                 790                 795                 800

Gln Val Tyr Thr Leu Pro Pro Ser Arg Glu Glu Met Thr Lys Asn Gln
                805                 810                 815

Val Ser Leu Thr Cys Leu Val Lys Gly Phe Tyr Pro Ser Asp Ile Ala
            820                 825                 830

Val Glu Trp Glu Ser Asn Gly Gln Pro Glu Asn Asn Tyr Lys Thr Thr
        835                 840                 845

Pro Pro Val Leu Asp Ser Asp Gly Ser Phe Phe Leu Tyr Ser Lys Leu
    850                 855                 860

Thr Val Asp Lys Ser Arg Trp Gln Gln Gly Asn Val Phe Ser Cys Ser
865                 870                 875                 880

Val Met His Glu Ala Leu His Asn His Tyr Thr Gln Lys Ser Leu Ser
                885                 890                 895

Leu Ser Pro Gly Lys
            900

<210> SEQ ID NO 29
<211> LENGTH: 871
<212> TYPE: PRT
<213> ORGANISM: Artificial Sequence
<220> FEATURE:
<223> OTHER INFORMATION: Synthetic Protein complex comprising VEGF and
      EGFR specific binding peptides #22

<400> SEQUENCE: 29

Met Gly Trp Ser Cys Ile Ile Leu Phe Leu Val Ala Thr Ala Thr Gly
1               5                   10                  15

```
Val His Ser Asp Ile Gln Met Thr Gln Ser Pro Ser Ser Leu Ser Ala
             20                  25                  30

Ser Val Gly Asp Arg Val Thr Ile Thr Cys Arg Ala Ser Gln Lys Ile
         35                  40                  45

Phe Asn Gly Leu Ser Trp Tyr Gln Gln Lys Pro Gly Lys Ala Pro Lys
     50                  55                  60

Leu Leu Ile Tyr His Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                 85                  90                  95

Leu Gln Pro Glu Asp Phe Ala Thr Tyr Tyr Cys Gln Gln Val Leu Leu
             100                 105                 110

Tyr Pro Tyr Thr Phe Gly Gln Gly Thr Lys Val Glu Ile Lys Arg Glu
         115                 120                 125

Pro Lys Ser Cys Asp Lys Thr His Thr Cys Pro Pro Cys Pro Ala Pro
130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                 165                 170                 175

Asp Val Ser His Glu Asp Pro Glu Val Lys Phe Asn Trp Tyr Val Asp
             180                 185                 190

Gly Val Glu Val His Asn Ala Lys Thr Lys Pro Arg Glu Glu Gln Tyr
         195                 200                 205

Asn Ser Thr Tyr Arg Val Val Ser Val Leu Thr Val Leu His Gln Asp
210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                 245                 250                 255

Glu Pro Gln Val Tyr Thr Leu Pro Pro Ser Arg Glu Glu Met Thr Lys
             260                 265                 270

Asn Gln Val Ser Leu Thr Cys Leu Val Lys Gly Phe Tyr Pro Ser Asp
         275                 280                 285

Ile Ala Val Glu Trp Glu Ser Asn Gly Gln Pro Glu Asn Asn Tyr Lys
290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                 325                 330                 335

Cys Ser Val Met His Glu Ala Leu His Asn His Tyr Thr Gln Lys Ser
             340                 345                 350

Leu Ser Leu Ser Pro Gly Lys Met Gln Ile Phe Val Lys Thr Leu Thr
         355                 360                 365

Gly Lys Thr Ile Thr Leu Glu Val Glu Pro Ser Asp Thr Ile Glu Asn
         370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                 405                 410                 415

Asp Tyr Asn Ile Gln Lys Glu Ser Thr Leu His Leu Val Leu Arg Leu
             420                 425                 430

Arg Gly Gly Gly Gly Gly Ser Gly Gly Gly Gly Ser Gly Gly Gly
```

-continued

```
                435                 440                 445
Gly Ser Gly Gly Gly Ser Met Gln Ile Phe Val Lys Thr Leu Thr
450                 455                 460
Gly Lys Thr Ile Thr Leu Glu Val Glu Pro Ser Asp Thr Ile Glu Asn
465                 470                 475                 480
Val Lys Ala Lys Ile Gln Asp Lys Glu Gly Ile Pro Pro Asp Gln Gln
                485                 490                 495
Arg Leu Ile Phe Ala Gly Lys Gln Leu Glu Asp Gly Arg Thr Leu Ser
                500                 505                 510
Asp Tyr Asn Ile Gln Lys Glu Ser Thr Leu His Leu Val Leu Arg Leu
                515                 520                 525
Arg Gly Gly Asp Ile Gln Met Thr Gln Ser Pro Thr Ser Leu Ser Ala
530                 535                 540
Ser Val Gly Asp Arg Val Thr Ile Thr Cys Arg Ala Ser Gln Trp Ile
545                 550                 555                 560
Gly Asn Leu Leu Asp Trp Tyr Gln Gln Lys Pro Gly Glu Ala Pro Lys
                565                 570                 575
Leu Leu Ile Tyr Tyr Ala Ser Phe Leu Gln Ser Gly Val Pro Ser Arg
                580                 585                 590
Phe Ser Gly Gly Gly Phe Gly Thr Asp Phe Thr Leu Thr Ile Ser Ser
                595                 600                 605
Leu Gln Pro Glu Asp Phe Ala Thr Tyr Tyr Cys Gln Gln Ala Asn Pro
                610                 615                 620
Ala Pro Leu Thr Phe Gly Gln Gly Thr Lys Val Glu Ile Lys Arg Glu
625                 630                 635                 640
Pro Lys Ser Cys Asp Lys Thr His Thr Cys Pro Pro Cys Pro Ala Pro
                645                 650                 655
Glu Leu Leu Gly Gly Pro Ser Val Phe Leu Phe Pro Pro Lys Pro Lys
                660                 665                 670
Asp Thr Leu Met Ile Ser Arg Thr Pro Glu Val Thr Cys Val Val Val
                675                 680                 685
Asp Val Ser His Glu Asp Pro Glu Val Lys Phe Asn Trp Tyr Val Asp
                690                 695                 700
Gly Val Glu Val His Asn Ala Lys Thr Lys Pro Arg Glu Glu Gln Tyr
705                 710                 715                 720
Asn Ser Thr Tyr Arg Val Val Ser Val Leu Thr Val Leu His Gln Asp
                725                 730                 735
Trp Leu Asn Gly Lys Glu Tyr Lys Cys Lys Val Ser Asn Lys Ala Leu
                740                 745                 750
Pro Ala Pro Ile Glu Lys Thr Ile Ser Lys Ala Lys Gly Gln Pro Arg
                755                 760                 765
Glu Pro Gln Val Tyr Thr Leu Pro Pro Ser Arg Glu Glu Met Thr Lys
                770                 775                 780
Asn Gln Val Ser Leu Thr Cys Leu Val Lys Gly Phe Tyr Pro Ser Asp
785                 790                 795                 800
Ile Ala Val Glu Trp Glu Ser Asn Gly Gln Pro Glu Asn Asn Tyr Lys
                805                 810                 815
Thr Thr Pro Pro Val Leu Asp Ser Asp Gly Ser Phe Phe Leu Tyr Ser
                820                 825                 830
Lys Leu Thr Val Asp Lys Ser Arg Trp Gln Gln Gly Asn Val Phe Ser
                835                 840                 845
Cys Ser Val Met His Glu Ala Leu His Asn His Tyr Thr Gln Lys Ser
850                 855                 860
```

```
Leu Ser Leu Ser Pro Gly Lys
865                 870

<210> SEQ ID NO 30
<211> LENGTH: 876
<212> TYPE: PRT
<213> ORGANISM: Artificial Sequence
<220> FEATURE:
<223> OTHER INFORMATION: Synthetic Protein complex comprising VEGF and
      EGFR specific binding peptides #23

<400> SEQU

-continued

```
                340                 345                 350
Leu Ser Leu Ser Pro Gly Lys Met Gln Ile Phe Val Lys Thr Leu Thr
            355                 360                 365
Gly Lys Thr Ile Thr Leu Glu Val Glu Pro Ser Asp Thr Ile Glu Asn
        370                 375                 380
Val Lys Ala Lys Ile Gln Asp Lys Glu Gly Ile Pro Pro Asp Gln Gln
385                 390                 395                 400
Arg Leu Ile Phe Ala Gly Lys Gln Leu Glu Asp Gly Arg Thr Leu Ser
                405                 410                 415
Asp Tyr Asn Ile Gln Lys Glu Ser Thr Leu His Leu Val Leu Arg Leu
            420                 425                 430
Arg Gly Gly Gly Gly Gly Ser Gly Gly Gly Ser Gly Gly Gly
        435                 440                 445
Gly Ser Gly Gly Gly Gly Ser Gly Gly Gly Gly Ser Met Gln Ile Phe
    450                 455                 460
Val Lys Thr Leu Thr Gly Lys Thr Ile Thr Leu Glu Val Glu Pro Ser
465                 470                 475                 480
Asp Thr Ile Glu Asn Val Lys Ala Lys Ile Gln Asp Lys Glu Gly Ile
                485                 490                 495
Pro Pro Asp Gln Gln Arg Leu Ile Phe Ala Gly Lys Gln Leu Glu Asp
            500                 505                 510
Gly Arg Thr Leu Ser Asp Tyr Asn Ile Gln Lys Glu Ser Thr Leu His
        515                 520                 525
Leu Val Leu Arg Leu Arg Gly Gly Asp Ile Gln Met Thr Gln Ser Pro
    530                 535                 540
Thr Ser Leu Ser Ala Ser Val Gly Asp Arg Val Thr Ile Thr Cys Arg
545                 550                 555                 560
Ala Ser Gln Trp Ile Gly Asn Leu Leu Asp Trp Tyr Gln Gln Lys Pro
                565                 570                 575
Gly Glu Ala Pro Lys Leu Leu Ile Tyr Tyr Ala Ser Phe Leu Gln Ser
            580                 585                 590
Gly Val Pro Ser Arg Phe Ser Gly Gly Gly Phe Gly Thr Asp Phe Thr
        595                 600                 605
Leu Thr Ile Ser Ser Leu Gln Pro Glu Asp Phe Ala Thr Tyr Tyr Cys
    610                 615                 620
Gln Gln Ala Asn Pro Ala Pro Leu Thr Phe Gly Gln Gly Thr Lys Val
625                 630                 635                 640
Glu Ile Lys Arg Glu Pro Lys Ser Cys Asp Lys Thr His Thr Cys Pro
                645                 650                 655
Pro Cys Pro Ala Pro Glu Leu Leu Gly Gly Pro Ser Val Phe Leu Phe
            660                 665                 670
Pro Pro Lys Pro Lys Asp Thr Leu Met Ile Ser Arg Thr Pro Glu Val
        675                 680                 685
Thr Cys Val Val Val Asp Val Ser His Glu Asp Pro Glu Val Lys Phe
    690                 695                 700
Asn Trp Tyr Val Asp Gly Val Glu Val His Asn Ala Lys Thr Lys Pro
705                 710                 715                 720
Arg Glu Glu Gln Tyr Asn Ser Thr Tyr Arg Val Val Ser Val Leu Thr
                725                 730                 735
Val Leu His Gln Asp Trp Leu Asn Gly Lys Glu Tyr Lys Cys Lys Val
            740                 745                 750
Ser Asn Lys Ala Leu Pro Ala Pro Ile Glu Lys Thr Ile Ser Lys Ala
        755                 760                 765
```

```
Lys Gly Gln Pro Arg Glu Pro Gln Val Tyr Thr Leu Pro Pro Ser Arg
        770                 775                 780

Glu Glu Met Thr Lys Asn Gln Val Ser Leu Thr Cys Leu Val Lys Gly
785                 790                 795                 800

Phe Tyr Pro Ser Asp Ile Ala Val Glu Trp Glu Ser Asn Gly Gln Pro
                805                 810                 815

Glu Asn Asn Tyr Lys Thr Thr Pro Pro Val Leu Asp Ser Asp Gly Ser
                820                 825                 830

Phe Phe Leu Tyr Ser Lys Leu Thr Val Asp Lys Ser Arg Trp Gln Gln
        835                 840                 845

Gly Asn Val Phe Ser Cys Ser Val Met His Glu Ala Leu His Asn His
        850                 855                 860

Tyr Thr Gln Lys Ser Leu Ser Leu Ser Pro Gly Lys
865                 870                 875
```

<210> SEQ ID NO 31
<211> LENGTH: 881
<212> TYPE: PRT
<213> ORGANISM: Artificial Sequence
<220> FEATURE:
<223> OTHER INFORMATION: Synthetic Protein complex comprising VEGF and
      EGFR specific binding peptides #24

<400> SEQUENCE: 31

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
```

-continued

```
                245                 250                 255
Glu Pro Gln Val Tyr Thr Leu Pro Pro Ser Arg Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
        290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
                355                 360                 365

Gly Lys Thr Ile Thr Leu Glu Val Glu Pro Ser Asp Thr Ile Glu Asn
        370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Ser Gly Gly Gly Ser Gly Gly Gly
            435                 440                 445

Gly Ser Gly Gly Gly Ser Gly Gly Gly Ser Gly Gly Gly
        450                 455                 460

Ser Met Gln Ile Phe Val Lys Thr Leu Thr Gly Lys Thr Ile Thr Leu
465                 470                 475                 480

Glu Val Glu Pro Ser Asp Thr Ile Glu Asn Val Lys Ala Lys Ile Gln
                485                 490                 495

Asp Lys Glu Gly Ile Pro Pro Asp Gln Gln Arg Leu Ile Phe Ala Gly
            500                 505                 510

Lys Gln Leu Glu Asp Gly Arg Thr Leu Ser Asp Tyr Asn Ile Gln Lys
        515                 520                 525

Glu Ser Thr Leu His Leu Val Leu Arg Leu Arg Gly Gly Asp Ile Gln
        530                 535                 540

Met Thr Gln Ser Pro Thr Ser Leu Ser Ala Ser Val Gly Asp Arg Val
545                 550                 555                 560

Thr Ile Thr Cys Arg Ala Ser Gln Trp Ile Gly Asn Leu Leu Asp Trp
                565                 570                 575

Tyr Gln Gln Lys Pro Gly Glu Ala Pro Lys Leu Leu Ile Tyr Tyr Ala
            580                 585                 590

Ser Phe Leu Gln Ser Gly Val Pro Ser Arg Phe Ser Gly Gly Gly Phe
        595                 600                 605

Gly Thr Asp Phe Thr Leu Thr Ile Ser Ser Leu Gln Pro Glu Asp Phe
    610                 615                 620

Ala Thr Tyr Tyr Cys Gln Gln Ala Asn Pro Ala Pro Leu Thr Phe Gly
625                 630                 635                 640

Gln Gly Thr Lys Val Glu Ile Lys Arg Glu Pro Lys Ser Cys Asp Lys
                645                 650                 655

Thr His Thr Cys Pro Pro Cys Pro Ala Pro Glu Leu Leu Gly Gly Pro
            660                 665                 670
```

```
Ser Val Phe Leu Phe Pro Pro Lys Pro Lys Asp Thr Leu Met Ile Ser
        675                 680                 685

Arg Thr Pro Glu Val Thr Cys Val Val Val Asp Val Ser His Glu Asp
690                 695                 700

Pro Glu Val Lys Phe Asn Trp Tyr Val Asp Gly Val Glu Val His Asn
705                 710                 715                 720

Ala Lys Thr Lys Pro Arg Glu Glu Gln Tyr Asn Ser Thr Tyr Arg Val
                725                 730                 735

Val Ser Val Leu Thr Val Leu His Gln Asp Trp Leu Asn Gly Lys Glu
            740                 745                 750

Tyr Lys Cys Lys Val Ser Asn Lys Ala Leu Pro Ala Pro Ile Glu Lys
        755                 760                 765

Thr Ile Ser Lys Ala Lys Gly Gln Pro Arg Glu Pro Gln Val Tyr Thr
    770                 775                 780

Leu Pro Pro Ser Arg Glu Glu Met Thr Lys Asn Gln Val Ser Leu Thr
785                 790                 795                 800

Cys Leu Val Lys Gly Phe Tyr Pro Ser Asp Ile Ala Val Glu Trp Glu
                805                 810                 815

Ser Asn Gly Gln Pro Glu Asn Asn Tyr Lys Thr Thr Pro Pro Val Leu
            820                 825                 830

Asp Ser Asp Gly Ser Phe Phe Leu Tyr Ser Lys Leu Thr Val Asp Lys
        835                 840                 845

Ser Arg Trp Gln Gln Gly Asn Val Phe Ser Cys Ser Val Met His Glu
    850                 855                 860

Ala Leu His Asn His Tyr Thr Gln Lys Ser Leu Ser Leu Ser Pro Gly
865                 870                 875                 880

Lys

<210> SEQ ID NO 32
<211> LENGTH: 886
<212> TYPE: PRT
<213> ORGANISM: Artificial Sequence
<220> FEATURE:
<223> OTHER INFORMATION: Synthetic Protein complex comprising VEGF and
      EGFR specific binding peptides #25

<400> SEQUENCE: 32

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val G

```
Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Ser Gly Gly Gly Ser Gly Gly Gly
        435                 440                 445

Gly Ser Gly Gly Gly Ser Gly Gly Gly Ser Gly Gly Gly
    450                 455                 460

Ser Gly Gly Gly Ser Met Gln Ile Phe Val Lys Thr Leu Thr Gly
465                 470                 475                 480

Lys Thr Ile Thr Leu Glu Val Glu Pro Ser Asp Thr Ile Glu Asn Val
                485                 490                 495

Lys Ala Lys Ile Gln Asp Lys Glu Gly Ile Pro Pro Asp Gln Gln Arg
            500                 505                 510

Leu Ile Phe Ala Gly Lys Gln Leu Glu Asp Gly Arg Thr Leu Ser Asp
        515                 520                 525

Tyr Asn Ile Gln Lys Glu Ser Thr Leu His Leu Val Leu Arg Leu Arg
    530                 535                 540

Gly Gly Asp Ile Gln Met Thr Gln Ser Pro Thr Ser Leu Ser Ala Ser
545                 550                 555                 560
```

Val Gly Asp Arg Val Thr Ile Thr Cys Arg Ala Ser Gln Trp Ile Gly
            565                 570                 575

Asn Leu Leu Asp Trp Tyr Gln Gln Lys Pro Gly Glu Ala Pro Lys Leu
        580                 585                 590

Leu Ile Tyr Tyr Ala Ser Phe Leu Gln Ser Gly Val Pro Ser Arg Phe
    595                 600                 605

Ser Gly Gly Gly Phe Gly Thr Asp Phe Thr Leu Thr Ile Ser Ser Leu
610                 615                 620

Gln Pro Glu Asp Phe Ala Thr Tyr Tyr Cys Gln Gln Ala Asn Pro Ala
625                 630                 635                 640

Pro Leu Thr Phe Gly Gln Gly Thr Lys Val Glu Ile Lys Arg Glu Pro
                645                 650                 655

Lys Ser Cys Asp Lys Thr His Thr Cys Pro Pro Cys Pro Ala Pro Glu
            660                 665                 670

Leu Leu Gly Gly Pro Ser Val Phe Leu Phe Pro Pro Lys Pro Lys Asp
        675                 680                 685

Thr Leu Met Ile Ser Arg Thr Pro Glu Val Thr Cys Val Val Val Asp
    690                 695                 700

Val Ser His Glu Asp Pro Glu Val Lys Phe Asn Trp Tyr Val Asp Gly
705                 710                 715                 720

Val Glu Val His Asn Ala Lys Thr Lys Pro Arg Glu Glu Gln Tyr Asn
                725                 730                 735

Ser Thr Tyr Arg Val Val Ser Val Leu Thr Val Leu His Gln Asp Trp
            740                 745                 750

Leu Asn Gly Lys Glu Tyr Lys Cys Lys Val Ser Asn Lys Ala Leu Pro
        755                 760                 765

Ala Pro Ile Glu Lys Thr Ile Ser Lys Ala Lys Gly Gln Pro Arg Glu
    770                 775                 780

Pro Gln Val Tyr Thr Leu Pro Pro Ser Arg Glu Glu Met Thr Lys Asn
785                 790                 795                 800

Gln Val Ser Leu Thr Cys Leu Val Lys Gly Phe Tyr Pro Ser Asp Ile
                805                 810                 815

Ala Val Glu Trp Glu Ser Asn Gly Gln Pro Glu Asn Asn Tyr Lys Thr
            820                 825                 830

Thr Pro Pro Val Leu Asp Ser Asp Gly Ser Phe Phe Leu Tyr Ser Lys
        835                 840                 845

Leu Thr Val Asp Lys Ser Arg Trp Gln Gln Gly Asn Val Phe Ser Cys
    850                 855                 860

Ser Val Met His Glu Ala Leu His Asn His Tyr Thr Gln Lys Ser Leu
865                 870                 875                 880

Ser Leu Ser Pro Gly Lys
                885

<210> SEQ ID NO 33
<211> LENGTH: 891
<212> TYPE: PRT
<213> ORGANISM: Artificial Sequence
<220> FEATURE:
<223> OTHER INFORMATION: Synthetic Protein complex comprising VEGF and
      EGFR specific binding peptides #26

<400> SEQUENCE: 33

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

```
Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
 50                  55                  60

Leu Leu Ile Tyr His Ser Ser Thr Leu Gln Ser Gly Val Pro Ser Arg
 65                  70                  75                  80

Phe Ser Gly Ser Gly Ser Gly Thr Asp Phe Thr Leu Thr Ile Ser Ser
                 85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
            115                 120                 125

Pro Lys Ser Cys Asp Lys Thr His Thr Cys Pro Pro Cys Pro Ala Pro
130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
            195                 200                 205

Asn Ser Thr Tyr Arg Val Val Ser Val Leu Thr Val Leu His Gln Asp
        210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
            275                 280                 285

Ile Ala Val Glu Trp Glu Ser Asn Gly Gln Pro Glu Asn Asn Tyr Lys
        290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
            355                 360                 365

Gly Lys Thr Ile Thr Leu Glu Val Glu Pro Ser Asp Thr Ile Glu Asn
370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Ser Gly Gly Gly Ser Gly Gly Gly
            435                 440                 445
```

```
Gly Ser Gly Gly Gly Gly Ser Gly Gly Gly Ser Gly Gly Gly
    450                 455                 460
Ser Gly Gly Gly Ser Gly Gly Gly Ser Met Gln Ile Phe Val
465                 470                 475                 480
Lys Thr Leu Thr Gly Lys Thr Ile Thr Leu Glu Val Glu Pro Ser Asp
                485                 490                 495
Thr Ile Glu Asn Val Lys Ala Lys Ile Gln Asp Lys Glu Gly Ile Pro
            500                 505                 510
Pro Asp Gln Gln Arg Leu Ile Phe Ala Gly Lys Gln Leu Glu Asp Gly
            515                 520                 525
Arg Thr Leu Ser Asp Tyr Asn Ile Gln Lys Glu Ser Thr Leu His Leu
    530                 535                 540
Val Leu Arg Leu Arg Gly Gly Asp Ile Gln Met Thr Gln Ser Pro Thr
545                 550                 555                 560
Ser Leu Ser Ala Ser Val Gly Asp Arg Val Thr Ile Thr Cys Arg Ala
                565                 570                 575
Ser Gln Trp Ile Gly Asn Leu Asp Trp Tyr Gln Gln Lys Pro Gly
            580                 585                 590
Glu Ala Pro Lys Leu Leu Ile Tyr Tyr Ala Ser Phe Leu Gln Ser Gly
            595                 600                 605
Val Pro Ser Arg Phe Ser Gly Gly Gly Phe Gly Thr Asp Phe Thr Leu
    610                 615                 620
Thr Ile Ser Ser Leu Gln Pro Glu Asp Phe Ala Thr Tyr Tyr Cys Gln
625                 630                 635                 640
Gln Ala Asn Pro Ala Pro Leu Thr Phe Gly Gln Gly Thr Lys Val Glu
                645                 650                 655
Ile Lys Arg Glu Pro Lys Ser Cys Asp Lys Thr His Thr Cys Pro Pro
            660                 665                 670
Cys Pro Ala Pro Glu Leu Leu Gly Gly Pro Ser Val Phe Leu Phe Pro
            675                 680                 685
Pro Lys Pro Lys Asp Thr Leu Met Ile Ser Arg Thr Pro Glu Val Thr
    690                 695                 700
Cys Val Val Val Asp Val Ser His Glu Asp Pro Glu Val Lys Phe Asn
705                 710                 715                 720
Trp Tyr Val Asp Gly Val Glu Val His Asn Ala Lys Thr Lys Pro Arg
                725                 730                 735
Glu Glu Gln Tyr Asn Ser Thr Tyr Arg Val Val Ser Val Leu Thr Val
            740                 745                 750
Leu His Gln Asp Trp Leu Asn Gly Lys Glu Tyr Lys Cys Lys Val Ser
    755                 760                 765
Asn Lys Ala Leu Pro Ala Pro Ile Glu Lys Thr Ile Ser Lys Ala Lys
    770                 775                 780
Gly Gln Pro Arg Glu Pro Gln Val Tyr Thr Leu Pro Pro Ser Arg Glu
785                 790                 795                 800
Glu Met Thr Lys Asn Gln Val Ser Leu Thr Cys Leu Val Lys Gly Phe
                805                 810                 815
Tyr Pro Ser Asp Ile Ala Val Glu Trp Glu Ser Asn Gly Gln Pro Glu
            820                 825                 830
Asn Asn Tyr Lys Thr Thr Pro Pro Val Leu Asp Ser Asp Gly Ser Phe
            835                 840                 845
Phe Leu Tyr Ser Lys Leu Thr Val Asp Lys Ser Arg Trp Gln Gln Gly
    850                 855                 860
Asn Val Phe Ser Cys Ser Val Met His Glu Ala Leu His Asn His Tyr
```

```
                865                 870                 875                 880
Thr Gln Lys Ser Leu Ser Leu Ser Pro Gly Lys
                885                 890

<210> SEQ ID NO 34
<211> LENGTH: 896
<212> TYPE: PRT
<213> ORGANISM: Artificial Sequence
<220> FEATURE:
<223> OTHER INFORMATION: Synthetic Protein complex comprising VEGF and
      EGFR specific binding peptides #27

<400> SEQUENCE: 34

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
                20                  25                  30

Ser Val Gly Asp Arg Val Thr Ile Thr Cys Arg Ala Ser Gln Lys Ile
            35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
                100                 105                 110

Tyr Pro Tyr Thr Phe Gly Gln Gly Thr Lys Val Glu Ile Lys Arg Glu
            115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
                180                 185                 190

Gly Val Glu Val His Asn Ala Lys Thr Lys Pro Arg Glu Glu Gln Tyr
            195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
                260                 265                 270

Asn Gln Val Ser Leu Thr Cys Leu Val Lys Gly Phe Tyr Pro Ser Asp
            275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335
```

```
Cys Ser Val Met His Glu Ala Leu His Asn His Tyr Thr Gln Lys Ser
             340                 345                 350

Leu Ser Leu Ser Pro Gly Lys Met Gln Ile Phe Val Lys Thr Leu Thr
         355                 360                 365

Gly Lys Thr Ile Thr Leu Glu Val Glu Pro Ser Asp Thr Ile Glu Asn
     370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                 405                 410                 415

Asp Tyr Asn Ile Gln Lys Glu Ser Thr Leu His Leu Val Leu Arg Leu
             420                 425                 430

Arg Gly Gly Gly Gly Gly Ser Gly Gly Gly Ser Gly Gly Gly
         435                 440                 445

Gly Ser Gly Gly Gly Ser Gly Gly Gly Ser Gly Gly Gly
         450                 455                 460

Ser Gly Gly Gly Ser Gly Gly Gly Ser Gly Gly Gly Ser
465                 470                 475                 480

Met Gln Ile Phe Val Lys Thr Leu Thr Gly Lys Thr Ile Thr Leu Glu
                 485                 490                 495

Val Glu Pro Ser Asp Thr Ile Glu Asn Val Lys Ala Lys Ile Gln Asp
             500                 505                 510

Lys Glu Gly Ile Pro Pro Asp Gln Gln Arg Leu Ile Phe Ala Gly Lys
         515                 520                 525

Gln Leu Glu Asp Gly Arg Thr Leu Ser Asp Tyr Asn Ile Gln Lys Glu
     530                 535                 540

Ser Thr Leu His Leu Val Leu Arg Leu Arg Gly Gly Asp Ile Gln Met
545                 550                 555                 560

Thr Gln Ser Pro Thr Ser Leu Ser Ala Ser Val Gly Asp Arg Val Thr
                 565                 570                 575

Ile Thr Cys Arg Ala Ser Gln Trp Ile Gly Asn Leu Leu Asp Trp Tyr
             580                 585                 590

Gln Gln Lys Pro Gly Glu Ala Pro Lys Leu Leu Ile Tyr Tyr Ala Ser
         595                 600                 605

Phe Leu Gln Ser Gly Val Pro Ser Arg Phe Ser Gly Gly Gly Phe Gly
     610                 615                 620

Thr Asp Phe Thr Leu Thr Ile Ser Ser Leu Gln Pro Glu Asp Phe Ala
625                 630                 635                 640

Thr Tyr Tyr Cys Gln Gln Ala Asn Pro Ala Pro Leu Thr Phe Gly Gln
                 645                 650                 655

Gly Thr Lys Val Glu Ile Lys Arg Glu Pro Lys Ser Cys Asp Lys Thr
             660                 665                 670

His Thr Cys Pro Pro Cys Pro Ala Pro Glu Leu Leu Gly Gly Pro Ser
         675                 680                 685

Val Phe Leu Phe Pro Pro Lys Pro Lys Asp Thr Leu Met Ile Ser Arg
     690                 695                 700

Thr Pro Glu Val Thr Cys Val Val Val Asp Val Ser His Glu Asp Pro
705                 710                 715                 720

Glu Val Lys Phe Asn Trp Tyr Val Asp Gly Val Glu Val His Asn Ala
                 725                 730                 735

Lys Thr Lys Pro Arg Glu Glu Gln Tyr Asn Ser Thr Tyr Arg Val Val
             740                 745                 750

Ser Val Leu Thr Val Leu His Gln Asp Trp Leu Asn Gly Lys Glu Tyr
```

```
                    755                 760                 765
Lys Cys Lys Val Ser Asn Lys Ala Leu Pro Ala Pro Ile Glu Lys Thr
        770                 775                 780

Ile Ser Lys Ala Lys Gly Gln Pro Arg Glu Pro Gln Val Tyr Thr Leu
785                 790                 795                 800

Pro Pro Ser Arg Glu Glu Met Thr Lys Asn Gln Val Ser Leu Thr Cys
                805                 810                 815

Leu Val Lys Gly Phe Tyr Pro Ser Asp Ile Ala Val Glu Trp Glu Ser
            820                 825                 830

Asn Gly Gln Pro Glu Asn Asn Tyr Lys Thr Thr Pro Pro Val Leu Asp
                835                 840                 845

Ser Asp Gly Ser Phe Phe Leu Tyr Ser Lys Leu Thr Val Asp Lys Ser
        850                 855                 860

Arg Trp Gln Gln Gly Asn Val Phe Ser Cys Ser Val Met His Glu Ala
865                 870                 875                 880

Leu His Asn His Tyr Thr Gln Lys Ser Leu Ser Leu Ser Pro Gly Lys
                885                 890                 895

<210> SEQ ID NO 35
<211> LENGTH: 901
<212> TYPE: PRT
<213> ORGANISM: Artificial Sequence
<220> FEATURE:
<223> OTHER INFORMATION: Synthetic Protein complex comprising VEGF and
      EGFR specific binding peptides #28

<400> SEQUENCE: 35

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220
```

```
Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
            245                 250                 255

Glu Pro Gln Val Tyr Thr Leu Pro Pro Ser Arg Glu Glu Met Thr Lys
        260                 265                 270

Asn Gln Val Ser Leu Thr Cys Leu Val Lys Gly Phe Tyr Pro Ser Asp
    275                 280                 285

Ile Ala Val Glu Trp Glu Ser Asn Gly Gln Pro Glu Asn Asn Tyr Lys
        290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
            405                 410                 415

Asp Tyr Asn Ile Gln Lys Glu Ser Thr Leu His Leu Val Leu Arg Leu
        420                 425                 430

Arg Gly Gly Gly Gly Gly Ser Gly Gly Gly Gly Ser Gly Gly Gly Gly
            435                 440                 445

Gly Ser Gly Gly Gly Ser Gly Gly Gly Ser Gly Gly Gly Gly
        450                 455                 460

Ser Gly Gly Gly Gly Ser Gly Gly Gly Ser Gly Gly Gly Ser
465                 470                 475                 480

Gly Gly Gly Gly Ser Met Gln Ile Phe Val Lys Thr Leu Thr Gly Lys
                485                 490                 495

Thr Ile Thr Leu Glu Val Glu Pro Ser Asp Thr Ile Glu Asn Val Lys
        500                 505                 510

Ala Lys Ile Gln Asp Lys Glu Gly Ile Pro Pro Asp Gln Gln Arg Leu
    515                 520                 525

Ile Phe Ala Gly Lys Gln Leu Glu Asp Gly Arg Thr Leu Ser Asp Tyr
530                 535                 540

Asn Ile Gln Lys Glu Ser Thr Leu His Leu Val Leu Arg Leu Arg Gly
545                 550                 555                 560

Gly Asp Ile Gln Met Thr Gln Ser Pro Thr Ser Leu Ser Ala Ser Val
            565                 570                 575

Gly Asp Arg Val Thr Ile Thr Cys Arg Ala Ser Gln Trp Ile Gly Asn
        580                 585                 590

Leu Leu Asp Trp Tyr Gln Gln Lys Pro Gly Glu Ala Pro Lys Leu Leu
        595                 600                 605

Ile Tyr Tyr Ala Ser Phe Leu Gln Ser Gly Val Pro Ser Arg Phe Ser
        610                 615                 620

Gly Gly Gly Phe Gly Thr Asp Phe Thr Leu Thr Ile Ser Ser Leu Gln
625                 630                 635                 640

Pro Glu Asp Phe Ala Thr Tyr Tyr Cys Gln Gln Ala Asn Pro Ala Pro
```

```
                    645                 650                 655

Leu Thr Phe Gly Gln Gly Thr Lys Val Glu Ile Lys Arg Glu Pro Lys
                660                 665                 670

Ser Cys Asp Lys Thr His Thr Cys Pro Pro Cys Pro Ala Pro Glu Leu
                675                 680                 685

Leu Gly Gly Pro Ser Val Phe Leu Phe Pro Pro Lys Pro Lys Asp Thr
                690                 695                 700

Leu Met Ile Ser Arg Thr Pro Glu Val Thr Cys Val Val Val Asp Val
705                 710                 715                 720

Ser His Glu Asp Pro Glu Val Lys Phe Asn Trp Tyr Val Asp Gly Val
                725                 730                 735

Glu Val His Asn Ala Lys Thr Lys Pro Arg Glu Glu Gln Tyr Asn Ser
                740                 745                 750

Thr Tyr Arg Val Val Ser Val Leu Thr Val Leu His Gln Asp Trp Leu
                755                 760                 765

Asn Gly Lys Glu Tyr Lys Cys Lys Val Ser Asn Lys Ala Leu Pro Ala
                770                 775                 780

Pro Ile Glu Lys Thr Ile Ser Lys Ala Lys Gly Gln Pro Arg Glu Pro
785                 790                 795                 800

Gln Val Tyr Thr Leu Pro Pro Ser Arg Glu Glu Met Thr Lys Asn Gln
                805                 810                 815

Val Ser Leu Thr Cys Leu Val Lys Gly Phe Tyr Pro Ser Asp Ile Ala
                820                 825                 830

Val Glu Trp Glu Ser Asn Gly Gln Pro Glu Asn Asn Tyr Lys Thr Thr
                835                 840                 845

Pro Pro Val Leu Asp Ser Asp Gly Ser Phe Phe Leu Tyr Ser Lys Leu
850                 855                 860

Thr Val Asp Lys Ser Arg Trp Gln Gln Gly Asn Val Phe Ser Cys Ser
865                 870                 875                 880

Val Met His Glu Ala Leu His Asn His Tyr Thr Gln Lys Ser Leu Ser
                885                 890                 895

Leu Ser Pro Gly Lys
                900

<210> SEQ ID NO 36
<211> LENGTH: 880
<212> TYPE: PRT
<213> ORGANISM: Artificial Sequence
<220> FEATURE:
<223> OTHER INFORMATION: Synthetic Protein complex comprising VEGF and
      EGFR specific binding peptides #29

<400> SEQUENCE: 36

Gly Trp Ser Cys Ile Ile Leu Phe Leu Val Ala Thr Ala Thr Gly Val
1               5                   10                  15

His Ser Asp Ile Gln Met Thr Gln Ser Pro Ser Ser Leu Ser Ala Ser
                20                  25                  30

Val Gly Asp Arg Val Thr Ile Thr Cys Arg Ala Ser Gln Lys Ile Phe
            35                  40                  45

Asn Gly Leu Ser Trp Tyr Gln Gln Lys Pro Gly Lys Ala Pro Lys Leu
        50                  55                  60

Leu Ile Tyr His Ser Ser Thr Leu Gln Ser Gly Val Pro Ser Arg Phe
65                  70                  75                  80

Ser Gly Ser Gly Ser Gly Thr Asp Phe Thr Leu Thr Ile Ser Ser Leu
                85                  90                  95
```

```
Gln Pro Glu Asp Phe Ala Thr Tyr Tyr Cys Gln Gln Val Leu Leu Tyr
                100                 105                 110

Pro Tyr Thr Phe Gly Gln Gly Thr Lys Val Glu Ile Lys Arg Glu Pro
            115                 120                 125

Lys Ser Cys Asp Lys Thr His Thr Cys Pro Pro Cys Pro Ala Pro Glu
        130                 135                 140

Leu Leu Gly Gly Pro Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
        195                 200                 205

Ser Thr Tyr Arg Val Val Ser Val Leu Thr Val Leu His Gln Asp Trp
210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Glu Glu Met Thr Lys Asn
            260                 265                 270

Gln Val Ser Leu Thr Cys Leu Val Lys Gly Phe Tyr Pro Ser Asp Ile
        275                 280                 285

Ala Val Glu Trp Glu Ser Asn Gly Gln Pro Glu Asn Asn Tyr Lys Thr
290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys Met Gln Ile Phe Val Lys Thr Leu Thr Gly
        355                 360                 365

Lys Thr Ile Thr Leu Glu Val Glu Pro Ser Asp Thr Ile Glu Asn Val
370                 375                 380

Lys Ala Lys Ile Gln Asp Lys Glu Gly Ile Pro Pro Asp Gln Gln Arg
385                 390                 395                 400

Leu Ile Phe Ala Gly Lys Gln Leu Glu Asp Gly Arg Thr Leu Ser Asp
                405                 410                 415

Tyr Asn Ile Gln Lys Glu Ser Thr Leu His Leu Val Leu Arg Leu Arg
            420                 425                 430

Gly Gly Gly Gly Gly Gly Ser Gly Gly Gly Gly Ser Gly Gly Gly Gly
        435                 440                 445

Ser Gly Gly Gly Gly Ser Gly Gly Gly Gly Ser Gly Gly Gly Gly Ser
450                 455                 460

Met Gln Ile Phe Val Lys Thr Leu Thr Gly Lys Thr Ile Thr Leu Glu
465                 470                 475                 480

Val Glu Pro Ser Asp Thr Ile Glu Asn Val Lys Ala Lys Ile Gln Asp
                485                 490                 495

Lys Glu Gly Ile Pro Pro Asp Gln Gln Arg Leu Ile Phe Ala Gly Lys
            500                 505                 510

Gln Leu Glu Asp Gly Arg Thr Leu Ser Asp Tyr Asn Ile Gln Lys Glu
```

```
            515                 520                 525
Ser Thr Leu His Leu Val Leu Arg Leu Arg Gly Gly Asp Ile Gln Met
    530                 535                 540

Thr Gln Ser Pro Thr Ser Leu Ser Ala Ser Val Gly Asp Arg Val Thr
545                 550                 555                 560

Ile Thr Cys Arg Ala Ser Gln Trp Ile Gly Asn Leu Leu Asp Trp Tyr
                565                 570                 575

Gln Gln Lys Pro Gly Glu Ala Pro Lys Leu Leu Ile Tyr Tyr Ala Ser
            580                 585                 590

Phe Leu Gln Ser Gly Val Pro Ser Arg Phe Ser Gly Gly Gly Phe Gly
        595                 600                 605

Thr Asp Phe Thr Leu Thr Ile Ser Ser Leu Gln Pro Glu Asp Phe Ala
    610                 615                 620

Thr Tyr Tyr Cys Gln Gln Ala Asn Pro Ala Pro Leu Thr Phe Gly Gln
625                 630                 635                 640

Gly Thr Lys Val Glu Ile Lys Arg Glu Pro Lys Ser Cys Asp Lys Thr
                645                 650                 655

His Thr Cys Pro Pro Cys Pro Ala Pro Glu Leu Leu Gly Gly Pro Ser
            660                 665                 670

Val Phe Leu Phe Pro Pro Lys Pro Lys Asp Thr Leu Met Ile Ser Arg
        675                 680                 685

Thr Pro Glu Val Thr Cys Val Val Val Asp Val Ser His Glu Asp Pro
    690                 695                 700

Glu Val Lys Phe Asn Trp Tyr Val Asp Gly Val Glu Val His Asn Ala
705                 710                 715                 720

Lys Thr Lys Pro Arg Glu Glu Gln Tyr Asn Ser Thr Tyr Arg Val Val
                725                 730                 735

Ser Val Leu Thr Val Leu His Gln Asp Trp Leu Asn Gly Lys Glu Tyr
            740                 745                 750

Lys Cys Lys Val Ser Asn Lys Ala Leu Pro Ala Pro Ile Glu Lys Thr
        755                 760                 765

Ile Ser Lys Ala Lys Gly Gln Pro Arg Glu Pro Gln Val Tyr Thr Leu
    770                 775                 780

Pro Pro Ser Arg Glu Glu Met Thr Lys Asn Gln Val Ser Leu Thr Cys
785                 790                 795                 800

Leu Val Lys Gly Phe Tyr Pro Ser Asp Ile Ala Val Glu Trp Glu Ser
                805                 810                 815

Asn Gly Gln Pro Glu Asn Asn Tyr Lys Thr Thr Pro Pro Val Leu Asp
            820                 825                 830

Ser Asp Gly Ser Phe Phe Leu Tyr Ser Lys Leu Thr Val Asp Lys Ser
        835                 840                 845

Arg Trp Gln Gln Gly Asn Val Phe Ser Cys Ser Val Met His Glu Ala
    850                 855                 860

Leu His Asn His Tyr Thr Gln Lys Ser Leu Ser Leu Ser Pro Gly Lys
865                 870                 875                 880

<210> SEQ ID NO 37
<211> LENGTH: 777
<212> TYPE: PRT
<213> ORGANISM: Artificial Sequence
<220> FEATURE:
<223> OTHER INFORMATION: Synthetic Protein complex comprising VEGF and
      EGFR specific binding peptides #30

<400> SEQU

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
    275                 280                 285

Ile Ala Val Glu Trp Glu Ser Asn Gly Gln Pro Glu Asn Asn Tyr Lys
        290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
```

```
            420                 425                 430

Arg Gly Gly Gly Gly Asp Ile Gln Met Thr Gln Ser Pro Thr Ser Leu
        435                 440                 445

Ser Ala Ser Val Gly Asp Arg Val Thr Ile Thr Cys Arg Ala Ser Gln
    450                 455                 460

Trp Ile Gly Asn Leu Leu Asp Trp Tyr Gln Gln Lys Pro Gly Glu Ala
465                 470                 475                 480

Pro Lys Leu Leu Ile Tyr Tyr Ala Ser Phe Leu Gln Ser Gly Val Pro
                485                 490                 495

Ser Arg Phe Ser Gly Gly Gly Phe Gly Thr Asp Phe Thr Leu Thr Ile
            500                 505                 510

Ser Ser Leu Gln Pro Glu Asp Phe Ala Thr Tyr Tyr Cys Gln Gln Ala
        515                 520                 525

Asn Pro Ala Pro Leu Thr Phe Gly Gln Gly Thr Lys Val Glu Ile Lys
    530                 535                 540

Arg Glu Pro Lys Ser Cys Asp Lys Thr His Thr Cys Pro Pro Cys Pro
545                 550                 555                 560

Ala Pro Glu Leu Leu Gly Gly Pro Ser Val Phe Leu Phe Pro Pro Lys
                565                 570                 575

Pro Lys Asp Thr Leu Met Ile Ser Arg Thr Pro Glu Val Thr Cys Val
            580                 585                 590

Val Val Asp Val Ser His Glu Asp Pro Glu Val Lys Phe Asn Trp Tyr
        595                 600                 605

Val Asp Gly Val Glu Val His Asn Ala Lys Thr Lys Pro Arg Glu Glu
    610                 615                 620

Gln Tyr Asn Ser Thr Tyr Arg Val Val Ser Val Leu Thr Val Leu His
625                 630                 635                 640

Gln Asp Trp Leu Asn Gly Lys Glu Tyr Lys Cys Lys Val Ser Asn Lys
                645                 650                 655

Ala Leu Pro Ala Pro Ile Glu Lys Thr Ile Ser Lys Ala Lys Gly Gln
            660                 665                 670

Pro Arg Glu Pro Gln Val Tyr Thr Leu Pro Pro Ser Arg Glu Glu Met
        675                 680                 685

Thr Lys Asn Gln Val Ser Leu Thr Cys Leu Val Lys Gly Phe Tyr Pro
    690                 695                 700

Ser Asp Ile Ala Val Glu Trp Glu Ser Asn Gly Gln Pro Glu Asn Asn
705                 710                 715                 720

Tyr Lys Thr Thr Pro Pro Val Leu Asp Ser Asp Gly Ser Phe Phe Leu
                725                 730                 735

Tyr Ser Lys Leu Thr Val Asp Lys Ser Arg Trp Gln Gln Gly Asn Val
            740                 745                 750

Phe Ser Cys Ser Val Met His Glu Ala Leu His Asn His Tyr Thr Gln
        755                 760                 765

Lys Ser Leu Ser Leu Ser Pro Gly Lys
    770                 775

<210> SEQ ID NO 38
<211> LENGTH: 886
<212> TYPE: PRT
<213> ORGANISM: Artificial Sequence
<220> FEATURE:
<223> OTHER INFORMATION: Synthetic Protein complex comprising VEGF and
      EGFR specific binding peptides #31

<400> SEQUENCE: 38
```

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Thr Leu Gln Ser Gly Val Pro Ser Arg
65              70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
```

-continued

```
                420             425             430
Arg Gly Gly Gly Gly Gly Ser Gly Gly Gly Ser Gly Gly Gly
            435             440             445
Gly Ser Gly Gly Gly Ser Gly Gly Gly Ser Gly Gly Gly Gly
450             455             460
Ser Met Gln Ile Phe Val Lys Thr Leu Thr Gly Lys Thr Ile Thr Leu
465                 470                 475                 480
Glu Val Glu Pro Ser Asp Thr Ile Glu Asn Val Lys Ala Lys Ile Gln
                485                 490                 495
Asp Lys Glu Gly Ile Pro Pro Asp Gln Gln Arg Leu Ile Phe Ala Gly
            500             505             510
Lys Gln Leu Glu Asp Gly Arg Thr Leu Ser Asp Tyr Asn Ile Gln Lys
        515             520             525
Glu Ser Thr Leu His Leu Val Leu Arg Leu Arg Gly Gly Gly Gly
    530             535             540
Gly Ser Asp Ile Gln Met Thr Gln Ser Pro Thr Ser Leu Ser Ala Ser
545             550             555             560
Val Gly Asp Arg Val Thr Ile Thr Cys Arg Ala Ser Gln Trp Ile Gly
                565             570             575
Asn Leu Leu Asp Trp Tyr Gln Gln Lys Pro Gly Glu Ala Pro Lys Leu
            580             585             590
Leu Ile Tyr Tyr Ala Ser Phe Leu Gln Ser Gly Val Pro Ser Arg Phe
        595             600             605
Ser Gly Gly Gly Phe Gly Thr Asp Phe Thr Leu Thr Ile Ser Ser Leu
    610             615             620
Gln Pro Glu Asp Phe Ala Thr Tyr Tyr Cys Gln Gln Ala Asn Pro Ala
625             630             635             640
Pro Leu Thr Phe Gly Gln Gly Thr Lys Val Glu Ile Lys Arg Glu Pro
                645             650             655
Lys Ser Cys Asp Lys Thr His Thr Cys Pro Pro Cys Pro Ala Pro Glu
            660             665             670
Leu Leu Gly Gly Pro Ser Val Phe Leu Phe Pro Pro Lys Pro Lys Asp
        675             680             685
Thr Leu Met Ile Ser Arg Thr Pro Glu Val Thr Cys Val Val Val Asp
    690             695             700
Val Ser His Glu Asp Pro Glu Val Lys Phe Asn Trp Tyr Val Asp Gly
705             710             715             720
Val Glu Val His Asn Ala Lys Thr Lys Pro Arg Glu Glu Gln Tyr Asn
                725             730             735
Ser Thr Tyr Arg Val Val Ser Val Leu Thr Val Leu His Gln Asp Trp
            740             745             750
Leu Asn Gly Lys Glu Tyr Lys Cys Lys Val Ser Asn Lys Ala Leu Pro
        755             760             765
Ala Pro Ile Glu Lys Thr Ile Ser Lys Ala Lys Gly Gln Pro Arg Glu
    770             775             780
Pro Gln Val Tyr Thr Leu Pro Pro Ser Arg Glu Glu Met Thr Lys Asn
785             790             795             800
Gln Val Ser Leu Thr Cys Leu Val Lys Gly Phe Tyr Pro Ser Asp Ile
                805             810             815
Ala Val Glu Trp Glu Ser Asn Gly Gln Pro Glu Asn Asn Tyr Lys Thr
            820             825             830
Thr Pro Pro Val Leu Asp Ser Asp Gly Ser Phe Phe Leu Tyr Ser Lys
        835             840             845
```

```
Leu Thr Val Asp Lys Ser Arg Trp Gln Gln Gly Asn Val Phe Ser Cys
        850                 855                 860

Ser Val Met His Glu Ala Leu His Asn His Tyr Thr Gln Lys Ser Leu
865                 870                 875                 880

Ser Leu Ser Pro Gly Lys
                885
```

<210> SEQ ID NO 39
<211> LENGTH: 883
<212> TYPE: PRT
<213> ORGANISM: Artificial Sequence
<220> FEATURE:
<223> OTHER INFORMATION: Synthetic Protein complex comprising VEGF and
      EGFR specific binding peptides #32

<400> SEQUENCE: 39

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
```

```
            305                 310                 315                 320
Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
                340                 345                 350

Leu Ser Leu Ser Pro Gly Lys Met Gln Ile Phe Val Lys Thr Leu Thr
                355                 360                 365

Gly Lys Thr Ile Thr Leu Glu Val Glu Pro Ser Asp Thr Ile Glu Asn
370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
                420                 425                 430

Arg Gly Gly Gly Gly Gly Ser Gly Gly Gly Gly Ser Gly Gly Gly Gly
                435                 440                 445

Gly Ser Gly Gly Gly Gly Ser Gly Gly Gly Gly Ser Gly Gly Gly Gly
450                 455                 460

Ser Met Gln Ile Phe Val Lys Thr Leu Thr Gly Lys Thr Ile Thr Leu
465                 470                 475                 480

Glu Val Glu Pro Ser Asp Thr Ile Glu Asn Val Lys Ala Lys Ile Gln
                485                 490                 495

Asp Lys Glu Gly Ile Pro Pro Asp Gln Gln Arg Leu Ile Phe Ala Gly
                500                 505                 510

Lys Gln Leu Glu Asp Gly Arg Thr Leu Ser Asp Tyr Asn Ile Gln Lys
                515                 520                 525

Glu Ser Thr Leu His Leu Val Leu Arg Leu Arg Gly Gly Gly Gly Asp
                530                 535                 540

Ile Gln Met Thr Gln Ser Pro Thr Ser Leu Ser Ala Ser Val Gly Asp
545                 550                 555                 560

Arg Val Thr Ile Thr Cys Arg Ala Ser Gln Trp Ile Gly Asn Leu Leu
                565                 570                 575

Asp Trp Tyr Gln Gln Lys Pro Gly Glu Ala Pro Lys Leu Leu Ile Tyr
                580                 585                 590

Tyr Ala Ser Phe Leu Gln Ser Gly Val Pro Ser Arg Phe Ser Gly Gly
                595                 600                 605

Gly Phe Gly Thr Asp Phe Thr Leu Thr Ile Ser Ser Leu Gln Pro Glu
                610                 615                 620

Asp Phe Ala Thr Tyr Tyr Cys Gln Gln Ala Asn Pro Ala Pro Leu Thr
625                 630                 635                 640

Phe Gly Gln Gly Thr Lys Val Glu Ile Lys Arg Glu Pro Lys Ser Cys
                645                 650                 655

Asp Lys Thr His Thr Cys Pro Pro Cys Pro Ala Pro Glu Leu Leu Gly
                660                 665                 670

Gly Pro Ser Val Phe Leu Phe Pro Pro Lys Pro Lys Asp Thr Leu Met
                675                 680                 685

Ile Ser Arg Thr Pro Glu Val Thr Cys Val Val Val Asp Val Ser His
                690                 695                 700

Glu Asp Pro Glu Val Lys Phe Asn Trp Tyr Val Asp Gly Val Glu Val
705                 710                 715                 720

His Asn Ala Lys Thr Lys Pro Arg Glu Glu Gln Tyr Asn Ser Thr Tyr
                725                 730                 735
```

```
Arg Val Val Ser Val Leu Thr Val Leu His Gln Asp Trp Leu Asn Gly
            740                 745                 750

Lys Glu Tyr Lys Cys Lys Val Ser Asn Lys Ala Leu Pro Ala Pro Ile
            755                 760                 765

Glu Lys Thr Ile Ser Lys Ala Lys Gly Gln Pro Arg Glu Pro Gln Val
770             775                 780

Tyr Thr Leu Pro Pro Ser Arg Glu Glu Met Thr Lys Asn Gln Val Ser
785             790                 795                 800

Leu Thr Cys Leu Val Lys Gly Phe Tyr Pro Ser Asp Ile Ala Val Glu
            805                 810                 815

Trp Glu Ser Asn Gly Gln Pro Glu Asn Asn Tyr Lys Thr Thr Pro Pro
            820                 825                 830

Val Leu Asp Ser Asp Gly Ser Phe Phe Leu Tyr Ser Lys Leu Thr Val
            835                 840                 845

Asp Lys Ser Arg Trp Gln Gln Gly Asn Val Phe Ser Cys Ser Val Met
            850                 855                 860

His Glu Ala Leu His Asn His Tyr Thr Gln Lys Ser Leu Ser Leu Ser
865             870                 875                 880

Pro Gly Lys

<210> SEQ ID NO 40
<211> LENGTH: 886
<212> TYPE: PRT
<213> ORGANISM: Artificial Sequence
<220> FEATURE:
<223> OTHER INFORMATION: Synthetic Protein complex comprising VEGF and
      EGFR specific binding peptides #33

<400> SEQUENCE: 40

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
50              55                  60

Leu Leu Ile Tyr His Ser Ser Thr Leu Gln Ser Gly Val Pro Ser Arg
65              70                  75                  80

Phe Ser Gly Ser Gly Ser Gly Thr Asp Phe Thr Leu Thr Ile Ser Ser
            85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
            115                 120                 125

Pro Lys Ser Cys Asp Lys Thr His Thr Cys Pro Pro Cys Pro Ala Pro
130             135                 140

Glu Leu Leu Gly Gly Pro Ser Val Phe Leu Phe Pro Pro Lys Pro Lys
145             150                 155                 160

Asp Thr Leu Met Ile Ser Arg Thr Pro Glu Val Thr Cys Val Val Val
            165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
            195                 200                 205
```

```
Asn Ser Thr Tyr Arg Val Val Ser Val Leu Thr Val Leu His Gln Asp
            210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
            275                 280                 285

Ile Ala Val Glu Trp Glu Ser Asn Gly Gln Pro Glu Asn Asn Tyr Lys
290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
                340                 345                 350

Leu Ser Leu Ser Pro Gly Lys Met Gln Ile Phe Val Lys Thr Leu Thr
            355                 360                 365

Gly Lys Thr Ile Thr Leu Glu Val Glu Pro Ser Asp Thr Ile Glu Asn
370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Ser Gly Gly Gly Ser Gly Gly Gly
            435                 440                 445

Gly Ser Gly Gly Gly Ser Gly Gly Gly Ser Gly Gly Gly Gly
        450                 455                 460

Ser Met Gln Ile Phe Val Lys Thr Leu Thr Gly Lys Thr Ile Thr Leu
465                 470                 475                 480

Glu Val Glu Pro Ser Asp Thr Ile Glu Asn Val Lys Ala Lys Ile Gln
                485                 490                 495

Asp Lys Glu Gly Ile Pro Pro Asp Gln Gln Arg Leu Ile Phe Ala Gly
            500                 505                 510

Lys Gln Leu Glu Asp Gly Arg Thr Leu Ser Asp Tyr Asn Ile Gln Lys
            515                 520                 525

Glu Ser Thr Leu His Leu Val Leu Arg Leu Arg Gly Gly Gly Gly Gly
            530                 535                 540

Gly Ser Asp Ile Gln Met Thr Gln Ser Pro Thr Ser Leu Ser Ala Ser
545                 550                 555                 560

Val Gly Asp Arg Val Thr Ile Thr Cys Arg Ala Ser Gln Trp Ile Gly
                565                 570                 575

Asn Leu Leu Asp Trp Tyr Gln Gln Lys Pro Gly Glu Ala Pro Lys Leu
            580                 585                 590

Leu Ile Tyr Tyr Ala Ser Phe Leu Gln Ser Gly Val Pro Ser Arg Phe
        595                 600                 605

Ser Gly Gly Gly Phe Gly Thr Asp Phe Thr Leu Thr Ile Ser Ser Leu
610                 615                 620
```

-continued

```
Gln Pro Glu Asp Phe Ala Thr Tyr Tyr Cys Gln Gln Ala Asn Pro Ala
625                 630                 635                 640

Pro Leu Thr Phe Gly Gln Gly Thr Lys Val Glu Ile Lys Arg Glu Pro
            645                 650                 655

Lys Ser Cys Asp Lys Thr His Thr Cys Pro Pro Cys Pro Ala Pro Glu
        660                 665                 670

Leu Leu Gly Gly Pro Ser Val Phe Leu Phe Pro Pro Lys Pro Lys Asp
    675                 680                 685

Thr Leu Met Ile Ser Arg Thr Pro Glu Val Thr Cys Val Val Val Asp
690                 695                 700

Val Ser His Glu Asp Pro Glu Val Lys Phe Asn Trp Tyr Val Asp Gly
705                 710                 715                 720

Val Glu Val His Asn Ala Lys Thr Lys Pro Arg Glu Glu Gln Tyr Asn
                725                 730                 735

Ser Thr Tyr Arg Val Val Ser Val Leu Thr Val Leu His Gln Asp Trp
            740                 745                 750

Leu Asn Gly Lys Glu Tyr Lys Cys Lys Val Ser Asn Lys Ala Leu Pro
        755                 760                 765

Ala Pro Ile Glu Lys Thr Ile Ser Lys Ala Lys Gly Gln Pro Arg Glu
    770                 775                 780

Pro Gln Val Tyr Thr Leu Pro Pro Ser Arg Glu Glu Met Thr Lys Asn
785                 790                 795                 800

Gln Val Ser Leu Thr Cys Leu Val Lys Gly Phe Tyr Pro Ser Asp Ile
                805                 810                 815

Ala Val Glu Trp Glu Ser Asn Gly Gln Pro Glu Asn Asn Tyr Lys Thr
            820                 825                 830

Thr Pro Pro Val Leu Asp Ser Asp Gly Ser Phe Phe Leu Tyr Ser Lys
        835                 840                 845

Leu Thr Val Asp Lys Ser Arg Trp Gln Gln Gly Asn Val Phe Ser Cys
    850                 855                 860

Ser Val Met His Glu Ala Leu His Asn His Tyr Thr Gln Lys Ser Leu
865                 870                 875                 880

Ser Leu Ser Pro Gly Lys
            885

<210> SEQ ID NO 41
<211> LENGTH: 777
<212> TYPE: PRT
<213> ORGANISM: Artificial Sequence
<220> FEATURE:
<223> OTHER INFORMATION: Synthetic Protein complex comprising VEGF and
      EGFR specific binding peptides #34

<400> SEQUENCE: 41

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95
```

```
Leu Gln Pro Glu Asp Phe Ala Thr Tyr Tyr Cys Gln Gln Val Leu Leu
                100                 105                 110

Tyr Pro Tyr Thr Phe Gly Gln Gly Thr Lys Val Glu Ile Lys Arg Glu
            115                 120                 125

Pro Lys Ser Cys Asp Lys Thr His Thr Cys Pro Pro Cys Pro Ala Pro
        130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
        290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Asp Ile Gln Met Thr Gln Ser Pro Thr Ser Leu
        435                 440                 445

Ser Ala Ser Val Gly Asp Arg Val Thr Ile Thr Cys Arg Ala Ser Gln
        450                 455                 460

Trp Ile Gly Asn Leu Leu Asp Trp Tyr Gln Gln Lys Pro Gly Glu Ala
465                 470                 475                 480

Pro Lys Leu Leu Ile Tyr Tyr Ala Ser Phe Leu Gln Ser Gly Val Pro
                485                 490                 495

Ser Arg Phe Ser Gly Gly Phe Gly Thr Asp Phe Thr Leu Thr Ile
            500                 505                 510
```

```
Ser Ser Leu Gln Pro Glu Asp Phe Ala Thr Tyr Tyr Cys Gln Gln Ala
        515                 520                 525

Asn Pro Ala Pro Leu Thr Phe Gly Gln Gly Thr Lys Val Glu Ile Lys
530                 535                 540

Arg Glu Pro Lys Ser Cys Asp Lys Thr His Thr Cys Pro Pro Cys Pro
545                 550                 555                 560

Ala Pro Glu Leu Leu Gly Gly Pro Ser Val Phe Leu Phe Pro Pro Lys
                565                 570                 575

Pro Lys Asp Thr Leu Met Ile Ser Arg Thr Pro Glu Val Thr Cys Val
            580                 585                 590

Val Val Asp Val Ser His Glu Asp Pro Glu Val Lys Phe Asn Trp Tyr
        595                 600                 605

Val Asp Gly Val Glu Val His Asn Ala Lys Thr Lys Pro Arg Glu Glu
    610                 615                 620

Gln Tyr Asn Ser Thr Tyr Arg Val Val Ser Val Leu Thr Val Leu His
625                 630                 635                 640

Gln Asp Trp Leu Asn Gly Lys Glu Tyr Lys Cys Lys Val Ser Asn Lys
                645                 650                 655

Ala Leu Pro Ala Pro Ile Glu Lys Thr Ile Ser Lys Ala Lys Gly Gln
            660                 665                 670

Pro Arg Glu Pro Gln Val Tyr Thr Leu Pro Pro Ser Arg Glu Glu Met
        675                 680                 685

Thr Lys Asn Gln Val Ser Leu Thr Cys Leu Val Lys Gly Phe Tyr Pro
    690                 695                 700

Ser Asp Ile Ala Val Glu Trp Glu Ser Asn Gly Gln Pro Glu Asn Asn
705                 710                 715                 720

Tyr Lys Thr Thr Pro Pro Val Leu Asp Ser Asp Gly Ser Phe Phe Leu
                725                 730                 735

Tyr Ser Lys Leu Thr Val Asp Lys Ser Arg Trp Gln Gln Gly Asn Val
            740                 745                 750

Phe Ser Cys Ser Val Met His Glu Ala Leu His Asn His Tyr Thr Gln
        755                 760                 765

Lys Ser Leu Ser Leu Ser Pro Gly Lys
    770                 775

<210> SEQ ID NO 42
<211> LENGTH: 780
<212> TYPE: PRT
<213> ORGANISM: Artificial Sequence
<220> FEATURE:
<223> OTHER INFORMATION: Synthetic Protein complex comprising VEGF and
      EGFR specific binding peptides #35

<400> SEQUENCE: 42

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95
```

Leu Gln Pro Glu Asp Phe Ala Thr Tyr Tyr Cys Gln Gln Val Leu Leu
                100                 105                 110

Tyr Pro Tyr Thr Phe Gly Gln Gly Thr Lys Val Glu Ile Lys Arg Glu
            115                 120                 125

Pro Lys Ser Cys Asp Lys Thr His Thr Cys Pro Pro Cys Pro Ala Pro
        130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Ser Asp Ile Gln Met Thr Gln Ser Pro
        435                 440                 445

Thr Ser Leu Ser Ala Ser Val Gly Asp Arg Val Thr Ile Thr Cys Arg
    450                 455                 460

Ala Ser Gln Trp Ile Gly Asn Leu Leu Asp Trp Tyr Gln Gln Lys Pro
465                 470                 475                 480

Gly Glu Ala Pro Lys Leu Leu Ile Tyr Tyr Ala Ser Phe Leu Gln Ser
                485                 490                 495

Gly Val Pro Ser Arg Phe Ser Gly Gly Phe Gly Thr Asp Phe Thr
            500                 505                 510

```
Leu Thr Ile Ser Ser Leu Gln Pro Glu Asp Phe Ala Thr Tyr Tyr Cys
            515                 520                 525

Gln Gln Ala Asn Pro Ala Pro Leu Thr Phe Gly Gln Gly Thr Lys Val
        530                 535                 540

Glu Ile Lys Arg Glu Pro Lys Ser Cys Asp Lys Thr His Thr Cys Pro
545                 550                 555                 560

Pro Cys Pro Ala Pro Glu Leu Leu Gly Gly Pro Ser Val Phe Leu Phe
                565                 570                 575

Pro Pro Lys Pro Lys Asp Thr Leu Met Ile Ser Arg Thr Pro Glu Val
            580                 585                 590

Thr Cys Val Val Val Asp Val Ser His Glu Asp Pro Glu Val Lys Phe
        595                 600                 605

Asn Trp Tyr Val Asp Gly Val Glu Val His Asn Ala Lys Thr Lys Pro
610                 615                 620

Arg Glu Glu Gln Tyr Asn Ser Thr Tyr Arg Val Val Ser Val Leu Thr
625                 630                 635                 640

Val Leu His Gln Asp Trp Leu Asn Gly Lys Glu Tyr Lys Cys Lys Val
                645                 650                 655

Ser Asn Lys Ala Leu Pro Ala Pro Ile Glu Lys Thr Ile Ser Lys Ala
            660                 665                 670

Lys Gly Gln Pro Arg Glu Pro Gln Val Tyr Thr Leu Pro Pro Ser Arg
        675                 680                 685

Glu Glu Met Thr Lys Asn Gln Val Ser Leu Thr Cys Leu Val Lys Gly
690                 695                 700

Phe Tyr Pro Ser Asp Ile Ala Val Glu Trp Glu Ser Asn Gly Gln Pro
705                 710                 715                 720

Glu Asn Asn Tyr Lys Thr Thr Pro Pro Val Leu Asp Ser Asp Gly Ser
                725                 730                 735

Phe Phe Leu Tyr Ser Lys Leu Thr Val Asp Lys Ser Arg Trp Gln Gln
            740                 745                 750

Gly Asn Val Phe Ser Cys Ser Val Met His Glu Ala Leu His Asn His
        755                 760                 765

Tyr Thr Gln Lys Ser Leu Ser Leu Ser Pro Gly Lys
770                 775                 780

<210> SEQ ID NO 43
<211> LENGTH: 825
<212> TYPE: PRT
<213> ORGANISM: Artificial Sequence
<220> FEATURE:
<223> OTHER INFORMATION: Synthetic Protein complex comprising VEGF and
      EGFR specific binding peptides #36

<400> SEQUENCE: 43

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val

-continued

```
Leu Gln Pro Glu Asp Phe Ala Thr Tyr Tyr Cys Gln Gln Val Leu Leu
                100                 105                 110
Tyr Pro Tyr Thr Phe Gly Gln Gly Thr Lys Val Glu Ile Lys Arg Glu
            115                 120                 125
Pro Lys Ser Cys Asp Lys Thr His Thr Cys Pro Pro Cys Pro Ala Pro
        130                 135                 140
Glu Leu Leu Gly Gly Pro Ser Val Phe Leu Phe Pro Pro Lys Pro Lys
145                 150                 155                 160
Asp Thr Leu Met Ile Ser Arg Thr Pro Glu Val Thr Cys Val Val Val
                165                 170                 175
Asp Val Ser His Glu Asp Pro Glu Val Lys Phe Asn Trp Tyr Val Asp
            180                 185                 190
Gly Val Glu Val His Asn Ala Lys Thr Lys Pro Arg Glu Glu Gln Tyr
        195                 200                 205
Asn Ser Thr Tyr Arg Val Val Ser Val Leu Thr Val Leu His Gln Asp
    210                 215                 220
Trp Leu Asn Gly Lys Glu Tyr Lys Cys Lys Val Ser Asn Lys Ala Leu
225                 230                 235                 240
Pro Ala Pro Ile Glu Lys Thr Ile Ser Lys Ala Lys Gly Gln Pro Arg
                245                 250                 255
Glu Pro Gln Val Tyr Thr Leu Pro Pro Ser Arg Glu Glu Met Thr Lys
            260                 265                 270
Asn Gln Val Ser Leu Thr Cys Leu Val Lys Gly Phe Tyr Pro Ser Asp
        275                 280                 285
Ile Ala Val Glu Trp Glu Ser Asn Gly Gln Pro Glu Asn Asn Tyr Lys
    290                 295                 300
Thr Thr Pro Pro Val Leu Asp Ser Asp Gly Ser Phe Phe Leu Tyr Ser
305                 310                 315                 320
Lys Leu Thr Val Asp Lys Ser Arg Trp Gln Gln Gly Asn Val Phe Ser
                325                 330                 335
Cys Ser Val Met His Glu Ala Leu His Asn His Tyr Thr Gln Lys Ser
            340                 345                 350
Leu Ser Leu Ser Pro Gly Lys Gly Gly Met Lys Arg Gln Gly Lys Glu
        355                 360                 365
Met Asp Ser Leu Arg Phe Leu Tyr Asp Gly Ile Arg Ile Gln Ala Asp
    370                 375                 380
Gln Ala Pro Glu Asp Leu Asp Met Glu Asp Asn Asp Ile Ile Glu Ala
385                 390                 395                 400
His Arg Glu Gln Ile Gly Gly Gly Gly Ser Gly Gly Gly
                405                 410                 415
Ser Gly Gly Gly Ser Gly Gly Gly Ser Gly Gly Gly Ser
            420                 425                 430
Gly Gly Gly Ser Met Lys Arg Gln Gly Lys Glu Met Asp Ser Leu
        435                 440                 445
Arg Phe Leu Tyr Asp Gly Ile Arg Ile Gln Ala Asp Gln Ala Pro Glu
    450                 455                 460
Asp Leu Asp Met Glu Asp Asn Asp Ile Ile Glu Ala His Arg Glu Gln
465                 470                 475                 480
Ile Gly Gly Gly Gly Asp Ile Gln Met Thr Gln Ser Pro Thr Ser Leu
                485                 490                 495
Ser Ala Ser Val Gly Asp Arg Val Thr Ile Thr Cys Arg Ala Ser Gln
            500                 505                 510
```

```
Trp Ile Gly Asn Leu Leu Asp Trp Tyr Gln Gln Lys Pro Gly Glu Ala
            515                 520                 525

Pro Lys Leu Leu Ile Tyr Tyr Ala Ser Phe Leu Gln Ser Gly Val Pro
        530                 535                 540

Ser Arg Phe Ser Gly Gly Gly Phe Gly Thr Asp Phe Thr Leu Thr Ile
545                 550                 555                 560

Ser Ser Leu Gln Pro Glu Asp Phe Ala Thr Tyr Tyr Cys Gln Gln Ala
                565                 570                 575

Asn Pro Ala Pro Leu Thr Phe Gly Gln Gly Thr Lys Val Glu Ile Lys
            580                 585                 590

Arg Glu Pro Lys Ser Cys Asp Lys Thr His Thr Cys Pro Pro Cys Pro
        595                 600                 605

Ala Pro Glu Leu Leu Gly Gly Pro Ser Val Phe Leu Phe Pro Pro Lys
    610                 615                 620

Pro Lys Asp Thr Leu Met Ile Ser Arg Thr Pro Glu Val Thr Cys Val
625                 630                 635                 640

Val Val Asp Val Ser His Glu Asp Pro Glu Val Lys Phe Asn Trp Tyr
                645                 650                 655

Val Asp Gly Val Glu Val His Asn Ala Lys Thr Lys Pro Arg Glu Glu
            660                 665                 670

Gln Tyr Asn Ser Thr Tyr Arg Val Val Ser Val Leu Thr Val Leu His
        675                 680                 685

Gln Asp Trp Leu Asn Gly Lys Glu Tyr Lys Cys Lys Val Ser Asn Lys
    690                 695                 700

Ala Leu Pro Ala Pro Ile Glu Lys Thr Ile Ser Lys Ala Lys Gly Gln
705                 710                 715                 720

Pro Arg Glu Pro Gln Val Tyr Thr Leu Pro Pro Ser Arg Glu Glu Met
                725                 730                 735

Thr Lys Asn Gln Val Ser Leu Thr Cys Leu Val Lys Gly Phe Tyr Pro
            740                 745                 750

Ser Asp Ile Ala Val Glu Trp Glu Ser Asn Gly Gln Pro Glu Asn Asn
        755                 760                 765

Tyr Lys Thr Thr Pro Pro Val Leu Asp Ser Asp Gly Ser Phe Phe Leu
    770                 775                 780

Tyr Ser Lys Leu Thr Val Asp Lys Ser Arg Trp Gln Gln Gly Asn Val
785                 790                 795                 800

Phe Ser Cys Ser Val Met His Glu Ala Leu His Asn His Tyr Thr Gln
                805                 810                 815

Lys Ser Leu Ser Leu Ser Pro Gly Lys
            820                 825

<210> SEQ ID NO 44
<211> LENGTH: 753
<212> TYPE: PRT
<213> ORGANISM: Artificial Sequence
<220> FEATURE:
<223> OTHER INFORMATION: Synthetic Protein complex comprising VEGF and
      EGFR specific binding peptides #37

<400> SEQUENCE: 44

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45
```

```
Phe Asn Gly Leu Ser Trp Tyr Gln Gln Lys Pro Gly Lys Ala Pro Lys
     50                  55                  60

Leu Leu Ile Tyr His Ser Ser Thr Leu Gln Ser Gly Val Pro Ser Arg
 65                  70                  75                  80

Phe Ser Gly Ser Gly Ser Gly Thr Asp Phe Thr Leu Thr Ile Ser Ser
                 85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Asp Tyr Asp Ile Pro Thr Thr Glu Asn
        355                 360                 365

Leu Tyr Phe Gln Gly Gly Gly Gly Ser Gly Gly Gly Ser Gly
    370                 375                 380

Gly Gly Ser Gly Gly Gly Gly Ser Gly Gly Gly Ser Gly Gly
385                 390                 395                 400

Gly Gly Ser Glu Asn Leu Tyr Phe Gln Gly Ser Gly Asp Ile Gln
            405                 410                 415

Met Thr Gln Ser Pro Thr Ser Leu Ser Ala Ser Val Gly Asp Arg Val
        420                 425                 430

Thr Ile Thr Cys Arg Ala Ser Gln Trp Ile Gly Asn Leu Leu Asp Trp
            435                 440                 445

Tyr Gln Gln Lys Pro Gly Glu Ala Pro Lys Leu Leu Ile Tyr Tyr Ala
    450                 455                 460
```

```
Ser Phe Leu Gln Ser Gly Val Pro Ser Arg Phe Ser Gly Gly Gly Phe
465                 470                 475                 480

Gly Thr Asp Phe Thr Leu Thr Ile Ser Ser Leu Gln Pro Glu Asp Phe
            485                 490                 495

Ala Thr Tyr Tyr Cys Gln Gln Ala Asn Pro Ala Pro Leu Thr Phe Gly
        500                 505                 510

Gln Gly Thr Lys Val Glu Ile Lys Arg Glu Pro Lys Ser Cys Asp Lys
    515                 520                 525

Thr His Thr Cys Pro Pro Cys Pro Ala Pro Glu Leu Leu Gly Gly Pro
530                 535                 540

Ser Val Phe Leu Phe Pro Pro Lys Pro Lys Asp Thr Leu Met Ile Ser
545                 550                 555                 560

Arg Thr Pro Glu Val Thr Cys Val Val Val Asp Val Ser His Glu Asp
                565                 570                 575

Pro Glu Val Lys Phe Asn Trp Tyr Val Asp Gly Val Glu Val His Asn
            580                 585                 590

Ala Lys Thr Lys Pro Arg Glu Glu Gln Tyr Asn Ser Thr Tyr Arg Val
        595                 600                 605

Val Ser Val Leu Thr Val Leu His Gln Asp Trp Leu Asn Gly Lys Glu
    610                 615                 620

Tyr Lys Cys Lys Val Ser Asn Lys Ala Leu Pro Ala Pro Ile Glu Lys
625                 630                 635                 640

Thr Ile Ser Lys Ala Lys Gly Gln Pro Arg Glu Pro Gln Val Tyr Thr
                645                 650                 655

Leu Pro Pro Ser Arg Glu Glu Met Thr Lys Asn Gln Val Ser Leu Thr
            660                 665                 670

Cys Leu Val Lys Gly Phe Tyr Pro Ser Asp Ile Ala Val Glu Trp Glu
        675                 680                 685

Ser Asn Gly Gln Pro Glu Asn Asn Tyr Lys Thr Thr Pro Pro Val Leu
    690                 695                 700

Asp Ser Asp Gly Ser Phe Phe Leu Tyr Ser Lys Leu Thr Val Asp Lys
705                 710                 715                 720

Ser Arg Trp Gln Gln Gly Asn Val Phe Ser Cys Ser Val Met His Glu
                725                 730                 735

Ala Leu His Asn His Tyr Thr Gln Lys Ser Leu Ser Leu Ser Pro Gly
            740                 745                 750

Lys
```

```
<210> SEQ ID NO 45
<211> LENGTH: 2634
<212> TYPE: DNA
<213> ORGANISM: Artificial Sequence
<220> FEATURE:
<223> OTHER INFORMATION: Synthetic Nucleotide sequence encoding the
      protein complex comprising VEGF and EGFR specific binding
      peptides #1

<400> SEQUENCE: 45
```

| | | | | | |
|---|---|---|---|---|---|
| gaattcgcca | ccatgggctg | gtcctgcatc | atcctgtttc | tggtggccac | cgccaccggc | 60 |
| gtgcactctg | atatccagat | gacccagagc | cccagcagcc | tgtctgcctc | tgtgggcgac | 120 |
| agagtgacca | tcacctgtag | agccagccag | tggatcggcc | ctgagctgag | ctggtatcag | 180 |
| cagaagcccg | gcaaggcccc | caagctgctg | atctaccaca | ccagcatcct | gcagagcggc | 240 |
| gtgcccagca | gattttctgg | cagcggcagc | ggcaccgact | tcaccctgac | aatcagcagc | 300 |
| ctgcagcccg | aggacttcgc | cacctactac | tgccagcagt | acatgttcca | gccccggacc | 360 |

```
tttggccagg gcaccaaggt ggaaatcaga agagagccca agagctgcga caagacccac    420
acctgtcccc cttgtcctgc ccctgaactg ctggggaggcc ctagcgtgtt cctgttcccc    480
ccaaagccca aggacaccct gatgatcagc cggaccccccg aagtgacctg cgtggtggtg    540
gatgtgtccc acgaggaccc tgaagtgaag ttcaattggt acgtggacgg cgtggaagtg    600
cacaacgcca agaccaagcc cagagaggaa cagtacaaca gcacctaccg ggtggtgtcc    660
gtgctgacag tgctgcacca ggactggctg aacggcaaag agtacaagtg caaggtgtcc    720
aacaaggccc tgcctgcccc catcgagaaa accatcagca aggccaaggg ccagcccaga    780
gaacccagg tgtacacact gccccccagc agagaagaga tgaccaagaa ccaggtgtcc    840
ctgacctgcc tggtcaaggg cttctacccc agcgatatcg ccgtggaatg ggagagcaac    900
ggccagcctg agaacaacta caagaccacc cccctgtgc tggacagcga cggctcattc    960
ttcctgtaca gcaagctgac cgtggacaag agccggtggc agcagggcaa cgtgttcagc    1020
tgcagcgtga tgcacgaggc cctgcacaac cactacaccc agaagtccct gagcctgagc    1080
cccggcaaga tgcagatctt cgtgaaaacc ctgaccggca agaccatcac cctggaagtg    1140
gaacccagcg acaccatcga gaacgtgaag gccaagatcc aggacaaaga gggcatcccc    1200
cccgaccagc agagactgat cttcgccggc aagcagctgg aagatggcag aaccctgagc    1260
gactacaaca tccagaaaga gtccacccctg cacctggtgc tgcggctgag aggcggaggt    1320
ggtggtggtt ctggtggcgg aggatctggc ggtggtggat ctgggggagg tggaagtatg    1380
cagattttg tcaagacact gaccggggaa acaatcacac tcgaagtcga gccctccgat    1440
acaattgaga atgtgaaagc caaaattcag gacaagaag ggattcctcc tgatcagcag    1500
cggctgattt tgccggaaa acagctgaa gatggacgga ccctgtccga ttacaatatt    1560
cagaaagaaa gcaccctcca tctggtcctg aggctgcggg gaggcgacat tcagatgaca    1620
cagtcccccca gctccctgag cgccagcgtg ggagatcgcg tgaccattac atgccgggcc    1680
tcccagtgga ttggcatcct ggtggattgg tatcagcaga acctgggga ggctcctaaa    1740
ctgctgatct attacgccag ctttctgcag tccggcgtgc cctctagatt cagcggctct    1800
ggcttcggca cagatttcac actgaccatc tctagcctgc acccctgaaga ttttgccaca    1860
tattactgtc agcaggccaa ccctgccccc ctgacattcg ccagggaac aaaggtcgag    1920
atcaagcgcg agcccaagtc ctgtgataag acacatacct gcccccctg cccagctcca    1980
gaactgctcg gaggaccttc tgtgtttctg tttccaccca agcctaagga tacactcatg    2040
atctccagaa cacctgaagt gacatgtgtg gtcgtcgacg tgtcacatga ggatccagaa    2100
gtcaagttta actggtatgt ggatggggtc gaggtgcaca atgccaaaac aaaacctcgg    2160
gaagaacagt ataattccac ctatagagtc gtgtctgtgc tcaccgtgct ccatcaggat    2220
tggctcaatg gaaagaata caaatgtaaa gtctctaaca agccctgcc cgctcctatc    2280
gaaaagacaa tctccaaggc caaggacag cctcgcgagc tcaggtcta caccctgcca    2340
ccttcccgcg aggaaatgac aaaaaatcag gtgtcactca cctgtctcgt gaagggtttt    2400
taccccctccg acattgccgt cgagtgggag tccaatggac agcccgagaa caattataag    2460
acaacacctc ccgtcctgga ctccgatgga tcatttttc tgtactccaa gctcaccgtc    2520
gataagtcca gatggcagca gggaaatgtc ttttcctgct ccgtgatgca tgaagctctc    2580
cacaatcatt acacacagaa aagcctgtcc ctgtcccccg gcaagtgact cgag          2634
```

<210> SEQ ID NO 46

<211> LENGTH: 2649
<212> TYPE: DNA
<213> ORGANISM: Artificial Sequence
<220> FEATURE:
<223> OTHER INFORMATION: Synthetic Nucleotide sequence encoding the protein complex comprising VEGF and EGFR specific binding peptides #2

<400> SEQUENCE: 46

| | | | | | |
|---|---|---|---|---|---|
| gaattcgcca | ccatgggctg | gtcctgcatc | atcctgtttc | tggtggccac | cgccaccggc | 60 |
| gtgcactctg | atatccagat | gacccagagc | cccagcagcc | tgtctgcctc | tgtgggcgac | 120 |
| agagtgacca | tcacctgtag | agccagccag | tggatcggcc | tgagctgag | ctggtatcag | 180 |
| cagaagcccg | gcaaggcccc | caagctgctg | atctaccaca | ccagcatcct | gcagagcggc | 240 |
| gtgcccagca | gattttctgg | cagcggcagc | ggcaccgact | tcaccctgac | aatcagcagc | 300 |
| ctgcagcccg | aggacttcgc | cacctactac | tgccagcagt | acatgttcca | gccccggacc | 360 |
| tttggccagg | gcaccaaggt | ggaaatcaga | agagagccca | gagctgcga | caagacccac | 420 |
| acctgtcccc | cttgtcctgc | ccctgaactg | ctgggaggcc | ctagcgtgtt | cctgttcccc | 480 |
| ccaaagccca | aggacaccct | gatgatcagc | cggaccccg | aagtgacctg | cgtggtggtg | 540 |
| gatgtgtccc | acgaggaccc | tgaagtgaag | ttcaattggt | acgtggacgg | cgtggaagtg | 600 |
| cacaacgcca | agaccaagcc | cagagaggaa | cagtacaaca | gcacctaccg | ggtggtgtcc | 660 |
| gtgctgacag | tgctgcacca | ggactggctg | aacggcaaag | agtacaagtg | caaggtgtcc | 720 |
| aacaaggccc | tgcctgcccc | catcgagaaa | accatcagca | aggccaaggg | ccagcccaga | 780 |
| gaacccagg | tgtacacact | gcccccagc | agagaagaga | tgaccaagaa | ccaggtgtcc | 840 |
| ctgacctgcc | tggtcaaggg | cttctacccc | agcgatatcg | ccgtggaatg | ggagagcaac | 900 |
| ggccagcctg | agaacaacta | caagaccacc | ccccctgtgc | tggacagcga | cggctcattc | 960 |
| ttcctgtaca | gcaagctgac | cgtggacaag | agccggtggc | agcagggcaa | cgtgttcagc | 1020 |
| tgcagcgtga | tgcacgaggc | cctgcacaac | cactacaccc | agaagtccct | gagcctgagc | 1080 |
| cccggcaaga | tgcagatctt | cgtgaaaacc | ctgaccggca | agaccatcac | cctggaagtg | 1140 |
| gaacccagcg | acaccatcga | gaacgtgaag | gccaagatcc | aggacaaaga | gggcatcccc | 1200 |
| cccgaccagc | agagactgat | cttcgccggc | aagcagctgg | aagatggcag | aaccctgagc | 1260 |
| gactacaaca | tccagaaaga | gtccaccctg | cacctggtgc | tgcggctgag | aggcggaggt | 1320 |
| ggtggtggtt | ctggtggcgg | aggatctggc | ggtggtggat | ctgggggagg | tggaagtggt | 1380 |
| ggcggtggta | gtatgcagat | ttttgtcaag | acactgaccg | ggaaaacaat | cacactcgaa | 1440 |
| gtcgagccct | ccgatacaat | tgagaatgtg | aaagccaaaa | ttcaggacaa | agaagggatt | 1500 |
| cctcctgatc | agcagcggct | gattttttgcc | ggaaaacagc | tcgaagatgg | acggaccctg | 1560 |
| tccgattaca | atattcagaa | agaaagcacc | ctccatctgg | tcctgaggct | gcggggaggc | 1620 |
| gacattcaga | tgacacagtc | ccccagctcc | ctgagcgcca | gcgtgggaga | tcgcgtgacc | 1680 |
| attacatgcc | gggcctccca | gtggattggc | atcctggtgg | attggtatca | gcagaaacct | 1740 |
| ggggaggctc | ctaaactgct | gatctattac | gccagctttc | tgcagtccgg | cgtgccctct | 1800 |
| agattcagcg | gctctggctt | cggcacagat | ttcacactga | ccatctctag | cctgcaccct | 1860 |
| gaagattttg | ccacatatta | ctgtcagcag | gccaaccctg | cccccctgac | attcggccag | 1920 |
| ggaacaaagg | tcgagatcaa | gcgcgagccc | aagtcctgtg | ataagacaca | tacctgcccc | 1980 |
| ccctgcccag | ctccagaact | gctcggagga | ccttctgtgt | ttctgtttcc | acccaagcct | 2040 |
| aaggatacac | tcatgatctc | cagaacacct | gaagtgacat | gtgtggtcgt | cgacgtgtca | 2100 |

| | |
|---|---|
| catgaggatc cagaagtcaa gtttaactgg tatgtggatg gggtcgaggt gcacaatgcc | 2160 |
| aaaacaaaac ctcgggaaga acagtataat tccacctata gagtcgtgtc tgtgctcacc | 2220 |
| gtgctccatc aggattggct caatgggaaa gaatacaaat gtaaagtctc taacaaagcc | 2280 |
| ctgcccgctc ctatcgaaaa gacaatctcc aaggccaaag acagcctcg cgagcctcag | 2340 |
| gtctacaccc tgccaccttc ccgcgaggaa atgacaaaaa atcaggtgtc actcacctgt | 2400 |
| ctcgtgaagg ggttttaccc ctccgacatt gccgtcgagt gggagtccaa tggacagccc | 2460 |
| gagaacaatt ataagacaac acctcccgtc ctggactccg atggatcatt ttttctgtac | 2520 |
| tccaagctca ccgtcgataa gtccagatgg cagcagggaa atgtcttttc ctgctccgtg | 2580 |
| atgcatgaag ctctccacaa tcattacaca cagaaaagcc tgtccctgtc ccccggcaag | 2640 |
| tgactcgag | 2649 |

<210> SEQ ID NO 47
<211> LENGTH: 2664
<212> TYPE: DNA
<213> ORGANISM: Artificial Sequence
<220> FEATURE:
<223> OTHER INFORMATION: Synthetic Nucleotide sequence encoding the
      protein complex comprising VEGF and EGFR specific binding
      peptides #3

<400> SEQUENCE: 47

| | |
|---|---|
| gaattcgcca ccatgggctg gtcctgcatc atcctgtttc tggtggccac cgccaccggc | 60 |
| gtgcactctg atatccagat gacccagagc cccagcagcc tgtctgcctc tgtgggcgac | 120 |
| agagtgacca tcacctgtag agccagccag tggatcggcc tgagctgag ctggtatcag | 180 |
| cagaagcccg gcaaggcccc caagctgctg atctaccaca ccagcatcct gcagagcggc | 240 |
| gtgcccagca gattttctgg cagcggcagc ggcaccgact tcaccctgac aatcagcagc | 300 |
| ctgcagcccg aggacttcgc cacctactac tgccagcagt acatgttcca gccccggacc | 360 |
| tttggccagg gcaccaaggt ggaaatcaga agagagccca gagctgcga caagacccac | 420 |
| acctgtcccc cttgtcctgc ccctgaactg ctgggaggcc tagcgtgtt cctgttcccc | 480 |
| ccaaagccca aggacaccct gatgatcagc cggacccccg aagtgacctg cgtggtggtg | 540 |
| gatgtgtccc acgaggaccc tgaagtgaag ttcaattggt acgtggacgg cgtggaagtg | 600 |
| cacaacgcca agaccaagcc cagagaggaa cagtacaaca gcacctaccg ggtggtgtcc | 660 |
| gtgctgacag tgctgcacca ggactggctg aacggcaaag agtacaagtg caaggtgtcc | 720 |
| aacaaggccc tgcctgcccc catcgagaaa accatcagca ggccaagggg ccagcccaga | 780 |
| gaaccccagg tgtacacact gccccccagc agagaagaga tgaccaagaa ccaggtgtcc | 840 |
| ctgacctgcc tggtcaaggg cttctacccc agcgatatcg ccgtggaatg ggagagcaac | 900 |
| ggccagcctg agaacaacta caagaccacc ccccctgtgc tggacagcga cggctcattc | 960 |
| ttcctgtaca gcaagctgac cgtggacaag agccggtggc agcagggcaa cgtgttcagc | 1020 |
| tgcagcgtga tgcacgaggc cctgcacaac cactacaccc agaagtccct gagcctgagc | 1080 |
| cccggcaaga tgcagatctt cgtgaaaacc ctgaccggca agaccatcac cctggaagtg | 1140 |
| gaacccagcg acaccatcga aacgtgaag gccaagatcc aggacaaaga gggcatcccc | 1200 |
| cccgaccagc agagactgat cttcgccggc aagcagctgg aagatggcag aaccctgagc | 1260 |
| gactacaaca tccagaaaga gtccaccctg cacctggtgc tgcggctgag aggcggaggt | 1320 |
| ggtggtggtt ctggtggcgg aggatctggc ggtggtggat ctgggggagg tggaagtggt | 1380 |

| ggcggtggta gtggtggtgg cggaagcatg cagattttg tcaagacact gaccgggaaa | 1440 |
| acaatcacac tcgaagtcga gccctccgat acaattgaga atgtgaaagc caaaattcag | 1500 |
| gacaaagaag ggattcctcc tgatcagcag cggctgattt ttgccggaaa acagctcgaa | 1560 |
| gatggacgga ccctgtccga ttacaatatt cagaaagaaa gcaccctcca tctggtcctg | 1620 |
| aggctgcggg gaggcgacat tcagatgaca cagtccccca gctccctgag cgccagcgtg | 1680 |
| ggagatcgcg tgaccattac atgccgggcc tcccagtgga ttggcatcct ggtggattgg | 1740 |
| tatcagcaga aacctgggga ggctcctaaa ctgctgatct attacgccag ctttctgcag | 1800 |
| tccggcgtgc cctctagatt cagcggctct ggcttcggca cagatttcac actgaccatc | 1860 |
| tctagcctgc accctgaaga ttttgccaca tattactgtc agcaggccaa ccctgccccc | 1920 |
| ctgacattcg ccagggaac aaaggtcgag atcaagcgcg agcccaagtc ctgtgataag | 1980 |
| acacatacct gccccccctg cccagctcca gaactgctcg gaggaccttc tgtgtttctg | 2040 |
| tttccaccca gcctaagga tacactcatg atctccagaa cacctgaagt gacatgtgtg | 2100 |
| gtcgtcgacg tgtcacatga ggatccagaa gtcaagttta actggtatgt ggatggggtc | 2160 |
| gaggtgcaca atgccaaaac aaaacctcgg gaagaacagt ataattccac ctatagagtc | 2220 |
| gtgtctgtgc tcaccgtgct ccatcaggat tggctcaatg gaaagaata caaatgtaaa | 2280 |
| gtctctaaca agcccctgcc cgctcctatc gaaaagacaa tctccaaggc caaggacag | 2340 |
| cctcgcgagc tcaggtcta caccctgcca ccttcccgcg aggaaatgac aaaaaatcag | 2400 |
| gtgtcactca cctgtctcgt gaaggggttt taccctccg acattgccgt cgagtgggag | 2460 |
| tccaatggac agcccgagaa caattataag acaacacctc ccgtcctgga ctccgatgga | 2520 |
| tcatttttc tgtactccaa gctcaccgtc gataagtcca gatggcagca gggaaatgtc | 2580 |
| tttcctgct ccgtgatgca tgaagctctc cacaatcatt acacacagaa aagcctgtcc | 2640 |
| ctgtcccccg gcaagtgact cgag | 2664 |

<210> SEQ ID NO 48
<211> LENGTH: 2679
<212> TYPE: DNA
<213> ORGANISM: Artificial Sequence
<220> FEATURE:
<223> OTHER INFORMATION: Synthetic Nucleotide sequence encoding the
    protein complex comprising VEGF and EGFR specific binding
    peptides #4

<400> SEQUENCE: 48

| gaattcgcca ccatgggctg gtcctgcatc atcctgtttc tggtggccac cgccaccggc | 60 |
| gtgcactctg atatccagat gacccagagc cccagcagcc tgtctgcctc tgtgggcgac | 120 |
| agagtgacca tcacctgtag agccagccag tggatcggcc ctgagctgag ctggtatcag | 180 |
| cagaagcccg gcaaggcccc caagctgctg atctaccaca ccagcatcct gcagagcggc | 240 |
| gtgcccagca gattttctgg cagcggcagc ggcaccgact tcaccctgac aatcagcagc | 300 |
| ctgcagcccg aggacttcgc cacctactac tgccagcagt acatgttcca gccccggacc | 360 |
| tttggccagg gcaccaaggt ggaaatcaga agagagccca gagctgcga caagacccac | 420 |
| acctgtcccc cttgtcctgc ccctgaactg ctggagcc ctagcgtgtt cctgttcccc | 480 |
| ccaaagccca aggacaccct gatgatcagc cggaccccg aagtgacctg cgtggtggtg | 540 |
| gatgtgtccc acgaggaccc tgaagtgaag ttcaattggt acgtggacgg cgtggaagtg | 600 |
| cacaacgcca agaccaagcc cagagaggaa cagtacaaca gcacctaccg ggtggtgtcc | 660 |
| gtgctgacag tgctgcacca ggactggctg aacggcaaag agtacaagtg caaggtgtcc | 720 |

```
aacaaggccc tgcctgcccc catcgagaaa accatcagca aggccaaggg ccagcccaga    780
gaacccagg tgtacacact gcccccagc agagaagaga tgaccaagaa ccaggtgtcc      840
ctgacctgcc tggtcaaggg cttctacccc agcgatatcg ccgtggaatg ggagagcaac    900
ggccagcctg agaacaacta caagaccacc cccctgtgc tggacagcga cggctcattc     960
ttcctgtaca gcaagctgac cgtggacaag agccggtggc agcagggcaa cgtgttcagc   1020
tgcagcgtga tgcacgaggc cctgcacaac cactacaccc agaagtccct gagcctgagc   1080
cccggcaaga tgcagatctt cgtgaaaacc ctgaccggca agaccatcac cctggaagtg   1140
gaacccagcg acaccatcga aacgtgaag gccaagatcc aggacaaaga gggcatcccc    1200
cccgaccagc agagactgat cttcgccggc aagcagctgg aagatggcag aaccctgagc   1260
gactacaaca tccagaaaga gtccaccctg cacctggtgc tgcggctgag aggcggaggt   1320
ggtggtggtt ctggtggcgg aggatctggc ggtggtggat ctggggagg tggaagtggt    1380
ggcggtggta gtggtggtgg cggaagcgga ggcggtggat caatgcagat ttttgtcaag   1440
acactgaccg ggaaaacaat cacactcgaa gtcgagccct ccgatacaat tgagaatgtg   1500
aaagccaaaa ttcaggacaa agaagggatt cctcctgatc agcagcggct gatttttgcc   1560
ggaaaacagc tcgaagatgg acggaccctg tccgattaca atattcagaa agaaagcacc   1620
ctccatctgg tcctgaggct gcggggaggc gacattcaga tgacacagtc ccccagctcc   1680
ctgagcgcca gcgtgggaga tcgcgtgacc attacatgcc gggcctccca gtggattggc   1740
atcctggtgg attggtatca gcagaaacct ggggaggctc ctaaactgct gatctattac   1800
gccagctttc tgcagtccgg cgtgccctct agattcagcg gctctggctt cggcacagat   1860
ttcacactga ccatctctag cctgcaccct gaagattttg ccacatatta ctgtcagcag   1920
gccaacccctg cccccctgac attcggccag ggaacaaagg tcgagatcaa gcgcgagccc   1980
aagtcctgtg ataagacaca tacctgcccc ccctgcccag ctccagaact gctcggagga   2040
ccttctgtgt ttctgttttcc acccaagcct aaggatacac tcatgatctc cagaacacct   2100
gaagtgacat gtgtggtcgt cgacgtgtca catgaggatc cagaagtcaa gtttaactgg   2160
tatgtggatg gggtcgaggt gcacaatgcc aaaacaaaac tcgggaagga acagtataat   2220
tccacctata gagtcgtgtc tgtgctcacc gtgctccatc aggattggct caatgggaaa   2280
gaatacaaat gtaaagtctc taacaaagcc ctgcccgctc ctatcgaaaa gacaatctcc   2340
aaggccaaag gacagcctcg cgagcctcag gtctacaccc tgccaccttc ccgcgaggaa   2400
atgacaaaaa atcaggtgtc actcacctgt ctcgtgaagg ggttttaccc ctccgacatt   2460
gccgtcgagt gggagtccaa tggacagccc gagaacaatt ataagacaac acctcccgtc   2520
ctggactccg atggatcatt ttttctgtac tccaagctca ccgtcgataa gtccagatgg   2580
cagcagggaa atgtctttc ctgctccgtg atgcatgaag ctctccacaa tcattacaca   2640
cagaaaagcc tgtccctgtc ccccggcaag tgactcgag                         2679
```

<210> SEQ ID NO 49
<211> LENGTH: 2694
<212> TYPE: DNA
<213> ORGANISM: Artificial Sequence
<220> FEATURE:
<223> OTHER INFORMATION: Synthetic Nucleotide sequence encoding the
      protein complex comprising VEGF and EGFR specific binding
      peptides #5

<400> SEQUENCE: 49

```
gaattcgcca ccatgggctg gtcctgcatc atcctgtttc tggtggccac cgccaccggc    60
gtgcactctg atatccagat gacccagagc cccagcagcc tgtctgcctc tgtgggcgac   120
agagtgacca tcacctgtag agccagccag tggatcggcc tgagctgag  ctggtatcag   180 cagaagcccg gcaaggcccc caagctgctg atctaccaca ccagcatcct gcagagcggc   240
gtgcccagca gattttctgg cagcggcagc ggcaccgact  tcaccctgac aatcagcagc   300
ctgcagcccg aggacttcgc cacctactac tgccagcagt acatgttcca gccccggacc   360
tttggccagg gcaccaaggt ggaaatcaga agagagccca gagctgcga  caagacccac   420 acctgtcccc cttgtcctgc ccctgaactg ctgggaggcc ctagcgtgtt cctgttcccc   480
ccaaagccca aggacaccct gatgatcagc cggacccccg aagtgacctg cgtggtggtg   540
gatgtgtccc acgaggaccc tgaagtgaag ttcaattggt acgtggacgg cgtggaagtg   600
cacaacgcca agaccaagcc cagagaggaa cagtacaaca gcacctaccg ggtggtgtcc   660
gtgctgacag tgctgcacca ggactggctg aacggcaaag agtacaagtg caaggtgtcc   720
aacaaggccc tgcctgcccc catcgagaaa accatcagca aggccaaggg ccagcccaga   780 gaacccagg  tgtacacact gccccccagc agagaagaga tgaccaagaa ccaggtgtcc   840
ctgacctgcc tggtcaaggg cttctacccc agcgatatcg ccgtggaatg ggagagcaac   900
ggccagcctg agaacaacta caagaccacc cccctgtgc  tggacagcga cggctcattc   960
ttcctgtaca gcaagctgac cgtggacaag agccggtggc agcagggcaa cgtgttcagc  1020
tgcagcgtga tgcacgaggc cctgcacaac cactacaccc agaagtccct gagcctgagc  1080
cccggcaaga tgcagatctt cgtgaaaacc ctgaccggca agaccatcac cctggaagtg  1140
gaacccagcg acaccatcga aacgtgaag  gccaagatcc aggacaaaga gggcatcccc  1200
cccgaccagc agagactgat cttcgccggc aagcagctgg aagatggcag aaccctgagc  1260
gactacaaca tccagaaaga gtccaccctg cacctggtgc tgcggctgag aggcggaggt  1320
ggtggtggtt ctggtggcgg aggatctggc ggtggtggat ctgggggagg tggaagtggt  1380
ggcggtggta gtggtggtgg cggaagcgga ggcggtggat caggcggagg cggatcaatg  1440
cagatttttg tcaagacact gaccgggaaa acaatcacac tcgaagtcga gccctccgat  1500
acaattgaga atgtgaaagc caaaattcag gacaaagaag ggattcctcc tgatcagcag  1560
cggctgattt ttgccggaaa acagctcgaa gatggacgga ccctgtccga ttacaatatt  1620
cagaaagaaa gcaccctcca tctggtcctg aggctgcggg gaggcgacat tcagatgaca  1680
cagtccccca gctccctgag cgccagcgtg ggagatcgcg tgaccattac atgccgggcc  1740
tcccagtgga ttggcatcct ggtggattgg tatcagcaga aacctgggga ggctcctaaa  1800
ctgctgatct attacgccag cttttctgcag tccggcgtgc cctctagatt cagcggctct  1860
ggcttcggca cagatttcac actgaccatc tctagcctgc accctgaaga tttttgccaca  1920 tattactgtc agcaggccaa ccctgccccc ctgacattcg ccagggaac  aaaggtcgag  1980 atcaagcgcg agcccaagtc ctgtgataag acacatacct gcccccctg  cccagctcca  2040 gaactgctcg gaggaccttc tgtgtttctg tttccaccca agcctaagga tacactcatg  2100
atctccagaa cacctgaagt gacatgtgtg gtcgtcgacg tgtcacatga ggatccagaa  2160
gtcaagttta actggtatgt ggatggggtc gaggtgcaca atgccaaaac aaaacctcgg  2220
gaagaacagt ataattccac ctatagagtc gtgtctgtgc tcaccgtgct ccatcaggat  2280
tggctcaatg gaaagaata  caaatgtaaa gtctctaaca aagccctgcc cgctcctatc  2340
gaaaagacaa tctccaaggc caaaggacag cctcgcgagc ctcaggtcta caccctgcca  2400
```

| | |
|---|---|
| ccttcccgcg aggaaatgac aaaaaatcag gtgtcactca cctgtctcgt gaagggtttt | 2460 |
| taccccctccg acattgccgt cgagtgggag tccaatggac agcccgagaa caattataag | 2520 |
| acaacacctc ccgtcctgga ctccgatgga tcattttttc tgtactccaa gctcaccgtc | 2580 |
| gataagtcca gatggcagca gggaaatgtc ttttcctgct ccgtgatgca tgaagctctc | 2640 |
| cacaatcatt acacacagaa aagcctgtcc ctgtcccccg gcaagtgact cgag | 2694 |

<210> SEQ ID NO 50
<211> LENGTH: 2709
<212> TYPE: DNA
<213> ORGANISM: Artificial Sequence
<220> FEATURE:
<223> OTHER INFORMATION: Synthetic Nucleotide sequence encoding the
protein complex comprising VEGF and EGFR specific binding
peptides #6

<400> SEQUENCE: 50

| | |
|---|---|
| gaattcgcca ccatgggctg gtcctgcatc atcctgtttc tggtggccac cgccaccggc | 60 |
| gtgcactctg atatccagat gacccagagc cccagcagcc tgtctgcctc tgtgggcgac | 120 |
| agagtgacca tcacctgtag agccagccag tggatcggcc tgagctgag ctggtatcag | 180 |
| cagaagcccg gcaaggcccc caagctgctg atctaccaca ccagcatcct gcagagcggc | 240 |
| gtgcccagca gattttctgg cagcggcagc ggcaccgact tcaccctgac aatcagcagc | 300 |
| ctgcagcccg aggacttcgc cacctactac tgccagcagt acatgttcca gccccggacc | 360 |
| tttggccagg gcaccaaggt ggaaatcaga gagagcccca gagctgcga caagaccccac | 420 |
| acctgtcccc cttgtcctgc ccctgaactg ctgggaggcc ctagcgtgtt cctgttcccc | 480 |
| ccaaagccca aggacaccct gatgatcagc cggaccccg aagtgacctg cgtggtggtg | 540 |
| gatgtgtccc acgaggaccc tgaagtgaag ttcaattggt acgtggacgg cgtggaagtg | 600 |
| cacaacgcca agaccaagcc cagagaggaa cagtacaaca gcacctaccg ggtggtgtcc | 660 |
| gtgctgacag tgctgcacca ggactggctg aacggcaaag agtacaagtg caaggtgtcc | 720 |
| aacaaggccc tgcctgcccc catcgagaaa accatcagca aggccaaggg ccagcccaga | 780 |
| gaaccccagg tgtacacact gccccccagc agagaagaga tgaccaagaa ccaggtgtcc | 840 |
| ctgacctgcc tggtcaaggg cttctacccc agcgatatcg ccgtggaatg ggagagcaac | 900 |
| ggccagcctg agaacaacta caagaccacc cccctgtgc tggacagcga cggctcattc | 960 |
| ttcctgtaca gcaagctgac cgtggacaag agccggtggc agcagggcaa cgtgttcagc | 1020 |
| tgcagcgtga tgcacgaggc cctgcacaac cactacaccc agaagtccct gagcctgagc | 1080 |
| cccggcaaga tgcagatctt cgtgaaaacc ctgaccggca gaccatcac cctggaagtg | 1140 |
| gaacccagcg acaccatcga gaacgtgaag gccaagatcc aggacaaaga gggcatcccc | 1200 |
| cccgaccagc agagactgat cttcgccggc aagcagctgg aagatggcag aaccctgagc | 1260 |
| gactacaaca tccagaaaga gtccaccctg cacctggtgc tgcggctgag aggcggaggt | 1320 |
| ggtggtggtt ctggtggcgg aggatctggc ggtggtggat ctgggggagg tggaagtggt | 1380 |
| ggcggtggta gtggtggtgg cggaagcgga ggcggtggat caggcggagg cggatcaggt | 1440 |
| ggcggggtt caatgcagat ttttgtcaag acactgaccg gaaaacaat cacactcgaa | 1500 |
| gtcgagccct ccgatacaat tgagaatgtg aaagccaaaa ttcaggacaa agaagggatt | 1560 |
| cctcctgatc agcagcggct gattttttgcc ggaaaacagc tcgaagatgg acggaccctg | 1620 |
| tccgattaca atattcagaa agaaagcacc ctccatctgg tcctgaggct gcggggaggc | 1680 |

```
gacattcaga tgacacagtc ccccagctcc ctgagcgcca gcgtgggaga tcgcgtgacc    1740
attacatgcc gggcctccca gtggattggc atcctggtgg attggtatca gcagaaacct    1800
ggggaggctc ctaaactgct gatctattac gccagctttc tgcagtccgg cgtgccctct    1860
agattcagcg gctctggctt cggcacagat ttcacactga ccatctctag cctgcaccct    1920
gaagattttg ccacatatta ctgtcagcag gccaaccctg ccccctgac attcggccag    1980 ggaacaaagg tcgagatcaa gcgcgagccc aagtcctgtg ataagacaca tacctgcccc    2040
ccctgcccag ctccagaact gctcggagga ccttctgtgt ttctgtttcc acccaagcct    2100
aaggatacac tcatgatctc cagaacacct gaagtgacat gtgtggtcgt cgacgtgtca    2160
catgaggatc cagaagtcaa gtttaactgg tatgtggatg gggtcgaggt gcacaatgcc    2220
aaaacaaaac ctcgggaaga acagtataat tccacctata gagtcgtgtc tgtgctcacc    2280
gtgctccatc aggattggct caatgggaaa gaatacaaat gtaaagtctc taacaaagcc    2340
ctgcccgctc ctatcgaaaa gacaatctcc aaggccaaag acagcctcg cgagcctcag    2400 gtctacaccc tgccaccttc ccgcgaggaa atgacaaaaa tcaggtgtc actcacctgt    2460 ctcgtgaagg ggttttaccc ctccgacatt gccgtcgagt gggagtccaa tggacagccc    2520
gagaacaatt ataagacaac acctcccgtc ctggactccg atggatcatt ttttctgtac    2580
tccaagctca ccgtcgataa gtccagatgg cagcagggaa atgtctttc ctgctccgtg    2640 atgcatgaag ctctccacaa tcattacaca cagaaaagcc tgtccctgtc ccccggcaag    2700
tgactcgag                                                           2709
```

<210> SEQ ID NO 51
<211> LENGTH: 2724
<212> TYPE: DNA
<213> ORGANISM: Artificial Sequence
<220> FEATURE:
<223> OTHER INFORMATION: Synthetic Nucleotide sequence encoding the protein complex comprising VEGF and EGFR specific binding peptides #7

<400> SEQUENCE: 51

```
gaattcgcca ccatgggctg gtcctgcatc atcctgtttc tggtggccac cgccaccggc     60
gtgcactctg atatccagat gacccagagc cccagcagcc tgtctgcctc tgtgggcgac    120
agagtgacca tcacctgtag agccagccag tggatcggcc tgagctgag ctggtatcag    180 cagaagcccg gcaaggcccc caagctgctg atctaccaca ccagcatcct gcagagcggc    240
gtgcccagca gattttctgg cagcggcagc ggcaccgact cacccctgac aatcagcagc    300
ctgcagcccg aggacttcgc cacctactac tgccagcagt acatgttcca gccccggacc    360
tttggccagg gcaccaaggt ggaaatcaga agagagccca gagctgcga caagacccac    420 acctgtcccc cttgtcctgc ccctgaactg ctgggaggcc ctagcgtgtt cctgttcccc    480
ccaaagccca aggacaccct gatgatcagc cggacccccg aagtgacctg cgtggtggtg    540
gatgtgtccc acgaggaccc tgaagtgaag ttcaattggt acgtggacgg cgtggaagtg    600
cacaacgcca agaccaagcc cagagaggaa cagtacaaca gcacctaccg ggtggtgtcc    660
gtgctgacag tgctgcacca ggactggctg aacggcaaag agtacaagtg caaggtgtcc    720
aacaaggccc tgcctgcccc catcgagaaa accatcagca aggccaaggg ccagcccaga    780
gaaccccagg tgtacacact gcccccagc agagaagaga tgaccaagaa ccaggtgtcc    840
ctgacctgcc tggtcaaggg cttctacccc agcgatatcg ccgtggaatg ggagagcaac    900
ggccagcctg agaacaacta caagaccacc cccctgtgc tggacagcga cggctcattc    960
```

```
ttcctgtaca gcaagctgac cgtggacaag agccggtggc agcagggcaa cgtgttcagc    1020
tgcagcgtga tgcacgaggc cctgcacaac cactacaccc agaagtccct gagcctgagc    1080
cccggcaaga tgcagatctt cgtgaaaacc ctgaccggca agaccatcac cctggaagtg    1140
gaacccagcg acaccatcga gaacgtgaag gccaagatcc aggacaaaga gggcatcccc    1200
cccgaccagc agagactgat cttcgccggc aagcagctgg aagatggcag aaccctgagc    1260
gactacaaca tccagaaaga gtccaccctg cacctggtgc tgcggctgag aggcggaggt    1320
ggtggtggtt ctggtggcgg aggatctggc ggtggtggat ctggggagg tggaagtggt    1380 ggcggtggta gtggtggtgg cggaagcgga ggcggtggat caggcggagg cggatcaggt    1440
ggcgggggtt caggggggtgg cggaagtatg cagattttg tcaagacact gaccgggaaa    1500
acaatcacac tcgaagtcga gccctccgat acaattgaga atgtgaaagc caaaattcag    1560
gacaaagaag ggattcctcc tgatcagcag cggctgattt tgccggaaa acagctcgaa    1620 gatgacgga ccctgtccga ttacaatatt cagaaagaaa gcaccctcca tctggtcctg    1680
aggctgcggg gaggcgacat tcagatgaca cagtccccca gctccctgag cgccagcgtg    1740
ggagatcgcg tgaccattac atgccgggcc tcccagtgga ttggcatcct ggtggattgg    1800
tatcagcaga aacctgggga ggctcctaaa ctgctgatct attacgccag ctttctgcag    1860
tccggcgtgc cctctagatt cagcggctct ggcttcggca cagatttcac actgaccatc    1920
tctagcctgc accctgaaga ttttgccaca tattactgtc agcaggccaa ccctgccccc    1980
ctgacattcg ccagggaac aaaggtcgag atcaagcgcg agcccaagtc tgtgataag    2040 acacatacct gccccccctg cccagctcca gaactgctcg gaggaccttc tgtgtttctg    2100
tttccaccca gcctaagga tacactcatg atctccagaa cacctgaagt gacatgtgtg    2160
gtcgtcgacg tgtcacatga ggatccagaa gtcaagttta actggtatgt ggatggggtc    2220
gaggtgcaca atgccaaaac aaaacctcgg gaagaacagt ataattccac ctatagagtc    2280
gtgtctgtgc tcaccgtgct ccatcaggat tggctcaatg gaaagaata caaatgtaaa    2340 gtctctaaca agcccctgcc cgctcctatc gaaaagacaa tctccaaggc caaggacag    2400 cctcgcgagc ctcaggtcta caccctgcca ccttcccgcg aggaaatgac aaaaaatcag    2460
gtgtcactca cctgtctcgt gaagggggttt tacccctccg acattgccgt cgagtgggag    2520
tccaatggac agcccgagaa caattataag acaacacctc ccgtcctgga ctccgatgga    2580
tcattttttc tgtactccaa gctcaccgtc gataagtcca gatggcagca gggaaatgtc    2640
ttttcctgct ccgtgatgca tgaagctctc cacaatcatt acacacagaa aagcctgtcc    2700 ctgtccccg gcaagtgact cgag                                             2724
```

<210> SEQ ID NO 52
<211> LENGTH: 2634
<212> TYPE: DNA
<213> ORGANISM: Artificial Sequence
<220> FEATURE:
<223> OTHER INFORMATION: Synthetic Nucleotide sequence encoding the
     protein complex comprising VEGF and EGFR specific binding
     peptides #8

<400> SEQUENCE: 52

```
gaattcgcca ccatgggctg gtcctgcatc atcctgtttc tggtggccac cgccaccggc     60
gtgcactctg atatccagat gacccagagc cccagcagcc tgtctgcctc tgtgggcgac    120
agagtgacca tcacctgtag agccagccag tggatcggcc tgagctgag ctggtatcag    180
```

```
cagaagcccg gcaaggcccc caagctgctg atctaccaca ccagcatcct gcagagcggc    240
gtgcccagca gattttctgg cagcggcagc ggcaccgact tcaccctgac aatcagcagc    300
ctgcagcccg aggacttcgc cacctactac tgccagcagt acatgttcca gccccggacc    360
tttggccagg gcaccaaggt ggaaatcaga gagagcccca gagctgcgca agacccac     420 acctgtcccc cttgtcctgc ccctgaactg ctgggaggcc ctagcgtgtt cctgttcccc    480
ccaaagccca aggacaccct gatgatcagc cggaccccg aagtgacctg cgtggtggtg     540
gatgtgtccc acgaggaccc tgaagtgaag ttcaattggt acgtggacgg cgtggaagtg    600
cacaacgcca agaccaagcc cagagaggaa cagtacaaca gcacctaccg ggtggtgtcc    660
gtgctgacag tgctgcacca ggactggctg aacggcaaag agtacaagtg caaggtgtcc    720
aacaaggccc tgcctgcccc catcgagaaa accatcagca aggccaaggg ccagcccaga    780 gaacccagg tgtacacact gccccccagc agagaagaga tgaccaagaa ccaggtgtcc     840
ctgacctgcc tggtcaaggg cttctacccc agcgatatcg ccgtggaatg ggagagcaac    900
ggccagcctg agaacaacta caagaccacc cccctgtgc tggacagcga cggctcattc     960
ttcctgtaca gcaagctgac cgtggacaag agccggtggc agcagggcaa cgtgttcagc   1020
tgcagcgtga tgcacgaggc cctgcacaac cactacaccc agaagtccct gagcctgagc   1080
cccggcaaga tgcagatctt cgtgaaaacc ctgaccggca agaccatcac cctggaagtg   1140
gaacccagcg acaccatcga gaacgtgaag gccaagatcc aggacaaaga gggcatcccc   1200
cccgaccagc agagactgat cttcgccggc aagcagctgg aagatggcag aaccctgagc   1260
gactacaaca tccagaaaga gtccaccctg cacctggtgc tgcggctgag aggcggaggt   1320
ggtggtggtt ctggtggcgg aggatctggc ggtggtggat ctgggggagg tggaagtatg   1380
cagatttttg tcaagacact gaccgggaaa acaatcacac tcgaagtcga gccctccgat   1440
acaattgaga atgtgaaagc caaaattcag gacaagaag ggattcctcc tgatcagcag    1500
cggctgattt ttgccggaaa acagctcgaa gatggacgga ccctgtccga ttacaatatt   1560
cagaaagaaa gcaccctcca tctggtcctg aggctgcggg gaggcgacat tcagatgaca   1620
cagtccccca cctccctgtc tgccagcgtg ggagatcgcg tgaccattac atgccgggcc   1680
tcccagtgga ttggcaacct gctggattgg tatcagcaga acctgggga ggctcctaaa    1740 ctgctgatct attacgccag cttttctgcag tccggcgtgc cctccagatt cagcggcgga   1800
ggcttcggca cagatttcac actgaccatc tcatccctgc agcctgaaga ttttgccaca   1860
tattattgcc agcaggccaa ccctgccccc ctgacattcg ccagggaac aaaggtcgag    1920 atcaagcgcg agcccaagtc ctgtgataag acacatacct gcccccctg cccagctcca    1980 gaactgctcg gaggaccttc tgtgtttctg tttccaccca gcctaagga tacactcatg     2040 atctccagaa caccgaagt gacatgtgtg gtcgtcgacg tgtcacatga ggatccagaa    2100
gtcaagttta actggtatgt ggatggggtc gaggtgcaca atgccaaaac aaaacctcgg   2160
gaagaacagt ataattccac ctatagagtc gtgtctgtgc tcaccgtgct ccatcaggat   2220
tggctcaatg gaaagaata caaatgtaaa gtctctaaca agccctgcc cgctcctatc     2280 gaaaagacaa tctccaaggc caaggacag cctcgcgagc tcaggtcta caccctgcca     2340 cctagccgcg aggaaatgac aaaaaatcag gtgtcactca cctgtctcgt gaagggttt    2400 taccccctccg acattgccgt cgagtgggag tccaatggac agcccgagaa caattataag    2460
acaacacctc ccgtcctgga ctccgatgga tcattttttc tgtactccaa gctcaccgtc   2520
gataagtcca gatggcagca gggaaatgtc ttttcctgct ccgtgatgca tgaagctctc   2580
```

```
cacaatcatt acacacagaa aagcctgtcc ctgtccccg gcaagtgact cgag        2634
```

<210> SEQ ID NO 53
<211> LENGTH: 2649
<212> TYPE: DNA
<213> ORGANISM: Artificial Sequence
<220> FEATURE:
<223> OTHER INFORMATION: Synthetic Nucleotide sequence encoding the
      protein complex comprising VEGF and EGFR specific binding
      peptides #9

<400> SEQUENCE: 53

```
gaattcgcca ccatgggctg gtcctgcatc atcctgtttc tggtggccac cgccaccggc     60
gtgcactctg atatccagat gacccagagc cccagcagcc tgtctgcctc tgtgggcgac    120
agagtgacca tcacctgtag agccagccag tggatcggcc tgagctgag ctggtatcag    180
cagaagcccg gcaaggcccc caagctgctg atctaccaca ccagcatcct gcagagcggc    240
gtgcccagca gatttctgg cagcggcagc ggcaccgact tcaccctgac aatcagcagc    300
ctgcagcccg aggacttcgc cacctactac tgccagcagt acatgttcca gccccggacc    360
tttggccagg gcaccaaggt ggaaatcaga gagagcccag agctgcga caagacccac    420
acctgtcccc cttgtcctgc ccctgaactg ctgggaggcc ctagcgtgtt cctgttcccc    480
ccaaagccca aggacaccct gatgatcagc ggacccccg aagtgacctg cgtggtggtg    540
gatgtgtccc acgaggaccc tgaagtgaag ttcaattggt acgtggacgg cgtggaagtg    600
cacaacgcca agaccaagcc cagagaggaa cagtacaaca gcacctaccg ggtggtgtcc    660
gtgctgacag tgctgcacca ggactggctg aacggcaaag agtacaagtg caaggtgtcc    720
aacaaggccc tgcctgcccc catcgagaaa accatcagca aggccaaggg ccagcccaga    780
gaaccccagg tgtacacact gccccccagc agagaagaga tgaccaagaa ccaggtgtcc    840
ctgacctgcc tggtcaaggg cttctacccc agcgatatcg ccgtggaatg ggagagcaac    900
ggccagcctg agaacaacta caagaccacc ccccctgtgc tggacagcga cggctcattc    960
ttcctgtaca gcaagctgac cgtggacaag agccggtggc agcagggcaa cgtgttcagc   1020
tgcagcgtga tgcacgaggc cctgcacaac cactacaccc agaagtccct gagcctgagc   1080
cccggcaaga tgcagatctt cgtgaaaacc ctgaccggca agaccatcac cctggaagtg   1140
gaacccagcg acaccatcga gaacgtgaag gccaagatcc aggacaaaga gggcatcccc   1200
cccgaccagc agagactgat cttcgccggc aagcagctgg aagatggcag aaccctgagc   1260
gactacaaca tccagaaaga gtccaccctg cacctggtgc tgcggctgag aggcggaggt   1320
ggtggtggtt ctggtggcgg aggatctggc ggtggtggat ctggggagg tggaagtggt   1380
ggcggtggta gtatgcagat ttttgtcaag acactgaccg gaaaacaat cactgtcgaa   1440
gtcgagccct ccgatacaat tgagaatgtg aaagccaaaa tcaggacaa gaagggatt   1500
cctcctgatc agcagcggct gattttttgcc ggaaaacagc tcgaagatgg acggaccctg   1560
tccgattaca atattcagaa agaaagcacc ctccatctgg tcctgaggct gcggggaggc   1620
gacattcaga tgacacagtc ccccaccctcc ctgtctgcca gcgtgggaga tcgcgtgacc   1680
attacatgcc gggcctccca gtggattggc aacctgctgg attggtatca gcagaaacct   1740
ggggaggctc ctaaactgct gatctattac gccagctttc tgcagtccgg cgtgccctcc   1800
agattcagcg gcgaggctt cggcacagat ttcacactga ccatctcatc cctgcagcct   1860
gaagattttg ccacatatta ttgccagcag ggcaaccctg cccccctgac attcggccag   1920
```
ggaacaaagg tcgagatcaa gcgcgagccc aagtcctgtg ataagacaca tacctgcccc 1980
ccctgcccag ctccagaact gctcggagga ccttctgtgt ttctgtttcc acccaagcct 2040
aaggatacac tcatgatctc cagaacacct gaagtgacat gtgtggtcgt cgacgtgtca 2100
catgaggatc cagaagtcaa gtttaactgg tatgtggatg ggtcgaggt gcacaatgcc 2160 aaaacaaaac ctcgggaaga acagtataat tccacctata gagtcgtgtc tgtgctcacc 2220
gtgctccatc aggattggct caatgggaaa gaatacaaat gtaaagtctc taacaaagcc 2280
ctgcccgctc ctatcgaaaa gacaatctcc aaggccaaag gacagcctcg cgagcctcag 2340
gtctacaccc tgccacctag ccgcgaggaa atgacaaaaa atcaggtgtc actcacctgt 2400
ctcgtgaagg ggttttaccc ctccgacatt gccgtcgagt gggagtccaa tggacagccc 2460
gagaacaatt ataagacaac acctcccgtc ctggactccg atggatcatt ttttctgtac 2520
tccaagctca ccgtcgataa gtccagatgg cagcagggaa atgtcttttc ctgctccgtg 2580
atgcatgaag ctctccacaa tcattacaca cagaaaagcc tgtccctgtc ccccggcaag 2640
tgactcgag 2649

<210> SEQ ID NO 54
<211> LENGTH: 2664
<212> TYPE: DNA
<213> ORGANISM: Artificial Sequence
<220> FEATURE:
<223> OTHER INFORMATION: Synthetic Nucleotide sequence encoding the protein complex comprising VEGF and EGFR specific binding peptides #10

<400> SEQUENCE: 54
gaattcgcca ccatgggctg gtcctgcatc atcctgtttc tggtggccac cgccaccggc 60
gtgcactctg atatccagat gacccagagc cccagcagcc tgtctgcctc tgtgggcgac 120
agagtgacca tcacctgtag agccagccag tggatcggcc ctgagctgag ctggtatcag 180
cagaagcccg gcaaggcccc caagctgctg atctaccaca ccagcatcct gcagagcggc 240
gtgcccagca gattttctgg cagcggcagc ggcaccgact tcaccctgac aatcagcagc 300
ctgcagcccg aggacttcgc cacctactac tgccagcagt acatgttcca gccccggacc 360
tttggccagg gcaccaaggt ggaaatcaga agagagccca agagctgcga caagacccac 420
acctgtcccc cttgtcctgc ccctgaactg ctgggaggcc ctagcgtgtt cctgttcccc 480
ccaaagccca aggacaccct gatgatcagc cggacccccg aagtgacctg cgtggtggtg 540
gatgtgtccc acgaggaccc tgaagtgaag ttcaattggt acgtggacgg cgtggaagtg 600
cacaacgcca agaccaagcc cagagaggaa cagtacaaca gcacctaccg ggtggtgtcc 660
gtgctgacag tgctgcacca ggactggctg aacggcaaag agtacaagtg caaggtgtcc 720
aacaaggccc tgcctgcccc catcgagaaa accatcagca aggccaaggg ccagcccaga 780
gaaccccagg tgtacacact gccccccagc agagaagaga tgaccaagaa ccaggtgtcc 840
ctgacctgcc tggtcaaggg cttctacccc agcgatatcg ccgtggaatg ggagagcaac 900
ggccagcctg agaacaacta caagaccacc ccccctgtgc tggacagcga cggctcattc 960
ttcctgtaca gcaagctgac cgtggacaag agccggtggc agcagggcaa cgtgttcagc 1020
tgcagcgtga tgcacgaggc cctgcacaac cactacaccc agaagtccct gagcctgagc 1080
cccggcaaga tgcagatctt cgtgaaaacc ctgaccggca agaccatcac cctggaagtg 1140
gaacccagcg acaccatcga gaacgtgaag gccaagatcc aggacaaaga gggcatcccc 1200
cccgaccagc agagactgat cttcgccggc aagcagctgg aagatggcag aaccctgagc 1260

```
gactacaaca tccagaaaga gtccaccctg cacctggtgc tgcggctgag aggcggaggt   1320
ggtggtggtt ctggtggcgg aggatctggc ggtggtggat ctgggggagg tggaagtggt   1380
ggcggtggta gtggtggtgg cggaagcatg cagatttttg tcaagacact gaccgggaaa   1440
acaatcacac tcgaagtcga gccctccgat acaattgaga atgtgaaagc caaaattcag   1500
gacaaagaag ggattcctcc tgatcagcag cggctgattt ttgccggaaa acagctcgaa   1560
gatggacgga ccctgtccga ttacaatatt cagaaagaaa gcaccctcca tctggtcctg   1620
aggctgcggg gaggcgacat tcagatgaca cagtccccca cctccctgtc tgccagcgtg   1680
ggagatcgcg tgaccattac atgccgggcc tcccagtgga ttggcaacct gctggattgg   1740
tatcagcaga aacctgggga ggctcctaaa ctgctgatct attacgccag ctttctgcag   1800
tccggcgtgc cctccagatt cagcggcgga ggcttcggca cagatttcac actgaccatc   1860
tcatccctgc agcctgaaga ttttgccaca tattattgcc agcaggccaa ccctgccccc   1920
ctgacattcg gccagggaac aaaggtcgag atcaagcgcg agcccaagtc ctgtgataag   1980
acacatacct gcccccccctg cccagctcca gaactgctcg gaggaccttc tgtgtttctg   2040
tttccaccca agcctaagga tacactcatg atctccagaa cacctgaagt gacatgtgtg   2100
gtcgtcgacg tgtcacatga ggatccagaa gtcaagttta actggtatgt ggatggggtc   2160
gaggtgcaca atgccaaaac aaaacctcgg gaagaacagt ataattccac ctatagagtc   2220
gtgtctgtgc tcaccgtgct ccatcaggat tggctcaatg ggaaagaata caaatgtaaa   2280
gtctctaaca aagccctgcc cgctcctatc gaaaagacaa tctccaaggc caaaggacag   2340
cctcgcgagc ctcaggtcta caccctgcca cctagccgcg aggaaatgac aaaaaatcag   2400
gtgtcactca cctgtctcgt gaaggggttt taccccctccg acattgccgt cgagtgggag   2460
tccaatggac agcccgagaa caattataag acaacacctc ccgtcctgga ctccgatgga   2520
tcattttttc tgtactccaa gctcaccgtc gataagtcca gatggcagca gggaaatgtc   2580
ttttcctgct ccgtgatgca tgaagctctc cacaatcatt acacacagaa aagcctgtcc   2640
ctgtcccccg gcaagtgact cgag                                          2664
```

```

<210> SEQ ID NO 55
<211> LENGTH: 2679
<212> TYPE: DNA
<213> ORGANISM: Artificial Sequence
<220> FEATURE:
<223> OTHER INFORMATION: Synthetic Nucleotide sequence encoding the
      protein complex comprising VEGF and EGFR specific binding
      peptides #11

<400> SEQUENCE: 55
gaattcgcca ccatgggctg gtcctgcatc atcctgtttc tggtggccac cgccaccggc     60
gtgcactctg atatccagat gacccagagc cccagcagcc tgtctgcctc tgtgggcgac    120
agagtgacca tcacctgtag agccagccag tggatcggcc ctgagctgag ctggtatcag    180
cagaagcccg gcaaggcccc caagctgctg atctaccaca ccagcatcct gcagagcggc    240
gtgcccagca gattttctgg cagcggcagc ggcaccgact tcaccctgac aatcagcagc    300
ctgcagcccg aggacttcgc cacctactac tgccagcagt acatgttcca gccccggacc    360
tttggccagg gcaccaaggt ggaaatcaga agagagccca agagctgcga caagacccac    420
acctgtcccc cttgtcctgc ccctgaactg ctgggaggcc ctagcgtgtt cctgttcccc    480
ccaaagccca aggacaccct gatgatcagc cggacccccg aagtgacctg cgtggtggtg    540
```

-continued

| | |
|---|---|
| gatgtgtccc acgaggaccc tgaagtgaag ttcaattggt acgtggacgg cgtggaagtg | 600 |
| cacaacgcca agaccaagcc cagagaggaa cagtacaaca gcacctaccg ggtggtgtcc | 660 |
| gtgctgacag tgctgcacca ggactggctg aacggcaaag agtacaagtg caaggtgtcc | 720 |
| aacaaggccc tgcctgcccc catcgagaaa accatcagca aggccaaggg ccagcccaga | 780 |
| gaacccccagg tgtacacact gccccccagc agagaagaga tgaccaagaa ccaggtgtcc | 840 |
| ctgacctgcc tggtcaaggg cttctacccc agcgatatcg ccgtggaatg ggagagcaac | 900 |
| ggccagcctg agaacaacta caagaccacc ccccctgtgc tggacagcga cggctcattc | 960 |
| ttcctgtaca gcaagctgac cgtggacaag agccggtggc agcagggcaa cgtgttcagc | 1020 |
| tgcagcgtga tgcacgaggc cctgcacaac cactacaccc agaagtccct gagcctgagc | 1080 |
| cccggcaaga tgcagatctt cgtgaaaacc ctgaccggca agaccatcac cctggaagtg | 1140 |
| gaacccagcg acaccatcga gaacgtgaag gccaagatcc aggacaaaga gggcatcccc | 1200 |
| cccgaccagc agagactgat cttcgccggc aagcagctgg aagatggcag aaccctgagc | 1260 |
| gactacaaca tccagaaaga gtccaccctg cacctggtgc tgcggctgag aggcggaggt | 1320 |
| ggtggtggtt ctggtggcgg aggatctggc ggtggtggat ctggggggagg tggaagtggt | 1380 |
| ggcggtggta gtggtggtgg cggaagcgga ggcggtggat caatgcagat ttttgtcaag | 1440 |
| acactgaccg ggaaaacaat cacactcgaa gtcgagccct ccgatacaat tgagaatgtg | 1500 |
| aaagccaaaa ttcaggacaa agaagggatt cctcctgatc agcagcggct gattttttgcc | 1560 |
| ggaaaacagc tcgaagatgg acggaccctg tccgattaca atattcagaa agaaagcacc | 1620 |
| ctccatctgg tcctgaggct gcggggaggc gacattcaga tgacacagtc ccccaccctcc | 1680 |
| ctgtctgcca gcgtgggaga tcgcgtgacc attacatgcc gggcctccca gtggattggc | 1740 |
| aacctgctgg attggtatca gcagaaacct ggggaggctc ctaaactgct gatctattac | 1800 |
| gccagctttc tgcagtccgg cgtgccctcc agattcagcg gcggaggctt cggcacagat | 1860 |
| ttcacactga ccatctcatc cctgcagcct gaagatttttg ccacatatta ttgccagcag | 1920 |
| gccaaccctg cccccctgac attcggccag ggaacaaagg tcgagatcaa gcgcgagccc | 1980 |
| aagtcctgtg ataagacaca tacctgcccc ccctgcccag ctccagaact gctcggagga | 2040 |
| ccttctgtgt ttctgtttcc acccaagcct aaggatacac tcatgatctc cagaacacct | 2100 |
| gaagtgacat gtgtggtcgt cgacgtgtca catgaggatc cagaagtcaa gtttaactgg | 2160 |
| tatgtggatg gggtcgaggt gcacaatgcc aaaacaaaac tcgggaagaa acagtataat | 2220 |
| tccacctata gagtcgtgtc tgtgctcacc gtgctccatc aggattggct caatgggaaa | 2280 |
| gaatacaaat gtaaagtctc taacaaagcc ctgcccgctc ctatcgaaaa gacaatctcc | 2340 |
| aaggccaaag acagcctcg cgagcctcag gtctacaccc tgccacctag ccgcgaggaa | 2400 |
| atgacaaaaa atcaggtgtc actcacctgt ctcgtgaagg ggttttaccc ctccgacatt | 2460 |
| gccgtcgagt gggagtccaa tggacagccc gagaacaatt ataagacaac acctcccgtc | 2520 |
| ctggactccg atggatcatt ttttctgtac tccaagctca ccgtcgataa gtccagatgg | 2580 |
| cagcagggaa atgtctttc ctgctccgtg atgcatgaag ctctccacaa tcattacaca | 2640 |
| cagaaaagcc tgtccctgtc ccccggcaag tgactcgag | 2679 |

<210> SEQ ID NO 56
<211> LENGTH: 2694
<212> TYPE: DNA
<213> ORGANISM: Artificial Sequence
<220> FEATURE:
<223> OTHER INFORMATION: Synthetic Nucleotide sequence encoding the protein complex comprising VEGF and EGFR specific binding
peptides #12

<400> SEQUENCE: 56

| | | | | |
|---|---|---|---|---|
| gaattcgcca | ccatgggctg | gtcctgcatc | atcctgtttc | tggtggccac | cgccaccggc | 60 |
| gtgcactctg | atatccagat | gacccagagc | cccagcagcc | tgtctgcctc | tgtgggcgac | 120 |
| agagtgacca | tcacctgtag | agccagccag | tggatcggcc | ctgagctgag | ctggtatcag | 180 |
| cagaagcccg | gcaaggcccc | caagctgctg | atctaccaca | ccagcatcct | gcagagcggc | 240 |
| gtgcccagca | gattttctgg | cagcggcagc | ggcaccgact | tcaccctgac | aatcagcagc | 300 |
| ctgcagcccg | aggacttcgc | cacctactac | tgccagcagt | acatgttcca | gccccggacc | 360 |
| tttggccagg | gcaccaaggt | ggaaatcaga | agagagccca | gagctgcga | caagacccac | 420 |
| acctgtcccc | cttgtcctgc | ccctgaactg | ctgggaggcc | ctagcgtgtt | cctgttcccc | 480 |
| ccaaagccca | aggacaccct | gatgatcagc | cggaccccg | aagtgacctg | cgtggtggtg | 540 |
| gatgtgtccc | acgaggaccc | tgaagtgaag | ttcaattggt | acgtggacgg | cgtggaagtg | 600 |
| cacaacgcca | agaccaagcc | cagagaggaa | cagtacaaca | gcacctaccg | ggtggtgtcc | 660 |
| gtgctgacag | tgctgcacca | ggactggctg | aacggcaaag | agtacaagtg | caaggtgtcc | 720 |
| aacaaggccc | tgcctgcccc | catcgagaaa | accatcagca | aggccaaggg | ccagcccaga | 780 |
| gaacccagg | tgtacacact | gccccccagc | agagaagaga | tgaccaagaa | ccaggtgtcc | 840 |
| ctgacctgcc | tggtcaaggg | cttctacccc | agcgatatcg | ccgtggaatg | ggagagcaac | 900 |
| ggccagcctg | agaacaacta | caagaccacc | ccccctgtgc | tggacagcga | cggctcattc | 960 |
| ttcctgtaca | gcaagctgac | cgtggacaag | agccggtggc | agcagggcaa | cgtgttcagc | 1020 |
| tgcagcgtga | tgcacgaggc | cctgcacaac | cactacaccc | agaagtccct | gagcctgagc | 1080 |
| cccggcaaga | tgcagatctt | cgtgaaaacc | ctgaccggca | agaccatcac | cctggaagtg | 1140 |
| gaacccagcg | acaccatcga | aacgtgaag | gccaagatcc | aggacaaaga | gggcatcccc | 1200 |
| cccgaccagc | agagactgat | cttcgccggc | aagcagctgg | aagatggcag | aaccctgagc | 1260 |
| gactacaaca | tccagaaaga | gtccaccctg | cacctggtgc | tgcggctgag | aggcggaggt | 1320 |
| ggtggtggtt | ctggtggcgg | aggatctggc | ggtggtggat | ctggggagg | tggaagtggt | 1380 |
| ggcggtggta | gtggtggtgg | cggaagcgga | ggcggtggat | caggcggagg | cggatcaatg | 1440 |
| cagattttg | tcaagacact | gaccgggaaa | acaatcacac | tcgaagtcga | gccctccgat | 1500 |
| acaattgaga | atgtgaaagc | caaaattcag | gacaagaag | ggattcctcc | tgatcagcag | 1560 |
| cggctgattt | ttgccggaaa | acagctcgaa | gatggacgga | ccctgtccga | ttacaatatt | 1620 |
| cagaaagaaa | gcaccctcca | tctggtcctg | aggctgcggg | gaggcgacat | tcagatgaca | 1680 |
| cagtccccca | cctccctgtc | tgccagcgtg | ggagatcgcg | tgaccattac | atgccgggcc | 1740 |
| tcccagtgga | ttggcaacct | gctggattgg | tatcagcaga | aacctgggga | ggctcctaaa | 1800 |
| ctgctgatct | attaccccag | cttttctgcag | tccggcgtgc | cctccagatt | cagcggcgga | 1860 |
| ggcttcggca | cagatttcac | actgaccatc | tcatccctgc | agcctgaaga | ttttgccaca | 1920 |
| tattattgcc | agcaggccaa | ccctgccccc | ctgacattcg | ccagggaac | aaaggtcgag | 1980 |
| atcaagcgcg | agcccaagtc | ctgtgataag | acacatacct | gccccccctg | cccagctcca | 2040 |
| gaactgctcg | gaggaccttc | tgtgtttctg | tttccaccca | agcctaagga | tacactcatg | 2100 |
| atctccagaa | cacctgaagt | gacatgtgtg | gtcgtcgacg | tgtcacatga | ggatccagaa | 2160 |
| gtcaagttta | actggtatgt | ggatggggtc | gaggtgcaca | atgccaaaac | aaaacctcgg | 2220 |

```
gaagaacagt ataattccac ctatagagtc gtgtctgtgc tcaccgtgct ccatcaggat   2280
tggctcaatg ggaaagaata caaatgtaaa gtctctaaca aagccctgcc cgctcctatc   2340
gaaaagacaa tctccaaggc caaaggacag cctcgcgagc tcaggtctac acccctgcca   2400
cctagccgcg aggaaatgac aaaaaatcag gtgtcactca cctgtctcgt gaagggtttt   2460 taccctccg acattgccgt cgagtgggag tccaatggac agcccgagaa caattataag    2520 acaacctc ccgtcctgga ctccgatgga tcattttttc tgtactccaa gctcaccgtc     2580
gataagtcca gatggcagca gggaaatgtc ttttcctgct ccgtgatgca tgaagctctc   2640
cacaatcatt acacacagaa aagcctgtcc ctgtccccg gcaagtgact cgag           2694
```

<210> SEQ ID NO 57
<211> LENGTH: 2709
<212> TYPE: DNA
<213> ORGANISM: Artificial Sequence
<220> FEATURE:
<223> OTHER INFORMATION: Synthetic Nucleotide sequence encoding the
      protein complex comprising VEGF and EGFR specific binding
      peptides #13

<400> SEQUENCE: 57

```
gaattcgcca ccatgggctg gtcctgcatc atcctgtttc tggtggccac cgccaccggc    60
gtgcactctg atatccagat gacccagagc cccagcagcc tgtctgcctc tgtgggcgac   120
agagtgacca tcacctgtag agccagccag tggatcggcc tgagctgag ctggtatcag   180 cagaagcccg gcaaggcccc caagctgctg atctaccaca ccagcatcct gcagagcggc   240
gtgcccagca gattttctgg cagcggcagc ggcaccgact tcaccctgac aatcagcagc   300
ctgcagcccg aggacttcgc cacctactac tgccagcagt acatgttcca gccccggacc   360
tttggccagg gcaccaaggt ggaaatcaga agagagccca gagctgcga caagacccac   420 acctgtcccc cttgtcctgc ccctgaactg ctgggaggcc ctagcgtgtt cctgttcccc   480
ccaaagccca aggacaccct gatgatcagc cggaccccg aagtgacctg cgtggtggtg   540
gatgtgtccc acgaggaccc tgaagtgaag ttcaattggt acgtggacgg cgtggaagtg   600
cacaacgcca agaccaagcc cagagaggaa cagtacaaca gcacctaccg ggtggtgtcc   660
gtgctgacag tgctgcacca ggactggctg aacggcaaag agtacaagtg caaggtgtcc   720
aacaaggccc tgcctgcccc catcgagaaa accatcagca aggccaaggg ccagccagag   780 aacccagag tgtacacact gcccccagc agagaagaga tgaccaagaa ccaggtgtcc   840
ctgacctgcc tggtcaaggg cttctacccc agcgatatcg ccgtggaatg ggagagcaac   900
ggccagcctg agaacaacta caagaccacc cccctgtgc tggacagcga cggctcattc   960
ttcctgtaca gcaagctgac cgtggacaag agccggtggc agcagggcaa cgtgttcagc   1020
tgcagcgtga tgcacgaggc cctgcacaac cactacaccc agaagtccct gagcctgagc   1080
cccggcaaga tgcagatctt cgtgaaaacc ctgaccggca gaccatcac cctggaagtg   1140 gaacccagcg acaccatcga gaacgtgaag gccaagatcc aggacaaaga gggcatcccc   1200
cccgaccagc agagactgat cttcgccggc aagcagctgg aagatggcag aaccctgagc   1260
gactacaaca tccagaaaga gtccaccctg cacctggtgc tgcggctgag aggcggaggt   1320
ggtggtggtt ctggtggcgg aggatctggc ggtggtggat ctggggagg tggaagtggt   1380 ggcggtggta gtggtggtgg cggaagcgga ggcggtggat caggcggagg cggatcaggt   1440
ggcggcggaa gtatgcagat ttttgtcaag acactgaccg ggaaaacaat cactctcgaa   1500
gtcgagccct ccgatacaat tgagaatgtg aaagccaaaa ttcaggacaa agaagggatt   1560
```

| | |
|---|---|
| cctcctgatc agcagcggct gattttttgcc ggaaaacagc tcgaagatgg acggaccctg | 1620 |
| tccgattaca atattcagaa agaaagcacc ctccatctgg tcctgaggct gcggggaggc | 1680 |
| gacattcaga tgacacagtc ccccacctcc ctgtctgcca gcgtgggaga tcgcgtgacc | 1740 |
| attacatgcc gggcctccca gtggattggc aacctgctgg attggtatca gcagaaacct | 1800 |
| ggggaggctc ctaaactgct gatctattac gccagctttc tgcagtccgg cgtgccctcc | 1860 |
| agattcagcg gcgaggctt cggcacagat ttcacactga ccatctcatc cctgcagcct | 1920 |
| gaagattttg ccacatatta ttgccagcag gccaaccctg cccccctgac attcggccag | 1980 |
| ggaacaaagg tcgagatcaa gcgcgagccc aagtcctgtg ataagacaca tacctgcccc | 2040 |
| ccctgcccag ctccagaact gctcggagga ccttctgtgt ttctgtttcc acccaagcct | 2100 |
| aaggatacac tcatgatctc cagaacacct gaagtgacat gtgtggtcgt cgacgtgtca | 2160 |
| catgaggatc cagaagtcaa gtttaactgg tatgtggatg gggtcgaggt gcacaatgcc | 2220 |
| aaaacaaaac tcgggaaga acagtataat ccacctata gagtcgtgtc tgtgctcacc | 2280 |
| gtgctccatc aggattggct caatgggaaa gaatacaaat gtaaagtctc taacaaagcc | 2340 |
| ctgcccgctc ctatcgaaaa dacaatctcc aaggccaaag acagcctcg cgagcctcag | 2400 |
| gtctacaccc tgccacctag ccgcgaggaa atgacaaaaa atcaggtgtc actcacctgt | 2460 |
| ctcgtgaagg ggttttaccc ctccgacatt gccgtcgagt gggagtccaa tggacagccc | 2520 |
| gagaacaatt ataagacaac acctcccgtc ctggactccg atggatcatt ttttctgtac | 2580 |
| tccaagctca ccgtcgataa gtccagatgg cagcagggaa atgtcttttc ctgctccgtg | 2640 |
| atgcatgaag ctctccacaa tcattacaca cagaaaagcc tgtccctgtc ccccggcaag | 2700 |
| tgactcgag | 2709 |

<210> SEQ ID NO 58
<211> LENGTH: 2724
<212> TYPE: DNA
<213> ORGANISM: Artificial Sequence
<220> FEATURE:
<223> OTHER INFORMATION: Synthetic Nucleotide sequence encoding the protein complex comprising VEGF and EGFR specific binding peptides #14

<400> SEQUENCE: 58

| | |
|---|---|
| gaattcgcca ccatgggctg gtcctgcatc atcctgtttc tggtggccac cgccaccggc | 60 |
| gtgcactctg atatccagat gacccagagc cccagcagcc tgtctgcctc tgtgggcgac | 120 |
| agagtgacca tcacctgtag agccagccag tggatcggcc tgagctgag ctggtatcag | 180 |
| cagaagcccg gcaaggcccc caagctgctg atctaccaca ccagcatcct gcagagcggc | 240 |
| gtgcccagca gattttctgg cagcggcagc ggcaccgact tcaccctgac aatcagcagc | 300 |
| ctgcagcccg aggacttcgc cacctactac tgccagcagt acatgttcca gccccggacc | 360 |
| tttggccagg gcaccaaggt ggaaatcaga agagagccca gagctgcga caagacccac | 420 |
| acctgtcccc cttgtcctgc ccctgaactg ctgggaggcc ctagcgtgtt cctgttcccc | 480 |
| ccaaagccca aggacaccct gatgatcagc cggaccccg aagtgacctg cgtggtggtg | 540 |
| gatgtgtccc acgaggaccc tgaagtgaag ttcaattggt acgtggacgg cgtggaagtg | 600 |
| cacaacgcca agaccaagcc cagagaggaa cagtacaaca gcacctaccg ggtggtgtcc | 660 |
| gtgctgacag tgctgcacca ggactggctg aacggcaaag agtacaagtg caaggtgtcc | 720 |
| aacaaggccc tgcctgcccc catcgagaaa accatcagca aggccaaggg ccagccagga | 780 |

```
gaaccccagg tgtacacact gccccccagc agagaagaga tgaccaagaa ccaggtgtcc      840
ctgacctgcc tggtcaaggg cttctacccc agcgatatcg ccgtggaatg ggagagcaac      900
ggccagcctg agaacaacta caagaccacc cccctgtgc tggacagcga cggctcattc       960
ttcctgtaca gcaagctgac cgtggacaag agccggtggc agcagggcaa cgtgttcagc     1020
tgcagcgtga tgcacgaggc cctgcacaac cactacaccc agaagtccct gagcctgagc     1080
cccggcaaga tgcagatctt cgtgaaaacc ctgaccggca agaccatcac cctggaagtg     1140
gaacccagcg acaccatcga gaacgtgaag gccaagatcc aggacaaaga gggcatcccc     1200
cccgaccagc agagactgat cttcgccggc aagcagctgg aagatggcag aaccctgagc     1260
gactacaaca tccagaaaga gtccaccctg cacctggtgc tgcggctgag aggcggaggt     1320
ggtggtggtt ctggtggcgg aggatctggc ggtggtggat ctggggagg tggaagtggt      1380 ggcggtggta gtggtggtgg cggaagcgga ggcggtggat caggcggagg cggatcaggt     1440
ggcggcggaa gtggcggagg cggcagcatg cagattttg tcaagacact gaccgggaaa      1500
acaatcacac tcgaagtcga gccctccgat acaattgaga atgtgaaagc caaaattcag     1560 gacaagaag ggattcctcc tgatcagcag cggctgattt tgccggaaa acagctcgaa       1620 gatggacgga ccctgtccga ttacaatatt cagaaagaaa gcaccctcca tctggtcctg     1680
aggctgcggg gaggcgacat tcagatgaca cagtccccca cctccctgtc tgccagcgtg     1740
ggagatcgcg tgaccattac atgccgggcc tcccagtgga ttggcaacct gctggattgg     1800
tatcagcaga aacctgggga ggctcctaaa ctgctgatct attacgccag ctttctgcag     1860
tccggcgtgc cctccagatt cagcggcgga ggcttcggca cagatttcac actgaccatc     1920
tcatccctgc agcctgaaga ttttgccaca tattattgcc agcaggccaa ccctgccccc     1980
ctgacattcg gccagggaac aaaggtcgag atcaagcgcg agcccaagtc ctgtgataag     2040
acacatacct gccccccctg cccagctcca gaactgctcg gaggaccttc tgtgtttctg     2100
tttccaccca gcctaagga tacactcatg atctccagaa cacctgaagt gacatgtgtg     2160
gtcgtcgacg tgtcacatga ggatccagaa gtcaagttta actggtatgt ggatggggtc     2220
gaggtgcaca atgccaaaac aaaacctcgg gaagaacagt ataattccac ctatagagtc     2280
gtgtctgtgc tcaccgtgct ccatcaggat tggctcaatg gaaagaata caaatgtaaa     2340 gtctctaaca agcccctgcc cgctcctatc gaaaagacaa tctccaaggc caaggacag      2400 cctcgcgagc tcaggtctta caccctgcca cctagccgcg aggaaatgac aaaaaatcag     2460
gtgtcactca cctgtctcgt gaaggggttt taccccttccg acattgccgt cgagtgggag     2520
tccaatggac agcccgagaa caattataag acaacacctc ccgtcctgga ctccgatgga     2580 tcatttttc tgtactccaa gctcaccgtc gataagtcca gatggcagca gggaaatgtc     2640
ttttcctgct ccgtgatgca tgaagctctc cacaatcatt acacacagaa aagcctgtcc     2700
ctgtcccccg gcaagtgact cgag                                            2724
```

<210> SEQ ID NO 59
<211> LENGTH: 2634
<212> TYPE: DNA
<213> ORGANISM: Artificial Sequence
<220> FEATURE:
<223> OTHER INFORMATION: Synthetic Nucleotide sequence encoding the
      protein complex comprising VEGF and EGFR specific binding
      peptides #15

<400> SEQUENCE: 59

```
gaattcgcca ccatgggctg gtcctgcatc atcctgtttc tggtggccac cgccaccggc       60
```

-continued

```
gtgcactctg atatccagat gacccagagc cccagcagcc tgtctgcctc tgtgggcgac    120
agagtgacca tcacctgtcg ggccagccag aagatcttca acggcctgag ctggtatcag    180
cagaagcccg gcaaggcccc caagctgctg atctaccaca gcagcaccct gcagagcggc    240
gtgccaagca gattttctgg cagcggcagc ggcaccgact tcaccctgac aatcagcagc    300
ctgcagcccg aggacttcgc cacctactac tgccagcagg tcctgctgta cccctacacc    360
tttggccagg gcaccaaggt ggaaatcaag agagagccca gagctgcga caagacccac    420 acctgtcccc cttgtcctgc ccctgaactg ctgggaggcc tagcgtgtt cctgttcccc    480 ccaaagccca aggacaccct gatgatcagc cggaccccg aagtgacctg cgtggtggtg    540
gatgtgtccc acgaggaccc tgaagtgaag ttcaattggt acgtggacgg cgtggaagtg    600
cacaacgcca agaccaagcc cagagaggaa cagtacaaca gcacctaccg ggtggtgtcc    660
gtgctgacag tgctgcacca ggactggctg aacggcaaag agtacaagtg caaggtgtcc    720
aacaaggccc tgcctgcccc catcgagaaa accatcagca aggccaaggg ccagcccaga    780 gaacccagg tgtacacact gcccccagc agagaagaga tgaccaagaa ccaggtgtcc    840
ctgacctgcc tggtcaaggg cttctacccc agcgatatcg ccgtggaatg ggagagcaac    900
ggccagcctg agaacaacta agaccacc ccctgtgc tggacagcga cggctcattc    960
ttcctgtaca gcaagctgac cgtggacaag agccggtggc agcagggcaa cgtgttcagc    1020
tgcagcgtga tgcacgaggc cctgcacaac cactacaccc agaagtccct gagcctgagc    1080
cccggcaaga tgcagatctt cgtgaaaacc ctgaccggca agaccatcac cctggaagtg    1140
gaacccagcg acaccatcga aacgtgaag gccaagatcc aggacaaaga gggcatcccc    1200
cccgaccagc agagactgat cttcgccggc aagcagctgg aagatggcag aaccctgagc    1260
gactacaaca tccagaaaga gtccaccctg cacctggtgc tgcggctgag aggcggaggt    1320
ggtggtggtt ctggtggcgg aggatctggc ggtggtggat ctgggggagg tggaagtatg    1380 cagattttg tcaagacact gaccgggaaa acaatcacac tcgaagtcga gccctccgat    1440
acaattgaga atgtgaaagc caaaattcag gacaagaag ggattcctcc tgatcagcag    1500
cggctgattt ttgccggaaa acagctcgaa gatggacgga ccctgtccga ttacaatatt    1560
cagaaagaaa gcaccctcca tctggtcctg aggctgcggg gaggcgacat tcagatgaca    1620
cagtccccca gctccctgag cgccagcgtg ggagatcgcg tgaccattac ctgcagagcc    1680
tcccagtgga tcggcatcct ggtgattgg tatcagcaga aacctgggga ggctcctaaa    1740
ctgctgatct attacgccag cttcctgcag tccggcgtgc cctctagatt cagcggctct    1800
ggcttcggca cagatttcac actgaccatc tctagcctgc accctgaaga ttttgccaca    1860
tattactgtc agcaggccaa ccctgccccc ctgacatttg gacagggaac aaaggtcgag    1920
atcaagcgcg agcctaagtc ctgtgacaag acacacacat gccctccctg cccagcccca    1980
gaactgctcg gtggaccctc tgtgtttctg tttccaccca gcctaagga tacactcatg    2040 atctccagaa caccctgaagt gacatgtgtg gtcgtcgacg tgtcacatga ggatccagaa    2100
gtcaagttta actggtatgt ggatggggtc gaggtgcaca atgccaaaac aaaacctcgg    2160
gaagaacagt ataattccac ctatagagtc gtgtctgtgc tcaccgtgct ccatcaggat    2220
tggctcaatg gaaagaata caatgtaaa gtctctaaca agccctgcc cgctcctatc    2280 gaaaagacaa tctccaaggc caaggacag cctcgcgagc ctcaggtcta caccctgcca    2340
ccttcccgcg aggaaatgac aaaaaatcag gtgtcactca cctgtctcgt gaaggggttt    2400
```

| | |
|---|---|
| taccccctccg acattgccgt cgagtgggag tccaatggac agcccgagaa caattataag | 2460 |
| acaacacctc ccgtcctgga ctccgatgga tcatttttc tgtactccaa gctcaccgtc | 2520 |
| gataagtcca gatggcagca gggaaatgtc ttttcctgct ccgtgatgca tgaagctctc | 2580 |
| cacaatcatt acacacagaa aagcctgtcc ctgtcccccg gcaagtgact cgag | 2634 |

<210> SEQ ID NO 60
<211> LENGTH: 2649
<212> TYPE: DNA
<213> ORGANISM: Artificial Sequence
<220> FEATURE:
<223> OTHER INFORMATION: Synthetic Nucleotide sequence encoding the
      protein complex comprising VEGF and EGFR specific binding
      peptides #16

<400> SEQUENCE: 60

| | |
|---|---|
| gaattcgcca ccatgggctg gtcctgcatc atcctgtttc tggtggccac cgccaccggc | 60 |
| gtgcactctg atatccagat gacccagagc cccagcagcc tgtctgcctc tgtgggcgac | 120 |
| agagtgacca tcacctgtcg ggccagccag aagatcttca cggcctgag ctggtatcag | 180 |
| cagaagcccg gcaaggcccc caagctgctg atctaccaca gcagcaccct gcagagcggc | 240 |
| gtgccaagca gatttctctgg cagcggcagc ggcaccgact cacccctgac aatcagcagc | 300 |
| ctgcagcccg aggacttcgc cacctactac tgccagcagg tcctgctgta ccctacacc | 360 |
| tttggccagg gcaccaaggt ggaaatcaag agagagccca gagctgcga caagacccac | 420 |
| acctgtcccc cttgtcctgc ccctgaactg ctgggaggcc tagcgtgtt cctgttcccc | 480 |
| ccaaagccca aggacaccct gatgatcagc cggacccccg aagtgacctg cgtggtggtg | 540 |
| gatgtgtccc acgaggaccc tgaagtgaag ttcaattggt acgtggacgg cgtggaagtg | 600 |
| cacaacgcca agaccaagcc cagagaggaa cagtacaaca gcacctaccg ggtggtgtcc | 660 |
| gtgctgacag tgctgcacca ggactggctg aacggcaaag agtacaagtg caaggtgtcc | 720 |
| aacaaggccc tgcctgcccc catcgagaaa accatcagca aggccaaggg ccagcccaga | 780 |
| gaaccccagg tgtacacact gcccccagc agagaagaga tgaccaagaa ccaggtgtcc | 840 |
| ctgacctgcc tggtcaaggg cttctacccc agcgatatcg ccgtggaatg ggagagcaac | 900 |
| ggccagcctg agaacaacta caagaccacc ccccctgtgc tggacagcga cggctcattc | 960 |
| ttcctgtaca gcaagctgac cgtggacaag agccggtggc agcagggcaa cgtgttcagc | 1020 |
| tgcagcgtga tgcacgaggc cctgcacaac cactacaccc agaagtccct gagcctgagc | 1080 |
| cccggcaaga tgcagatctt cgtgaaaacc ctgaccggca gaccatcac cctggaagtg | 1140 |
| gaacccagcg acaccatcga aacgtgaag gccaagatcc aggacaaaga gggcatcccc | 1200 |
| cccgaccagc agagactgat cttcgccggc aagcagctgg aagatggcag acccctgagc | 1260 |
| gactacaaca tccagaaaga gtccacccctg cacctggtgc tgcggctgag aggcggaggt | 1320 |
| ggtggtggtt ctggtggcgg aggatctggc ggtggtggat ctggggagg tggaagtggt | 1380 |
| ggcggtggta gtatgcagat tttgtcaag acactgaccg ggaaaacaat cacactcgaa | 1440 |
| gtcgagccct ccgatacaat tgagaatgtg aaagccaaaa ttcaggacaa agaagggatt | 1500 |
| cctcctgatc agcagcggct gattttttgcc ggaaaacagc tcgaagatgg acggaccctg | 1560 |
| tccgattaca atattcagaa agaaagcacc ctccatctgg tcctgaggct gcggggaggc | 1620 |
| gacattcaga tgcacagtc ccccagctcc ctgagcgcca gcgtgggaga tcgcgtgacc | 1680 |
| attacctgca gagcctccca gtggatcggc atcctggtgg attggtatca gcagaaacct | 1740 |
| ggggaggctc taaactgct gatctattac gccagcttcc tgcagtccgg cgtgccctct | 1800 |

| | |
|---|---|
| agattcagcg gctctggctt cggcacagat ttcacactga ccatctctag cctgcaccct | 1860 |
| gaagattttg ccacatatta ctgtcagcag gccaaccctg cccccctgac atttggacag | 1920 |
| ggaacaaagg tcgagatcaa gcgcgagcct aagtcctgtg acaagacaca cacatgccct | 1980 |
| ccctgcccag ccccagaact gctcggtgga ccctctgtgt ttctgtttcc acccaagcct | 2040 |
| aaggatacac tcatgatctc cagaacacct gaagtgacat gtgtggtcgt cgacgtgtca | 2100 |
| catgaggatc cagaagtcaa gtttaactgg tatgtggatg gggtcgaggt gcacaatgcc | 2160 |
| aaaacaaaac ctcgggaaga acagtataat tccacctata gagtcgtgtc tgtgctcacc | 2220 |
| gtgctccatc aggattggct caatgggaaa gaatacaaat gtaaagtctc taacaaagcc | 2280 |
| ctgcccgctc ctatcgaaaa gacaatctcc aaggccaaag acagcctcg cgagcctcag | 2340 |
| gtctacaccc tgccaccttc ccgcgaggaa atgacaaaaa atcaggtgtc actcacctgt | 2400 |
| ctcgtgaagg ggttttaccc ctccgacatt gccgtcgagt gggagtccaa tggacagccc | 2460 |
| gagaacaatt ataagacaac acctcccgtc ctggactccg atggatcatt ttttctgtac | 2520 |
| tccaagctca ccgtcgataa gtccagatgg cagcagggaa atgtctttc ctgctccgtg | 2580 |
| atgcatgaag ctctccacaa tcattacaca cagaaaagcc tgtccctgtc ccccggcaag | 2640 |
| tgactcgag | 2649 |

<210> SEQ ID NO 61
<211> LENGTH: 2664
<212> TYPE: DNA
<213> ORGANISM: Artificial Sequence
<220> FEATURE:
<223> OTHER INFORMATION: Synthetic Nucleotide sequence encoding the
       protein complex comprising VEGF and EGFR specific binding
       peptides #17

<400> SEQUENCE: 61

| | |
|---|---|
| gaattcgcca ccatgggctg gtcctgcatc atcctgtttc tggtggccac cgccaccggc | 60 |
| gtgcactctg atatccagat gacccagagc cccagcagcc tgtctgcctc tgtgggcgac | 120 |
| agagtgacca tcacctgtcg ggccagccag aagatcttca cggcctgag ctggtatcag | 180 |
| cagaagcccg gcaaggcccc caagctgctg atctaccaca gcagcaccct gcagagcggc | 240 |
| gtgccaagca gatttctgg cagcggcagc ggcaccgact tcaccctgac aatcagcagc | 300 |
| ctgcagcccg aggacttcgc cacctactac tgccagcagg tcctgctgta ccctacaccc | 360 |
| tttggccagg gcaccaaggt ggaaatcaag agagagccca gagctgcga caagacccac | 420 |
| acctgtcccc cttgtcctgc ccctgaactg ctgggaggcc ctagcgtgtt cctgttcccc | 480 |
| ccaaagccca aggacaccct gatgatcagc cggacccccg aagtgacctg cgtggtggtg | 540 |
| gatgtgtccc acgaggaccc tgaagtgaag ttcaattggt acgtggacgg cgtggaagtg | 600 |
| cacaacgcca agaccaagcc cagagaggaa cagtacaaca gcacctaccg ggtggtgtcc | 660 |
| gtgctgacag tgctgcacca ggactggctg aacggcaaag agtacaagtg caaggtgtcc | 720 |
| aacaaggccc tgcctgcccc catcgagaaa accatcagca aggccaaggg ccagcccaga | 780 |
| gaaccccagg tgtacacact gcccccagc agagaagaga tgaccaagaa ccaggtgtcc | 840 |
| ctgacctgcc tggtcaaggg cttctacccc agcgatatcg ccgtggaatg ggagagcaac | 900 |
| ggccagcctg agaacaacta caagaccacc ccccctgtgc tggacagcga cggctcattc | 960 |
| ttcctgtaca gcaagctgac cgtggacaag agccggtggc agcagggcaa cgtgttcagc | 1020 |
| tgcagcgtga tgcacgaggc cctgcacaac cactacaccc agaagtccct gagcctgagc | 1080 |

```
cccggcaaga tgcagatctt cgtgaaaacc ctgaccggca agaccatcac cctggaagtg   1140
gaacccagcg acaccatcga gaacgtgaag gccaagatcc aggacaaaga gggcatcccc   1200
cccgaccagc agagactgat cttcgccggc aagcagctgg aagatggcag aaccctgagc   1260
gactacaaca tccagaaaga gtccacccTg cacctggtgc tgcggctgag aggcggaggt   1320
ggtggtggtt ctggtggcgg aggatctggc ggtggtggat ctggggaggg tggaagtggt   1380
ggcggtggta gtggtggtgg cggaagcatg cagatttttg tcaagacact gaccgggaaa   1440
acaatcacac tcgaagtcga gccctccgat acaattgaga atgtgaaagc caaaattcag   1500
gacaaagaag ggattcctcc tgatcagcag cggctgattt tgccggaaac acagctcgaa   1560
gatggacgga ccctgtccga ttacaatatt cagaaagaaa gcaccctcca tctggtcctg   1620
aggctgcggg gaggcgacat tcagatgaca cagtccccca gctccctgag cgccagcgtg   1680
ggagatcgcg tgaccattac ctgcagagcc tcccagtgga tcgcatcct ggtggattgg   1740 tatcagcaga aacctgggga ggctcctaaa ctgctgatct attacgccag cttcctgcag   1800
tccggcgtgc cctctagatt cagcggctct ggcttcggca cagatttcac actgaccatc   1860
tctagcctgc accctgaaga ttttgccaca tattactgtc agcaggccaa ccctgccccc   1920
ctgacatttg gacagggaac aaaggtcgag atcaagcgcg agcctaagtc ctgtgacaag   1980
acacacacat gccctcc ctg cccagcccca gaactgctcg gtgga ccctc tgtgtttctg   2040 tttccaccca gcctaagga tacactcatg atctccagaa cacctgaagt gacatgtgtg   2100
gtcgtcgacg tgtcacatga ggatccagaa gtcaagttta actggtatgt ggatggggtc   2160
gaggtgcaca atgccaaaac aaaacctcgg gaagaacagt ataattccac ctatagagtc   2220
gtgtctgtgc tcaccgtgct ccatcaggat tggctcaatg gaaagaata caaatgtaaa   2280 gtctctaaca agccctgcc cgctcctatc gaaaagacaa tctccaaggc caaggacag   2340 cctcgcgagc ctcaggtcta caccctgcca ccttcccgcg aggaaatgac aaaaaatcag   2400
gtgtcactca cctgtctcgt gaaggggttt taccccctccg acattgccgt cgagtgggag   2460
tccaatggac agcccgagaa caattataag acaacacctc ccgtcctgga ctccgatgga   2520 tcatttttc tgtactccaa gctcaccgtc gataagtcca gatggcagca gggaaatgtc   2580
ttttcctgct ccgtgatgca tgaagctctc cacaatcatt acacacagaa aagcctgtcc   2640 ctgtccccg caagtgact cgag                                            2664
```

<210> SEQ ID NO 62
<211> LENGTH: 2679
<212> TYPE: DNA
<213> ORGANISM: Artificial Sequence
<220> FEATURE:
<223> OTHER INFORMATION: Synthetic Nucleotide sequence encoding the
      protein complex comprising VEGF and EGFR specific binding
      peptides #18

<400> SEQUENCE: 62

```
gaattcgcca ccatgggctg gtcctgcatc atcctgtttc tggtggccac cgccaccggc     60
gtgcactctg atatccagat gacccagagc cccagcagcc tgtctgcctc tgtgggcgac    120
agagtgacca tcacctgtcg ggccagccag aagatcttca cggcctgag ctggtatcag    180 cagaagcccg gcaaggcccc caagctgctg atctaccaca gcagcaccct gcagagcggc    240
gtgccaagca gattttctgg cagcggcagc ggcaccgact tcaccctgac aatcagcagc    300
ctgcagcccg aggacttcgc cacctactac tgccagcagg cctgctgta ccctacacc    360 tttggccagg gcaccaaggt ggaaatcaag agagagccca gagctgcga caagacccac    420
```

```
acctgtcccc cttgtcctgc ccctgaactg ctgggaggcc ctagcgtgtt cctgttcccc    480
ccaaagccca aggacaccct gatgatcagc cggaccccg aagtgacctg cgtggtggtg    540
gatgtgtccc acgaggaccc tgaagtgaag ttcaattggt acgtggacgg cgtggaagtg    600
cacaacgcca agaccaagcc cagagaggaa cagtacaaca gcacctaccg ggtggtgtcc    660
gtgctgacag tgctgcacca ggactggctg aacggcaaag agtacaagtg caaggtgtcc    720
aacaaggccc tgcctgcccc catcgagaaa accatcagca aggccaaggg ccagcccaga    780 gaacccagg tgtacacact gccccccagc agagaagaga tgaccaagaa ccaggtgtcc    840
ctgacctgcc tggtcaaggg cttctacccc agcgatatcg ccgtggaatg ggagagcaac    900
ggccagcctg agaacaacta caagaccacc cccctgtgc tggacagcga cggctcattc    960
ttcctgtaca gcaagctgac cgtggacaag agccggtggc agcagggcaa cgtgttcagc    1020
tgcagcgtga tgcacgaggc cctgcacaac cactacaccc agaagtccct gagcctgagc    1080
cccggcaaga tgcagatctt cgtgaaaacc ctgaccggca agaccatcac cctggaagtg    1140
gaacccagcg acaccatcga gaacgtgaag gccaagatcc aggacaaaga gggcatcccc    1200
cccgaccagc agagactgat cttcgccggc aagcagctgg aagatggcag aaccctgagc    1260
gactacaaca tccagaaaga gtccaccctg cacctggtgc tgcggctgag aggcggaggt    1320
ggtggtggtt ctggtggcgg aggatctggc ggtggtggat ctgggggagg tggaagtggt    1380
ggcggtggta gtggtggtgg cggaagcgga ggcggtggat caatgcagat ttttgtcaag    1440
acactgaccg ggaaaacaat cacactcgaa gtcgagccct ccgatacaat tgagaatgtg    1500
aaagccaaaa ttcaggacaa agaagggatt cctcctgatc agcagcggct gattttgcc    1560 ggaaaacagc tcgaagatgg acggaccctg tccgattaca atattcagaa agaaagcacc    1620
ctccatctgg tcctgaggct gcggggaggc gacattcaga tgacacagtc ccccagctcc    1680
ctgagcgcca gcgtgggaga tcgcgtgacc attacctgca gagcctccca gtggatcggc    1740
atcctggtgg attggtatca gcagaaacct ggggaggctc ctaaaactgct gatctattac    1800 gccagcttcc tgcagtccgg cgtgccctct agattcagcg gctctggctt cggcacagat    1860
ttcacactga ccatctctag cctgcaccct gaagattttg ccacatatta ctgtcagcag    1920
gccaaccctg ccccctgac atttggacag ggaacaaagg tcgagatcaa gcgcgagcct    1980
aagtcctgtg acaagacaca cacatgccct cctgcccag ccccagaact gctcggtgga    2040
ccctctgtgt ttctgtttcc acccaagcct aaggatacac tcatgatctc cagaacacct    2100
gaagtgacat gtgtggtcgt cgacgtgtca catgaggatc cagaagtcaa gtttaactgg    2160
tatgtggatg gggtcgaggt gcacaatgcc aaaacaaaac tcgggaaga acagtataat    2220 tccacctata gagtcgtgtc tgtgctcacc gtgctccatc aggattggct caatgggaaa    2280
gaatacaaat gtaaagtctc taacaaagcc ctgcccgctc ctatcgaaaa gacaatctcc    2340
aaggccaaag acagcctccg cgagcctcag gtctacaccc tgccaccttc ccgcgaggaa    2400
atgacaaaaa atcaggtgtc actcacctgt ctcgtgaagg ggttttaccc ctccgacatt    2460
gccgtcgagt gggagtccaa tggacagccc gagaacaatt ataagacaac acctcccgtc    2520
ctggactccg atggatcatt ttttctgtac tccaagctca ccgtcgataa gtccagatgg    2580
cagcagggaa atgtcttttc ctgctccgtg atgcatgaag ctctccacaa tcattacaca    2640
cagaaaagcc tgtccctgtc ccccggcaag tgactcgag                          2679
```

<210> SEQ ID NO 63

<211> LENGTH: 2694
<212> TYPE: DNA
<213> ORGANISM: Artificial Sequence
<220> FEATURE:
<223> OTHER INFORMATION: Synthetic Nucleotide sequence encoding the
      protein complex comprising VEGF and EGFR specific binding
      peptides #19

<400> SEQUENCE: 63

| | | | | | |
|---|---|---|---|---|---|
| gaattcgcca | ccatgggctg | gtcctgcatc | atcctgtttc | tggtggccac | cgccaccggc | 60 |
| gtgcactctg | atatccagat | gacccagagc | cccagcagcc | tgtctgcctc | tgtgggcgac | 120 |
| agagtgacca | tcacctgtcg | ggccagccag | aagatcttca | cggcctgag | ctggtatcag | 180 |
| cagaagcccg | gcaaggcccc | caagctgctg | atctaccaca | gcagcaccct | gcagagcggc | 240 |
| gtgccaagca | gattttctgg | cagcggcagc | ggcaccgact | tcaccctgac | aatcagcagc | 300 |
| ctgcagcccg | aggacttcgc | cacctactac | tgccagcagg | tcctgctgta | ccctacacc | 360 |
| tttggccagg | gcaccaaggt | ggaaatcaag | agagagccca | gagctgcga | caagacccac | 420 |
| acctgtcccc | cttgtcctgc | ccctgaactg | ctgggaggcc | ctagcgtgtt | cctgttcccc | 480 |
| ccaaagccca | aggacaccct | gatgatcagc | cggaccccg | aagtgacctg | cgtggtggtg | 540 |
| gatgtgtccc | acgaggaccc | tgaagtgaag | ttcaattggt | acgtggacgg | cgtggaagtg | 600 |
| cacaacgcca | agaccaagcc | cagagaggaa | cagtacaaca | gcacctaccg | ggtggtgtcc | 660 |
| gtgctgacag | tgctgcacca | ggactggctg | aacggcaaag | agtacaagtg | caaggtgtcc | 720 |
| aacaaggccc | tgcctgcccc | catcgagaaa | accatcagca | aggccaaggg | ccagcccaga | 780 |
| gaacccagg | tgtacacact | gcccccagc | agagaagaga | tgaccaagaa | ccaggtgtcc | 840 |
| ctgacctgcc | tggtcaaggg | cttctacccc | agcgatatcg | ccgtggaatg | ggagagcaac | 900 |
| ggccagcctg | agaacaacta | caagaccacc | ccccctgtgc | tggacagcga | cggctcattc | 960 |
| ttcctgtaca | gcaagctgac | cgtggacaag | agccggtggc | agcagggcaa | cgtgttcagc | 1020 |
| tgcagcgtga | tgcacgaggc | cctgcacaac | cactacaccc | agaagtccct | gagcctgagc | 1080 |
| cccggcaaga | tgcagatctt | cgtgaaaacc | ctgaccggca | agaccatcac | cctggaagtg | 1140 |
| gaacccagcg | acaccatcga | gaacgtgaag | gccaagatcc | aggacaaaga | gggcatcccc | 1200 |
| cccgaccagc | agagactgat | cttcgccggc | aagcagctgg | aagatggcag | aaccctgagc | 1260 |
| gactacaaca | tccagaaaga | gtccaccctg | cacctggtgc | tgcggctgag | aggcggaggt | 1320 |
| ggtggtggtt | ctggtggcgg | aggatctggc | ggtggtggat | ctggggagg | tggaagtggt | 1380 |
| ggcggtggta | gtggtggtgg | cggaagcgga | ggcggtggat | caggcggagg | cggatcaatg | 1440 |
| cagattttg | tcaagacact | gaccgggaaa | acaatcacac | tcgaagtcga | gccctccgat | 1500 |
| acaattgaga | atgtgaaagc | caaaattcag | gacaaagaag | ggattcctcc | tgatcagcag | 1560 |
| cggctgattt | ttgccggaaa | acagctcgaa | gatggacgga | ccctgtccga | ttacaatatt | 1620 |
| cagaaagaaa | gcaccctcca | tctggtcctg | aggctgcggg | gaggcgacat | tcagatgaca | 1680 |
| cagtccccca | gctccctgag | cgccagcgtg | ggagatcgcg | tgaccattac | ctgcagagcc | 1740 |
| tcccagtgga | tcggcatcct | ggtggattgg | tatcagcaga | aacctgggga | ggctcctaaa | 1800 |
| ctgctgatct | attaccgcag | cttcctgcag | tccggcgtgc | cctctagatt | cagcggctct | 1860 |
| ggcttcggca | cagatttcac | actgaccatc | tctagcctgc | accctgaaga | ttttgccaca | 1920 |
| tattactgtc | agcaggccaa | ccctgccccc | ctgacatttg | gacagggaac | aaaggtcgag | 1980 |
| atcaagcgcg | agcctaagtc | ctgtgacaag | acacacacat | gccctccctg | cccagcccca | 2040 |
| gaactgctcg | gtgaccctc | tgtgtttctg | tttccaccca | agcctaagga | tacactcatg | 2100 |

```
atctccagaa cacctgaagt gacatgtgtg gtcgtcgacg tgtcacatga ggatccagaa    2160
gtcaagttta actggtatgt ggatggggtc gaggtgcaca atgccaaaac aaaacctcgg    2220
gaagaacagt ataattccac ctatagagtc gtgtctgtgc tcaccgtgct ccatcaggat    2280
tggctcaatg ggaaagaata caaatgtaaa gtctctaaca agccctgcc cgctcctatc     2340 gaaaagacaa tctccaaggc caaggacag cctcgcgagc ctcaggtcta caccctgcca     2400
ccttcccgcg aggaaatgac aaaaaatcag gtgtcactca cctgtctcgt gaaggggttt    2460 taccccctccg acattgccgt cgagtgggag tccaatggac agcccgagaa caattataag    2520
acaacacctc ccgtcctgga ctccgatgga tcattttttc tgtactccaa gctcaccgtc    2580
gataagtcca gatggcagca gggaaatgtc tttctgcct ccgtgatgca tgaagctctc     2640
cacaatcatt acacacagaa aagcctgtcc ctgtcccccg gcaagtgact cgag           2694
```

<210> SEQ ID NO 64
<211> LENGTH: 2709
<212> TYPE: DNA
<213> ORGANISM: Artificial Sequence
<220> FEATURE:
<223> OTHER INFORMATION: Synthetic Nucleotide sequence encoding the
      protein complex comprising VEGF and EGFR specific binding
      peptides #20

<400> SEQUENCE: 64

```
gaattcgcca ccatgggctg gtcctgcatc atcctgtttc tggtggccac cgccaccggc      60
gtgcactctg atatccagat gacccagagc cccagcagcc tgtctgcctc tgtgggcgac     120
agagtgacca tcacctgtcg ggccagccag aagatcttca acggcctgag ctggtatcag     180
cagaagcccg gcaaggcccc caagctgctg atctaccaca gcagcaccct gcagagcggc     240
gtgccaagca gatttttctgg cagcggcagc ggcaccgact cacccctgac aatcagcagc     300
ctgcagcccg aggacttcgc cacctactac tgccagcagg tcctgctgta ccccta cacc     360 tttggccagg gcaccaaggt ggaaatcaag agagagccca gagctgcga caagacccac     420 acctgtcccc cttgtcctgc ccctgaactg ctgggaggcc ctagcgtgtt cctgttcccc     480
ccaaagccca aggacaccct gatgatcagc cggacccccg aagtgacctg cgtggtggtg     540
gatgtgtccc acgaggaccc tgaagtgaag ttcaattggt acgtggacgg cgtggaagtg     600
cacaacgcca agaccaagcc cagagaggaa cagtacaaca gcacctaccg ggtggtgtcc     660
gtgctgacag tgctgcacca ggactggctg aacggcaaag agtacaagtg caaggtgtcc     720
aacaaggccc tgcctgcccc catcgagaaa accatcagca aggccaaggg ccagcccaga     780 gaacccagg tgtacacact gcccccagc agagaagaga tgaccaagaa ccaggtgtcc      840
ctgacctgcc tggtcaaggg cttctacccc agcgatatcg ccgtggaatg ggagagcaac     900
ggccagcctg agaacaacta caagaccacc ccccctgtgc tggacagcga cggctcattc     960
ttcctgtaca gcaagctgac cgtggacaag agccggtggc agcagggcaa cgtgttcagc    1020
tgcagcgtga tgcacgaggc cctgcacaac cactacaccc agaagtccct gagcctgagc    1080
cccggcaaga tgcagatctt cgtgaaaacc ctgaccggca agaccatcac cctggaagtg    1140
gaacccagcg acaccatcga gaacgtgaag gccaagatcc aggacaaaga gggcatcccc    1200
cccgaccagc agagactgat cttcgccggc aagcagctgg aagatggcag aaccctgagc    1260
gactacaaca tccagaaaga gtccacccctg cacctggtgc tgcggctgag aggcggaggt    1320
ggtggtggtt ctggtggcgg aggatctggc ggtggtggat ctgggggagg tggaagtggt    1380
```

-continued

```
ggcggtggta gtggtggtgg cggaagcgga ggcggtggat caggcggagg cggatcaggt     1440
ggcgggggtt caatgcagat ttttgtcaag acactgaccg ggaaaacaat cacactcgaa     1500
gtcgagccct ccgatacaat tgagaatgtg aaagccaaaa ttcaggacaa agaagggatt     1560
cctcctgatc agcagcggct gattttttgcc ggaaaacagc tcgaagatgg acggaccctg    1620
tccgattaca atattcagaa agaaagcacc ctccatctgg tcctgaggct gcggggaggc    1680
gacattcaga tgacacagtc ccccagctcc ctgagcgcca gcgtgggaga tcgcgtgacc    1740
attacctgca gagcctccca gtggatcggc atcctggtgg attggtatca gcagaaacct    1800
ggggaggctc ctaaactgct gatctattac gccagcttcc tgcagtccgg cgtgccctct    1860
agattcagcg gctctggctt cggcacagat ttcacactga ccatctctag cctgcaccct    1920
gaagattttg ccacatatta ctgtcagcag gccaaccctg ccccctgac atttggacag     1980 ggaacaaagg tcgagatcaa gcgcgagcct aagtcctgtg acaagacaca cacatgccct    2040
ccctgcccag ccccagaact gctcggtgga ccctctgtgt tctgtttcc acccaagcct     2100 aaggatacac tcatgatctc cagaacacct gaagtgacat gtgtggtcgt cgacgtgtca    2160
catgaggatc cagaagtcaa gtttaactgg tatgtggatg gggtcgaggt gcacaatgcc    2220
aaaacaaaac ctcgggaaga acagtataat tccacctata gagtcgtgtc tgtgctcacc    2280
gtgctccatc aggattggct caatgggaaa gaatacaaat gtaaagtctc taacaaagcc    2340
ctgcccgctc ctatcgaaaa gacaatctcc aaggccaaag acagcctcg cgagcctcag     2400 gtctacaccc tgccaccttc ccgcgaggaa atgacaaaaa tcaggtgtc actcacctgt     2460 ctcgtgaagg ggttttaccc ctccgacatt gccgtcgagt gggagtccaa tggacagccc    2520
gagaacaatt ataagacaac acctcccgtc ctggactccg atggatcatt ttttctgtac    2580
tccaagctca ccgtcgataa gtccagatgg cagcagggaa atgtctttc ctgctccgtg     2640 atgcatgaag ctctccacaa tcattacaca cagaaaagcc tgtccctgtc ccccggcaag    2700
tgactcgag                                                            2709
```

<210> SEQ ID NO 65
<211> LENGTH: 2724
<212> TYPE: DNA
<213> ORGANISM: Artificial Sequence
<220> FEATURE:
<223> OTHER INFORMATION: Synthetic Nucleotide sequence encoding the protein complex comprising VEGF and EGFR specific binding peptides #21

<400> SEQUENCE: 65

```
gaattcgcca ccatgggctg gtcctgcatc atcctgtttc tggtggccac cgccaccggc     60
gtgcactctg atatccagat gacccagagc cccagcagcc tgtctgcctc tgtgggcgac    120
agagtgacca tcacctgtcg ggccagccag aagatcttca cggcctgag ctggtatcag    180 cagaagcccg gcaaggcccc caagctgctg atctaccaca gcagcaccct gcagagcggc    240
gtgccaagca gattttctgg cagcggcagc ggcaccgact tcaccctgac aatcagcagc    300
ctgcagcccg aggacttcgc cacctactac tgccagcagg tcctgctgta ccctacacc     360 tttggccagg gcaccaaggt ggaaatcaag agagagccca gagctgcga caagacccac    420 acctgtcccc cttgtcctgc cctgaactg ctgggaggcc ctagcgtgtt cctgttcccc    480
ccaaagccca aggacaccct gatgatcagc cggacccccg aagtgacctg cgtggtggtg    540
gatgtgtccc acgaggaccc tgaagtgaag ttcaattggt acgtggacgg cgtggaagtg    600
cacaacgcca agaccaagcc cagagaggaa cagtacaaca gcacctaccg ggtggtgtcc    660
```

```
gtgctgacag tgctgcacca ggactggctg aacggcaaag agtacaagtg caaggtgtcc    720
aacaaggccc tgcctgcccc catcgagaaa accatcagca aggccaaggg ccagcccaga    780 gaacccagg tgtacacact gccccccagc agagaagaga tgaccaagaa ccaggtgtcc    840
ctgacctgcc tggtcaaggg cttctacccc agcgatatcg ccgtggaatg ggagagcaac    900
ggccagcctg agaacaacta caagaccacc cccctgtgc tggacagcga cggctcattc    960
ttcctgtaca gcaagctgac cgtggacaag agccggtggc agcagggcaa cgtgttcagc   1020
tgcagcgtga tgcacgaggc cctgcacaac cactacaccc agaagtccct gagcctgagc   1080
cccggcaaga tgcagatctt cgtgaaaacc ctgaccggca agaccatcac cctggaagtg   1140
gaacccagcg acaccatcga aacgtgaag gccaagatcc aggacaaaga gggcatcccc   1200
cccgaccagc agagactgat cttcgccggc aagcagctgg aagatggcag aaccctgagc   1260
gactacaaca tccagaaaga gtccaccctg cacctggtgc tgcggctgag aggcggaggt   1320
ggtggtggtt ctggtggcgg aggatctggc ggtggtggat ctgggggagg tggaagtggt   1380
ggcggtggta gtggtggtgg cggaagcgga ggcggtggat caggcggagg cggatcaggt   1440 ggcggggtt caggggtgg cggaagtatg cagattttg tcaagacact gaccgggaaa   1500
acaatcacac tcgaagtcga gccctccgat acaattgaga atgtgaaagc caaaattcag   1560
gacaaagaag ggattcctcc tgatcagcag cggctgattt ttgccggaaa acagctcgaa   1620
gatggacgga ccctgtccga ttacaatatt cagaaagaaa gcaccctcca tctggtcctg   1680
aggctgcggg gaggcgacat tcagatgaca cagtcccccca gctccctgag cgccagcgtg   1740
ggagatcgcg tgaccattac ctgcagagcc tccagtggaa tcggcatcct ggtggattgg   1800
tatcagcaga aacctgggga ggctcctaaa ctgctgatct attacgccag cttcctgcag   1860
tccggcgtgc cctctagatt cagcggctct ggcttcggca cagatttcac actgaccatc   1920
tctagcctgc accctgaaga ttttgccaca tattactgtc agcaggccaa ccctgccccc   1980
ctgacatttg gacagggaac aaaggtcgag atcaagcgcg agcctaagtc ctgtgacaag   2040
acacacacat gcctccctg cccagcccca gaactgctcg gtggaccctc tgtgtttctg   2100
tttccaccca gcctaagga tacactcatg atctccagaa cacctgaagt gacatgtgtg   2160
gtcgtcgacg tgtcacatga ggatccagaa gtcaagttta actggtatgt ggatggggtc   2220
gaggtgcaca atgccaaaac aaaacctcgg gaagaacagt ataattccac ctatagagtc   2280
gtgtctgtgc tcaccgtgct ccatcaggat tggctcaatg gaaagaata caatgtaaa   2340 gtctctaaca agccctgcc cgctcctatc gaaaagacaa tctccaaggc caaggacag   2400 cctcgcgagc ctcaggtcta caccctgcca ccttcccgcg aggaaatgac aaaaaatcag   2460
gtgtcactca cctgtctcgt gaaggggttt taccctccg acattgccgt cgagtgggag   2520
tccaatggac agcccgagaa caattataag acaacacctc ccgtcctgga ctccgatgga   2580 tcatttttttc tgtactccaa gctcaccgtc gataagtcca gatggcagca gggaaatgtc   2640
ttttcctgct ccgtgatgca tgaagctctc cacaatcatt acacacagaa aagcctgtcc   2700 ctgtccccccg gcaagtgact cgag                                         2724
```

<210> SEQ ID NO 66
<211> LENGTH: 2634
<212> TYPE: DNA
<213> ORGANISM: Artificial Sequence
<220> FEATURE:
<223> OTHER INFORMATION: Synthetic Nucleotide sequence encoding the
    protein complex comprising VEGF and EGFR specific binding peptides #22

<400> SEQUENCE: 66

| | | | | | |
|---|---|---|---|---|---|
| gaattcgcca | ccatgggctg | gtcctgcatc | atcctgtttc | tggtggccac | cgccaccggc | 60 |
| gtgcactctg | atatccagat | gacccagagc | cccagcagcc | tgtctgcctc | tgtgggcgac | 120 |
| agagtgacca | tcacctgtcg | ggccagccag | aagatcttca | acggcctgag | ctggtatcag | 180 |
| cagaagcccg | gcaaggcccc | caagctgctg | atctaccaca | gcagcaccct | gcagagcggc | 240 |
| gtgccaagca | gattttctgg | cagcggcagc | ggcaccgact | tcaccctgac | aatcagcagc | 300 |
| ctgcagcccg | aggacttcgc | cacctactac | tgccagcagg | tcctgctgta | ccccctacacc | 360 |
| tttggccagg | gcaccaaggt | ggaaatcaag | agagagccca | gagctgcga | caagacccac | 420 |
| acctgtcccc | cttgtcctgc | ccctgaactg | ctgggaggcc | tagcgtgtt | cctgttcccc | 480 |
| ccaaagccca | aggacaccct | gatgatcagc | cggacccccg | aagtgacctg | cgtggtggtg | 540 |
| gatgtgtccc | acgaggaccc | tgaagtgaag | ttcaattggt | acgtggacgg | cgtggaagtg | 600 |
| cacaacgcca | agaccaagcc | cagagaggaa | cagtacaaca | gcacctaccg | ggtggtgtcc | 660 |
| gtgctgacag | tgctgcacca | ggactggctg | aacggcaaag | agtacaagtg | caaggtgtcc | 720 |
| aacaaggccc | tgcctgcccc | catcgagaaa | accatcagca | aggccaaggg | ccagcccaga | 780 |
| gaacccagg | tgtacacact | gccccccagc | agagaagaga | tgaccaagaa | ccaggtgtcc | 840 |
| ctgacctgcc | tggtcaaggg | cttctacccc | agcgatatcg | ccgtggaatg | ggagagcaac | 900 |
| ggccagcctg | agaacaacta | caagaccacc | cccctgtgc | tggacagcga | cggctcattc | 960 |
| ttcctgtaca | gcaagctgac | cgtggacaag | agccggtggc | agcagggcaa | cgtgttcagc | 1020 |
| tgcagcgtga | tgcacgaggc | cctgcacaac | cactacaccc | agaagtccct | gagcctgagc | 1080 |
| cccggcaaga | tgcagatctt | cgtgaaaacc | ctgaccggca | agaccatcac | cctggaagtg | 1140 |
| gaacccagcg | acaccatcga | gaacgtgaag | gccaagatcc | aggacaaaga | gggcatcccc | 1200 |
| cccgaccagc | agagactgat | cttcgccggc | aagcagctgg | aagatggcag | aaccctgagc | 1260 |
| gactacaaca | tccagaaaga | gtccaccctg | cacctggtgc | tgcggctgag | aggcggaggt | 1320 |
| ggtggtggtt | ctggtggcgg | aggatctggc | ggtggtggat | ctgggggagg | tggaagtatg | 1380 |
| cagattttg | tcaagacact | gaccgggaaa | acaatcacac | tcgaagtcga | gccctccgat | 1440 |
| acaattgaga | atgtgaaagc | caaaattcag | gacaaagaag | ggattcctcc | tgatcagcag | 1500 |
| cggctgattt | ttgccggaaa | acagctcgaa | gatggacgga | ccctgtccga | ttacaatatt | 1560 |
| cagaaagaaa | gcaccctcca | tctggtcctg | aggctgcggg | gaggcgacat | tcagatgaca | 1620 |
| cagtccccca | cctccctgtc | tgccagcgtg | ggagatcgcg | tgaccattac | ctgcagagcc | 1680 |
| tcccagtgga | tcggcaacct | gctggattgg | tatcagcaga | aacctgggga | ggctcctaaa | 1740 |
| ctgctgatct | attacgccag | cttcctgcag | tccggcgtgc | cctctagatt | ttccggcgga | 1800 |
| ggcttcggca | cagatttcac | actgaccatc | tcatccctgc | agcctgaaga | ttttgccaca | 1860 |
| tattattgcc | agcaggccaa | ccctgccccc | ctgacatttg | gcagggaac | aaaggtcgag | 1920 |
| atcaagcgcg | agcctaagtc | ctgtgacaag | acacacacat | gccctccctg | cccagcccca | 1980 |
| gaactgctcg | gtggaccctc | tgtgtttctg | tttccaccca | agcctaagga | tacactcatg | 2040 |
| atctccagaa | cacctgaagt | gacatgtgtg | gtcgtcgacg | tgtcacatga | ggatccagaa | 2100 |
| gtcaagttta | actggtatgt | ggatggggtc | gaggtgcaca | atgccaaaac | aaaacctcgg | 2160 |
| gaagaacagt | ataattccac | ctatagagtc | gtgtctgtgc | tcaccgtgct | ccatcaggat | 2220 |
| tggctcaatg | gaaagaaata | caaatgtaaa | gtctctaaca | aagccctgcc | cgctcctatc | 2280 |

| gaaaagacaa tctccaaggc caaaggacag cctcgcgagc ctcaggtcta caccctgcca | 2340 |
| cctteccgcg aggaaatgac aaaaaatcag gtgtcactca cctgtctcgt gaagggttt | 2400 |
| taccctccg acattgccgt cgagtgggag tccaatggac agcccgagaa caattataag | 2460 |
| acaacacctc ccgtcctgga ctccgatgga tcattttttc tgtactccaa gctcaccgtc | 2520 |
| gataagtcca gatggcagca gggaaatgtc ttttcctgct ccgtgatgca tgaagctctc | 2580 |
| cacaatcatt acacacagaa aagcctgtcc ctgtccccg gcaagtgact cgag | 2634 |

<210> SEQ ID NO 67
<211> LENGTH: 2649
<212> TYPE: DNA
<213> ORGANISM: Artificial Sequence
<220> FEATURE:
<223> OTHER INFORMATION: Synthetic Nucleotide sequence encoding the
      protein complex comprising VEGF and EGFR specific binding
      peptides #23

<400> SEQUENCE: 67

| gaattcgcca ccatgggctg gtcctgcatc atcctgtttc tggtggccac cgccaccggc | 60 |
| gtgcactctg atatccagat gacccagagc cccagcagcc tgtctgcctc tgtgggcgac | 120 |
| agagtgacca tcacctgtcg ggccagccag aagatcttca cggcctgag ctggtatcag | 180 |
| cagaagcccg gcaaggcccc caagctgctg atctaccaca gcagcaccct gcagagcggc | 240 |
| gtgccaagca gattttctgg cagcggcagc ggcaccgact caccctgac aatcagcagc | 300 |
| ctgcagcccg aggacttcgc cacctactac tgccagcagg gcctgctgta ccctacacc | 360 |
| tttggccagg gcaccaaggt ggaaatcaag agagagccca gagctgcga caagacccac | 420 |
| acctgtcccc cttgtcctgc ccctgaactg ctgggaggcc ctagcgtgtt cctgttcccc | 480 |
| ccaaagccca aggacaccct gatgatcagc cggaccccg aagtgacctg cgtggtggtg | 540 |
| gatgtgtccc acgaggaccc tgaagtgaag ttcaattggt acgtggacgg cgtggaagtg | 600 |
| cacaacgcca agaccaagcc cagagaggaa cagtacaaca gcacctaccg ggtggtgtcc | 660 |
| gtgctgacag tgctgcacca ggactggctg aacggcaaag agtacaagtg caaggtgtcc | 720 |
| aacaaggccc tgcctgcccc catcgagaaa accatcagca aggccaaggg ccagcccaga | 780 |
| gaacccagg tgtacacact gccccccagc agagaagaga tgaccaagaa ccaggtgtcc | 840 |
| ctgacctgcc tggtcaaggg cttctacccc agcgatatcg ccgtggaatg ggagagcaac | 900 |
| ggccagcctg agaacaacta caagaccacc ccctgtgc tggacagcga cggctcattc | 960 |
| ttcctgtaca gcaagctgac cgtggacaag agccggtggc agcagggcaa cgtgttcagc | 1020 |
| tgcagcgtga tgcacgaggc cctgcacaac cactacaccc agaagtccct gagcctgagc | 1080 |
| cccggcaaga tgcagatctt cgtgaaaacc ctgaccggca gaccatcac cctggaagtg | 1140 |
| gaacccagcg acaccatcga gaacgtgaag gccaagatcc aggacaaaga gggcatcccc | 1200 |
| cccgaccagc agagactgat cttcgccggc aagcagctgg aagatggcag aaccctgagc | 1260 |
| gactacaaca tccagaaaga gtccacctg cacctggtgc tgcggctgag aggcggaggt | 1320 |
| ggtggtggtt ctggtggcgg aggatctggc ggtggtggat ctgggggagg tggaagtggt | 1380 |
| ggcggtggta gtatgcagat ttttgtcaag acactgaccg gaaaacaat cacactcgaa | 1440 |
| gtcgagccct ccgatacaat tgagaatgtg aaagccaaaa ttcaggacaa agaagggatt | 1500 |
| cctcctgatc agcagcggct gattttttgcc ggaaaacagc tcgaagatgg acggaccctg | 1560 |
| tccgattaca atattcagaa agaaagcacc ctccatctgg tcctgaggct gcggggaggc | 1620 |

-continued

```
gacattcaga tgacacagtc ccccacctcc ctgtctgcca gcgtgggaga tcgcgtgacc    1680
attacctgca gagcctccca gtggatcggc aacctgctgg attggtatca gcagaaacct    1740
ggggaggctc ctaaactgct gatctattac gccagcttcc tgcagtccgg cgtgccctct    1800
agattttccg gcggaggctt cggcacagat ttcacactga ccatctcatc cctgcagcct    1860
gaagattttg ccacatatta ttgccagcag gccaaccctg cccccctgac atttggacag    1920
ggaacaaagg tcgagatcaa gcgcgagcct aagtcctgtg acaagacaca cacatgccct    1980
ccctgcccag ccccagaact gctcggtgga ccctctgtgt ttctgtttcc acccaagcct    2040
aaggatacac tcatgatctc cagaacacct gaagtgacat gtgtggtcgt cgacgtgtca    2100
catgaggatc cagaagtcaa gtttaactgg tatgtggatg gggtcgaggt gcacaatgcc    2160
aaaacaaaac ctcgggaaga acagtataat tccacctata gagtcgtgtc tgtgctcacc    2220
gtgctccatc aggattggct caatgggaaa gaatacaaat gtaaagtctc taacaaagcc    2280
ctgcccgctc ctatcgaaaa gacaatctcc aaggccaaag acagcctcg cgagcctcag    2340
gtctacaccc tgccaccttc ccgcgaggaa atgacaaaaa tcaggtgtc actcacctgt    2400
ctcgtgaagg ggttttaccc ctccgacatt gccgtcgagt gggagtccaa tggacagccc    2460
gagaacaatt ataagacaac acctcccgtc ctggactccg atggatcatt ttttctgtac    2520
tccaagctca ccgtcgataa gtccagatgg cagcagggaa atgtcttttc ctgctccgtg    2580
atgcatgaag ctctccacaa tcattacaca cagaaaagcc tgtccctgtc ccccggcaag    2640
tgactcgag    2649
```

<210> SEQ ID NO 68
<211> LENGTH: 2664
<212> TYPE: DNA
<213> ORGANISM: Artificial Sequence
<220> FEATURE:
<223> OTHER INFORMATION: Synthetic Nucleotide sequence encoding the protein complex comprising VEGF and EGFR specific binding peptides #24

<400> SEQUENCE: 68

```
gaattcgcca ccatgggctg gtcctgcatc atcctgtttc tggtggccac cgccaccggc     60
gtgcactctg atatccagat gacccagagc cccagcagcc tgtctgcctc tgtgggcgac    120
agagtgacca tcacctgtcg ggccagccag aagatcttca acggcctgag ctggtatcag    180
cagaagcccg gcaaggcccc caagctgctg atctaccaca gcagcaccct gcagagcggc    240
gtgccaagca gattttctgg cagcggcagc ggcaccgact tcaccctgac aatcagcagc    300
ctgcagcccg aggacttcgc cacctactac tgccagcagg tcctgctgta cccctacacc    360
tttggccagg gcaccaaggt ggaaatcaag agagagccca agagctgcga caagacccac    420
acctgtcccc cttgtcctgc ccctgaactg ctgggaggcc ctagcgtgtt cctgttcccc    480
ccaaagccca aggacaccct gatgatcagc cggacccccg aagtgacctg cgtggtggtg    540
gatgtgtccc acgaggaccc tgaagtgaag ttcaattggt acgtggacgg cgtggaagtg    600
cacaacgcca agaccaagcc cagagaggaa cagtacaaca gcacctaccg ggtggtgtcc    660
gtgctgacag tgctgcacca ggactggctg aacggcaaag agtacaagtg caaggtgtcc    720
aacaaggccc tgcctgcccc catcgagaaa accatcagca aggccaaggg ccagcccaga    780
gaaccccagg tgtacacact gccccccagc agagaagaga tgaccaagaa ccaggtgtcc    840
ctgacctgcc tggtcaaggg cttctacccc agcgatatcg ccgtggaatg ggagagcaac    900
ggccagcctg agaacaacta caagaccacc ccccctgtgc tggacagcga cggctcattc    960
```

```
ttcctgtaca gcaagctgac cgtggacaag agccggtggc agcagggcaa cgtgttcagc    1020
tgcagcgtga tgcacgaggc cctgcacaac cactacaccc agaagtccct gagcctgagc    1080
cccggcaaga tgcagatctt cgtgaaaacc ctgaccggca agaccatcac cctggaagtg    1140
gaacccagcg acaccatcga gaacgtgaag gccaagatcc aggacaaaga gggcatcccc    1200
cccgaccagc agagactgat cttcgccggc aagcagctgg aagatggcag aaccctgagc    1260
gactacaaca tccagaaaga gtccaccctg cacctggtgc tgcggctgag aggcggaggt    1320
ggtggtggtt ctggtggcgg aggatctggc ggtggtggat ctggggagg tggaagtggt    1380 ggcggtggta gtggtggtgg cggaagcatg cagattttg tcaagacact gaccgggaaa    1440
acaatcacac tcgaagtcga gccctccgat acaattgaga atgtgaaagc caaaattcag    1500
gacaaagaag ggattcctcc tgatcagcag cggctgattt ttgccggaaa acagctcgaa    1560
gatggacgga ccctgtccga ttacaatatt cagaaagaaa gcaccctcca tctggtcctg    1620
aggctgcggg gaggcgacat tcagatgaca cagtccccca cctccctgtc tgccagcgtg    1680
ggagatcgcg tgaccattac ctgcagagcc tcccagtgga tcggcaacct gctggattgg    1740
tatcagcaga aacctgggga ggctcctaaa ctgctgatct attacgccag cttcctgcag    1800
tccggcgtgc cctctagatt ttccggcgga ggcttcggca cagatttcac actgaccatc    1860
tcatccctgc agcctgaaga ttttgccaca tattattgcc agcaggccaa ccctgccccc    1920
ctgacatttg acagggaac aaaggtcgag atcaagcgcg agcctaagtc ctgtgacaag    1980
acacacacat gccctcctg cccagcccca gaactgctcg gtggaccctc tgtgtttctg    2040 tttccacccca agcctaagga tacactcatg atctccagaa cacctgaagt gacatgtgtg    2100
gtcgtcgacg tgtcacatga ggatccgaaa gtcaagttta actggtatgt ggatggggtc    2160
gaggtgcaca atgccaaaac aaaaacctcgg gaagaacagt ataattccac ctatagagtc    2220
gtgtctgtgc tcaccgtgct ccatcaggat tggctcaatg ggaaagaata caaatgtaaa    2280
gtctctaaca agcccctgcc cgctcctatc gaaaagacaa tctccaaggc caaggacag    2340 cctcgcgagc ctcaggtcta caccctgcca ccttcccgcg aggaaatgac aaaaaatcag    2400
gtgtcactca cctgtctcgt gaagggttt taccctccg acattgccgt cgagtgggag    2460
tccaatggac agcccgagaa caattataag acaacacctc ccgtcctgga ctccgatgga    2520 tcatttttttc tgtactccaa gctcaccgtc gataagtcca gatggcagca gggaaatgtc    2580
ttttcctgct ccgtgatgca tgaagctctc cacaatcatt acacacagaa aagcctgtcc    2640
ctgtcccccg gcaagtgact cgag                                         2664
```

<210> SEQ ID NO 69
<211> LENGTH: 2679
<212> TYPE: DNA
<213> ORGANISM: Artificial Sequence
<220> FEATURE:
<223> OTHER INFORMATION: Synthetic Nucleotide sequence encoding the
      protein complex comprising VEGF and EGFR specific binding
      peptides #25

<400> SEQUENCE: 69

```
gaattcgcca ccatgggctg gtcctgcatc atcctgtttc tggtggccac cgccaccggc     60
gtgcactctg atatccagat gacccagagc ccagcagcc tgtctgcctc tgtgggcgac    120
agagtgacca tcacctgtcg ggccagccag aagatcttca cggcctgag ctggtatcag    180 cagaagcccg gcaaggcccc caagctgctg atctaccaca gcagcaccct gcagagcggc    240
```

-continued

```
gtgccaagca gattttctgg cagcggcagc ggcaccgact tcaccctgac aatcagcagc    300
ctgcagcccg aggacttcgc cacctactac tgccagcagg tcctgctgta ccctacacc     360 tttggccagg gcaccaaggt ggaaatcaag agagagccca gagctgcga caagacccac    420 acctgtcccc cttgtcctgc ccctgaactg ctgggaggcc tagcgtgtt cctgttcccc    480 ccaaagccca aggacaccct gatgatcagc cggaccccg aagtgacctg cgtggtggtg    540
gatgtgtccc acgaggaccc tgaagtgaag ttcaattggt acgtggacgg cgtggaagtg    600
cacaacgcca agaccaagcc cagagaggaa cagtacaaca gcacctaccg ggtggtgtcc    660
gtgctgacag tgctgcacca ggactggctg aacggcaaag agtacaagtg caaggtgtcc    720
aacaaggccc tgcctgcccc catcgagaaa accatcagca aggccaaggg ccagcccaga    780 gaacccagg tgtacacact gcccccagc agagaagaga tgaccaagaa ccaggtgtcc    840
ctgacctgcc tggtcaaggg cttctacccc agcgatatcg ccgtggaatg ggagagcaac    900
ggccagcctg agaacaacta caagaccacc cccctgtgc tggacagcga cggctcattc    960
ttcctgtaca gcaagctgac cgtggacaag agccggtggc agcagggcaa cgtgttcagc   1020
tgcagcgtga tgcacgaggc cctgcacaac cactacaccc agaagtccct gagcctgagc   1080
cccggcaaga tgcagatctt cgtgaaaacc ctgaccggca agaccatcac cctggaagtg   1140
gaacccagcg acaccatcga gaacgtgaag gccaagatcc aggacaaaga gggcatcccc   1200
cccgaccagc agagactgat cttcgccggc aagcagctgg aagatggcag aaccctgagc   1260
gactacaaca tccagaaaga gtccaccctg cacctggtgc tgcggctgag aggcggaggt   1320
ggtggtggtt ctggtggcgg aggatctggc ggtggtggat ctgggggagg tggaagtggt   1380
ggcggtggta gtggtggtgg cggaagcgga ggcggtggat caatgcagat ttttgtcaag   1440
acactgaccg gaaaacaat cacactcgaa gtcgagccct ccgatacaat tgagaatgtg   1500
aaagccaaaa ttcaggacaa agaagggatt cctcctgatc agcagcggct gattttttgcc   1560 ggaaaacagc tcgaagatgg acggaccctg tccgattaca atattcagaa agaaagcacc   1620
ctccatctgg tcctgaggct gcggggaggc gacattcaga tgacacagtc ccccacctcc   1680
ctgtctgcca gcgtgggaga tcgcgtgacc attacctgca gagcctccca gtggatcggc   1740
aacctgctgg attggtatca gcagaaacct ggggaggctc ctaaactgct gatctattac   1800
gccagcttcc tgcagtccgg cgtgccctct agatttcccg gcggaggctt cggcacagat   1860
ttcacactga ccatctcatc cctgcagcct gaagattttg ccacatatta ttgccagcag   1920
gccaaccctg ccccctgac atttggacag ggaacaaagg tcgagatcaa gcgcgagcct   1980
aagtcctgtg acaagacaca cacatgccct ccctgcccag cccagaact gctcggtgga   2040 ccctctgtgt ttctgttccc acccaagcct aaggatacac tcatgatctc cagaacacct   2100
gaagtgacat gtgtggtcgt cgacgtgtca catgaggatc cagaagtcaa gtttaactgg   2160
tatgtggatg gggtcgaggt gcacaatgcc aaaacaaaac tcgggaaga acagtataat   2220 tccacctata gagtcgtgtc tgtgctcacc gtgctccatc aggattggct caatgggaaa   2280
gaatacaaat gtaaagtctc taacaaagcc ctgcccgctc ctatcgaaaa gacaatctcc   2340
aaggccaaag acagcctcg cgagcctcag gtctacaccc tgccaccttc ccgcgaggaa   2400
atgacaaaaa atcaggtgtc actcacctgt ctcgtgaagg ggttttaccc ctccgacatt   2460
gccgtcgagt gggagtccaa tggacagccc gagaacaatt ataagacaac acctcccgtc   2520
ctggactccg atggatcatt ttttctgtac tccaagctca ccgtcgataa gtccagatgg   2580
cagcagggaa atgtcttttc ctgctccgtg atgcatgaag ctctccacaa tcattacaca   2640
```

```
cagaaaagcc tgtccctgtc ccccggcaag tgactcgag                      2679
```

<210> SEQ ID NO 70
<211> LENGTH: 2694
<212> TYPE: DNA
<213> ORGANISM: Artificial Sequence
<220> FEATURE:
<223> OTHER INFORMATION: Synthetic Nucleotide sequence encoding the
      protein complex comprising VEGF and EGFR specific binding
      peptides #26

<400> SEQUENCE: 70

```
gaattcgcca ccatgggctg gtcctgcatc atcctgtttc tggtggccac cgccaccggc      60
gtgcactctg atatccagat gacccagagc ccagcagcc tgtctgcctc tgtgggcgac     120
agagtgacca tcacctgtcg ggccagccag aagatcttca cggcctgag ctggtatcag     180
cagaagcccg gcaaggcccc caagctgctg atctaccaca gcagcaccct gcagagcggc     240
gtgccaagca gattttctgg cagcggcagc ggcaccgact tcaccctgac aatcagcagc     300
ctgcagcccg aggacttcgc cacctactac tgccagcagg tcctgctgta ccctacacc      360
tttggccagg gcaccaaggt ggaaatcaag agagagccca gagctgcga caagacccac     420
acctgtcccc cttgtcctgc ccctgaactg ctgggaggcc tagcgtgtt cctgttcccc      480
ccaaagccca aggacaccct gatgatcagc ggacccccg aagtgacctg cgtggtggtg      540
gatgtgtccc acgaggaccc tgaagtgaag ttcaattggt acgtggacgg cgtggaagtg      600
cacaacgcca agaccaagcc cagagaggaa cagtacaaca gcacctaccg ggtggtgtcc      660
gtgctgacag tgctgcacca ggactggctg aacggcaaag agtacaagtg caaggtgtcc      720
aacaaggccc tgcctgcccc catcgagaaa accatcagca aggccaaggg ccagcccaga      780
gaaccccagg tgtacacact gcccccagc agagaagaga tgaccaagaa ccaggtgtcc     840
ctgacctgcc tggtcaaggg cttctacccc agcgatatcg ccgtggaatg ggagagcaac      900
ggccagcctg agaacaacta caagaccacc cccctgtgc tggacagcga cggctcattc      960
ttcctgtaca gcaagctgac cgtggacaag agcggtggc agcagggcaa cgtgttcagc     1020
tgcagcgtga tgcacgaggc cctgcacaac cactacaccc agaagtccct gagcctgagc     1080
cccggcaaga tgcagatctt cgtgaaaacc ctgaccggca agaccatcac cctggaagtg     1140
gaacccagcg acaccatcga gaacgtgaag gccaagatcc aggacaaaga gggcatcccc     1200
cccgaccagc agagactgat cttcgccggc aagcagctgg aagatggcag aaccctgagc     1260
gactacaaca tccagaaaga gtccaccctg cacctggtgc tgcggctgag aggcggaggt     1320
ggtggtggtt ctggtggcgg aggatctggc ggtggtggat ctggggagg tggaagtggt     1380
ggcggtggta gtggtggtgg cggaagcgga ggcggtggat caggcggagg cggatcaatg     1440
cagattttg tcaagacact gaccgggaaa acaatcacac tcgaagtcga gccctccgat     1500
acaattgaga atgtgaaagc caaaattcag gacaaagaag ggattcctcc tgatcagcag     1560
cggctgattt ttgccggaaa acagctcgaa gatggacgga ccctgtccga ttacaatatt     1620
cagaaagaaa gcaccctcca tctggtcctg aggctgcggg gaggcgacat tcagatgaca     1680
cagtccccca cctccctgtc tgccagcgtg ggagatcgcg tgaccattac ctgcagagcc     1740
tcccagtgga tcggcaacct gctggattgg tatcagcaga aacctgggga ggctcctaaa     1800
ctgctgatct attaccgcag cttcctgcag tccggcgtgc cctctagatt ttccggcgga     1860
ggcttcggca cagatttcac actgaccatc tcatccctgc agcctgaaga ttttgccaca     1920
```

```
tattattgcc agcaggccaa ccctgccccc ctgacatttg gacagggaac aaaggtcgag    1980
atcaagcgcg agcctaagtc ctgtgacaag acacacacat gccctccctg cccagcccca    2040
gaactgctcg gtggaccctc tgtgtttctg tttccaccca agcctaagga tacactcatg    2100
atctccagaa cacctgaagt gacatgtgtg gtcgtcgacg tgtcacatga ggatccagaa    2160
gtcaagttta actggtatgt ggatggggtc gaggtgcaca atgccaaaac aaaacctcgg    2220
gaagaacagt ataattccac ctatagagtc gtgtctgtgc tcaccgtgct ccatcaggat    2280
tggctcaatg gaaagaata caaatgtaaa gtctctaaca agcccctgcc cgctcctatc    2340
gaaaagacaa tctccaaggc caaggacag cctcgcgagc ctcaggtcta caccctgcca    2400
ccttcccgcg aggaaatgac aaaaaatcag gtgtcactca cctgtctcgt gaagggggttt    2460 taccccctccg acattgccgt cgagtgggag tccaatggac agcccgagaa caattataag    2520
acaacacctc ccgtcctgga ctccgatgga tcatttttc tgtactccaa gctcaccgtc    2580
gataagtcca gatggcagca gggaaatgtc ttttcctgct ccgtgatgca tgaagctctc    2640
cacaatcatt acacacagaa aagcctgtcc ctgtccccccg gcaagtgact cgag         2694
```

<210> SEQ ID NO 71
<211> LENGTH: 2709
<212> TYPE: DNA
<213> ORGANISM: Artificial Sequence
<220> FEATURE:
<223> OTHER INFORMATION: Synthetic Nucleotide sequence encoding the
      protein complex comprising VEGF and EGFR specific binding
      peptides #27

<400> SEQUENCE: 71

```
gaattcgcca ccatgggctg gtcctgcatc atcctgtttc tggtggccac cgccaccggc      60
gtgcactctg atatccagat gacccagagc cccagcagcc tgtctgcctc tgtgggcgac     120
agagtgacca tcacctgtcg ggccagccag aagatcttca acggcctgag ctggtatcag     180
cagaagcccg gcaaggcccc caagctgctg atctaccaca gcagcaccct gcagagcggc     240
gtgccaagca gattttctgg cagcggcagc ggcaccgact tcaccctgac aatcagcagc     300
ctgcagcccg aggacttcgc cacctactac tgccagcagg tcctgctgta ccccctacacc     360 tttggccagg gcaccaaggt ggaaatcaag agagagccca gagctgcga caagacccac     420 acctgtcccc cttgtcctgc ccctgaactg ctgggaggcc ctagcgtgtt cctgttcccc     480
ccaaagccca aggacaccct gatgatcagc cggacccccg aagtgacctg cgtggtggtg     540
gatgtgtccc acgaggaccc tgaagtgaag ttcaattggt acgtggacgg cgtggaagtg     600
cacaacgcca agaccaagcc cagagaggaa cagtacaaca gcacctaccg ggtggtgtcc     660
gtgctgacag tgctgcacca ggactggctg aacggcaaag agtacaagtg caaggtgtcc     720
aacaaggccc tgcctgcccc catcgagaaa accatcagca aggccaaggg ccagcccaga     780 gaacccagg tgtacacact gccccccagc agagaagaga tgaccaagaa ccaggtgtcc     840
ctgacctgcc tggtcaaggg cttctacccc agcgatatcg ccgtggaatg ggagagcaac     900
ggccagcctg agaacaacta caagaccacc ccccctgtgc tggacagcga cggctcattc     960
ttcctgtaca gcaagctgac cgtggacaag agccggtggc agcagggcaa cgtgttcagc    1020
tgcagcgtga tgcacgaggc cctgcacaac cactacaccc agaagtccct gagcctgagc    1080
cccggcaaga tgcagatctt cgtgaaaacc ctgaccggca agaccatcac cctggaagtg    1140
gaacccagcg acaccatcga gaacgtgaag gccaagatcc aggacaaaga gggcatcccc    1200
cccgaccagc agagactgat cttcgccggc aagcagctgg aagatggcag aacccctgagc    1260
```

```
gactacaaca tccagaaaga gtccaccctg cacctggtgc tgcggctgag aggcggaggt   1320
ggtggtggtt ctggtggcgg aggatctggc ggtggtggat ctggggaggg tggaagtggt   1380
ggcggtggta gtggtggtgg cggaagcgga ggcggtggat caggcggagg cggatcaggt   1440
ggcgggggtt caatgcagat ttttgtcaag acactgaccg ggaaaacaat cacactcgaa   1500
gtcgagccct ccgatacaat tgagaatgtg aaagccaaaa ttcaggacaa agaagggatt   1560
cctcctgatc agcagcggct gattttttgcc ggaaaacagc tcgaagatgg acggaccctg   1620
tccgattaca atattcagaa agaaagcacc ctccatctgg tcctgaggct gcggggaggc   1680
gacattcaga tgacacagtc ccccacctcc ctgtctgcca gcgtgggaga tcgcgtgacc   1740
attacctgca gagcctccca gtggatcggc aacctgctgg attggtatca gcagaaacct   1800
ggggaggctc ctaaactgct gatctattac gccagcttcc tgcagtccgg cgtgccctct   1860 agatttccg gcggaggctt cggcacagat ttcacactga ccatctcatc cctgcagcct   1920
gaagattttg ccacatatta ttgccagcag gccaaccctg ccccctgac atttggacag   1980 ggaacaaagg tcgagatcaa gcgcgagcct aagtcctgtg acaagacaca cacatgccct   2040
ccctgcccag ccccagaact gctcggtgga ccctctgtgt ttctgtttcc acccaagcct   2100
aaggatacac tcatgatctc cagaacacct gaagtgacat gtgtggtcgt cgacgtgtca   2160
catgaggatc cagaagtcaa gtttaactgg tatgtggatg gggtcgaggt gcacaatgcc   2220
aaaacaaaac ctcgggaaga acagtataat tccacctata gagtcgtgtc tgtgctcacc   2280
gtgctccatc aggattggct caatgggaaa gaatacaaat gtaaagtctc taacaaagcc   2340
ctgcccgctc ctatcgaaaa gacaatctcc aaggccaaag acagcctcg cgagcctcag   2400 gtctacaccc tgccaccttc ccgcgaggaa atgacaaaaa atcaggtgtc actcacctgt   2460
ctcgtgaagg ggttttaccc ctccgacatt gccgtcgagt gggagtccaa tggacagccc   2520
gagaacaatt ataagacaac acctcccgtc ctggactccg atggatcatt ttttctgtac   2580
tccaagctca ccgtcgataa gtccagatgg cagcaggaa atgtcttttc ctgctccgtg   2640
atgcatgaag ctctccacaa tcattacaca cagaaaagcc tgtccctgtc ccccggcaag   2700
tgactcgag                                                           2709
```

<210> SEQ ID NO 72
<211> LENGTH: 2724
<212> TYPE: DNA
<213> ORGANISM: Artificial Sequence
<220> FEATURE:
<223> OTHER INFORMATION: Synthetic Nucleotide sequence encoding the
      protein complex comprising VEGF and EGFR specific binding
      peptides #28

<400> SEQUENCE: 72

```
gaattcgcca ccatgggctg gtcctgcatc atcctgtttc tggtggccac cgccaccggc    60
gtgcactctg atatccagat gacccagagc cccagcagcc tgtctgcctc tgtgggcgac   120
agagtgacca tcacctgtcg ggccagccag aagatcttca cggcctgag ctggtatcag   180 cagaagcccg gcaaggcccc caagctgctg atctaccaca gcagcaccct gcagagcggc   240
gtgccaagca gattttctgg cagcggcagc ggcaccgact tcaccctgac aatcagcagc   300
ctgcagcccg aggacttcgc cacctactac tgccagcagg tcctgctgta cccctacacc   360
tttggccagg gcaccaaggt ggaaatcaag agagagccca gagctgcga caagacccac   420 acctgtcccc cttgtcctgc ccctgaactg ctgggaggcc ctagcgtgtt cctgttcccc   480
```

| | |
|---|---|
| ccaaagccca aggacaccct gatgatcagc cggaccccg aagtgacctg cgtggtggtg | 540 |
| gatgtgtccc acgaggaccc tgaagtgaag ttcaattggt acgtggacgg cgtggaagtg | 600 |
| cacaacgcca agaccaagcc cagagaggaa cagtacaaca gcacctaccg ggtggtgtcc | 660 |
| gtgctgacag tgctgcacca ggactggctg aacggcaaag agtacaagtg caaggtgtcc | 720 |
| aacaaggccc tgcctgcccc catcgagaaa accatcagca aggccaaggg ccagcccaga | 780 |
| gaacccagg tgtacacact gcccccagc agagaagaga tgaccaagaa ccaggtgtcc | 840 |
| ctgacctgcc tggtcaaggg cttctacccc agcgatatcg ccgtggaatg ggagagcaac | 900 |
| ggccagcctg agaacaacta caagaccacc cccctgtgc tggacagcga cggctcattc | 960 |
| ttcctgtaca gcaagctgac cgtggacaag agccggtggc agcagggcaa cgtgttcagc | 1020 |
| tgcagcgtga tgcacgaggc cctgcacaac cactacaccc agaagtccct gagcctgagc | 1080 |
| cccggcaaga tgcagatctt cgtgaaaacc ctgaccggca gaccatcac cctggaagtg | 1140 |
| gaacccagcg acaccatcga gaacgtgaag gccaagatcc aggacaaaga gggcatcccc | 1200 |
| cccgaccagc agagactgat cttcgccggc aagcagctgg aagatggcag aaccctgagc | 1260 |
| gactacaaca tccagaaaga gtccaccctg cacctggtgc tgcggctgag aggcggaggt | 1320 |
| ggtggtggtt ctggtggcgg aggatctggc ggtggtggat ctggggagg tggaagtggt | 1380 |
| ggcggtggta gtggtggtgg cggaagcgga ggcggtggat caggcggag cggatcaggt | 1440 |
| ggcggggtt caggggtggg cggaagtatg cagattttg tcaagacact gaccgggaaa | 1500 |
| acaatcacac tcgaagtcga gccctccgat acaattgaga atgtgaaagc caaaattcag | 1560 |
| gacaaagaag ggattcctcc tgatcagcag cggctgattt tgccggaaaa acagctcgaa | 1620 |
| gatggacgga ccctgtccga ttacaatatt cagaaagaaa gcaccctcca tctggtcctg | 1680 |
| aggctgcggg gaggcgacat tcagatgaca cagtccccca cctccctgtc tgccagcgtg | 1740 |
| ggagatcgcg tgaccattac ctgcagagcc tcccagtgga tcggcaacct gctggattgg | 1800 |
| tatcagcaga aacctgggga ggctcctaaa ctgctgatct attacgccag cttcctgcag | 1860 |
| tccggcgtgc cctctagatt ttccggcgga ggcttcggca cagatttcac actgaccatc | 1920 |
| tcatccctgc agcctgaaga ttttgccaca tattattgcc agcaggccaa ccctgccccc | 1980 |
| ctgacatttg gacagggaac aaaggtcgag atcaagcgcg agcctaagtc ctgtgacaag | 2040 |
| acacacacat gccctccctg cccagcccca gaactgctcg gtggaccctc tgtgtttctg | 2100 |
| tttccaccca gcctaagga tacactcatg atctccagaa cacctgaagt gacatgtgtg | 2160 |
| gtcgtcgacg tgtcacatga ggatccagaa gtcaagttta actggtatgt ggatggggtc | 2220 |
| gaggtgcaca atgccaaaac aaaacctcgg gaagaacagt ataattccac ctatagagtc | 2280 |
| gtgtctgtgc tcaccgtgct ccatcaggat tggctcaatg ggaaagaata caatgtaaa | 2340 |
| gtctctaaca agccctgcc cgctcctatc gaaaagacaa tctccaaggc caaggacag | 2400 |
| cctcgcgagc tcaggtcta caccctgcca ccttcccgcg aggaaatgac aaaaaatcag | 2460 |
| gtgtcactca cctgtctcgt gaagggggttt taccctcccg acattgccgt cgagtgggag | 2520 |
| tccaatggac agcccgagaa caattataag acaacacctc ccgtcctgga ctccgatgga | 2580 |
| tcatttttc tgtactccaa gctcaccgtc gataagtcca gatggcagca gggaaatgtc | 2640 |
| ttttcctgct ccgtgatgca tgaagctctc cacaatcatt acacacagaa aagcctgtcc | 2700 |
| ctgtccccg gcaagtgact cgag | 2724 |

<210> SEQ ID NO 73
<211> LENGTH: 2664

<212> TYPE: DNA
<213> ORGANISM: Artificial Sequence
<220> FEATURE:
<223> OTHER INFORMATION: Synthetic Nucleotide sequence encoding the
protein complex comprising VEGF and EGFR specific binding
peptides #29

<400> SEQUENCE: 73

| | | | | | |
|---|---|---|---|---|---|
| gaattcgcca | ccatgggctg | gtcctgcatc | atcctgtttc | tggtggccac | cgccaccggc | 60 |
| gtgcactctg | atatccagat | gacccagagc | cccagcagcc | tgtctgcctc | tgtgggcgac | 120 |
| agagtgacca | tcacctgtcg | ggccagccag | aagatcttca | acggcctgag | ctggtatcag | 180 |
| cagaagcccg | gcaaggcccc | caagctgctg | atctaccaca | gcagcaccct | gcagagcggc | 240 |
| gtgccaagca | gattttctgg | cagcggcagc | ggcaccgact | tcaccctgac | aatcagcagc | 300 |
| ctgcagcccg | aggacttcgc | cacctactac | tgccagcagg | tcctgctgta | ccccta cacc | 360 |
| tttggccagg | gcaccaaggt | ggaaatcaag | agagagccca | gagctgcga | caagacccac | 420 |
| acctgtcccc | cttgtcctgc | ccctgaactg | ctgggaggcc | ctagcgtgtt | cctgttcccc | 480 |
| ccaaagccca | aggacaccct | gatgatcagc | cggaccccg | aagtgacctg | cgtggtggtg | 540 |
| gatgtgtccc | acgaggaccc | tgaagtgaag | ttcaattggt | acgtggacgg | cgtggaagtg | 600 |
| cacaacgcca | agaccaagcc | cagagaggaa | cagtacaaca | gcacctaccg | ggtggtgtcc | 660 |
| gtgctgacag | tgctgcacca | ggactggctg | aacggcaaag | agtacaagtg | caaggtgtcc | 720 |
| aacaaggccc | tgcctgcccc | catcgagaaa | accatcagca | aggccaaggg | ccagcccaga | 780 |
| gaacccagg | tgtacacact | gccccccagc | agagaagaga | tgaccaagaa | ccaggtgtcc | 840 |
| ctgacctgcc | tggtcaaggg | cttctacccc | agcgatatcg | ccgtggaatg | ggagagcaac | 900 |
| ggccagcctg | agaacaacta | caagaccacc | cccctgtgc | tggacagcga | cggctcattc | 960 |
| ttcctgtaca | gcaagctgac | cgtggacaag | agccggtggc | agcagggcaa | cgtgttcagc | 1020 |
| tgcagcgtga | tgcacgaggc | cctgcacaac | cactacaccc | agaagtccct | gagcctgagc | 1080 |
| cccggcaaga | tgcagatctt | cgtgaaaacc | ctgaccggca | agaccatcac | cctggaagtg | 1140 |
| gaacccagcg | acaccatcga | aacgtgaag | gccaagatcc | aggacaaaga | gggcatcccc | 1200 |
| cccgaccagc | agagactgat | cttcgccggc | aagcagctgg | aagatggcag | aaccctgagc | 1260 |
| gactacaaca | tccagaaaga | gtccacccotg | cacctggtgc | tgcggctgag | aggcggaggt | 1320 |
| ggtggtggtt | ctggtggcgg | aggatctggc | ggtggtggat | ctggggggagg | tggaagtggt | 1380 |
| ggcggtggta | gtggtggtgg | cggaagcatg | cagattttg | tcaagacact | gaccgggaaa | 1440 |
| acaatcacac | tcgaagtcga | gccctccgat | acaattgaga | atgtgaaagc | caaaattcag | 1500 |
| gacaaagaag | ggattcctcc | tgatcagcag | cggctgattt | ttgccggaaa | acagctcgaa | 1560 |
| gatggacgga | ccctgtccga | ttacaatatt | cagaaagaaa | gcaccctcca | tctggtcctg | 1620 |
| aggctgcggg | gaggcgacat | tcagatgaca | cagtcccoca | cctccctgtc | tgccagcgtg | 1680 |
| ggagatcgcg | tgaccattac | ctgcagagcc | tcccagtgga | tcgcaacct | gctggattgg | 1740 |
| tatcagcaga | aacctgggga | ggctcctaaa | ctgctgatct | attacgccag | cttcctgcag | 1800 |
| tccggcgtgc | cctctagatt | ttccggcgga | ggcttcggca | cagatttcac | actgaccatc | 1860 |
| tcatccctgc | agcctgaaga | ttttgccaca | tattattgcc | agcaggccaa | ccctgccccc | 1920 |
| ctgacatttg | gacagggaac | aaaggtcgag | atcaagcgcg | agcctaagtc | ctgtgacaag | 1980 |
| acacacacat | gccctccctg | cccagcccca | gaactgctcg | gtggaccctc | tgtgtttctg | 2040 |
| tttccaccca | agcctaagga | tacactcatg | atctccagaa | cacctgaagt | gacatgtgtg | 2100 |

| | |
|---|---|
| gtcgtcgacg tgtcacatga ggatccagaa gtcaagttta actggtatgt ggatggggtc | 2160 |
| gaggtgcaca atgccaaaac aaaacctcgg gaagaacagt ataattccac ctatagagtc | 2220 |
| gtgtctgtgc tcaccgtgct ccatcaggat tggctcaatg ggaaagaata caaatgtaaa | 2280 |
| gtctctaaca aagccctgcc cgctcctatc gaaaagacaa tctccaaggc caaaggacag | 2340 |
| cctcgcgagc tcaggtcta caccctgcca ccttcccgcg aggaaatgac aaaaaatcag | 2400 |
| gtgtcactca cctgtctcgt gaaggggttt taccccctccg acattgccgt cgagtgggag | 2460 |
| tccaatggac agcccgagaa caattataag acaacacctc ccgtcctgga ctccgatgga | 2520 |
| tcatttttc tgtactccaa gctcaccgtg gataagtcca gatggcagca gggaaatgtc | 2580 |
| ttttcctgct ccgtgatgca tgaagctctc cacaatcatt acacacagaa aagcctgtcc | 2640 |
| ctgtcccccg gcaagtgact cgag | 2664 |

<210> SEQ ID NO 74
<211> LENGTH: 2352
<212> TYPE: DNA
<213> ORGANISM: Artificial Sequence
<220> FEATURE:
<223> OTHER INFORMATION: Synthetic Nucleotide sequence encoding the
      protein complex comprising VEGF and EGFR specific binding
      peptides #30

<400> SEQUENCE: 74

| | |
|---|---|
| gaattcgcca ccatgggctg gtcctgcatc atcctgtttc tggtggccac cgccaccggc | 60 |
| gtgcactctg atatccagat gacccagagc cccagcagcc tgtctgcctc tgtgggcgac | 120 |
| agagtgacca tcacctgtcg ggccagccag aagatcttca cggcctgag ctggtatcag | 180 |
| cagaagcccg gcaaggcccc caagctgctg atctaccaca gcagcaccct gcagagcggc | 240 |
| gtgccaagca gattttctgg cagcggcagc ggcaccgact tcaccctgac aatcagcagc | 300 |
| ctgcagcccg aggacttcgc cacctactac tgccagcagg tcctgctgta ccctacacc | 360 |
| tttggccagg gcaccaaggt ggaaatcaag agagagccca gagctgcga caagacccac | 420 |
| acctgtcccc cttgtcctgc ccctgaactg ctgggaggcc ctagcgtgtt cctgttcccc | 480 |
| ccaaagccca aggacaccct gatgatcagc cggacccccg aagtgacctg cgtggtggtg | 540 |
| gatgtgtccc acgaggaccc tgaagtgaag ttcaattggt acgtggacgg cgtggaagtg | 600 |
| cacaacgcca agaccaagcc cagagaggaa cagtacaaca gcacctaccg ggtggtgtcc | 660 |
| gtgctgacag tgctgcacca ggactggctg aacggcaaag agtacaagtg caaggtgtcc | 720 |
| aacaaggccc tgcctgcccc catcgagaaa accatcagca aggccaaggg ccagcccaga | 780 |
| gaacccagg tgtacacact gccccccagc agagaagaga tgaccaagaa ccaggtgtcc | 840 |
| ctgacctgcc tggtcaaggg cttctacccc agcgatatcg ccgtggaatg ggagagcaac | 900 |
| ggccagcctg agaacaacta caagaccacc cccctgtgc tggacagcga cggctcattc | 960 |
| ttcctgtaca gcaagctgac cgtggacaag agccggtggc agcagggcaa cgtgttcagc | 1020 |
| tgcagcgtga tgcacgaggc cctgcacaac cactacaccc agaagtccct gagcctgagc | 1080 |
| cccggcaaga tgcagatctt cgtgaaaacc ctgaccggca agaccatcac cctggaagtg | 1140 |
| gaacccagcg acaccatcga aacgtgaag gccaagatcc aggacaaaga gggcatcccc | 1200 |
| cccgaccagc agagactgat cttcgccggc aagcagctgg aagatggcag aaccctgagc | 1260 |
| gactacaaca tccagaaaga gtccaccctg cacctggtgc tgcggctgag aggcggaggt | 1320 |
| ggtgacattc agatgacaca gtccccccacc tccctgtctg ccagcgtggg agatcgcgtg | 1380 |
| accattacct gcagagcctc ccagtggatc ggcaacctgc tggattggta tcagcagaaa | 1440 |

```
cctggggagg ctcctaaact gctgatctat tacgccagct tcctgcagtc cggcgtgccc    1500
tctagatttt ccggcggagg cttcggcaca gatttcacac tgaccatctc atccctgcag    1560
cctgaagatt ttgccacata ttattgccag caggccaacc ctgcccccct gacatttgga    1620
cagggaacaa aggtcgagat caagcgcgag cctaagtcct gtgacaagac acacacatgc    1680
cctccctgcc cagccccaga actgctcggt ggaccctctg tgtttctgtt tccacccaag    1740
cctaaggata cactcatgat ctccagaaca cctgaagtga catgtgtggt cgtcgacgtg    1800
tcacatgagg atccagaagt caagtttaac tggtatgtgg atggggtcga ggtgcacaat    1860
gccaaaacaa aacctcggga agaacagtat aattccacct atagagtcgt gtctgtgctc    1920
accgtgctcc atcaggattg gctcaatggg aaagaataca aatgtaaagt ctctaacaaa    1980
gccctgcccg ctcctatcga aaagacaatc tccaaggcca aaggacagcc tcgcgagcct    2040
caggtctaca ccctgccacc ttcccgcgag gaaatgacaa aaaatcaggt gtcactcacc    2100
tgtctcgtga aggggtttta cccctccgac attgccgtcg agtgggagtc caatggacag    2160
cccgagaaca attataagac aacacctccc gtcctggact ccgatggatc attttttctg    2220
tactccaagc tcaccgtcga taagtccaga tggcagcagg gaaatgtctt ttcctgctcc    2280
gtgatgcatg aagctctcca caatcattac acacagaaaa gcctgtccct gtccccggc    2340 aagtgactcg ag    2352
```

<210> SEQ ID NO 75
<211> LENGTH: 2679
<212> TYPE: DNA
<213> ORGANISM: Artificial Sequence
<220> FEATURE:
<223> OTHER INFORMATION: Synthetic Nucleotide sequence encoding the
      protein complex comprising VEGF and EGFR specific binding
      peptides #31

<400> SEQUENCE: 75

```
gaattcgcca ccatgggctg gtcctgcatc atcctgtttc tggtggccac cgccaccggc     60
gtgcactctg atatccagat gacccagagc cccagcagcc tgtctgcctc tgtgggcgac    120
agagtgacca tcacctgtcg ggccagccag aagatcttca cggcctgag ctggtatcag    180 cagaagcccg gcaaggcccc caagctgctg atctaccaca gcagcaccct gcagagcggc    240
gtgccaagca gattttctgg cagcggcagc ggcaccgact caccctgac aatcagcagc    300 ctgcagcccg aggacttcgc cacctactac tgccagcagg tcctgctgta ccctacacc    360 tttggccagg gcaccaaggt ggaaatcaag agagagccca gagctgcga caagacccac    420 acctgtcccc cttgtcctgc ccctgaactg ctgggaggcc ctagcgtgtt cctgttcccc    480
ccaaagccca aggacaccct gatgatcagc cggacccccg aagtgacctg cgtggtggtg    540
gatgtgtccc acgaggaccc tgaagtgaag ttcaattggt acgtggacgg cgtggaagtg    600
cacaacgcca agaccaagcc cagagaggaa cagtacaaca gcacctaccg ggtggtgtcc    660
gtgctgacag tgctgcacca ggactggctg aacggcaaag agtacaagtg caaggtgtcc    720
aacaaggccc tgcctgcccc catcgagaaa accatcagca aggccaaggg ccagcccaga    780
gaaccccagg tgtacacact gccccccagc agagaagaga tgaccaagaa ccaggtgtcc    840
ctgacctgcc tggtcaaggg cttctacccc agcgatatcg ccgtggaatg ggagagcaac    900
ggccagcctg agaacaacta caagaccacc cccctgtgc tggacagcga cggctcattc    960
ttcctgtaca gcaagctgac cgtggacaag agccggtggc agcagggcaa cgtgttcagc    1020
```

```
tgcagcgtga tgcacgaggc cctgcacaac cactacaccc agaagtccct gagcctgagc    1080
cccggcaaga tgcagatctt cgtgaaaacc ctgaccggca agaccatcac cctggaagtg    1140
gaacccagcg acaccatcga aacgtgaag gccaagatcc aggacaaaga gggcatcccc     1200
cccgaccagc agagactgat cttcgccggc aagcagctgg aagatggcag aaccctgagc    1260
gactacaaca tccagaaaga gtccaccctg cacctggtgc tgcggctgag aggcggaggt    1320
ggtggtggtt ctggtggcgg aggatctggc ggtggtggat ctgggggagg tggaagtggt    1380
ggcggtggta gtggtggtgg cggaagcatg cagattttg tcaagacact gaccgggaaa     1440
acaatcacac tcgaagtcga gccctccgat acaattgaga atgtgaaagc caaaattcag    1500
gacaaagaag ggattcctcc tgatcagcag cggctgattt ttgccggaaa acagctcgaa    1560
gatggacgga ccctgtccga ttacaatatt cagaaagaaa gcaccctcca tctggtcctg    1620
aggctgcggg gaggcggcgg cggcggcagc gacattcaga tgacacagtc ccccacctcc    1680
ctgtctgcca gcgtgggaga tcgcgtgacc attacctgca gagcctccca gtggatcggc    1740
aacctgctgg attggtatca gcagaaacct ggggaggctc ctaaactgct gatctattac    1800
gccagcttcc tgcagtccgg cgtgccctct agattttccg gcggaggctt cggcacagat    1860
ttcacactga ccatctcatc cctgcagcct gaagattttg ccacatatta ttgccagcag    1920
gccaaccctg cccccctgac atttggacag ggaacaaagg tcgagatcaa gcgcgagcct    1980
aagtcctgtg acaagacaca cacatgccct ccctgcccag cccagaact gctcggtgga    2040 ccctctgtgt ttctgtttcc acccaagcct aaggatacac tcatgatctc cagaacacct    2100
gaagtgacat gtgtggtcgt cgacgtgtca catgaggatc cagaagtcaa gtttaactgg    2160
tatgtggatg gggtcgaggt gcacaatgcc aaaacaaaac tcgggaaga acagtataat    2220 tccacctata gagtcgtgtc tgtgctcacc gtgctccatc aggattggct caatgggaaa    2280
gaatacaaat gtaaagtctc taacaaagcc ctgcccgctc ctatcgaaaa gacaatctcc    2340
aaggccaaag acagcctccg cgagcctcag gtctacaccc tgccaccttc ccgcgaggaa    2400
atgacaaaaa atcaggtgtc actcacctgt ctcgtgaagg ggttttaccc ctccgacatt    2460
gccgtcgagt gggagtccaa tggacagccc gagaacaatt ataagacaac acctcccgtc    2520
ctggactccg atggatcatt ttttctgtac tccaagctca ccgtcgataa gtccagatgg    2580
cagcagggaa atgtcttttc ctgctccgtg atgcatgaag ctctccacaa tcattacaca    2640
cagaaaagcc tgtccctgtc ccccggcaag tgactcgag                           2679

<210> SEQ ID NO 76
<211> LENGTH: 2670
<212> TYPE: DNA
<213> ORGANISM: Artificial Sequence
<220> FEATURE:
<223> OTHER INFORMATION: Synthetic Nucleotide sequence encoding the
      protein complex comprising VEGF and EGFR specific binding
      peptides #32

<400> SEQUENCE: 76
gaattcgcca ccatgggctg gtcctgcatc atcctgtttc tggtggccac cgccaccggc     60
gtgcactctg atatccagat gacccagagc cccagcagcc tgtctgcctc tgtgggcgac    120
agagtgacca tcacctgtcg ggccagccag aagatcttca cggcctgag ctggtatcag    180 cagaagcccg gcaaggcccc caagctgctg atctaccaca gcagcaccct gcagagcggc    240
gtgccaagca gattttctgg cagcggcagc ggcaccgact tcaccctgac aatcagcagc    300
ctgcagcccg aggacttcgc cacctactac tgccagcagg tcctgctgta ccccctacacc    360
```

-continued

```
tttggccagg gcaccaaggt ggaaatcaag agagagccca agagctgcga caagacccac    420
acctgtcccc cttgtcctgc ccctgaactg ctggaggcc ctagcgtgtt cctgttcccc     480
ccaaagccca aggacaccct gatgatcagc cggaccccg aagtgacctg cgtggtggtg    540
gatgtgtccc acgaggaccc tgaagtgaag ttcaattggt acgtggacgg cgtggaagtg    600
cacaacgcca agaccaagcc cagagaggaa cagtacaaca gcacctaccg ggtggtgtcc    660
gtgctgacag tgctgcacca ggactggctg aacggcaaag agtacaagtg caaggtgtcc    720
aacaaggccc tgcctgcccc catcgagaaa accatcagca aggccaaggg ccagcccaga    780 gaacccagg tgtacacact gcccccagc agagaagaga tgaccaagaa ccaggtgtcc      840
ctgacctgcc tggtcaaggg cttctacccc agcgatatcg ccgtggaatg ggagagcaac    900
ggccagcctg agaacaacta caagaccacc cccctgtgc tggacagcga cggctcattc     960
ttcctgtaca gcaagctgac cgtggacaag agccggtggc agcagggcaa cgtgttcagc   1020
tgcagcgtga tgcacgaggc cctgcacaac cactacaccc agaagtccct gagcctgagc   1080
cccggcaaga tgcagatctt cgtgaaaacc ctgaccggca agaccatcac cctggaagtg   1140
gaacccagcg acaccatcga gaacgtgaag gccaagatcc aggacaaaga gggcatcccc   1200
cccgaccagc agagactgat cttcgccggc aagcagctgg aagatggcag aaccctgagc   1260
gactacaaca tccagaaaga gtccaccctg cacctggtgc tgcggctgag aggcggaggt   1320
ggtggtggtt ctggtggcgg aggatctggc ggtggtggat ctggggagg tggaagtggt    1380 ggcggtggta gtggtggtgg cggaagcatg cagattttg tcaagacact gaccgggaaa    1440
acaatcacac tcgaagtcga gccctccgat acaattgaga atgtgaaagc caaaattcag   1500
gacaaagaag ggattcctcc tgatcagcag cggctgattt ttgccggaaa acagctcgaa   1560
gatggacgga ccctgtccga ttacaatatt cagaaagaaa gcaccctcca tctggtcctg   1620
aggctgcggg gaggcggcgg cgacattcag atgacacagt cccccaccte cctgtctgcc   1680 agcgtgggag atcgcgtgac cattacctgc agagcctccc agtggatcgg caacctgctg   1740
gattggtatc agcagaaacc tgggagggct cctaaactgc tgatctatta cgccagcttc   1800
ctgcagtccg gcgtgccctc tagattttcc ggcggaggct tcggcacaga tttcacactg   1860
accatctcat ccctgcagcc tgaagatttt gccacatatt attgccagca ggccaaccct   1920
gcccccctga catttggaca gggaacaaag gtcgagatca agcgcgagcc taagtcctgt   1980
gacaagacac acacatgccc tccctgccca gccccagaac tgctcggtgg accctctgtg   2040
tttctgtttc cacccaagcc taaggataca ctcatgatct ccagaacacc tgaagtgaca   2100
tgtgtggtcg tcgacgtgtc acatgaggat ccagaagtca gtttaactg gtatgtggat    2160 ggggtcgagg tgcacaatgc caaaacaaaa cctcgggaag aacagtataa ttccacctat    2220
agagtcgtgt ctgtgctcac cgtgctccat caggattggc tcaatgggaa agaatacaaa    2280
tgtaaagtct ctaacaaagc cctgcccgct cctatcgaaa agacaatctc caaggccaaa    2340
ggacagcctc gcgagcctca ggtctacacc ctgccacctt cccgcgagga aatgacaaaa    2400
aatcaggtgt cactcacctg tctcgtgaag gggttttacc cctccgacat tgccgtcgag    2460
tgggagtcca atggacagcc cgagaacaat tataagacaa cacctcccgt cctggactcc    2520
gatggatcat ttttcctgta ctccaagctc accgtcgata gtccagatgg cagcaggga    2580 aatgtctttt cctgctccgt gatgcatgaa gctctccaca atcattacac acagaaaagc    2640
ctgtccctgt ccccggcaa gtgactcgag                                       2670
```

<210> SEQ ID NO 77
<211> LENGTH: 2679
<212> TYPE: DNA
<213> ORGANISM: Artificial Sequence
<220> FEATURE:
<223> OTHER INFORMATION: Synthetic Nucleotide sequence encoding the
    protein complex comprising VEGF and EGFR specific binding
    peptides #33

<400> SEQUENCE: 77

| | | | | | |
|---|---|---|---|---|---|
| gaattcgcca | ccatgggctg | gtcctgcatc | atcctgtttc | tggtggccac | cgccaccggc | 60 |
| gtgcactctg | atatccagat | gacccagagc | cccagcagcc | tgtctgcctc | tgtgggcgac | 120 |
| agagtgacca | tcacctgtcg | ggccagccag | aagatcttca | acggcctgag | ctggtatcag | 180 |
| cagaagcccg | gcaaggcccc | caagctgctg | atctaccaca | gcagcaccct | gcagagcggc | 240 |
| gtgccaagca | gattttctgg | cagcggcagc | ggcaccgact | tcaccctgac | aatcagcagc | 300 |
| ctgcagcccg | aggacttcgc | cacctactac | tgccagcagg | tcctgctgta | cccctacacc | 360 |
| tttggccagg | gcaccaaggt | ggaaatcaag | agagagccca | gagctgcgca | caagacccac | 420 |
| acctgtcccc | cttgtcctgc | ccctgaactg | ctgggaggcc | ctagcgtgtt | cctgttcccc | 480 |
| ccaaagccca | aggacaccct | gatgatcagc | cggacccccg | aagtgacctg | cgtggtggtg | 540 |
| gatgtgtccc | acgaggaccc | tgaagtgaag | ttcaattggt | acgtggacgg | cgtggaagtg | 600 |
| cacaacgcca | agaccaagcc | cagagaggaa | cagtacaaca | gcacctaccg | ggtggtgtcc | 660 |
| gtgctgacag | tgctgcacca | ggactggctg | aacggcaaag | agtacaagtg | caaggtgtcc | 720 |
| aacaaggccc | tgcctgcccc | catcgagaaa | accatcagca | aggccaaggg | ccagcccaga | 780 |
| gaacccccagg | tgtacacact | gccccccagc | agagaagaga | tgaccaagaa | ccaggtgtcc | 840 |
| ctgacctgcc | tggtcaaggg | cttctacccc | agcgatatcg | ccgtggaatg | ggagagcaac | 900 |
| ggccagcctg | agaacaacta | caagaccacc | cccctgtgc | tggacagcga | cggctcattc | 960 |
| ttcctgtaca | gcaagctgac | cgtggacaag | agccggtggc | agcagggcaa | cgtgttcagc | 1020 |
| tgcagcgtga | tgcacgaggc | cctgcacaac | cactacaccc | agaagtccct | gagcctgagc | 1080 |
| cccggcaaga | tgcagatctt | cgtgaaaacc | ctgaccggca | agaccatcac | cctggaagtg | 1140 |
| gaacccagcg | acaccatcga | gaacgtgaag | gccaagatcc | aggacaaaga | gggcatcccc | 1200 |
| cccgaccagc | agagactgat | cttcgccggc | aagcagctgg | aagatggcag | aaccctgagc | 1260 |
| gactacaaca | tccagaaaga | gtccacctg | cacctggtgc | tgcggctgag | aggcggaggt | 1320 |
| ggtggtggtt | ctggtggcgg | aggatctggc | ggtggtggat | ctgggggagg | tggaagtggt | 1380 |
| ggcggtggta | gtggtggtgg | cggaagcatg | cagattttg | tcaagacact | gaccgggaaa | 1440 |
| acaatcacac | tcgaagtcga | gccctccgat | acaattgaga | atgtgaaagc | caaaattcag | 1500 |
| gacaaagaag | ggattcctcc | tgatcagcag | cggctgattt | ttgccggaaa | acagctcgaa | 1560 |
| gatggacgga | ccctgtccga | ttacaatatt | cagaaagaaa | gcaccctcca | tctggtcctg | 1620 |
| aggctgcggg | gaggcggcgg | cggcggcagc | gacattcaga | tgacacagtc | ccccacctcc | 1680 |
| ctgtctgcca | gcgtgggaga | tcgcgtgacc | attacctgca | gagcctccca | gtggatcggc | 1740 |
| aacctgctgg | attggtatca | gcagaaacct | ggggaggctc | ctaaactgct | gatctattac | 1800 |
| gccagcttcc | tgcagtccgg | cgtgccctct | agattttccg | gcggaggctt | cggcacagat | 1860 |
| ttcacactga | ccatctcatc | cctgcagcct | gaagattttg | ccacatatta | ttgccagcag | 1920 |
| gccaaccctg | cccccctgac | atttggacag | ggaacaaagg | tcgagatcaa | gcgcgagcct | 1980 |
| aagtcctgtg | acaagacaca | cacatgccct | ccctgcccag | ccccagaact | gctcggtgga | 2040 |

```
ccctctgtgt ttctgtttcc acccaagcct aaggatacac tcatgatctc cagaacacct    2100
gaagtgacat gtgtggtcgt cgacgtgtca catgaggatc cagaagtcaa gtttaactgg    2160
tatgtggatg gggtcgaggt gcacaatgcc aaaacaaaac ctcgggaaga acagtataat    2220
tccacctata gagtcgtgtc tgtgctcacc gtgctccatc aggattggct caatgggaaa    2280
gaatacaaat gtaaagtctc taacaaagcc ctgcccgctc ctatcgaaaa gacaatctcc    2340
aaggccaaag acagcctcg cgagcctcag gtctacaccc tgccaccttc ccgcgaggaa     2400
atgacaaaaa atcaggtgtc actcacctgt ctcgtgaagg ggttttaccc ctccgacatt    2460
gccgtcgagt gggagtccaa tggacagccc gagaacaatt ataagacaac acctcccgtc    2520
ctggactccg atggatcatt ttttctgtac tccaagctca ccgtcgataa gtccagatgg    2580
cagcagggaa atgtcttttc ctgctccgtg atgcatgaag ctctccacaa tcattacaca    2640
cagaaaagcc tgtccctgtc ccccggcaag tgactcgag                           2679
```

<210> SEQ ID NO 78
<211> LENGTH: 2352
<212> TYPE: DNA
<213> ORGANISM: Artificial Sequence
<220> FEATURE:
<223> OTHER INFORMATION: Synthetic Nucleotide sequence encoding the
      protein complex comprising VEGF and EGFR specific binding
      peptides #34

<400> SEQUENCE: 78

```
gaattcgcca ccatgggctg gtcctgcatc atcctgtttc tggtggccac cgccaccggc      60
gtgcactctg atatccagat gacccagagc cccagcagcc tgtctgcctc tgtgggcgac     120
agagtgacca tcacctgtcg ggccagccag aagatcttca acggcctgag ctggtatcag     180
cagaagcccg gcaaggcccc caagctgctg atctaccaca gcagcaccct gcagagcggc     240
gtgccaagca gattttctgg cagcggcagc ggcaccgact tcaccctgac aatcagcagc     300
ctgcagcccg aggacttcgc cacctactac tgccagcagg tcctgctgta ccctacacc      360
tttggccagg gcaccaaggt ggaaatcaag agagagccca gagctgcga caagacccac     420
acctgtcccc cttgtcctgc ccctgaactg ctgggaggcc ctagcgtgtt cctgttcccc     480
ccaaagccca aggacaccct gatgatcagc cggacccccg aagtgacctg cgtggtggtg     540
gatgtgtccc acgaggaccc tgaagtgaag ttcaattggt acgtggacgg cgtggaagtg     600
cacaacgcca agaccaagcc cagagaggaa cagtacaaca gcacctaccg ggtggtgtcc     660
gtgctgacag tgctgcacca ggactggctg aacggcaaag agtacaagtg caaggtgtcc     720
aacaaggccc tgcctgcccc catcgagaaa accatcagca aggccaaggg ccagcccaga     780
gaacccagg tgtacacact gccccccagc agagaagaga tgaccaagaa ccaggtgtcc     840
ctgacctgcc tggtcaaggg cttctacccc agcgatatcg ccgtggaatg ggagagcaac     900
ggccagcctg agaacaacta caagaccacc ccccctgtgc tggacagcga cggctcattc     960
ttcctgtaca gcaagctgac cgtggacaag agccggtggc agcagggcaa cgtgttcagc    1020
tgcagcgtga tgcacgaggc cctgcacaac cactacaccc agaagtccct gagcctgagc    1080
cccggcaaga tgcagatctt cgtgaaaacc ctgaccggca agaccatcac cctggaagtg    1140
gaacccagcg acaccatcga gaacgtgaag gccaagatcc aggacaaaga gggcatcccc    1200
cccgaccagc agagactgat cttcgccggc aagcagctgg aagatggcag aaccctgagc    1260
gactacaaca tccagaaaga gtccaccctg cacctggtgc tgcggctgag aggcggaggt    1320
```

```
ggtgacattc agatgacaca gtcccccacc tccctgtctg ccagcgtggg agatcgcgtg      1380
accattacct gcagagcctc ccagtggatc ggcaacctgc tggattggta tcagcagaaa      1440
cctggggagg ctcctaaact gctgatctat tacgccagct cctgcagtc cggcgtgccc      1500 tctagatttt ccggcggagg cttcggcaca gatttcacac tgaccatctc atccctgcag      1560
cctgaagatt ttgccacata ttattgccag caggccaacc ctgccccct gacatttgga       1620 cagggaacaa aggtcgagat caagcgcgag cctaagtcct gtgacaagac acacacatgc      1680
cctccctgcc cagccccaga actgctcggt ggaccctctg tgtttctgtt tccacccaag      1740
cctaaggata cactcatgat ctccagaaca cctgaagtga catgtgtggt cgtcgacgtg      1800
tcacatgagg atccagaagt caagtttaac tggtatgtgg atggggtcga ggtgcacaat      1860
gccaaaacaa aacctcggga agaacagtat aattccacct atagagtcgt gtctgtgctc      1920
accgtgctcc atcaggattg gctcaatggg aaagaataca aatgtaaagt ctctaacaaa      1980
gccctgcccg ctcctatcga aaagacaatc tccaaggcca aggacagcc tcgcgagcct       2040 caggtctaca ccctgccacc ttcccgcgag gaaatgacaa aaaatcaggt gtcactcacc      2100
tgtctcgtga aggggtttta ccctccgac attgccgtcg agtgggagtc caatggacag       2160
cccgagaaca attataagac aacacctccc gtcctggact ccgatggatc attttttctg      2220
tactccaagc tcaccgtcga taagtccaga tggcagcagg gaaatgtctt ttcctgctcc      2280
gtgatgcatg aagctctcca caatcattac acacagaaaa gcctgtccct gtcccccggc      2340
aagtgactcg ag                                                          2352
```

<210> SEQ ID NO 79
<211> LENGTH: 2361
<212> TYPE: DNA
<213> ORGANISM: Artificial Sequence
<220> FEATURE:
<223> OTHER INFORMATION: Synthetic Nucleotide sequence encoding the protein complex comprising VEGF and EGFR specific binding peptides #35

<400> SEQUENCE: 79

```
gaattcgcca ccatgggctg gtcctgcatc atcctgtttc tggtggccac cgccaccggc       60
gtgcactctg atatccagat gacccagagc cccagcagcc tgtctgcctc tgtgggcgac      120
agagtgacca tcacctgtcg ggccagccag aagatcttca cggcctgag ctggtatcag       180 cagaagcccg gcaaggcccc caagctgctg atctaccaca gcagcaccct gcagagcggc      240
gtgccaagca gatttctgg cagcggcagc ggcaccgact cacccctgac aatcagcagc       300
ctgcagcccg aggacttcgc cacctactac tgccagcagg tcctgctgta ccctacacc       360 tttggccagg gcaccaaggt ggaaatcaag agagagccca gagctgcga caagacccac       420 acctgtcccc cttgtcctgc ccctgaactg ctgggaggcc ctagcgtgtt cctgttcccc      480
ccaaagccca aggacaccct gatgatcagc cggacccccg aagtgacctg cgtggtggtg      540
gatgtgtccc acgaggaccc tgaagtgaag ttcaattggt acgtggacgg cgtggaagtg      600
cacaacgcca agaccaagcc cagagaggaa cagtacaaca gcacctaccg ggtggtgtcc      660
gtgctgacag tgctgcacca ggactggctg aacggcaaag agtacaagtg caaggtgtcc      720
aacaaggccc tgcctgcccc catcgagaaa accatcagca aggccaaggg ccagccagaa      780 gaacccagg tgtacacact gccccccagc agagaagaga tgaccaagaa ccaggtgtcc      840
ctgacctgcc tggtcaaggg cttctacccc agcgatatcg ccgtggaatg ggagagcaac      900
ggccagcctg agaacaacta caagaccacc ccccctgtgc tggacagcga cggctcattc      960
```

```
ttcctgtaca gcaagctgac cgtggacaag agccggtggc agcagggcaa cgtgttcagc      1020
tgcagcgtga tgcacgaggc cctgcacaac cactacaccc agaagtccct gagcctgagc      1080
cccggcaaga tgcagatctt cgtgaaaacc ctgaccggca agaccatcac cctggaagtg      1140
gaacccagcg acaccatcga gaacgtgaag gccaagatcc aggacaaaga gggcatcccc      1200
cccgaccagc agagactgat cttcgccggc aagcagctgg aagatggcag aaccctgagc      1260
gactacaaca tccagaaaga gtccaccctg cacctggtgc tgcggctgag aggcggaggt      1320
ggtggtggtt ctgacattca gatgacacag tcccccacct ccctgtctgc cagcgtggga      1380
gatcgcgtga ccattacctg cagagcctcc cagtggatcg gcaacctgct ggattggtat      1440
cagcagaaac tggggaggc tcctaaactg ctgatctatt acgccagctt cctgcagtcc      1500
ggcgtgccct ctagatttc cggcggaggc ttcggcacag atttcacact gaccatctca      1560
tccctgcagc ctgaagattt tgccacatat tattgccagc aggccaaccc tgccccctg      1620 acatttggac agggaacaaa ggtcgagatc aagcgcgagc taagtcctg tgacaagaca      1680 cacacatgcc ctccctgccc agccccagaa ctgctcggtg accctctgt gtttctgttt      1740 ccacccaagc ctaaggatac actcatgatc tccagaacac ctgaagtgac atgtgtggtc      1800
gtcgacgtgt cacatgagga tccagaagtc aagtttaact ggtatgtgga tggggtcgag      1860
gtgcacaatg ccaaaacaaa acctcgggaa gaacagtata attccaccta tagagtcgtg      1920
tctgtgctca ccgtgctcca tcaggattgg ctcaatggga agaatacaa atgtaaagtc      1980 tctaacaaag ccctgcccgc tcctatcgaa aagacaatct ccaaggccaa aggacagcct      2040
cgcgagcctc aggtctacac cctgccacct tcccgcgagg aaatgacaaa aaatcaggtg      2100
tcactcacct gtctcgtgaa ggggtttac ccctccgaca ttgccgtcga gtgggagtcc      2160
aatggacagc ccgagaacaa ttataagaca acacctcccg tcctggactc cgatggatca      2220
ttttttctgt actccaagct caccgtcgat aagtccagat ggcagcaggg aaatgtcttt      2280
tcctgctccg tgatgcatga agctctccac aatcattaca cacagaaaag cctgtccctg      2340
tcccccggca gtgactcga g                                                2361
```

<210> SEQ ID NO 80
<211> LENGTH: 2496
<212> TYPE: DNA
<213> ORGANISM: Artificial Sequence
<220> FEATURE:
<223> OTHER INFORMATION: Synthetic Nucleotide sequence encoding the
      protein complex comprising VEGF and EGFR specific binding
      peptides #36

<400> SEQUENCE: 80

```
gaattcgcca ccatgggctg gtcctgcatc atcctgtttc tggtggccac cgccaccggc       60
gtgcactctg atatccagat gacccagagc ccagcagcc tgtctgcctc tgtgggcgac      120
agagtgacca tcacctgtcg ggccagccag aagatcttca acggcctgag ctggtatcag      180
cagaagcccg gcaaggcccc caagctgctg atctaccaca gcagcaccct gcagagcggc      240
gtgccaagca gatttctctgg cagcggcagc ggcaccgact tcaccctgac aatcagcagc      300
ctgcagcccg aggacttcgc cacctactac tgccagcagg tcctgctgta ccctacacc      360 tttggccagg gcaccaaggt ggaaatcaag agagagccca gagctgcga caagacccac      420 acctgtcccc cttgtcctgc ccctgaactg ctggggaggc ctagcgtgtt cctgttccc      480 ccaaagccca aggacaccct gatgatcagc cggacccccg aagtgacctg cgtggtggtg      540
```

```
gatgtgtccc acgaggaccc tgaagtgaag ttcaattggt acgtggacgg cgtggaagtg    600
cacaacgcca agaccaagcc cagagaggaa cagtacaaca gcacctaccg ggtggtgtcc    660
gtgctgacag tgctgcacca ggactggctg aacggcaaag agtacaagtg caaggtgtcc    720
aacaaggccc tgcctgcccc catcgagaaa accatcagca aggccaaggg ccagcccaga    780
gaacccacgg tgtacacact gccccccagc agagaagaga tgaccaagaa ccaggtgtcc    840
ctgacctgcc tggtcaaggg cttctacccc agcgatatcg ccgtggaatg ggagagcaac    900
ggccagcctg agaacaacta caagaccacc cccctgtgc tggacagcga cggctcattc    960
ttcctgtaca gcaagctgac cgtggacaag agccggtggc agcagggcaa cgtgttcagc   1020
tgcagcgtga tgcacgaggc cctgcacaac cactacaccc agaagtccct gagcctgagc   1080
cccggcaagg gcggcatgaa cgccagggc aaggagatgg acagcctgcg cttcctgtac   1140
gacggcatcc gcatccaggc cgaccaggcc cccgaggacc tggacatgga ggacaacgac   1200
atcatcgagg cccaccgcga gcagatcggc ggcggtggtg gtggttctgg tggcggagga   1260
tctggcggtg gtggatctgg gggaggtgga agtggtggcg gtggtagtgg tggtggcgga   1320
agcatgaagc gccagggcaa ggagatggac agcctgcgct tcctgtacga cggcatccgc   1380
atccaggccg accaggcccc cgaggacctg acatggagg acaacgacat catcgaggcc   1440
caccgcgagc agatcggcgg cggcggcgac attcagatga cacagtcccc cacctccctg   1500
tctgccagcg tgggagatcg cgtgaccatt acctgcagag cctcccagtg gatcggcaac   1560
ctgctggatt ggtatcagca gaaacctggg gaggctccta aactgctgat ctattacgcc   1620
agcttcctgc agtccggcgt gccctctaga ttttccggcg gaggcttcgg cacagatttc   1680
acactgacca tctcatccct gcagcctgaa gattttgcca catattattg ccagcaggcc   1740
aaccctgccc cctgacatt tggacaggga acaaaggtcg agatcaagcg cgagcctaag   1800
tcctgtgaca agacacacac atgccctccc tgcccagccc cagaactgct cggtggaccc   1860
tctgtgtttc tgtttccacc caagcctaag gatacactca tgatctccag aacacctgaa   1920
gtgacatgtg tggtcgtcga cgtgtcacat gaggatccag aagtcaagtt taactggtat   1980
gtggatgggg tcgaggtgca caatgccaaa acaaaaccct gggaagaaca gtataattcc   2040
acctatagag tcgtgtctgt gctcaccgtg ctccatcagg attggctcaa tgggaaagaa   2100
tacaaatgta agtctctaa caaagccctg cccgctccta tcgaaaagac aatctccaag   2160
gccaaaggac agcctcgcga gcctcaggtc tacaccctgc caccttcccg cgaggaaatg   2220
acaaaaaatc aggtgtcact cacctgtctc gtgaaggggt tttacccctc cgacattgcc   2280
gtcgagtggg agtccaatgg acagcccgag aacaattata agacaacacc tcccgtcctg   2340
gactccgatg gatcattttt tctgtactcc aagctcaccg tcgataagtc cagatggcag   2400
cagggaaatg tcttttcctg ctccgtgatg catgaagctc tccacaatca ttacacacag   2460
aaaagcctgt ccctgtcccc cggcaagtga ctcgag                              2496
```

<210> SEQ ID NO 81
<211> LENGTH: 2280
<212> TYPE: DNA
<213> ORGANISM: Artificial Sequence
<220> FEATURE:
<223> OTHER INFORMATION: Synthetic Nucleotide sequence encoding the
      protein complex comprising VEGF and EGFR specific binding
      peptides #37

<400> SEQUENCE: 81

```
gaattcgcca ccatgggctg gtcctgcatc atcctgtttc tggtggccac cgccaccggc     60
```

-continued

```
gtgcactctg atatccagat gacccagagc cccagcagcc tgtctgcctc tgtgggcgac    120
agagtgacca tcacctgtcg ggccagccag aagatcttca acggcctgag ctggtatcag    180
cagaagcccg gcaaggcccc caagctgctg atctaccaca gcagcaccct gcagagcggc    240
gtgccaagca gattttctgg cagcggcagc ggcaccgact tcaccctgac aatcagcagc    300
ctgcagcccg aggacttcgc cacctactac tgccagcagg tcctgctgta ccctacacc     360 tttggccagg gcaccaaggt ggaaatcaag agagagccca gagctgcga caagacccac     420 acctgtcccc cttgtcctgc ccctgaactg ctgggaggcc ctagcgtgtt cctgttcccc    480
ccaaagccca aggacaccct gatgatcagc cggacccccg aagtgacctg cgtggtggtg    540
gatgtgtccc acgaggaccc tgaagtgaag ttcaattggt acgtggacgg cgtggaagtg    600
cacaacgcca agaccaagcc cagagaggaa cagtacaaca gcacctaccg ggtggtgtcc    660
gtgctgacag tgctgcacca ggactggctg aacggcaaag agtacaagtg caaggtgtcc    720
aacaaggccc tgcctgcccc catcgagaaa accatcagca aggccaaggg ccagcccaga    780 gaacccagg tgtacacact gcccccagc agagaagaga tgaccaagaa ccaggtgtcc      840
ctgacctgcc tggtcaaggg cttctacccc agcgatatcg ccgtggaatg ggagagcaac    900
ggccagcctg agaacaacta agaccacc cccctgtgc tggacagcga cggctcattc       960
ttcctgtaca gcaagctgac cgtggacaag agccggtggc agcagggcaa cgtgttcagc    1020
tgcagcgtga tgcacgaggc cctgcacaac cactacaccc agaagtccct gagcctgagc    1080
cccggcaagg actacgacat ccccaccacc gagaacctgt acttccaggg cggtggtggt    1140
ggttctggtg gcggaggatc tggcggtggt ggatctgggg gaggtggaag tggtggcggt    1200
ggtagtggtg gtggcggaag cgagaacctg tacttccagg gctctggcgg cgacattcag    1260
atgacacagt ccccccacctc cctgtctgcc agcgtgggag atcgcgtgac cattacctgc    1320
agagcctccc agtggatcgg caacctgctg gattggtatc agcagaaacc tgggaggct    1380 cctaaactgc tgatctatta cgccagcttc ctgcagtccg gcgtgccctc tagattttcc    1440 ggcgaggct tcggcacaga tttcacactg accatctcat ccctgcagcc tgaagatttt    1500
gccacatatt attgccagca ggccaaccct gccccctga catttggaca gggaacaaag    1560
gtcgagatca agcgcgagcc taagtcctgt gacaagacac acacatgccc tccctgccca    1620
gccccagaac tgctcggtgg accctctgtg tttctgtttc cacccaagcc taaggataca    1680
ctcatgatct ccagaacacc tgaagtgaca tgtgtggtcg tcgacgtgtc acatgaggat    1740
ccagaagtca agtttaactg gtatgtggat ggggtcgagg tgcacaatgc caaaacaaaa    1800
cctcgggaag aacagtataa ttccacctat agagtcgtgt ctgtgctcac cgtgctccat    1860
caggattggc tcaatgggaa agaatacaaa tgtaaagtct ctaacaaagc cctgcccgct    1920
cctatcgaaa agacaatctc caaggccaaa ggacagcctc gcgagcctca ggtctacacc    1980 ctgccaccctt cccgcgagga aatgacaaaa atcaggtgt cactcacctg tctcgtgaag    2040
gggttttacc cctccgacat tgccgtcgag tgggagtcca atggacagcc cgagaacaat    2100
tataagacaa cacctcccgt cctggactcc gatggtcat ttttctgta ctccaagctc      2160 accgtcgata agtccagatg gcagcaggga aatgtcttt cctgctccgt gatgcatgaa     2220
gctctccaca atcattacac acagaaaagc ctgtccctgt cccccggcaa gtgactcgag    2280
```